(12) United States Patent
Kim et al.

(10) Patent No.: US 12,163,149 B2
(45) Date of Patent: Dec. 10, 2024

(54) ARTIFICIAL GENOME MANIPULATION FOR GENE EXPRESSION REGULATION

(71) Applicant: TOOLGEN INCORPORATED, Seoul (KR)

(72) Inventors: Seokjoong Kim, Seoul (KR); Dong Woo Song, Seoul (KR); Jae Young Lee, Seoul (KR); Jung Min Lee, Gyeongsangbuk-do (KR); Gyu-bon Cho, Seoul (KR); Hee Sook Bae, Gyeonggi-do (KR)

(73) Assignee: TOOLGEN INCORPORATED, Seoul (KR)

( * ) Notice: Subject to any disclaimer, the term of this patent is extended or adjusted under 35 U.S.C. 154(b) by 0 days.

(21) Appl. No.: 18/147,156

(22) Filed: Dec. 28, 2022

(65) Prior Publication Data

US 2023/0295652 A1    Sep. 21, 2023

Related U.S. Application Data

(63) Continuation of application No. 16/776,707, filed on Jan. 30, 2020, now Pat. No. 11,572,574, which is a continuation-in-part of application No. PCT/KR2018/011424, filed on Sep. 27, 2018.

(60) Provisional application No. 62/799,169, filed on Jan. 31, 2019, provisional application No. 62/565,868, filed on Sep. 29, 2017, provisional application No. 62/564,478, filed on Sep. 28, 2017.

(51) Int. Cl.
| | | |
|---|---|---|
| C07H 21/02 | (2006.01) | |
| C12N 9/22 | (2006.01) | |
| C12N 15/113 | (2010.01) | |
| C12N 15/85 | (2006.01) | |

(52) U.S. Cl.
CPC ............... *C12N 15/85* (2013.01); *C12N 9/22* (2013.01); *C12N 15/113* (2013.01); *C12N 2310/20* (2017.05)

(58) Field of Classification Search
CPC ............ C12N 15/111; C12N 2310/20
See application file for complete search history.

(56) References Cited

U.S. PATENT DOCUMENTS

| 5,215,982 | A  | 6/1993 | Sakane et al. |
| 7,384,928 | B2 | 6/2008 | Nishitani et al. |
| 2014/0242664 | A1 | 8/2014 | Zhang et al. |
| 2015/0071898 | A1 | 3/2015 | Liu et al. |
| 2015/0284727 | A1 | 10/2015 | Kim et al. |

FOREIGN PATENT DOCUMENTS

| CA | 2894701 A1 | 6/2014 | |
| CA | 3046199 A1 | 6/2018 | |
| CN | 105121648 A | 12/2015 | |
| CN | 105899658 A | 8/2016 | |
| EP | 3539980 A2 | 9/2019 | |
| KR | 10-2015-0101446 A | 9/2015 | |
| KR | 10-2015-0105633 A | 9/2015 | |
| KR | 10-2016-0050069 A | 5/2016 | |
| RU | 2015148637 A | 5/2017 | |
| WO | WO 2013/176772 A1 * | 11/2013 | ........... C12N 15/111 |
| WO | WO-2014/065596 A1 | 5/2014 | |
| WO | WO-2014-093712 A1 | 6/2014 | |
| WO | WO-2014-197748 A2 | 12/2014 | |
| WO | WO-2014-204728 A1 | 12/2014 | |
| WO | WO-2015-035162 A2 | 3/2015 | |
| WO | WO-2015/048577 A2 | 4/2015 | |
| WO | WO-2015-139139 A1 | 9/2015 | |
| WO | WO-2016-205613 A1 | 12/2016 | |
| WO | WO-2017/035416 A2 | 3/2017 | |
| WO | WO-2017-053431 A2 | 3/2017 | |
| WO | WO-2017/083852 A1 | 5/2017 | |
| WO | WO-2018-088694 A2 | 5/2018 | |
| WO | WO-2018/106782 A1 | 6/2018 | |

OTHER PUBLICATIONS

Wight (ASN Neuro, 9, 4, Jul.-Aug. 2017, 1-6).*
Office Action From Corresponding Canadian Application No. 3077153, Issued May 17, 2023.
Hudson, L.D. et al., "Human PLP gene encoding proteolipid protein, upstream region", GenBank, Accession M27111.1, Jan. 1995 (Jan. 1995).
International Search Report from corresponding PCT Application No. PCT/KR2018/011424, dated May 7, 2019.
Hamdan, H, et al.; "Control of Human PLP1 Expression Through Transcriptional Regulatory Elements and Alternatively Spliced Exons in Intron 1", American Society for Neurochemistry, 2015, pp. 1-12.
Hamdan, H., et al.; "The wmN1 Enhancer Region in Intron 1 is Required for Expression of Human PLP1", Glia. Aug. 2018 ; 66(8): 1763-1774.
Meng, F., et al.; "Characterization of an Intronic Enhancer That Regulates Myelin Proteolipid Protein (Plp) Gene Expression in Oligodendrocytes", Journal of Neuroscience Research 82:346-356 (2005).
Tuason, M. C., et al.,; "Separate Proteolipid Protein/DM20 Enhancers Serve Different Lineages and Stages of Development", The Journal of Neuroscience, Jul. 2, 2008 . 28(27):6895-6903.
Wight, P. A., et al.; "Effects of Intron 1 Sequences on Human PLP1 Expression: Implications for PLP1-Related Disorders", American Society for Neurochemistry, 2017, pp. 1-6.
Ji-Su Lee et al.: "Targeted PMP22 TATA-box editing by CRISPR/Cas9 reduces demyelinating neuropathy of Charcot-Marie-Tooth disease type 1A in mice", Nucleic Acids Research, vol. 48, Issue 1, Jan. 10, 2020, pp. 130-140, https://doi.org/10.1093/nar/gkz1070.

(Continued)

*Primary Examiner* — Amy Rose Hudson
(74) *Attorney, Agent, or Firm* — Harness, Dickey & Pierce, P.L.C.

(57) ABSTRACT

The present invention relates to an expression control composition for controlling the expression of a duplicate gene or a method using the same. In addition, the present invention relates to a method of treating or improving a disease caused by gene duplication using the expression control composition for controlling the expression of a duplicate gene.

5 Claims, 45 Drawing Sheets

Specification includes a Sequence Listing.

(56) References Cited

OTHER PUBLICATIONS

Wojtal D et al. "Spell Checking Nature: Versatility of CRISPR/Cas9 for Developing Treatments for Inherited Disorders", The American Journal of Human Genetics, 2016, vol. 98, pp. 90-101, the abstract, p. 94 the left column, the last paragraph. p. 95, the right column. paragraph 1, p. 97, the right column. paragraph 2, p. 98, the left column. Paragraph 2.

Office Action from corresponding Russian Patent Application No. 2020114785, dated Oct. 9, 2020.

Office Action of RU Patent Application No. 2020114785, Mar. 10, 2021.

Search Report of RU Patent Application No. 2020114785, Mar. 10, 2021.

Office Action of CA Patent Application No. 3,077,153, Mar. 29, 2021.

Iobodin, B. et al., "Transcription Impacts the Efficiency of mRNA Translation via Co transcriptional N6-adenosine Methylation", Cell, 169(2), pp. 326-337.e12, Apr. 6, 2017.

Search Report of SG Patent Application No. 11202002130W, Apr. 20, 2021.

Written Opinion of SG Patent Application No. 11202002130W, Apr. 20, 2021.

"Pantera, Harrison, et al. ""A Genome Editing Approach to Studying Pmp22 Enhancer Functionality"" FASEB Journal, vol. 30, No. Suppl. 1[online] Apr. 1, 2016, pp. 584.2".

"Kim H. and Kim S-J., A guide to genome engineering with programmable nucleases. Nat Rev Genet, Apr. 2, 2014, vol. 15, No. 5, pp. 321-334".

Office Action of JP Patent Application No. 2020-513755, May 18, 2021.

Rennoll, Sherri A. et al., Cancers, 2016, vol. 8, No. 52, pp. 1-15, doi:10.3390/cancers805005.

JBC, 1994, vol. 269, No. 41, pp. 25795-25808.

Supplementary Partial European Search Report of EP Patent Application No. 18862957.0, May 19, 2021.

"Luke A Gilbert et al., ""Genome-Scale CRISPR-Mediated Control of Gene Repression and Activation"" Cell. Oct. 23, 2014;159(3):pp. 647-661".

Luke A Gilbert et al, "Genome-Scale CRISPR-Mediated Control of Gene Repression and Activation" Cell. Oct. 23, 2014, pp. 647-661.

Sabrina Mahalia Heman-Ackah et al., "Precision Modulation of Neurodegenerative Disease-Related Gene Expression in Human iPSC-Derived Neurons", Science Reports, vol. 6, Jun. 24, 2016.

Sabrina Mahalia Heman-Ackah et al, "Supplementary information to Precision Modulation of Neurodegenerative Disease-Related Gene Expression in Human iPSC-Derived Neurons", Nature. Jun. 24, 2016, pp. 1-14.

Extended European Search Report from corresponding European Patent Application No. 18862957.0, dated Oct. 6, 2021.

Gilbert Luke A et al: "excerpt of table S2 of Genome-Scale CRISPR-Mediated Control of Gene Repression and Activation" Cell, Oct. 9, 2014 (Oct. 9, 2014), pp. 1-2.

Erming Wang et al: "MicroRNA expression in mouse oligodendrocytes and regulation of proteolipid protein gene expression", Journal of Neuroscience Research, vol. 90, No. 9, Apr. 14, 2012 (Apr. 14, 2012), pp. 1701-1712.

Office Action from corresponding Japanese Patent Application No. 2020-513755, dated Mar. 1, 2022.

Fu, Y., et al.; "Improving CRISPR-Cas nuclease specificity using truncated guide RNAs", Nature Biotechnology, vol. 32, No. 3, Mar. 2014, pp. 279-284.

O'Connell, M. R., et al.; "Programmable RNA recognition and cleavage by CRISPR/Cas9", Nature, 2014, vol. 516, pp. 263-266.

Osaka, H., et al.; "Pathophysiology and emerging therapeutic strategy in Pelizaeus-Merzbacher disease", Expert Opinion on Orphan Drugs, 3; 12, pp. 1447-1459.

Notice of Allowance from corresponding Russian Patent Application No. 2020114785, dated Dec. 17, 2021.

Office Action (Non-Final) from corresponding U.S. Appl. No. 16/776,707, dated Apr. 26, 2022.

Notice of Allowance from corresponding U.S. Appl. No. 16/776,707, dated Sep. 29, 2022.

Office Action from corresponding Chinese Patent Application No. 201880052875.2, dated Feb. 28, 2023.

Huang Wei et al. Diagnosis and treatment progress of common neurological diseases, 2014, pp. 195-196.

Written Decision on Registration for Korean Patent Application No. 10-2018-0114900, dated Feb. 29, 2024.

Search Report for Brazilian Patent Application No. 11 2020 006428 9, dated Feb. 27, 2024.

\* cited by examiner

FIG. 1

| sgRNAs | Direction | Mismatch 0 | Mismatch 1 | Mismatch 2 | Indel ratio(%) |
|---|---|---|---|---|---|
| sgRNA_TATA_Sp#1 | - | 1 | 0 | 1 | 32.80 |
| sgRNA_TATA_Sp#2 | + | 1 | 0 | 0 | 42.00 |
| sgRNA_TATA_Sp#3 | + | 1 | 0 | 0 | 25.20 |
| sgRNA_TATA_Sp#4 | + | 1 | 0 | 2 | 59.10 |
| sgRNA_TATA_Sp#5 | + | 1 | 0 | 0 | 16.20 |
| sgRNA_TATA_Sp#6 | + | 1 | 0 | 1 | 30.30 |
| sgRNA_TATA_Sp#7 | - | 1 | 0 | 1 | 53.80 |
| sgRNA_TATA_Sp#8 | + | 1 | 0 | 0 | 7.30 |
| sgRNA_TATA_Sp#9 | - | 1 | 0 | 1 | 26.90 |
| sgRNA_TATA_Sp#10 | - | 1 | 0 | 1 | 15.90 |
| sgRNA_TATA_Sp#11 | - | 1 | 0 | 2 | 24.20 |
| sgRNA_TATA_Sp#12 | - | 1 | 0 | 2 | 38.20 |
| sgRNA_TATA_Sp#13 | - | 1 | 0 | 0 | 6.90 |
| sgRNA_TATA_Sp#14 | + | 1 | 0 | 1 | 62.00 |
| sgRNA_TATA_Sp#15 | + | 1 | 0 | 1 | 54.60 |
| sgRNA_TATA_Sp#16 | - | 1 | 0 | 1 | 32.50 |

FIG. 2

| sgRNAs | Direction | Mismatch 0 | Mismatch 1 | Mismatch 2 | Indel ratio(%) |
|---|---|---|---|---|---|
| sgRNA_Enh_Sp#1 | - | 1 | 0 | 1 | 66.30 |
| sgRNA_Enh_Sp#2 | - | 1 | 0 | 0 | 18.80 |
| sgRNA_Enh_Sp#3 | - | 1 | 0 | 1 | 24.40 |
| sgRNA_Enh_Sp#4 | - | 1 | 0 | 0 | 44.00 |
| sgRNA_Enh_Sp#5 | - | 1 | 0 | 2 | 41.30 |
| sgRNA_Enh_Sp#6 | + | 1 | 0 | 1 | 8.60 |
| sgRNA_Enh_Sp#10 | - | 1 | 0 | 2 | 19.30 |
| sgRNA_Enh_Sp#11 | - | 1 | 0 | 2 | 21.90 |
| sgRNA_Enh_Sp#12 | - | 1 | 0 | 2 | 2.50 |
| sgRNA_Enh_Sp#13 | - | 1 | 0 | 1 | 12.80 |
| sgRNA_Enh_Sp#14 | - | 1 | 0 | 1 | 11.40 |
| sgRNA_Enh_Sp#15 | + | 1 | 0 | 1 | 21.80 |
| sgRNA_Enh_Sp#16 | + | 1 | 0 | 1 | 47.40 |

FIG. 3

| sgRNAs | Direction | Mismatch 0 | Mismatch 1 | Mismatch 2 | Indel ratio(%) |
|---|---|---|---|---|---|
| sgRNA_TATA_Cj#1 | + | 1 | 0 | 0 | 0.35 |
| sgRNA_TATA_Cj#2 | + | 1 | 0 | 0 | 0.07 |
| sgRNA_TATA_Cj#3 | + | 1 | 0 | 0 | 0.04 |
| sgRNA_TATA_Cj#4 | + | 1 | 0 | 1 | 3.80 |
| sgRNA_TATA_Cj#5 | + | 1 | 0 | 0 | 36.10 |
| sgRNA_TATA_Cj#6 | - | 1 | 0 | 0 | 0.02 |
| sgRNA_TATA_Cj#7 | + | 1 | 0 | 0 | 0.02 |
| sgRNA_TATA_Cj#8 | - | 1 | 0 | 0 | 0.06 |
| sgRNA_TATA_Cj#9 | - | 1 | 0 | 0 | 0.15 |
| sgRNA_TATA_Cj#10 | - | 1 | 0 | 0 | 13.10 |
| sgRNA_TATA_Cj#11 | - | 1 | 0 | 0 | 0.12 |

FIG. 4

| sgRNAs | Direction | Mismatch 0 | Mismatch 1 | Mismatch 2 | Indel ratio(%) |
|---|---|---|---|---|---|
| sgRNA_Enh_Cj#1 | + | 1 | 0 | 0 | 16.70 |
| sgRNA_Enh_Cj#2 | + | 1 | 0 | 0 | 0.07 |
| sgRNA_Enh_Cj#3 | - | 1 | 0 | 0 | 0 |
| sgRNA_Enh_Cj#4 | + | 1 | 0 | 0 | 1.18 |
| sgRNA_Enh_Cj#5 | - | 1 | 0 | 0 | 0.03 |
| sgRNA_Enh_Cj#6 | - | 1 | 0 | 0 | 0.05 |
| sgRNA_Enh_Cj#7 | - | 1 | 0 | 0 | 0.09 |
| sgRNA_Enh_Cj#8 | + | 1 | 0 | 0 | 0.28 |
| sgRNA_Enh_Cj#9 | - | 1 | 0 | 0 | 41.40 |
| sgRNA_Enh_Cj#10 | + | 1 | 0 | 0 | 0.45 |
| sgRNA_Enh_Cj#11 | - | 1 | 0 | 0 | 0.55 |
| sgRNA_Enh_Cj#12 | + | 1 | 0 | 0 | 2.83 |
| sgRNA_Enh_Cj#13 | + | 1 | 0 | 0 | 0.03 |

FIG. 5

| Name | sgRNAs | More than minimum frequency | Insertions | Deletions | Indel ratio(%) |
|---|---|---|---|---|---|
| TATA WT |  | 26730 | 28 | 70 | 0.40 |
| TATA-1 | sgRNA_TATA_Sp#15 | 30466 | 3110 | 6357 | 31.10 |
| TATA-2 | sgRNA_TATA_Sp#12 | 9286 | 0 | 6929 | 74.60 |
|  | sgRNA_TATA_Sp#14 | 5651 | 118 | 4972 | 90.10 |
| Enh WT |  | 27917 | 0 | 11 | 0.00 |
| Enh-3 | sgRNA_Enh_Sp#1 | 32148 | 8744 | 10126 | 58.70 |
| Enh-4 | sgRNA_Enh_Sp#5 | 37486 | 23 | 30928 | 82.60 |
|  | sgRNA_Enh_Sp#16 | 37277 | 69 | 35000 | 94.10 |
| Enh-5 | sgRNA_Enh_Sp#1 | 30576 | 2782 | 14544 | 56.70 |
|  | sgRNA_Enh_Sp#4 | 30399 | 217 | 11894 | 39.80 |
| CDS-SP1 WT |  | 35424 | 0 | 40 | 0.10 |
| CDS-SP1 | sgRNA_CDS_Sp#1 | 32206 | 4613 | 9077 | 42.50 |
| CDS-SP3 WT |  | 21997 | 0 | 0 | 0.00 |
| CDS-SP3 | sgRNA_CDS_Sp#3 | 27511 | 3441 | 11877 | 55.70 |

FIG. 6

| sgRNAs | CDS-SP1 | | CDS-SP3 | |
|---|---|---|---|---|
| | Reads | Ratio | Reads | Ratio |
| Total indels | 13690 | 1 | 15312 | 1 |
| 3N±1, 3N±2 | 10063 | 0.74 | 12795 | 0.84 |
| 3N±0 | 3627 | 0.26 | 2517 | 0.16 |

% Indel Reads

FIG. 15

| Indel | Local Sequence | Frequency (%) |
|---|---|---|
| WT | ACTGAAGCCAGACCAGGCGTCTTTCCAGTTTATTCAGGGGCTGGTCCAATGCTGGGATATGTCATGGTGGCCTGAGAGGTTCTCAGCCTC | |
| -1 | ACTGAAGCCAGACCAGGCGTCTTTCCAG-TTATTCAGGGGCTGGTCCAATGCTGGGATATGTCATGGCGGCCTGAGAGGTTCTCAGCCTC | 14.00 |
| -2 | ACTGAAGCCAGACCAGGCGTCTTTCCAGTT--TTCAGGGGCTGGTCCAATGCTGGGATATGTCATGGTGGCCTGAGAGGTTCTCAGCCTC | 8.86 |
| +1 | ACTGAAGCCAGACCAGGCGTCTTTCCAGTTTATTCAGGGGCTGGTCCAATGCTGGGATATGTCATGGCGGCCTGAGAGGTTCTCAGCCTC | 3.84 |
| -3 | ACTGAAGCCAGACCAGGCGTCTTTCCAGT---TTCAGGGGCTGGTCCAATGCTGGGATATGTCATGGCGGCCTGAGAGGTTCTCAGCCTC | 3.53 |
| -4 | ACTGAAGCCAGACCAGGCGTCTTTCCAG----TTCAGGGGCTGGTCCAATGCTGGGATATGTCATGGCGGCCTGAGAGGTTCTCAGCCTC | 2.81 |

FIG. 16

| | Location | Position | Target sequence (5' to 3') | Gene |
|---|---|---|---|---|
| On-target | chr17 | 15265347 | GGACCAGCCCCTGAATAAACTGG | hPMP22-TATA |
| Off1 | chr5 | 135488419 | GGACCAGCCaCaGAATAAACAAG | Intergenic |
| Off2 | chr8 | 140735957 | tGACCAGtCCaTGAATAAACAAG | PTK2 (Intron) |
| Off3 | chr12 | 14124312 | GGACCAGaCaCTGAATAtACCAG | Intergenic |
| Off4 | chr4 | 97775621 | GGACCAGCCaGAATAAAtTGG | STPG2 (Intron) |
| Off5 | chr5 | 26531145 | GGAtCAGCCCCaGAATAAAtTAG | Intergenic |
| Off6 | chr1 | 41780482 | GGAgCAtCCCaGAATAAACAAG | HIVEP3 (Intron) |
| Off7 | chr1 | 157564675 | GGAtCAGCgtCTGAATAAACAAG | Intergenic |
| Off8 | chr13 | 20254256 | aGACCAGCCCCaGAAcAAACAAG | Intergenic |
| Off9 | chr15 | 100401183 | GtACgAGCCCCTGAATAAAtAGG | CERS3 (Exon) |
| Off10 | chr6 | 26006396 | GGACCAaaCaCTGAATAAACAAG | Intergenic |
| Off11 | chr20 | 10136908 | GcACCAGCCaCTGAATtAACAAG | SNAP25 (Intron) |
| Off12 | chrX | 7525146 | GtACCAGCCaCTGAAaAAACAAG | Intergenic |
| Off13 | chr18 | 1972251 | GaACCAGCCCCTGAttAgACCAG | Intergenic |
| Off14 | chr18 | 77536261 | GtACCAGCCCCTGAAaAAACAGG | Intergenic |
| Off15 | chr11 | 30065750 | GtACCAGCCCCTGcAaAAACAGG | Intergenic |
| Off16 | chr11 | 30579429 | GcACCAGgCCtTGAATAAACAAG | MPP2D2 (Intron) |
| Off17 | chr11 | 35726323 | GGcCCAGCCaCTGAgTAAACTAG | TRIM44 (Intron) |
| Off18 | chr11 | 112468286 | GGAattGCCCCTGAATAAACAAG | RP11-65M17.3 (Intron) |

FIG. 18

| | Location | Position | Target sequence (5' to 3') | Gene |
|---|---|---|---|---|
| On-target | chr17 | 15265347 | GGACCAGCCCTGAATAAAC*TGG* | hPMP22-TATA |
| Off1 | chr5 | 38420810 | GGgaacagCCCTGAATAAAC*CTG* | EGFLAM (Intron) |
| Off2 | chr7 | 28618099 | aGgaCCagCtCTGAATAAAC*AGG* | CREB5 (Intron) |
| Off3 | chr5 | 38420811 | GGAaCAGCCCtgaATAAAC*TGG* | EGFLAM (Intron) |
| Off4 | chr10 | 93462291 | GagttcAGCCCTGAATAAC*AGG* | Intergenic |
| Off5 | chr3 | 78627344 | GGgaCcagCCCAGAATAAa*GGG* | Intergenic |
| Off6 | chr2 | 131586033 | aagCCAaCCCTGAATAAAC*AGG* | Intergenic |
| Off7 | chr18 | 56254369 | cacaCAGCCCTcAATAAAC*TGG* | ALPK2 (Intron) |
| Off8 | chr22 | 27477459 | GaggCAGCCCTGtATAAAC*TGG* | Intergenic |
| Off9 | chr6 | 91586787 | GacCagccCCTGAATAAca*TGG* | Intergenic |

FIG. 22

| | Location | Position | Target sequence (5' to 3') | Gene |
|---|---|---|---|---|
| On-target | chr17 | 15265347 | GGACCAGCCCCTGAATAAAC*TGG* | hPMP22-TATA |
| Off1 | chr12 | 118558427 | GtACCAGCCCCTGAcaAAAC*AGG* | Intergenic |
| Off2 | chr1 | 74579514 | GGAgCAGCCCCgGAATgAAC*AGG* | Zfp142 (Exon) |
| Off3 | chr13 | 50187695 | GGACCAGCCCCTGtATAccC*TGG* | Intergenic |
| Off4 | chr13 | 50319559 | GGACCAGCCCCTGtATAccC*TGG* | Intergenic |
| Off5 | chr13 | 50623450 | GGACCAGCCCCTGtATAccC*TGG* | Intergenic |
| Off6 | chr2 | 29191358 | GGcCCtgCCCCTaAATAAAC*AGG* | Intergenic |
| Off7 | chr9 | 102823783 | GGAtCAGCCCCaGAATAAcC*TGG* | Intergenic |
| Off8 | chrX | 101405421 | GGACtAGCCCCTGAgTAcAC*TGG* | Zmym3 (Exon) |

SEQUENCE LISTING

```
Sequence total quantity: 633
SEQ ID NO: 1            moltype = DNA  length = 20
FEATURE                 Location/Qualifiers
source                  1..20
                        mol_type = genomic DNA
                        organism = Homo sapiens
SEQUENCE: 1
ggaccagccc ctgaataaac                                                 20

SEQ ID NO: 2            moltype = DNA  length = 20
FEATURE                 Location/Qualifiers
source                  1..20
                        mol_type = genomic DNA
                        organism = Homo sapiens
SEQUENCE: 2
ggcgtctttc cagtttattc                                                 20

SEQ ID NO: 3            moltype = DNA  length = 20
FEATURE                 Location/Qualifiers
source                  1..20
                        mol_type = genomic DNA
                        organism = Homo sapiens
```

| | | |
|---|---|---|
| SEQUENCE: 3<br>gcgtctttcc agtttattca | | 20 |
| SEQ ID NO: 4<br>FEATURE<br>source<br><br>SEQUENCE: 4<br>cgtctttcca gtttattcag | moltype = DNA   length = 20<br>Location/Qualifiers<br>1..20<br>mol_type = genomic DNA<br>organism = Homo sapiens | <br><br><br><br><br>20 |
| SEQ ID NO: 5<br>FEATURE<br>source<br><br>SEQUENCE: 5<br>ttcagggget ggtccaatgc | moltype = DNA   length = 20<br>Location/Qualifiers<br>1..20<br>mol_type = genomic DNA<br>organism = Homo sapiens | <br><br><br><br><br>20 |
| SEQ ID NO: 6<br>FEATURE<br>source<br><br>SEQUENCE: 6<br>tcagggctg gtccaatgct | moltype = DNA   length = 20<br>Location/Qualifiers<br>1..20<br>mol_type = genomic DNA<br>organism = Homo sapiens | <br><br><br><br><br>20 |
| SEQ ID NO: 7<br>FEATURE<br>source<br><br>SEQUENCE: 7<br>accatgacat atcccagcat | moltype = DNA   length = 20<br>Location/Qualifiers<br>1..20<br>mol_type = genomic DNA<br>organism = Homo sapiens | <br><br><br><br><br>20 |
| SEQ ID NO: 8<br>FEATURE<br>source<br><br>SEQUENCE: 8<br>tttccagttt attcaggggc | moltype = DNA   length = 20<br>Location/Qualifiers<br>1..20<br>mol_type = genomic DNA<br>organism = Homo sapiens | <br><br><br><br><br>20 |
| SEQ ID NO: 9<br>FEATURE<br>source<br><br>SEQUENCE: 9<br>cagttacagg gagcaccacc | moltype = DNA   length = 20<br>Location/Qualifiers<br>1..20<br>mol_type = genomic DNA<br>organism = Homo sapiens | <br><br><br><br><br>20 |
| SEQ ID NO: 10<br>FEATURE<br>source<br><br>SEQUENCE: 10<br>ctggtctggc ttcagttaca | moltype = DNA   length = 20<br>Location/Qualifiers<br>1..20<br>mol_type = genomic DNA<br>organism = Homo sapiens | <br><br><br><br><br>20 |
| SEQ ID NO: 11<br>FEATURE<br>source<br><br>SEQUENCE: 11<br>cctggtctgg cttcagttac | moltype = DNA   length = 20<br>Location/Qualifiers<br>1..20<br>mol_type = genomic DNA<br>organism = Homo sapiens | <br><br><br><br><br>20 |
| SEQ ID NO: 12<br>FEATURE<br>source<br><br>SEQUENCE: 12<br>aactggaaag acgcctggtc | moltype = DNA   length = 20<br>Location/Qualifiers<br>1..20<br>mol_type = genomic DNA<br>organism = Homo sapiens | <br><br><br><br><br>20 |
| SEQ ID NO: 13<br>FEATURE<br>source | moltype = DNA   length = 20<br>Location/Qualifiers<br>1..20<br>mol_type = genomic DNA | |

```
                              organism = Homo sapiens
SEQUENCE: 13
gaataaactg gaaagacgcc                                                   20

SEQ ID NO: 14            moltype = DNA  length = 20
FEATURE                  Location/Qualifiers
source                   1..20
                         mol_type = genomic DNA
                         organism = Homo sapiens
SEQUENCE: 14
tccaatgctg ggatatgtca                                                   20

SEQ ID NO: 15            moltype = DNA  length = 20
FEATURE                  Location/Qualifiers
source                   1..20
                         mol_type = genomic DNA
                         organism = Homo sapiens
SEQUENCE: 15
aatgctggga tatgtcatgg                                                   20

SEQ ID NO: 16            moltype = DNA  length = 20
FEATURE                  Location/Qualifiers
source                   1..20
                         mol_type = genomic DNA
                         organism = Homo sapiens
SEQUENCE: 16
atagaggctg agaacctctc                                                   20

SEQ ID NO: 17            moltype = DNA  length = 20
FEATURE                  Location/Qualifiers
source                   1..20
                         mol_type = genomic DNA
                         organism = Homo sapiens
SEQUENCE: 17
ttgggcatgt ttgagctggt                                                   20

SEQ ID NO: 18            moltype = DNA  length = 20
FEATURE                  Location/Qualifiers
source                   1..20
                         mol_type = genomic DNA
                         organism = Homo sapiens
SEQUENCE: 18
tttgggcatg tttgagctgg                                                   20

SEQ ID NO: 19            moltype = DNA  length = 20
FEATURE                  Location/Qualifiers
source                   1..20
                         mol_type = genomic DNA
                         organism = Homo sapiens
SEQUENCE: 19
gagctggtgg gcgaagcata                                                   20

SEQ ID NO: 20            moltype = DNA  length = 20
FEATURE                  Location/Qualifiers
source                   1..20
                         mol_type = genomic DNA
                         organism = Homo sapiens
SEQUENCE: 20
agctggtggg cgaagcatat                                                   20

SEQ ID NO: 21            moltype = DNA  length = 20
FEATURE                  Location/Qualifiers
source                   1..20
                         mol_type = genomic DNA
                         organism = Homo sapiens
SEQUENCE: 21
tgggcgaagc atatgggcaa                                                   20

SEQ ID NO: 22            moltype = DNA  length = 20
FEATURE                  Location/Qualifiers
source                   1..20
                         mol_type = genomic DNA
                         organism = Homo sapiens
SEQUENCE: 22
ggcctccatc ctaaacaatg                                                   20

SEQ ID NO: 23            moltype = DNA  length = 20
FEATURE                  Location/Qualifiers
source                   1..20
```

```
                            mol_type = genomic DNA
                            organism = Homo sapiens
SEQUENCE: 23
gggttgggag gtttgggcgt                                                   20

SEQ ID NO: 24               moltype = DNA   length = 20
FEATURE                     Location/Qualifiers
source                      1..20
                            mol_type = genomic DNA
                            organism = Homo sapiens
SEQUENCE: 24
aggtttgggc gtgggagtcc                                                   20

SEQ ID NO: 25               moltype = DNA   length = 19
FEATURE                     Location/Qualifiers
source                      1..19
                            mol_type = genomic DNA
                            organism = Homo sapiens
SEQUENCE: 25
ttcagagact cagctattt                                                    19

SEQ ID NO: 26               moltype = DNA   length = 19
FEATURE                     Location/Qualifiers
source                      1..19
                            mol_type = genomic DNA
                            organism = Homo sapiens
SEQUENCE: 26
ggccacattg tttaggatg                                                    19

SEQ ID NO: 27               moltype = DNA   length = 19
FEATURE                     Location/Qualifiers
source                      1..19
                            mol_type = genomic DNA
                            organism = Homo sapiens
SEQUENCE: 27
ggctttgggc atgtttgag                                                    19

SEQ ID NO: 28               moltype = DNA   length = 19
FEATURE                     Location/Qualifiers
source                      1..19
                            mol_type = genomic DNA
                            organism = Homo sapiens
SEQUENCE: 28
aacatgccca aagcccagc                                                    19

SEQ ID NO: 29               moltype = DNA   length = 19
FEATURE                     Location/Qualifiers
source                      1..19
                            mol_type = genomic DNA
                            organism = Homo sapiens
SEQUENCE: 29
acatgcccaa agcccagcg                                                    19

SEQ ID NO: 30               moltype = DNA   length = 20
FEATURE                     Location/Qualifiers
source                      1..20
                            mol_type = genomic DNA
                            organism = Homo sapiens
SEQUENCE: 30
cgatgatact cagcaacagg                                                   20

SEQ ID NO: 31               moltype = DNA   length = 20
FEATURE                     Location/Qualifiers
source                      1..20
                            mol_type = genomic DNA
                            organism = Homo sapiens
SEQUENCE: 31
atggacacgc aactgatctc                                                   20

SEQ ID NO: 32               moltype = DNA   length = 22
FEATURE                     Location/Qualifiers
source                      1..22
                            mol_type = genomic DNA
                            organism = Homo sapiens
SEQUENCE: 32
gccctctgaa tctccagtca at                                                22

SEQ ID NO: 33               moltype = DNA   length = 22
FEATURE                     Location/Qualifiers
```

```
source                 1..22
                       mol_type = genomic DNA
                       organism = Homo sapiens
SEQUENCE: 33
aatctccagt caattccaac ac                                                 22

SEQ ID NO: 34          moltype = DNA   length = 22
FEATURE                Location/Qualifiers
source                 1..22
                       mol_type = genomic DNA
                       organism = Homo sapiens
SEQUENCE: 34
aattaggcaa ttcttgtaaa gc                                                 22

SEQ ID NO: 35          moltype = DNA   length = 22
FEATURE                Location/Qualifiers
source                 1..22
                       mol_type = genomic DNA
                       organism = Homo sapiens
SEQUENCE: 35
ttaggcaatt cttgtaaagc at                                                 22

SEQ ID NO: 36          moltype = DNA   length = 22
FEATURE                Location/Qualifiers
source                 1..22
                       mol_type = genomic DNA
                       organism = Homo sapiens
SEQUENCE: 36
aaagcatagg cacacatcac cc                                                 22

SEQ ID NO: 37          moltype = DNA   length = 22
FEATURE                Location/Qualifiers
source                 1..22
                       mol_type = genomic DNA
                       organism = Homo sapiens
SEQUENCE: 37
gcctggtctg gcttcagtta ca                                                 22

SEQ ID NO: 38          moltype = DNA   length = 22
FEATURE                Location/Qualifiers
source                 1..22
                       mol_type = genomic DNA
                       organism = Homo sapiens
SEQUENCE: 38
gtgtccaact ttgtttgctt tc                                                 22

SEQ ID NO: 39          moltype = DNA   length = 22
FEATURE                Location/Qualifiers
source                 1..22
                       mol_type = genomic DNA
                       organism = Homo sapiens
SEQUENCE: 39
gtattctgga aagcaaacaa ag                                                 22

SEQ ID NO: 40          moltype = DNA   length = 22
FEATURE                Location/Qualifiers
source                 1..22
                       mol_type = genomic DNA
                       organism = Homo sapiens
SEQUENCE: 40
cagtcttggc atcacaggct tc                                                 22

SEQ ID NO: 41          moltype = DNA   length = 22
FEATURE                Location/Qualifiers
source                 1..22
                       mol_type = genomic DNA
                       organism = Homo sapiens
SEQUENCE: 41
ggacctcttg gctattacac ag                                                 22

SEQ ID NO: 42          moltype = DNA   length = 22
FEATURE                Location/Qualifiers
source                 1..22
                       mol_type = genomic DNA
                       organism = Homo sapiens
SEQUENCE: 42
ggagccagtg ggacctcttg gc                                                 22

SEQ ID NO: 43          moltype = DNA   length = 22
```

```
FEATURE                 Location/Qualifiers
source                  1..22
                        mol_type = genomic DNA
                        organism = Homo sapiens
SEQUENCE: 43
taaatcacag aggcaaagag tt                                                  22

SEQ ID NO: 44           moltype = DNA   length = 22
FEATURE                 Location/Qualifiers
source                  1..22
                        mol_type = genomic DNA
                        organism = Homo sapiens
SEQUENCE: 44
ttgcatagtg ctagactgtt tt                                                  22

SEQ ID NO: 45           moltype = DNA   length = 22
FEATURE                 Location/Qualifiers
source                  1..22
                        mol_type = genomic DNA
                        organism = Homo sapiens
SEQUENCE: 45
gggtcatgtg ttttgaaaac ag                                                  22

SEQ ID NO: 46           moltype = DNA   length = 22
FEATURE                 Location/Qualifiers
source                  1..22
                        mol_type = genomic DNA
                        organism = Homo sapiens
SEQUENCE: 46
cccaaacctc ccaacccaca ac                                                  22

SEQ ID NO: 47           moltype = DNA   length = 22
FEATURE                 Location/Qualifiers
source                  1..22
                        mol_type = genomic DNA
                        organism = Homo sapiens
SEQUENCE: 47
actcagctat ttctggaatg ac                                                  22

SEQ ID NO: 48           moltype = DNA   length = 22
FEATURE                 Location/Qualifiers
source                  1..22
                        mol_type = genomic DNA
                        organism = Homo sapiens
SEQUENCE: 48
tcatcgcctt tgtgagctcc at                                                  22

SEQ ID NO: 49           moltype = DNA   length = 22
FEATURE                 Location/Qualifiers
source                  1..22
                        mol_type = genomic DNA
                        organism = Homo sapiens
SEQUENCE: 49
cagacacagg ctttgctcta gc                                                  22

SEQ ID NO: 50           moltype = DNA   length = 22
FEATURE                 Location/Qualifiers
source                  1..22
                        mol_type = genomic DNA
                        organism = Homo sapiens
SEQUENCE: 50
caaagcctgt gtctggccac ta                                                  22

SEQ ID NO: 51           moltype = DNA   length = 22
FEATURE                 Location/Qualifiers
source                  1..22
                        mol_type = genomic DNA
                        organism = Homo sapiens
SEQUENCE: 51
agcagtttgt gcccactagt gg                                                  22

SEQ ID NO: 52           moltype = DNA   length = 22
FEATURE                 Location/Qualifiers
source                  1..22
                        mol_type = genomic DNA
                        organism = Homo sapiens
SEQUENCE: 52
atgtcaaggt attccagcta ac                                                  22
```

```
SEQ ID NO: 53          moltype = DNA   length = 22
FEATURE                Location/Qualifiers
source                 1..22
                       mol_type = genomic DNA
                       organism = Homo sapiens
SEQUENCE: 53
gaataactgt atcaaagtta gc                                             22

SEQ ID NO: 54          moltype = DNA   length = 22
FEATURE                Location/Qualifiers
source                 1..22
                       mol_type = genomic DNA
                       organism = Homo sapiens
SEQUENCE: 54
ttcctaatta agaggctttg tg                                             22

SEQ ID NO: 55          moltype = DNA   length = 22
FEATURE                Location/Qualifiers
source                 1..22
                       mol_type = genomic DNA
                       organism = Homo sapiens
SEQUENCE: 55
gagctagttt gtcagggtct ag                                             22

SEQ ID NO: 56          moltype = DNA   length = 23
FEATURE                Location/Qualifiers
source                 1..23
                       mol_type = genomic DNA
                       organism = Homo sapiens
SEQUENCE: 56
gactttggga gctaatatct agg                                            23

SEQ ID NO: 57          moltype = DNA   length = 23
FEATURE                Location/Qualifiers
source                 1..23
                       mol_type = genomic DNA
                       organism = Homo sapiens
SEQUENCE: 57
ccctttcatc ttcccattcg tgg                                            23

SEQ ID NO: 58          moltype = DNA   length = 23
FEATURE                Location/Qualifiers
source                 1..23
                       mol_type = genomic DNA
                       organism = Homo sapiens
SEQUENCE: 58
cctttcatct tcccattcgt ggg                                            23

SEQ ID NO: 59          moltype = DNA   length = 23
FEATURE                Location/Qualifiers
source                 1..23
                       mol_type = genomic DNA
                       organism = Homo sapiens
SEQUENCE: 59
cccacgaatg ggaagatgaa agg                                            23

SEQ ID NO: 60          moltype = DNA   length = 23
FEATURE                Location/Qualifiers
source                 1..23
                       mol_type = genomic DNA
                       organism = Homo sapiens
SEQUENCE: 60
catcttccca ttcgtgggca agg                                            23

SEQ ID NO: 61          moltype = DNA   length = 23
FEATURE                Location/Qualifiers
source                 1..23
                       mol_type = genomic DNA
                       organism = Homo sapiens
SEQUENCE: 61
tctccacctt gcccacgaat ggg                                            23

SEQ ID NO: 62          moltype = DNA   length = 23
FEATURE                Location/Qualifiers
source                 1..23
                       mol_type = genomic DNA
                       organism = Homo sapiens
SEQUENCE: 62
gtctccacct tgcccacgaa tgg                                            23
```

```
SEQ ID NO: 63           moltype = DNA  length = 23
FEATURE                 Location/Qualifiers
source                  1..23
                        mol_type = genomic DNA
                        organism = Homo sapiens
SEQUENCE: 63
cccaatgctt gcacataaat tgg                                           23

SEQ ID NO: 64           moltype = DNA  length = 23
FEATURE                 Location/Qualifiers
source                  1..23
                        mol_type = genomic DNA
                        organism = Homo sapiens
SEQUENCE: 64
ccaatttatg tgcaagcatt ggg                                           23

SEQ ID NO: 65           moltype = DNA  length = 23
FEATURE                 Location/Qualifiers
source                  1..23
                        mol_type = genomic DNA
                        organism = Homo sapiens
SEQUENCE: 65
tccaatttat gtgcaagcat tgg                                           23

SEQ ID NO: 66           moltype = DNA  length = 23
FEATURE                 Location/Qualifiers
source                  1..23
                        mol_type = genomic DNA
                        organism = Homo sapiens
SEQUENCE: 66
tgtgcgcgtc tgaagaggag tgg                                           23

SEQ ID NO: 67           moltype = DNA  length = 23
FEATURE                 Location/Qualifiers
source                  1..23
                        mol_type = genomic DNA
                        organism = Homo sapiens
SEQUENCE: 67
gtgcgcgtct gaagaggagt ggg                                           23

SEQ ID NO: 68           moltype = DNA  length = 23
FEATURE                 Location/Qualifiers
source                  1..23
                        mol_type = genomic DNA
                        organism = Homo sapiens
SEQUENCE: 68
tgcgcgtctg aagaggagtg ggg                                           23

SEQ ID NO: 69           moltype = DNA  length = 23
FEATURE                 Location/Qualifiers
source                  1..23
                        mol_type = genomic DNA
                        organism = Homo sapiens
SEQUENCE: 69
tagtccagat gctgttgccg tgg                                           23

SEQ ID NO: 70           moltype = DNA  length = 23
FEATURE                 Location/Qualifiers
source                  1..23
                        mol_type = genomic DNA
                        organism = Homo sapiens
SEQUENCE: 70
attaccacgg caacagcatc tgg                                           23

SEQ ID NO: 71           moltype = DNA  length = 23
FEATURE                 Location/Qualifiers
source                  1..23
                        mol_type = genomic DNA
                        organism = Homo sapiens
SEQUENCE: 71
gacacgattt agtattacca cgg                                           23

SEQ ID NO: 72           moltype = DNA  length = 23
FEATURE                 Location/Qualifiers
source                  1..23
                        mol_type = genomic DNA
                        organism = Homo sapiens
SEQUENCE: 72
```

```
ctaaatcgtg tccaaagagg agg                                            23

SEQ ID NO: 73          moltype = DNA   length = 23
FEATURE                Location/Qualifiers
source                 1..23
                       mol_type = genomic DNA
                       organism = Homo sapiens
SEQUENCE: 73
aggaatctca gcctcctctt tgg                                            23

SEQ ID NO: 74          moltype = DNA   length = 23
FEATURE                Location/Qualifiers
source                 1..23
                       mol_type = genomic DNA
                       organism = Homo sapiens
SEQUENCE: 74
gtggacaagg ttaactaaaa agg                                            23

SEQ ID NO: 75          moltype = DNA   length = 23
FEATURE                Location/Qualifiers
source                 1..23
                       mol_type = genomic DNA
                       organism = Homo sapiens
SEQUENCE: 75
atagtcaaat catgtggaca agg                                            23

SEQ ID NO: 76          moltype = DNA   length = 23
FEATURE                Location/Qualifiers
source                 1..23
                       mol_type = genomic DNA
                       organism = Homo sapiens
SEQUENCE: 76
tgctggatag tcaaatcatg tgg                                            23

SEQ ID NO: 77          moltype = DNA   length = 23
FEATURE                Location/Qualifiers
source                 1..23
                       mol_type = genomic DNA
                       organism = Homo sapiens
SEQUENCE: 77
acatgatttg actatccagc agg                                            23

SEQ ID NO: 78          moltype = DNA   length = 23
FEATURE                Location/Qualifiers
source                 1..23
                       mol_type = genomic DNA
                       organism = Homo sapiens
SEQUENCE: 78
atttgactat ccagcaggct tgg                                            23

SEQ ID NO: 79          moltype = DNA   length = 23
FEATURE                Location/Qualifiers
source                 1..23
                       mol_type = genomic DNA
                       organism = Homo sapiens
SEQUENCE: 79
gtcccgaagt ctctggggcc tgg                                            23

SEQ ID NO: 80          moltype = DNA   length = 23
FEATURE                Location/Qualifiers
source                 1..23
                       mol_type = genomic DNA
                       organism = Homo sapiens
SEQUENCE: 80
aaaacagtcc cgaagtctct ggg                                            23

SEQ ID NO: 81          moltype = DNA   length = 23
FEATURE                Location/Qualifiers
source                 1..23
                       mol_type = genomic DNA
                       organism = Homo sapiens
SEQUENCE: 81
gaaaacagtc ccgaagtctc tgg                                            23

SEQ ID NO: 82          moltype = DNA   length = 23
FEATURE                Location/Qualifiers
source                 1..23
                       mol_type = genomic DNA
                       organism = Homo sapiens
```

```
SEQUENCE: 82
tatataccac attcaagtgc tgg                                              23

SEQ ID NO: 83           moltype = DNA   length = 23
FEATURE                 Location/Qualifiers
source                  1..23
                        mol_type = genomic DNA
                        organism = Homo sapiens
SEQUENCE: 83
tggatataac gaagttgtgt ggg                                              23

SEQ ID NO: 84           moltype = DNA   length = 23
FEATURE                 Location/Qualifiers
source                  1..23
                        mol_type = genomic DNA
                        organism = Homo sapiens
SEQUENCE: 84
atggatataa cgaagttgtg tgg                                              23

SEQ ID NO: 85           moltype = DNA   length = 23
FEATURE                 Location/Qualifiers
source                  1..23
                        mol_type = genomic DNA
                        organism = Homo sapiens
SEQUENCE: 85
atatgtttgt tcaccccaac agg                                              23

SEQ ID NO: 86           moltype = DNA   length = 23
FEATURE                 Location/Qualifiers
source                  1..23
                        mol_type = genomic DNA
                        organism = Homo sapiens
SEQUENCE: 86
gaaaacttga aatcctgttg ggg                                              23

SEQ ID NO: 87           moltype = DNA   length = 23
FEATURE                 Location/Qualifiers
source                  1..23
                        mol_type = genomic DNA
                        organism = Homo sapiens
SEQUENCE: 87
tagacattag gagaaacaga agg                                              23

SEQ ID NO: 88           moltype = DNA   length = 23
FEATURE                 Location/Qualifiers
source                  1..23
                        mol_type = genomic DNA
                        organism = Homo sapiens
SEQUENCE: 88
ctagcagtga catagacatt agg                                              23

SEQ ID NO: 89           moltype = DNA   length = 23
FEATURE                 Location/Qualifiers
source                  1..23
                        mol_type = genomic DNA
                        organism = Homo sapiens
SEQUENCE: 89
agccacctga ctttgatgaa agg                                              23

SEQ ID NO: 90           moltype = DNA   length = 23
FEATURE                 Location/Qualifiers
source                  1..23
                        mol_type = genomic DNA
                        organism = Homo sapiens
SEQUENCE: 90
tgagaaatgt tattactata tgg                                              23

SEQ ID NO: 91           moltype = DNA   length = 23
FEATURE                 Location/Qualifiers
source                  1..23
                        mol_type = genomic DNA
                        organism = Homo sapiens
SEQUENCE: 91
agactgcgag atgagagagt tgg                                              23

SEQ ID NO: 92           moltype = DNA   length = 23
FEATURE                 Location/Qualifiers
source                  1..23
                        mol_type = genomic DNA
```

```
                        organism = Homo sapiens
SEQUENCE: 92
ctcgcagtct gtacttagac tgg                                              23

SEQ ID NO: 93           moltype = DNA  length = 23
FEATURE                 Location/Qualifiers
source                  1..23
                        mol_type = genomic DNA
                        organism = Homo sapiens
SEQUENCE: 93
aatgtctctt gagagagcca agg                                              23

SEQ ID NO: 94           moltype = DNA  length = 30
FEATURE                 Location/Qualifiers
source                  1..30
                        mol_type = genomic DNA
                        organism = Homo sapiens
SEQUENCE: 94
atgggaagat gaaagggaag taactggtac                                       30

SEQ ID NO: 95           moltype = DNA  length = 30
FEATURE                 Location/Qualifiers
source                  1..30
                        mol_type = genomic DNA
                        organism = Homo sapiens
SEQUENCE: 95
actttgattg ttaaaactta tccttggcac                                       30

SEQ ID NO: 96           moltype = DNA  length = 30
FEATURE                 Location/Qualifiers
source                  1..30
                        mol_type = genomic DNA
                        organism = Homo sapiens
SEQUENCE: 96
agtcctacct cagcttccca atgcttgcac                                       30

SEQ ID NO: 97           moltype = DNA  length = 30
FEATURE                 Location/Qualifiers
source                  1..30
                        mol_type = genomic DNA
                        organism = Homo sapiens
SEQUENCE: 97
caatgcttgc acataaattg gaatgtgtac                                       30

SEQ ID NO: 98           moltype = DNA  length = 30
FEATURE                 Location/Qualifiers
source                  1..30
                        mol_type = genomic DNA
                        organism = Homo sapiens
SEQUENCE: 98
acacagagag agacagaatg aatgatgtac                                       30

SEQ ID NO: 99           moltype = DNA  length = 30
FEATURE                 Location/Qualifiers
source                  1..30
                        mol_type = genomic DNA
                        organism = Homo sapiens
SEQUENCE: 99
tcctcttcag acgcgcacac acacacacac                                       30

SEQ ID NO: 100          moltype = DNA  length = 30
FEATURE                 Location/Qualifiers
source                  1..30
                        mol_type = genomic DNA
                        organism = Homo sapiens
SEQUENCE: 100
actcctcttc agacgcgcac acacacacac                                       30

SEQ ID NO: 101          moltype = DNA  length = 30
FEATURE                 Location/Qualifiers
source                  1..30
                        mol_type = genomic DNA
                        organism = Homo sapiens
SEQUENCE: 101
ccactcctct tcagacgcgc acacacacac                                       30

SEQ ID NO: 102          moltype = DNA  length = 30
FEATURE                 Location/Qualifiers
source                  1..30
```

```
                        mol_type = genomic DNA
                        organism = Homo sapiens
SEQUENCE: 102
ccccactcct cttcagacgc gcacacacac                                              30

SEQ ID NO: 103          moltype = DNA   length = 30
FEATURE                 Location/Qualifiers
source                  1..30
                        mol_type = genomic DNA
                        organism = Homo sapiens
SEQUENCE: 103
ctccccactc ctcttcagac gcgcacacac                                              30

SEQ ID NO: 104          moltype = DNA   length = 30
FEATURE                 Location/Qualifiers
source                  1..30
                        mol_type = genomic DNA
                        organism = Homo sapiens
SEQUENCE: 104
tactccccac tcctcttcag acgcgcacac                                              30

SEQ ID NO: 105          moltype = DNA   length = 30
FEATURE                 Location/Qualifiers
source                  1..30
                        mol_type = genomic DNA
                        organism = Homo sapiens
SEQUENCE: 105
tatactcccc actcctcttc agacgcgcac                                              30

SEQ ID NO: 106          moltype = DNA   length = 30
FEATURE                 Location/Qualifiers
source                  1..30
                        mol_type = genomic DNA
                        organism = Homo sapiens
SEQUENCE: 106
acagcatctg gactatcttg tttcctatac                                              30

SEQ ID NO: 107          moltype = DNA   length = 30
FEATURE                 Location/Qualifiers
source                  1..30
                        mol_type = genomic DNA
                        organism = Homo sapiens
SEQUENCE: 107
atagtccaga tgctgttgcc gtggtaatac                                              30

SEQ ID NO: 108          moltype = DNA   length = 30
FEATURE                 Location/Qualifiers
source                  1..30
                        mol_type = genomic DNA
                        organism = Homo sapiens
SEQUENCE: 108
aaaaggaatc tcagcctcct ctttggacac                                              30

SEQ ID NO: 109          moltype = DNA   length = 30
FEATURE                 Location/Qualifiers
source                  1..30
                        mol_type = genomic DNA
                        organism = Homo sapiens
SEQUENCE: 109
tgtcactgct agtgtgctta attcttgtac                                              30

SEQ ID NO: 110          moltype = DNA   length = 30
FEATURE                 Location/Qualifiers
source                  1..30
                        mol_type = genomic DNA
                        organism = Homo sapiens
SEQUENCE: 110
atgtgaattc agtacaagaa ttaagcacac                                              30

SEQ ID NO: 111          moltype = DNA   length = 30
FEATURE                 Location/Qualifiers
source                  1..30
                        mol_type = genomic DNA
                        organism = Homo sapiens
SEQUENCE: 111
ttatgtgaat tcagtacaag aattaagcac                                              30

SEQ ID NO: 112          moltype = DNA   length = 30
FEATURE                 Location/Qualifiers
```

```
source                  1..30
                        mol_type = genomic DNA
                        organism = Homo sapiens
SEQUENCE: 112
ctttcatttc tgtttatgtg aattcagtac                                              30

SEQ ID NO: 113          moltype = DNA   length = 30
FEATURE                 Location/Qualifiers
source                  1..30
                        mol_type = genomic DNA
                        organism = Homo sapiens
SEQUENCE: 113
ttcacataaa cagaaatgaa agaaaaacac                                              30

SEQ ID NO: 114          moltype = DNA   length = 30
FEATURE                 Location/Qualifiers
source                  1..30
                        mol_type = genomic DNA
                        organism = Homo sapiens
SEQUENCE: 114
atgccaactc tctcatctcg cagtctgtac                                              30

SEQ ID NO: 115          moltype = DNA   length = 30
FEATURE                 Location/Qualifiers
source                  1..30
                        mol_type = genomic DNA
                        organism = Homo sapiens
SEQUENCE: 115
gagacattct cacatttcca gtctaagtac                                              30

SEQ ID NO: 116          moltype = DNA   length = 23
FEATURE                 Location/Qualifiers
source                  1..23
                        mol_type = genomic DNA
                        organism = Mus musculus
SEQUENCE: 116
tgtttggtag tatagtaagt agg                                                     23

SEQ ID NO: 117          moltype = DNA   length = 23
FEATURE                 Location/Qualifiers
source                  1..23
                        mol_type = genomic DNA
                        organism = Mus musculus
SEQUENCE: 117
ggtctagaaa agatcaagcc agg                                                     23

SEQ ID NO: 118          moltype = DNA   length = 23
FEATURE                 Location/Qualifiers
source                  1..23
                        mol_type = genomic DNA
                        organism = Mus musculus
SEQUENCE: 118
gccaggactg tgacctgata agg                                                     23

SEQ ID NO: 119          moltype = DNA   length = 23
FEATURE                 Location/Qualifiers
source                  1..23
                        mol_type = genomic DNA
                        organism = Mus musculus
SEQUENCE: 119
tcaccttcac actttaacca agg                                                     23

SEQ ID NO: 120          moltype = DNA   length = 23
FEATURE                 Location/Qualifiers
source                  1..23
                        mol_type = genomic DNA
                        organism = Mus musculus
SEQUENCE: 120
caaggttgag acaatgttcc agg                                                     23

SEQ ID NO: 121          moltype = DNA   length = 23
FEATURE                 Location/Qualifiers
source                  1..23
                        mol_type = genomic DNA
                        organism = Mus musculus
SEQUENCE: 121
ccaattcatg tgcaaacatt tgg                                                     23

SEQ ID NO: 122          moltype = DNA   length = 23
```

```
FEATURE              Location/Qualifiers
source               1..23
                     mol_type = genomic DNA
                     organism = Mus musculus
SEQUENCE: 122
catcacagtt tatacttagc tgg                                               23

SEQ ID NO: 123       moltype = DNA   length = 23
FEATURE              Location/Qualifiers
source               1..23
                     mol_type = genomic DNA
                     organism = Mus musculus
SEQUENCE: 123
atcacagttt atacttagct ggg                                               23

SEQ ID NO: 124       moltype = DNA   length = 23
FEATURE              Location/Qualifiers
source               1..23
                     mol_type = genomic DNA
                     organism = Mus musculus
SEQUENCE: 124
ggaataccte aggctcaaca ggg                                               23

SEQ ID NO: 125       moltype = DNA   length = 23
FEATURE              Location/Qualifiers
source               1..23
                     mol_type = genomic DNA
                     organism = Mus musculus
SEQUENCE: 125
tctctgtttc ggaataccte agg                                               23

SEQ ID NO: 126       moltype = DNA   length = 23
FEATURE              Location/Qualifiers
source               1..23
                     mol_type = genomic DNA
                     organism = Mus musculus
SEQUENCE: 126
ctgtcgacta ctttgatgaa agg                                               23

SEQ ID NO: 127       moltype = DNA   length = 23
FEATURE              Location/Qualifiers
source               1..23
                     mol_type = genomic DNA
                     organism = Mus musculus
SEQUENCE: 127
tgaaccaaga tgattatttg tgg                                               23

SEQ ID NO: 128       moltype = DNA   length = 23
FEATURE              Location/Qualifiers
source               1..23
                     mol_type = genomic DNA
                     organism = Mus musculus
SEQUENCE: 128
atcttggttc atagaaattt ggg                                               23

SEQ ID NO: 129       moltype = DNA   length = 23
FEATURE              Location/Qualifiers
source               1..23
                     mol_type = genomic DNA
                     organism = Mus musculus
SEQUENCE: 129
agccttgcat ggcagagctt ggg                                               23

SEQ ID NO: 130       moltype = DNA   length = 23
FEATURE              Location/Qualifiers
source               1..23
                     mol_type = genomic DNA
                     organism = Mus musculus
SEQUENCE: 130
acactttaac caaggaaaga ggg                                               23

SEQ ID NO: 131       moltype = DNA   length = 23
FEATURE              Location/Qualifiers
source               1..23
                     mol_type = genomic DNA
                     organism = Mus musculus
SEQUENCE: 131
taccagatcc cctctttcct tgg                                               23
```

```
SEQ ID NO: 132         moltype = DNA  length = 23
FEATURE                Location/Qualifiers
source                 1..23
                       mol_type = genomic DNA
                       organism = Mus musculus
SEQUENCE: 132
catttggagg ccaaaataca agg                                                  23

SEQ ID NO: 133         moltype = DNA  length = 23
FEATURE                Location/Qualifiers
source                 1..23
                       mol_type = genomic DNA
                       organism = Mus musculus
SEQUENCE: 133
ccaaatgttt gcacatgaat tgg                                                  23

SEQ ID NO: 134         moltype = DNA  length = 23
FEATURE                Location/Qualifiers
source                 1..23
                       mol_type = genomic DNA
                       organism = Mus musculus
SEQUENCE: 134
agtccagatg ctgtccctga agg                                                  23

SEQ ID NO: 135         moltype = DNA  length = 23
FEATURE                Location/Qualifiers
source                 1..23
                       mol_type = genomic DNA
                       organism = Mus musculus
SEQUENCE: 135
cgcaagccat tcaaacacaa agg                                                  23

SEQ ID NO: 136         moltype = DNA  length = 23
FEATURE                Location/Qualifiers
source                 1..23
                       mol_type = genomic DNA
                       organism = Mus musculus
SEQUENCE: 136
tcaaaaccct gttgagcctg agg                                                  23

SEQ ID NO: 137         moltype = DNA  length = 23
FEATURE                Location/Qualifiers
source                 1..23
                       mol_type = genomic DNA
                       organism = Mus musculus
SEQUENCE: 137
cggaatacct caggctcaac agg                                                  23

SEQ ID NO: 138         moltype = DNA  length = 23
FEATURE                Location/Qualifiers
source                 1..23
                       mol_type = genomic DNA
                       organism = Mus musculus
SEQUENCE: 138
gtcaaaatgt gaattctaac agg                                                  23

SEQ ID NO: 139         moltype = DNA  length = 23
FEATURE                Location/Qualifiers
source                 1..23
                       mol_type = genomic DNA
                       organism = Mus musculus
SEQUENCE: 139
ttatctattc tattagagct cgg                                                  23

SEQ ID NO: 140         moltype = DNA  length = 23
FEATURE                Location/Qualifiers
source                 1..23
                       mol_type = genomic DNA
                       organism = Mus musculus
SEQUENCE: 140
atcaagtaat gaaatggaca agg                                                  23

SEQ ID NO: 141         moltype = DNA  length = 23
FEATURE                Location/Qualifiers
source                 1..23
                       mol_type = genomic DNA
                       organism = Mus musculus
SEQUENCE: 141
ctcccactgc cttattaggc agg                                                  23
```

```
SEQ ID NO: 142          moltype = DNA  length = 23
FEATURE                 Location/Qualifiers
source                  1..23
                        mol_type = genomic DNA
                        organism = Mus musculus
SEQUENCE: 142
agagctcaaa tgggttctaa agg                                                 23

SEQ ID NO: 143          moltype = DNA  length = 23
FEATURE                 Location/Qualifiers
source                  1..23
                        mol_type = genomic DNA
                        organism = Mus musculus
SEQUENCE: 143
accacattca agagctcaaa tgg                                                 23

SEQ ID NO: 144          moltype = DNA  length = 23
FEATURE                 Location/Qualifiers
source                  1..23
                        mol_type = genomic DNA
                        organism = Mus musculus
SEQUENCE: 144
ttacagattg gttacacttg ggg                                                 23

SEQ ID NO: 145          moltype = DNA  length = 23
FEATURE                 Location/Qualifiers
source                  1..23
                        mol_type = genomic DNA
                        organism = Mus musculus
SEQUENCE: 145
atcactgctg ctactactta tgg                                                 23

SEQ ID NO: 146          moltype = DNA  length = 23
FEATURE                 Location/Qualifiers
source                  1..23
                        mol_type = genomic DNA
                        organism = Mus musculus
SEQUENCE: 146
atacctgcct aataaggcag tgg                                                 23

SEQ ID NO: 147          moltype = DNA  length = 23
FEATURE                 Location/Qualifiers
source                  1..23
                        mol_type = genomic DNA
                        organism = Mus musculus
SEQUENCE: 147
gatcaggaga gtcagtggga tgg                                                 23

SEQ ID NO: 148          moltype = DNA  length = 23
FEATURE                 Location/Qualifiers
source                  1..23
                        mol_type = genomic DNA
                        organism = Mus musculus
SEQUENCE: 148
ctattgtgag tctcagatta agg                                                 23

SEQ ID NO: 149          moltype = DNA  length = 23
FEATURE                 Location/Qualifiers
source                  1..23
                        mol_type = genomic DNA
                        organism = Mus musculus
SEQUENCE: 149
tattacagat tggttacact tgg                                                 23

SEQ ID NO: 150          moltype = DNA  length = 23
FEATURE                 Location/Qualifiers
source                  1..23
                        mol_type = genomic DNA
                        organism = Mus musculus
SEQUENCE: 150
attacagatt ggttacactt ggg                                                 23

SEQ ID NO: 151          moltype = DNA  length = 23
FEATURE                 Location/Qualifiers
source                  1..23
                        mol_type = genomic DNA
                        organism = Mus musculus
SEQUENCE: 151
```
tacagattgg ttacacttgg ggg                                          23

SEQ ID NO: 152           moltype = DNA   length = 23
FEATURE                  Location/Qualifiers
source                   1..23
                         mol_type = genomic DNA
                         organism = Mus musculus
SEQUENCE: 152
acagattggt tacacttggg ggg                                          23

SEQ ID NO: 153           moltype = DNA   length = 30
FEATURE                  Location/Qualifiers
source                   1..30
                         mol_type = genomic DNA
                         organism = Mus musculus
SEQUENCE: 153
ctacttacta tactaccaaa cacaccgcac                                   30

SEQ ID NO: 154           moltype = DNA   length = 30
FEATURE                  Location/Qualifiers
source                   1..30
                         mol_type = genomic DNA
                         organism = Mus musculus
SEQUENCE: 154
aaagcctact tactatacta ccaaacacac                                   30

SEQ ID NO: 155           moltype = DNA   length = 30
FEATURE                  Location/Qualifiers
source                   1..30
                         mol_type = genomic DNA
                         organism = Mus musculus
SEQUENCE: 155
caaaagccta cttactatac taccaaacac                                   30

SEQ ID NO: 156           moltype = DNA   length = 30
FEATURE                  Location/Qualifiers
source                   1..30
                         mol_type = genomic DNA
                         organism = Mus musculus
SEQUENCE: 156
gggtctgaat caaaagccta cttactatac                                   30

SEQ ID NO: 157           moltype = DNA   length = 30
FEATURE                  Location/Qualifiers
source                   1..30
                         mol_type = genomic DNA
                         organism = Mus musculus
SEQUENCE: 157
agagtgggat tctacaagtc accttcacac                                   30

SEQ ID NO: 158           moltype = DNA   length = 30
FEATURE                  Location/Qualifiers
source                   1..30
                         mol_type = genomic DNA
                         organism = Mus musculus
SEQUENCE: 158
ggaaagaggg gatctggtag cataaagtac                                   30

SEQ ID NO: 159           moltype = DNA   length = 30
FEATURE                  Location/Qualifiers
source                   1..30
                         mol_type = genomic DNA
                         organism = Mus musculus
SEQUENCE: 159
gggatctggt agcataaagt acagctacac                                   30

SEQ ID NO: 160           moltype = DNA   length = 30
FEATURE                  Location/Qualifiers
source                   1..30
                         mol_type = genomic DNA
                         organism = Mus musculus
SEQUENCE: 160
atctgtcact agcgacaagt gtagctgtac                                   30

SEQ ID NO: 161           moltype = DNA   length = 30
FEATURE                  Location/Qualifiers
source                   1..30
                         mol_type = genomic DNA
                         organism = Mus musculus

```
SEQUENCE: 161
tcatgtgcaa acatttggag gccaaaatac                                              30

SEQ ID NO: 162         moltype = DNA   length = 30
FEATURE                Location/Qualifiers
source                 1..30
                       mol_type = genomic DNA
                       organism = Mus musculus
SEQUENCE: 162
gacatacaga gaggggcgg agagaaatac                                               30

SEQ ID NO: 163         moltype = DNA   length = 30
FEATURE                Location/Qualifiers
source                 1..30
                       mol_type = genomic DNA
                       organism = Mus musculus
SEQUENCE: 163
atactgacgc catcacatca cagtttatac                                              30

SEQ ID NO: 164         moltype = DNA   length = 30
FEATURE                Location/Qualifiers
source                 1..30
                       mol_type = genomic DNA
                       organism = Mus musculus
SEQUENCE: 164
taaaactata agctctctgt ttcggaatac                                              30

SEQ ID NO: 165         moltype = DNA   length = 30
FEATURE                Location/Qualifiers
source                 1..30
                       mol_type = genomic DNA
                       organism = Mus musculus
SEQUENCE: 165
tcatcaaagt agtcgacagt caaagcatac                                              30

SEQ ID NO: 166         moltype = DNA   length = 30
FEATURE                Location/Qualifiers
source                 1..30
                       mol_type = genomic DNA
                       organism = Mus musculus
SEQUENCE: 166
tgaattctaa caggaaaact cagaacatac                                              30

SEQ ID NO: 167         moltype = DNA   length = 30
FEATURE                Location/Qualifiers
source                 1..30
                       mol_type = genomic DNA
                       organism = Mus musculus
SEQUENCE: 167
actgctgcta ctacttatgg tgactagtac                                              30

SEQ ID NO: 168         moltype = DNA   length = 30
FEATURE                Location/Qualifiers
source                 1..30
                       mol_type = genomic DNA
                       organism = Mus musculus
SEQUENCE: 168
agtcaccata agtagtagca gcagtgatac                                              30

SEQ ID NO: 169         moltype = DNA   length = 30
FEATURE                Location/Qualifiers
source                 1..30
                       mol_type = genomic DNA
                       organism = Mus musculus
SEQUENCE: 169
cataagtagt agcagcagtg atactaatac                                              30

SEQ ID NO: 170         moltype = DNA   length = 30
FEATURE                Location/Qualifiers
source                 1..30
                       mol_type = genomic DNA
                       organism = Mus musculus
SEQUENCE: 170
ttgaatggct tgcgaacaaa gattaaacac                                              30

SEQ ID NO: 171         moltype = DNA   length = 30
FEATURE                Location/Qualifiers
source                 1..30
                       mol_type = genomic DNA
```

```
                                       organism = Mus musculus
SEQUENCE: 171
ttaatctttg ttcgcaagcc attcaaacac                                        30

SEQ ID NO: 172          moltype = DNA   length = 30
FEATURE                 Location/Qualifiers
source                  1..30
                        mol_type = genomic DNA
                        organism = Mus musculus
SEQUENCE: 172
ttgctgcatc tctaacgtga actctaacac                                        30

SEQ ID NO: 173          moltype = DNA   length = 30
FEATURE                 Location/Qualifiers
source                  1..30
                        mol_type = genomic DNA
                        organism = Mus musculus
SEQUENCE: 173
ttcacgttag agatgcagca aagtctatac                                        30

SEQ ID NO: 174          moltype = DNA   length = 30
FEATURE                 Location/Qualifiers
source                  1..30
                        mol_type = genomic DNA
                        organism = Mus musculus
SEQUENCE: 174
tggaagcaac tctaaatcac cacccgatac                                        30

SEQ ID NO: 175          moltype = DNA   length = 30
FEATURE                 Location/Qualifiers
source                  1..30
                        mol_type = genomic DNA
                        organism = Mus musculus
SEQUENCE: 175
ttccaaagtt ctgtcaccca gtaaaaacac                                        30

SEQ ID NO: 176          moltype = DNA   length = 30
FEATURE                 Location/Qualifiers
source                  1..30
                        mol_type = genomic DNA
                        organism = Mus musculus
SEQUENCE: 176
ttcaagagct caaatgggtt ctaaaggcac                                        30

SEQ ID NO: 177          moltype = DNA   length = 30
FEATURE                 Location/Qualifiers
source                  1..30
                        mol_type = genomic DNA
                        organism = Mus musculus
SEQUENCE: 177
ttgaatgtgg tataagtgct aatatcatac                                        30

SEQ ID NO: 178          moltype = DNA   length = 30
FEATURE                 Location/Qualifiers
source                  1..30
                        mol_type = genomic DNA
                        organism = Mus musculus
SEQUENCE: 178
gtataagtgc taatatcata caggaaacac                                        30

SEQ ID NO: 179          moltype = DNA   length = 30
FEATURE                 Location/Qualifiers
source                  1..30
                        mol_type = genomic DNA
                        organism = Mus musculus
SEQUENCE: 179
gtgtttcctg tatgatatta gcacttatac                                        30

SEQ ID NO: 180          moltype = DNA   length = 30
FEATURE                 Location/Qualifiers
source                  1..30
                        mol_type = genomic DNA
                        organism = Mus musculus
SEQUENCE: 180
gactttgtgt ttcctgtatg atattagcac                                        30

SEQ ID NO: 181          moltype = DNA   length = 30
FEATURE                 Location/Qualifiers
source                  1..30
```

```
                              mol_type = genomic DNA
                              organism = Mus musculus
SEQUENCE: 181
aaaacaatta tcaggcagtg acagagacac                                          30

SEQ ID NO: 182            moltype = DNA  length = 30
FEATURE                   Location/Qualifiers
source                    1..30
                          mol_type = genomic DNA
                          organism = Mus musculus
SEQUENCE: 182
ccaagatact agagtagctg tgactggcac                                          30

SEQ ID NO: 183            moltype = DNA  length = 30
FEATURE                   Location/Qualifiers
source                    1..30
                          mol_type = genomic DNA
                          organism = Mus musculus
SEQUENCE: 183
ggcctatagc cattcaaatg gccaagatac                                          30

SEQ ID NO: 184            moltype = DNA  length = 30
FEATURE                   Location/Qualifiers
source                    1..30
                          mol_type = genomic DNA
                          organism = Mus musculus
SEQUENCE: 184
gtcccatctc cctaagtctc gaatctgcac                                          30

SEQ ID NO: 185            moltype = DNA  length = 20
FEATURE                   Location/Qualifiers
misc_feature              1..20
                          note = Primer
source                    1..20
                          mol_type = other DNA
                          organism = synthetic construct
SEQUENCE: 185
cacagggcag tcagagaccc                                                     20

SEQ ID NO: 186            moltype = DNA  length = 20
FEATURE                   Location/Qualifiers
misc_feature              1..20
                          note = Primer
source                    1..20
                          mol_type = other DNA
                          organism = synthetic construct
SEQUENCE: 186
gcaaacaaag ttggacactg                                                     20

SEQ ID NO: 187            moltype = DNA  length = 24
FEATURE                   Location/Qualifiers
misc_feature              1..24
                          note = Primer
source                    1..24
                          mol_type = other DNA
                          organism = synthetic construct
SEQUENCE: 187
agactcccgc ccatcttcta gaaa                                                24

SEQ ID NO: 188            moltype = DNA  length = 24
FEATURE                   Location/Qualifiers
misc_feature              1..24
                          note = Primer
source                    1..24
                          mol_type = other DNA
                          organism = synthetic construct
SEQUENCE: 188
aagtcgctct gagttgttat cagt                                                24

SEQ ID NO: 189            moltype = DNA  length = 19
FEATURE                   Location/Qualifiers
misc_feature              1..19
                          note = Primer
source                    1..19
                          mol_type = other DNA
                          organism = synthetic construct
SEQUENCE: 189
cagtgaaacg caccagacg                                                      19
```

```
SEQ ID NO: 190            moltype = DNA  length = 20
FEATURE                   Location/Qualifiers
misc_feature              1..20
                          note = Primer
source                    1..20
                          mol_type = other DNA
                          organism = synthetic construct
SEQUENCE: 190
aatctgccta acaggaggtg                                                  20

SEQ ID NO: 191            moltype = DNA  length = 24
FEATURE                   Location/Qualifiers
misc_feature              1..24
                          note = Primer
source                    1..24
                          mol_type = other DNA
                          organism = synthetic construct
SEQUENCE: 191
gagggaatgg ggaccaaagg catt                                             24

SEQ ID NO: 192            moltype = DNA  length = 24
FEATURE                   Location/Qualifiers
misc_feature              1..24
                          note = Primer
source                    1..24
                          mol_type = other DNA
                          organism = synthetic construct
SEQUENCE: 192
tcatgtgggg tgatgttcag gaag                                             24

SEQ ID NO: 193            moltype = DNA  length = 23
FEATURE                   Location/Qualifiers
misc_feature              1..23
                          note = Primer
source                    1..23
                          mol_type = other DNA
                          organism = synthetic construct
SEQUENCE: 193
agagcagctg acctgaggtc caa                                              23

SEQ ID NO: 194            moltype = DNA  length = 24
FEATURE                   Location/Qualifiers
misc_feature              1..24
                          note = Primer
source                    1..24
                          mol_type = other DNA
                          organism = synthetic construct
SEQUENCE: 194
cccaagggta gagtgcaagt aaac                                             24

SEQ ID NO: 195            moltype = DNA  length = 24
FEATURE                   Location/Qualifiers
misc_feature              1..24
                          note = Primer
source                    1..24
                          mol_type = other DNA
                          organism = synthetic construct
SEQUENCE: 195
gcatcctagc tcatttggtc tgct                                             24

SEQ ID NO: 196            moltype = DNA  length = 24
FEATURE                   Location/Qualifiers
misc_feature              1..24
                          note = Primer
source                    1..24
                          mol_type = other DNA
                          organism = synthetic construct
SEQUENCE: 196
gagaggattc ctcatgaatg ggat                                             24

SEQ ID NO: 197            moltype = DNA  length = 24
FEATURE                   Location/Qualifiers
misc_feature              1..24
                          note = Primer
source                    1..24
                          mol_type = other DNA
                          organism = synthetic construct
SEQUENCE: 197
accaaacact acacttggtt actg                                             24
```

```
SEQ ID NO: 198          moltype = DNA   length = 24
FEATURE                 Location/Qualifiers
misc_feature            1..24
                        note = Primer
source                  1..24
                        mol_type = other DNA
                        organism = synthetic construct
SEQUENCE: 198
ctcccactag caattttaaa gtct                                              24

SEQ ID NO: 199          moltype = DNA   length = 24
FEATURE                 Location/Qualifiers
misc_feature            1..24
                        note = Primer
source                  1..24
                        mol_type = other DNA
                        organism = synthetic construct
SEQUENCE: 199
gaatgttcag cacaggtttc cttg                                              24

SEQ ID NO: 200          moltype = DNA   length = 24
FEATURE                 Location/Qualifiers
misc_feature            1..24
                        note = Primer
source                  1..24
                        mol_type = other DNA
                        organism = synthetic construct
SEQUENCE: 200
ggtcaaaagg agctccatat ttga                                              24

SEQ ID NO: 201          moltype = DNA   length = 24
FEATURE                 Location/Qualifiers
misc_feature            1..24
                        note = Primer
source                  1..24
                        mol_type = other DNA
                        organism = synthetic construct
SEQUENCE: 201
caggacaccc atggccaaat ccag                                              24

SEQ ID NO: 202          moltype = DNA   length = 24
FEATURE                 Location/Qualifiers
misc_feature            1..24
                        note = Primer
source                  1..24
                        mol_type = other DNA
                        organism = synthetic construct
SEQUENCE: 202
cagagcctcc tgcagggatg tcaa                                              24

SEQ ID NO: 203          moltype = DNA   length = 24
FEATURE                 Location/Qualifiers
misc_feature            1..24
                        note = Primer
source                  1..24
                        mol_type = other DNA
                        organism = synthetic construct
SEQUENCE: 203
gcctgccaag gtgactctca tcta                                              24

SEQ ID NO: 204          moltype = DNA   length = 24
FEATURE                 Location/Qualifiers
misc_feature            1..24
                        note = Primer
source                  1..24
                        mol_type = other DNA
                        organism = synthetic construct
SEQUENCE: 204
tgcccaggct gatcttgaac tcct                                              24

SEQ ID NO: 205          moltype = DNA   length = 24
FEATURE                 Location/Qualifiers
misc_feature            1..24
                        note = Primer
source                  1..24
                        mol_type = other DNA
                        organism = synthetic construct
SEQUENCE: 205
```

```
cccagagtta agaggttctt tcct                                              24

SEQ ID NO: 206           moltype = DNA   length = 24
FEATURE                  Location/Qualifiers
misc_feature             1..24
                         note = Primer
source                   1..24
                         mol_type = other DNA
                         organism = synthetic construct
SEQUENCE: 206
gaagctactc cagtgcaact agct                                              24

SEQ ID NO: 207           moltype = DNA   length = 23
FEATURE                  Location/Qualifiers
misc_feature             1..23
                         note = Primer
source                   1..23
                         mol_type = other DNA
                         organism = synthetic construct
SEQUENCE: 207
acgcagtctg ttctgtgcag tgt                                               23

SEQ ID NO: 208           moltype = DNA   length = 24
FEATURE                  Location/Qualifiers
misc_feature             1..24
                         note = Primer
source                   1..24
                         mol_type = other DNA
                         organism = synthetic construct
SEQUENCE: 208
aggccttccc aaggaagacc ctga                                              24

SEQ ID NO: 209           moltype = DNA   length = 24
FEATURE                  Location/Qualifiers
misc_feature             1..24
                         note = Primer
source                   1..24
                         mol_type = other DNA
                         organism = synthetic construct
SEQUENCE: 209
gctgatcact ggccaaatcc agct                                              24

SEQ ID NO: 210           moltype = DNA   length = 24
FEATURE                  Location/Qualifiers
misc_feature             1..24
                         note = Primer
source                   1..24
                         mol_type = other DNA
                         organism = synthetic construct
SEQUENCE: 210
gggaaacaat gggatcaagc tgca                                              24

SEQ ID NO: 211           moltype = DNA   length = 24
FEATURE                  Location/Qualifiers
misc_feature             1..24
                         note = Primer
source                   1..24
                         mol_type = other DNA
                         organism = synthetic construct
SEQUENCE: 211
gccccttttgt aagttgagga gcat                                             24

SEQ ID NO: 212           moltype = DNA   length = 24
FEATURE                  Location/Qualifiers
misc_feature             1..24
                         note = Primer
source                   1..24
                         mol_type = other DNA
                         organism = synthetic construct
SEQUENCE: 212
ccctctacct ctctcaatgg gctt                                              24

SEQ ID NO: 213           moltype = DNA   length = 24
FEATURE                  Location/Qualifiers
misc_feature             1..24
                         note = Primer
source                   1..24
                         mol_type = other DNA
                         organism = synthetic construct
```

```
SEQUENCE: 213
cagacaagca aatgctgaga gatt                                              24

SEQ ID NO: 214          moltype = DNA   length = 24
FEATURE                 Location/Qualifiers
misc_feature            1..24
                        note = Primer
source                  1..24
                        mol_type = other DNA
                        organism = synthetic construct
SEQUENCE: 214
cctgtcatta tgatgttcgc tagt                                              24

SEQ ID NO: 215          moltype = DNA   length = 24
FEATURE                 Location/Qualifiers
misc_feature            1..24
                        note = Primer
source                  1..24
                        mol_type = other DNA
                        organism = synthetic construct
SEQUENCE: 215
ccagagttgg cctcctacag agat                                              24

SEQ ID NO: 216          moltype = DNA   length = 24
FEATURE                 Location/Qualifiers
misc_feature            1..24
                        note = Primer
source                  1..24
                        mol_type = other DNA
                        organism = synthetic construct
SEQUENCE: 216
gtggatgccc cactactgtt catt                                              24

SEQ ID NO: 217          moltype = DNA   length = 24
FEATURE                 Location/Qualifiers
misc_feature            1..24
                        note = Primer
source                  1..24
                        mol_type = other DNA
                        organism = synthetic construct
SEQUENCE: 217
tacccaattt gccagtctgt gtct                                              24

SEQ ID NO: 218          moltype = DNA   length = 23
FEATURE                 Location/Qualifiers
misc_feature            1..23
                        note = Primer
source                  1..23
                        mol_type = other DNA
                        organism = synthetic construct
SEQUENCE: 218
accaccaggc ctgccctaca aga                                               23

SEQ ID NO: 219          moltype = DNA   length = 24
FEATURE                 Location/Qualifiers
misc_feature            1..24
                        note = Primer
source                  1..24
                        mol_type = other DNA
                        organism = synthetic construct
SEQUENCE: 219
tgtgaatttg atcctggcat tatg                                              24

SEQ ID NO: 220          moltype = DNA   length = 24
FEATURE                 Location/Qualifiers
misc_feature            1..24
                        note = Primer
source                  1..24
                        mol_type = other DNA
                        organism = synthetic construct
SEQUENCE: 220
tacagacaag cagatgctga gaga                                              24

SEQ ID NO: 221          moltype = DNA   length = 24
FEATURE                 Location/Qualifiers
misc_feature            1..24
                        note = Primer
source                  1..24
                        mol_type = other DNA
```

```
                        organism = synthetic construct
SEQUENCE: 221
cagtcaacag agctctaacc tcct                                                  24

SEQ ID NO: 222          moltype = DNA   length = 23
FEATURE                 Location/Qualifiers
misc_feature            1..23
                        note = Primer
source                  1..23
                        mol_type = other DNA
                        organism = synthetic construct
SEQUENCE: 222
agcacctggt tgcacatcaa ctt                                                   23

SEQ ID NO: 223          moltype = DNA   length = 24
FEATURE                 Location/Qualifiers
misc_feature            1..24
                        note = Primer
source                  1..24
                        mol_type = other DNA
                        organism = synthetic construct
SEQUENCE: 223
catgtggtcc ctgaacgtga atga                                                  24

SEQ ID NO: 224          moltype = DNA   length = 23
FEATURE                 Location/Qualifiers
misc_feature            1..23
                        note = Primer
source                  1..23
                        mol_type = other DNA
                        organism = synthetic construct
SEQUENCE: 224
gtctgtcgct tgccctcttc tct                                                   23

SEQ ID NO: 225          moltype = DNA   length = 24
FEATURE                 Location/Qualifiers
misc_feature            1..24
                        note = Primer
source                  1..24
                        mol_type = other DNA
                        organism = synthetic construct
SEQUENCE: 225
atgcagggcc tctagaccat ttca                                                  24

SEQ ID NO: 226          moltype = DNA   length = 23
FEATURE                 Location/Qualifiers
misc_feature            1..23
                        note = Primer
source                  1..23
                        mol_type = other DNA
                        organism = synthetic construct
SEQUENCE: 226
ctcagcccttt tgtgcactca cct                                                  23

SEQ ID NO: 227          moltype = DNA   length = 20
FEATURE                 Location/Qualifiers
misc_feature            1..20
                        note = Primer
source                  1..20
                        mol_type = other DNA
                        organism = synthetic construct
SEQUENCE: 227
tgcacatcgc aaacatttcg                                                       20

SEQ ID NO: 228          moltype = DNA   length = 20
FEATURE                 Location/Qualifiers
misc_feature            1..20
                        note = Primer
source                  1..20
                        mol_type = other DNA
                        organism = synthetic construct
SEQUENCE: 228
tgggtatcgc actgtgtcag                                                       20

SEQ ID NO: 229          moltype = DNA   length = 20
FEATURE                 Location/Qualifiers
misc_feature            1..20
                        note = Primer
source                  1..20
```

```
                        mol_type = other DNA
                        organism = synthetic construct
SEQUENCE: 229
aggttcacat ggcttgtggt                                                    20

SEQ ID NO: 230          moltype = DNA   length = 20
FEATURE                 Location/Qualifiers
misc_feature            1..20
                        note = Primer
source                  1..20
                        mol_type = other DNA
                        organism = synthetic construct
SEQUENCE: 230
atatctgaaa tgcccgcagg                                                    20

SEQ ID NO: 231          moltype = DNA   length = 20
FEATURE                 Location/Qualifiers
misc_feature            1..20
                        note = Primer
source                  1..20
                        mol_type = other DNA
                        organism = synthetic construct
SEQUENCE: 231
tgcacatcgc aaacatttcg                                                    20

SEQ ID NO: 232          moltype = DNA   length = 20
FEATURE                 Location/Qualifiers
misc_feature            1..20
                        note = Primer
source                  1..20
                        mol_type = other DNA
                        organism = synthetic construct
SEQUENCE: 232
tgggtatcgc actgtgtcag                                                    20

SEQ ID NO: 233          moltype = DNA   length = 20
FEATURE                 Location/Qualifiers
misc_feature            1..20
                        note = Primer
source                  1..20
                        mol_type = other DNA
                        organism = synthetic construct
SEQUENCE: 233
tctttaaagg ccttatctcc                                                    20

SEQ ID NO: 234          moltype = DNA   length = 20
FEATURE                 Location/Qualifiers
misc_feature            1..20
                        note = Primer
source                  1..20
                        mol_type = other DNA
                        organism = synthetic construct
SEQUENCE: 234
ttctgcttga gaattcatcc                                                    20

SEQ ID NO: 235          moltype = DNA   length = 20
FEATURE                 Location/Qualifiers
misc_feature            1..20
                        note = Primer
source                  1..20
                        mol_type = other DNA
                        organism = synthetic construct
SEQUENCE: 235
ctcctaatct ttcacttagg                                                    20

SEQ ID NO: 236          moltype = DNA   length = 20
FEATURE                 Location/Qualifiers
misc_feature            1..20
                        note = Primer
source                  1..20
                        mol_type = other DNA
                        organism = synthetic construct
SEQUENCE: 236
caaagcctgg tataacatag                                                    20

SEQ ID NO: 237          moltype = DNA   length = 19
FEATURE                 Location/Qualifiers
misc_feature            1..19
                        note = Primer
```

```
source                  1..19
                        mol_type = other DNA
                        organism = synthetic construct
SEQUENCE: 237
tcacttcgag catctgtgg                                              19

SEQ ID NO: 238          moltype = DNA  length = 19
FEATURE                 Location/Qualifiers
misc_feature            1..19
                        note = Primer
source                  1..19
                        mol_type = other DNA
                        organism = synthetic construct
SEQUENCE: 238
ccaaatgaca ggctgagct                                              19

SEQ ID NO: 239          moltype = DNA  length = 20
FEATURE                 Location/Qualifiers
misc_feature            1..20
                        note = Primer
source                  1..20
                        mol_type = other DNA
                        organism = synthetic construct
SEQUENCE: 239
agcaggaagt gaaggctaag                                             20

SEQ ID NO: 240          moltype = DNA  length = 20
FEATURE                 Location/Qualifiers
misc_feature            1..20
                        note = Primer
source                  1..20
                        mol_type = other DNA
                        organism = synthetic construct
SEQUENCE: 240
atgtaacgtg gcaactctgg                                             20

SEQ ID NO: 241          moltype = DNA  length = 20
FEATURE                 Location/Qualifiers
misc_feature            1..20
                        note = Primer
source                  1..20
                        mol_type = other DNA
                        organism = synthetic construct
SEQUENCE: 241
gtgttgctct cgtcaattag                                             20

SEQ ID NO: 242          moltype = DNA  length = 20
FEATURE                 Location/Qualifiers
misc_feature            1..20
                        note = Primer
source                  1..20
                        mol_type = other DNA
                        organism = synthetic construct
SEQUENCE: 242
aggtgttgta catggagaag                                             20

SEQ ID NO: 243          moltype = DNA  length = 20
FEATURE                 Location/Qualifiers
misc_feature            1..20
                        note = Primer
source                  1..20
                        mol_type = other DNA
                        organism = synthetic construct
SEQUENCE: 243
tgtgagccac catacccagc                                             20

SEQ ID NO: 244          moltype = DNA  length = 20
FEATURE                 Location/Qualifiers
misc_feature            1..20
                        note = Primer
source                  1..20
                        mol_type = other DNA
                        organism = synthetic construct
SEQUENCE: 244
cctgcagtcc tttgcggatc                                             20

SEQ ID NO: 245          moltype = DNA  length = 20
FEATURE                 Location/Qualifiers
misc_feature            1..20
```

```
                        note = Primer
source                  1..20
                        mol_type = other DNA
                        organism = synthetic construct
SEQUENCE: 245
tcgctgccag tataacatgc                                                   20

SEQ ID NO: 246          moltype = DNA  length = 20
FEATURE                 Location/Qualifiers
misc_feature            1..20
                        note = Primer
source                  1..20
                        mol_type = other DNA
                        organism = synthetic construct
SEQUENCE: 246
aactccagtc tctagactcg                                                   20

SEQ ID NO: 247          moltype = DNA  length = 20
FEATURE                 Location/Qualifiers
misc_feature            1..20
                        note = Primer
source                  1..20
                        mol_type = other DNA
                        organism = synthetic construct
SEQUENCE: 247
aatagtttga cgttggagcc                                                   20

SEQ ID NO: 248          moltype = DNA  length = 20
FEATURE                 Location/Qualifiers
misc_feature            1..20
                        note = Primer
source                  1..20
                        mol_type = other DNA
                        organism = synthetic construct
SEQUENCE: 248
actcccaaca tgttctcctg                                                   20

SEQ ID NO: 249          moltype = DNA  length = 19
FEATURE                 Location/Qualifiers
misc_feature            1..19
                        note = Primer
source                  1..19
                        mol_type = other DNA
                        organism = synthetic construct
SEQUENCE: 249
atcatcgctc acagagtcc                                                    19

SEQ ID NO: 250          moltype = DNA  length = 20
FEATURE                 Location/Qualifiers
misc_feature            1..20
                        note = Primer
source                  1..20
                        mol_type = other DNA
                        organism = synthetic construct
SEQUENCE: 250
acgactgcag gatcttaatg                                                   20

SEQ ID NO: 251          moltype = DNA  length = 20
FEATURE                 Location/Qualifiers
misc_feature            1..20
                        note = Primer
source                  1..20
                        mol_type = other DNA
                        organism = synthetic construct
SEQUENCE: 251
tggatggagg ttgggaatcc                                                   20

SEQ ID NO: 252          moltype = DNA  length = 20
FEATURE                 Location/Qualifiers
misc_feature            1..20
                        note = Primer
source                  1..20
                        mol_type = other DNA
                        organism = synthetic construct
SEQUENCE: 252
ttgaggcagc agcactctcc                                                   20

SEQ ID NO: 253          moltype = DNA  length = 19
FEATURE                 Location/Qualifiers
```

```
                              -continued misc_feature              1..19
                          note = Primer
source                    1..19
                          mol_type = other DNA
                          organism = synthetic construct
SEQUENCE: 253
agtctatcct agcagctcc                                                    19

SEQ ID NO: 254            moltype = DNA   length = 20
FEATURE                   Location/Qualifiers
misc_feature              1..20
                          note = Primer
source                    1..20
                          mol_type = other DNA
                          organism = synthetic construct
SEQUENCE: 254
actgagacca gataatgcag                                                   20

SEQ ID NO: 255            moltype = DNA   length = 19
FEATURE                   Location/Qualifiers
misc_feature              1..19
                          note = Primer
source                    1..19
                          mol_type = other DNA
                          organism = synthetic construct
SEQUENCE: 255
aagagatgcg agttgttcc                                                    19

SEQ ID NO: 256            moltype = DNA   length = 19
FEATURE                   Location/Qualifiers
misc_feature              1..19
                          note = Primer
source                    1..19
                          mol_type = other DNA
                          organism = synthetic construct
SEQUENCE: 256
cctcttctac tctgagtgg                                                    19

SEQ ID NO: 257            moltype = DNA   length = 20
FEATURE                   Location/Qualifiers
misc_feature              1..20
                          note = Primer
source                    1..20
                          mol_type = other DNA
                          organism = synthetic construct
SEQUENCE: 257
acctggttta tcacaagcta                                                   20

SEQ ID NO: 258            moltype = DNA   length = 20
FEATURE                   Location/Qualifiers
misc_feature              1..20
                          note = Primer
source                    1..20
                          mol_type = other DNA
                          organism = synthetic construct
SEQUENCE: 258
aacgtgaaca gaaggatttc                                                   20

SEQ ID NO: 259            moltype = DNA   length = 20
FEATURE                   Location/Qualifiers
misc_feature              1..20
                          note = Primer
source                    1..20
                          mol_type = other DNA
                          organism = synthetic construct
SEQUENCE: 259
atcactccat cagagtcagg                                                   20

SEQ ID NO: 260            moltype = DNA   length = 20
FEATURE                   Location/Qualifiers
misc_feature              1..20
                          note = Primer
source                    1..20
                          mol_type = other DNA
                          organism = synthetic construct
SEQUENCE: 260
tggctccttc tattctctcc                                                   20

SEQ ID NO: 261            moltype =    length =
```

```
SEQUENCE: 261
000

SEQ ID NO: 262         moltype =    length =
SEQUENCE: 262
000

SEQ ID NO: 263         moltype =    length =
SEQUENCE: 263
000

SEQ ID NO: 264         moltype =    length =
SEQUENCE: 264
000

SEQ ID NO: 265         moltype =    length =
SEQUENCE: 265
000

SEQ ID NO: 266         moltype =    length =
SEQUENCE: 266
000

SEQ ID NO: 267         moltype =    length =
SEQUENCE: 267
000

SEQ ID NO: 268         moltype =    length =
SEQUENCE: 268
000

SEQ ID NO: 269         moltype = DNA   length = 15
FEATURE                Location/Qualifiers
source                 1..15
                       mol_type = genomic DNA
                       organism = Homo sapiens
SEQUENCE: 269
tatatatata tataa                                                       15

SEQ ID NO: 270         moltype =    length =
SEQUENCE: 270
000

SEQ ID NO: 271         moltype =    length =
SEQUENCE: 271
000

SEQ ID NO: 272         moltype =    length =
SEQUENCE: 272
000

SEQ ID NO: 273         moltype =    length =
SEQUENCE: 273
000

SEQ ID NO: 274         moltype =    length =
SEQUENCE: 274
000

SEQ ID NO: 275         moltype =    length =
SEQUENCE: 275
000

SEQ ID NO: 276         moltype =    length =
SEQUENCE: 276
000

SEQ ID NO: 277         moltype =    length =
SEQUENCE: 277
000

SEQ ID NO: 278         moltype =    length =
SEQUENCE: 278
000

SEQ ID NO: 279         moltype =    length =
SEQUENCE: 279
000
```

-continued

| | | |
|---|---|---|
| SEQ ID NO: 280<br>SEQUENCE: 280<br>000 | moltype = length = | |
| SEQ ID NO: 281<br>SEQUENCE: 281<br>000 | moltype = length = | |
| SEQ ID NO: 282<br>SEQUENCE: 282<br>000 | moltype = length = | |
| SEQ ID NO: 283<br>SEQUENCE: 283<br>000 | moltype = length = | |
| SEQ ID NO: 284<br>SEQUENCE: 284<br>000 | moltype = length = | |
| SEQ ID NO: 285<br>SEQUENCE: 285<br>000 | moltype = length = | |
| SEQ ID NO: 286<br>SEQUENCE: 286<br>000 | moltype = length = | |
| SEQ ID NO: 287<br>SEQUENCE: 287<br>000 | moltype = length = | |
| SEQ ID NO: 288<br>SEQUENCE: 288<br>000 | moltype = length = | |
| SEQ ID NO: 289<br>SEQUENCE: 289<br>000 | moltype = length = | |
| SEQ ID NO: 290<br>SEQUENCE: 290<br>000 | moltype = length = | |
| SEQ ID NO: 291<br>SEQUENCE: 291<br>000 | moltype = length = | |
| SEQ ID NO: 292<br>SEQUENCE: 292<br>000 | moltype = length = | |
| SEQ ID NO: 293<br>SEQUENCE: 293<br>000 | moltype = length = | |
| SEQ ID NO: 294<br>FEATURE<br>source<br><br>SEQUENCE: 294<br>tatatataaa aaaaa | moltype = DNA length = 15<br>Location/Qualifiers<br>1..15<br>mol_type = genomic DNA<br>organism = Homo sapiens | <br><br><br><br><br>15 |
| SEQ ID NO: 295<br>FEATURE<br>source<br><br>SEQUENCE: 295<br>cataaataaa aaaaatta | moltype = DNA length = 18<br>Location/Qualifiers<br>1..18<br>mol_type = genomic DNA<br>organism = Homo sapiens | <br><br><br><br><br>18 |
| SEQ ID NO: 296<br>FEATURE<br>source<br><br>SEQUENCE: 296<br>gttttagagc ta | moltype = RNA length = 12<br>Location/Qualifiers<br>1..12<br>mol_type = other RNA<br>organism = Streptococcus pyogenes | <br><br><br><br><br>12 |

```
SEQ ID NO: 297         moltype = RNA  length = 25
FEATURE                Location/Qualifiers
source                 1..25
                       mol_type = other RNA
                       organism = Campylobacter jejuni
SEQUENCE: 297
gttttagtcc cttttaaat ttctt                                              25

SEQ ID NO: 298         moltype =     length =
SEQUENCE: 298
000

SEQ ID NO: 299         moltype = RNA  length = 14
FEATURE                Location/Qualifiers
source                 1..14
                       mol_type = other RNA
                       organism = Streptococcus pyogenes
SEQUENCE: 299
tagcaagtta aaat                                                         14

SEQ ID NO: 300         moltype = RNA  length = 25
FEATURE                Location/Qualifiers
source                 1..25
                       mol_type = other RNA
                       organism = Campylobacter jejuni
SEQUENCE: 300
aagaaattta aaagggact aaaat                                              25

SEQ ID NO: 301         moltype = RNA  length = 11
FEATURE                Location/Qualifiers
misc_feature           1..11
                       note = Parcubacteria bacterium
source                 1..11
                       mol_type = other RNA
                       organism = unidentified
SEQUENCE: 301
aaatttctac t                                                            11

SEQ ID NO: 302         moltype = RNA  length = 12
FEATURE                Location/Qualifiers
source                 1..12
                       mol_type = other RNA
                       organism = Streptococcus pyogenes
SEQUENCE: 302
aaggctagtc cg                                                           12

SEQ ID NO: 303         moltype = RNA  length = 11
FEATURE                Location/Qualifiers
source                 1..11
                       mol_type = other RNA
                       organism = Campylobacter jejuni
SEQUENCE: 303
aaagagtttg c                                                            11

SEQ ID NO: 304         moltype = RNA  length = 34
FEATURE                Location/Qualifiers
source                 1..34
                       mol_type = other RNA
                       organism = Streptococcus pyogenes
SEQUENCE: 304
ttatcaactt gaaaaagtgg caccgagtcg gtgc                                   34

SEQ ID NO: 305         moltype = RNA  length = 38
FEATURE                Location/Qualifiers
source                 1..38
                       mol_type = other RNA
                       organism = Campylobacter jejuni
SEQUENCE: 305
gggactctgc ggggttacaa tcccctaaaa ccgctttt                               38

SEQ ID NO: 306         moltype = RNA  length = 22
FEATURE                Location/Qualifiers
source                 1..22
                       mol_type = other RNA
                       organism = Streptococcus thermophilus
SEQUENCE: 306
gttttagagc tgtgttgttt cg                                                22
```

```
SEQ ID NO: 307              moltype = RNA  length = 24
FEATURE                     Location/Qualifiers
source                      1..24
                            mol_type = other RNA
                            organism = Streptococcus thermophilus
SEQUENCE: 307
cgaaacaaca cagcgagtta aaat                                              24

SEQ ID NO: 308              moltype = RNA  length = 13
FEATURE                     Location/Qualifiers
source                      1..13
                            mol_type = other RNA
                            organism = Streptococcus thermophilus
SEQUENCE: 308
aaggcttagt ccg                                                          13

SEQ ID NO: 309              moltype = RNA  length = 38
FEATURE                     Location/Qualifiers
source                      1..38
                            mol_type = other RNA
                            organism = Streptococcus thermophilus
SEQUENCE: 309
tactcaactt gaaaaggtgg caccgattcg gtgttttt                               38

SEQ ID NO: 310              moltype = DNA  length = 20
FEATURE                     Location/Qualifiers
misc_feature                1..20
                            note = target sequence
source                      1..20
                            mol_type = other DNA
                            organism = synthetic construct
SEQUENCE: 310
atcattggca gactagttcg                                                   20

SEQ ID NO: 311              moltype = DNA  length = 20
FEATURE                     Location/Qualifiers
misc_feature                1..20
                            note = target sequence
source                      1..20
                            mol_type = other DNA
                            organism = synthetic construct
SEQUENCE: 311
cgaactagtc tgccaatgat                                                   20

SEQ ID NO: 312              moltype = AA  length = 7
FEATURE                     Location/Qualifiers
REGION                      1..7
                            note = Nuclear localization sequence
source                      1..7
                            mol_type = protein
                            organism = synthetic construct
SEQUENCE: 312
PKKKRKV                                                                  7

SEQ ID NO: 313              moltype = AA  length = 16
FEATURE                     Location/Qualifiers
REGION                      1..16
                            note = Nuclear localization sequence
source                      1..16
                            mol_type = protein
                            organism = synthetic construct
SEQUENCE: 313
KRPAATKKAG QAKKKK                                                       16

SEQ ID NO: 314              moltype = AA  length = 9
FEATURE                     Location/Qualifiers
REGION                      1..9
                            note = Nuclear localization sequence
source                      1..9
                            mol_type = protein
                            organism = synthetic construct
SEQUENCE: 314
PAAKRVKLD                                                                9

SEQ ID NO: 315              moltype = AA  length = 11
FEATURE                     Location/Qualifiers
REGION                      1..11
                            note = Nuclear localization sequence
source                      1..11
```

```
                        mol_type = protein
                        organism = synthetic construct
SEQUENCE: 315
RQRRNELKRS P                                                      11

SEQ ID NO: 316          moltype = AA   length = 38
FEATURE                 Location/Qualifiers
REGION                  1..38
                        note = Nuclear localization sequence
source                  1..38
                        mol_type = protein
                        organism = synthetic construct
SEQUENCE: 316
NQSSNFGPMK GGNFGGRSSG PYGGGGQYFA KPRNQGGY                          38

SEQ ID NO: 317          moltype = AA   length = 42
FEATURE                 Location/Qualifiers
REGION                  1..42
                        note = Nuclear localization sequence
source                  1..42
                        mol_type = protein
                        organism = synthetic construct
SEQUENCE: 317
RMRIZFKNKG KDTAELRRRR VEVSVELRKA KKDEQILKRR NV                     42

SEQ ID NO: 318          moltype = AA   length = 8
FEATURE                 Location/Qualifiers
REGION                  1..8
                        note = Nuclear localization sequence
source                  1..8
                        mol_type = protein
                        organism = synthetic construct
SEQUENCE: 318
VSRKRPRP                                                           8

SEQ ID NO: 319          moltype = AA   length = 8
FEATURE                 Location/Qualifiers
REGION                  1..8
                        note = Nuclear localization sequence
source                  1..8
                        mol_type = protein
                        organism = synthetic construct
SEQUENCE: 319
PPKKARED                                                           8

SEQ ID NO: 320          moltype = AA   length = 8
FEATURE                 Location/Qualifiers
REGION                  1..8
                        note = Nuclear localization sequence
source                  1..8
                        mol_type = protein
                        organism = synthetic construct
SEQUENCE: 320
PQPKKKPL                                                           8

SEQ ID NO: 321          moltype = AA   length = 12
FEATURE                 Location/Qualifiers
REGION                  1..12
                        note = Nuclear localization sequence
source                  1..12
                        mol_type = protein
                        organism = synthetic construct
SEQUENCE: 321
SALIKKKKKM AP                                                     12

SEQ ID NO: 322          moltype = AA   length = 5
FEATURE                 Location/Qualifiers
REGION                  1..5
                        note = Nuclear localization sequence
source                  1..5
                        mol_type = protein
                        organism = synthetic construct
SEQUENCE: 322
DRLRR                                                              5

SEQ ID NO: 323          moltype = AA   length = 7
FEATURE                 Location/Qualifiers
REGION                  1..7
                        note = Nuclear localization sequence
```

```
source                          1..7
                                mol_type = protein
                                organism = synthetic construct
SEQUENCE: 323
PKQKKRK                                                                    7

SEQ ID NO: 324                  moltype = AA  length = 10
FEATURE                         Location/Qualifiers
REGION                          1..10
                                note = Nuclear localization sequence
source                          1..10
                                mol_type = protein
                                organism = synthetic construct
SEQUENCE: 324
RKLKKKIKKL                                                                10

SEQ ID NO: 325                  moltype = AA  length = 10
FEATURE                         Location/Qualifiers
REGION                          1..10
                                note = Nuclear localization sequence
source                          1..10
                                mol_type = protein
                                organism = synthetic construct
SEQUENCE: 325
REKKKFLKRR                                                                10

SEQ ID NO: 326                  moltype = AA  length = 20
FEATURE                         Location/Qualifiers
REGION                          1..20
                                note = Nuclear localization sequence
source                          1..20
                                mol_type = protein
                                organism = synthetic construct
SEQUENCE: 326
KRKGDEVDGV DEVAKKKSKK                                                     20

SEQ ID NO: 327                  moltype = AA  length = 17
FEATURE                         Location/Qualifiers
REGION                          1..17
                                note = Nuclear localization sequence
source                          1..17
                                mol_type = protein
                                organism = synthetic construct
SEQUENCE: 327
RKCLQAGMNL EARKTKK                                                        17

SEQ ID NO: 328                  moltype = RNA  length = 77
FEATURE                         Location/Qualifiers
misc_feature                    1..77
                                note = Backbone sequence of chimeric single stranded RNA
source                          1..77
                                mol_type = other RNA
                                organism = synthetic construct
SEQUENCE: 328
gttttagtcc ctgaaaaggg actaaaataa agagtttgcg ggactctgcg gggttacaat         60
cccctaaaac cgctttt                                                        77

SEQ ID NO: 329                  moltype = RNA  length = 76
FEATURE                         Location/Qualifiers
misc_feature                    1..76
                                note = Backbone sequence of chimeric single stranded RNA
source                          1..76
                                mol_type = other RNA
                                organism = synthetic construct
SEQUENCE: 329
gttttagagc tagaaatagc aagttaaaat aaggctagtc cgttatcaac ttgaaaaagt         60
ggcaccgagt cggtgc                                                         76

SEQ ID NO: 330                  moltype = DNA  length = 23
FEATURE                         Location/Qualifiers
source                          1..23
                                mol_type = genomic DNA
                                organism = Homo sapiens
SEQUENCE: 330
agttacaggg agcaccacca ggg                                                 23

SEQ ID NO: 331                  moltype = DNA  length = 23
FEATURE                         Location/Qualifiers
source                          1..23
```

```
                          mol_type = genomic DNA
                          organism = Homo sapiens
SEQUENCE: 331
cagttacagg gagcaccacc agg                                         23

SEQ ID NO: 332            moltype = DNA  length = 23
FEATURE                   Location/Qualifiers
source                    1..23
                          mol_type = genomic DNA
                          organism = Homo sapiens
SEQUENCE: 332
ctggtctggc ttcagttaca ggg                                         23

SEQ ID NO: 333            moltype = DNA  length = 23
FEATURE                   Location/Qualifiers
source                    1..23
                          mol_type = genomic DNA
                          organism = Homo sapiens
SEQUENCE: 333
cctggtctgg cttcagttac agg                                         23

SEQ ID NO: 334            moltype = DNA  length = 23
FEATURE                   Location/Qualifiers
source                    1..23
                          mol_type = genomic DNA
                          organism = Homo sapiens
SEQUENCE: 334
cctggtctgg cttcagttac agg                                         23

SEQ ID NO: 335            moltype = DNA  length = 23
FEATURE                   Location/Qualifiers
source                    1..23
                          mol_type = genomic DNA
                          organism = Homo sapiens
SEQUENCE: 335
tctgcagaat tcactgggag ggg                                         23

SEQ ID NO: 336            moltype = DNA  length = 23
FEATURE                   Location/Qualifiers
source                    1..23
                          mol_type = genomic DNA
                          organism = Homo sapiens
SEQUENCE: 336
ctctgcagaa ttcactggga ggg                                         23

SEQ ID NO: 337            moltype = DNA  length = 23
FEATURE                   Location/Qualifiers
source                    1..23
                          mol_type = genomic DNA
                          organism = Homo sapiens
SEQUENCE: 337
tctctgcaga attcactggg agg                                         23

SEQ ID NO: 338            moltype = DNA  length = 23
FEATURE                   Location/Qualifiers
source                    1..23
                          mol_type = genomic DNA
                          organism = Homo sapiens
SEQUENCE: 338
taatctctgc agaattcact ggg                                         23

SEQ ID NO: 339            moltype = DNA  length = 23
FEATURE                   Location/Qualifiers
source                    1..23
                          mol_type = genomic DNA
                          organism = Homo sapiens
SEQUENCE: 339
ttaatctctg cagaattcac tgg                                         23

SEQ ID NO: 340            moltype = DNA  length = 30
FEATURE                   Location/Qualifiers
source                    1..30
                          mol_type = genomic DNA
                          organism = Homo sapiens
SEQUENCE: 340
gcctggtctg gcttcagtta cagggagcac                                  30

SEQ ID NO: 341            moltype = DNA  length = 30
FEATURE                   Location/Qualifiers
```

```
source                  1..30
                        mol_type = genomic DNA
                        organism = Homo sapiens
SEQUENCE: 341
gtgtccaact ttgtttgctt tccagaatac                                      30

SEQ ID NO: 342          moltype = DNA   length = 30
FEATURE                 Location/Qualifiers
source                  1..30
                        mol_type = genomic DNA
                        organism = Homo sapiens
SEQUENCE: 342
gtattctgga aagcaaacaa agttggacac                                      30

SEQ ID NO: 343          moltype = DNA   length = 30
FEATURE                 Location/Qualifiers
source                  1..30
                        mol_type = genomic DNA
                        organism = Homo sapiens
SEQUENCE: 343
cagtcttggc atcacaggct tcaggcatac                                      30

SEQ ID NO: 344          moltype = DNA   length = 30
FEATURE                 Location/Qualifiers
source                  1..30
                        mol_type = genomic DNA
                        organism = Homo sapiens
SEQUENCE: 344
ggacctcttg gctattacac aggttggcac                                      30

SEQ ID NO: 345          moltype = DNA   length = 30
FEATURE                 Location/Qualifiers
source                  1..30
                        mol_type = genomic DNA
                        organism = Homo sapiens
SEQUENCE: 345
ggagccagtg ggacctcttg gctattacac                                      30

SEQ ID NO: 346          moltype = DNA   length = 30
FEATURE                 Location/Qualifiers
source                  1..30
                        mol_type = genomic DNA
                        organism = Homo sapiens
SEQUENCE: 346
cccagtgaat tctgcagaga ttaaatatac                                      30

SEQ ID NO: 347          moltype = DNA   length = 30
FEATURE                 Location/Qualifiers
source                  1..30
                        mol_type = genomic DNA
                        organism = Homo sapiens
SEQUENCE: 347
ggaaggatct gtgtctacag tgttacatac                                      30

SEQ ID NO: 348          moltype = DNA   length = 30
FEATURE                 Location/Qualifiers
source                  1..30
                        mol_type = genomic DNA
                        organism = Homo sapiens
SEQUENCE: 348
ttacctgcac gtatgtaaca ctgtagacac                                      30

SEQ ID NO: 349          moltype = DNA   length = 30
FEATURE                 Location/Qualifiers
source                  1..30
                        mol_type = genomic DNA
                        organism = Homo sapiens
SEQUENCE: 349
aaataaaact tacctgcacg tatgtaacac                                      30

SEQ ID NO: 350          moltype = DNA   length = 30
FEATURE                 Location/Qualifiers
source                  1..30
                        mol_type = genomic DNA
                        organism = Homo sapiens
SEQUENCE: 350
aagtttattt aaaataaaac ttacctgcac                                      30

SEQ ID NO: 351          moltype = DNA   length = 30
```

| | | |
|---|---|---|
| FEATURE | Location/Qualifiers | |
| source | 1..30<br>mol_type = genomic DNA<br>organism = Homo sapiens | |
| SEQUENCE: 351 | | |
| aaagcatagg cacacatcac ccagaggcac | | 30 |
| SEQ ID NO: 352 | moltype = DNA  length = 30 | |
| FEATURE | Location/Qualifiers | |
| source | 1..30<br>mol_type = genomic DNA<br>organism = Homo sapiens | |
| SEQUENCE: 352 | | |
| ttaggcaatt cttgtaaagc ataggcacac | | 30 |
| SEQ ID NO: 353 | moltype = DNA  length = 30 | |
| FEATURE | Location/Qualifiers | |
| source | 1..30<br>mol_type = genomic DNA<br>organism = Homo sapiens | |
| SEQUENCE: 353 | | |
| aattaggcaa ttcttgtaaa gcataggcac | | 30 |
| SEQ ID NO: 354 | moltype = DNA  length = 30 | |
| FEATURE | Location/Qualifiers | |
| source | 1..30<br>mol_type = genomic DNA<br>organism = Homo sapiens | |
| SEQUENCE: 354 | | |
| aatctccagt caattccaac acaaatgcac | | 30 |
| SEQ ID NO: 355 | moltype = DNA  length = 30 | |
| FEATURE | Location/Qualifiers | |
| source | 1..30<br>mol_type = genomic DNA<br>organism = Homo sapiens | |
| SEQUENCE: 355 | | |
| gccctctgaa tctccagtca attccaacac | | 30 |
| SEQ ID NO: 356 | moltype = DNA  length = 30 | |
| FEATURE | Location/Qualifiers | |
| source | 1..30<br>mol_type = genomic DNA<br>organism = Homo sapiens | |
| SEQUENCE: 356 | | |
| tatatccttg gttaaaaggt ggatatatac | | 30 |
| SEQ ID NO: 357 | moltype = DNA  length = 30 | |
| FEATURE | Location/Qualifiers | |
| source | 1..30<br>mol_type = genomic DNA<br>organism = Mus musculus | |
| SEQUENCE: 357 | | |
| ctcttgggat cactctatcc tggaagatac | | 30 |
| SEQ ID NO: 358 | moltype = DNA  length = 30 | |
| FEATURE | Location/Qualifiers | |
| source | 1..30<br>mol_type = genomic DNA<br>organism = Mus musculus | |
| SEQUENCE: 358 | | |
| cttgggatca ctctatcctg gaagatacac | | 30 |
| SEQ ID NO: 359 | moltype = DNA  length = 30 | |
| FEATURE | Location/Qualifiers | |
| source | 1..30<br>mol_type = genomic DNA<br>organism = Mus musculus | |
| SEQUENCE: 359 | | |
| tctatcctgg aagatacaca agctggacac | | 30 |
| SEQ ID NO: 360 | moltype = DNA  length = 30 | |
| FEATURE | Location/Qualifiers | |
| source | 1..30<br>mol_type = genomic DNA<br>organism = Mus musculus | |
| SEQUENCE: 360 | | |
| gagacatcca agtggaggaa ggggttacac | | 30 |

```
SEQ ID NO: 361          moltype = DNA  length = 30
FEATURE                 Location/Qualifiers
source                  1..30
                        mol_type = genomic DNA
                        organism = Mus musculus
SEQUENCE: 361
ctctataaag cacaccctac ccagagatac                                          30

SEQ ID NO: 362          moltype = DNA  length = 30
FEATURE                 Location/Qualifiers
source                  1..30
                        mol_type = genomic DNA
                        organism = Mus musculus
SEQUENCE: 362
acaaaaactg agccactcta taaagcacac                                          30

SEQ ID NO: 363          moltype = DNA  length = 30
FEATURE                 Location/Qualifiers
source                  1..30
                        mol_type = genomic DNA
                        organism = Mus musculus
SEQUENCE: 363
ggacaaaaac tgagccactc tataaagcac                                          30

SEQ ID NO: 364          moltype = DNA  length = 20
FEATURE                 Location/Qualifiers
misc_feature            1..20
                        note = Primer
source                  1..20
                        mol_type = other DNA
                        organism = synthetic construct
SEQUENCE: 364
cttagtctgt cggctgcggg                                                     20

SEQ ID NO: 365          moltype = DNA  length = 20
FEATURE                 Location/Qualifiers
misc_feature            1..20
                        note = Primer
source                  1..20
                        mol_type = other DNA
                        organism = synthetic construct
SEQUENCE: 365
ggccaaacag cgtaacccct                                                     20

SEQ ID NO: 366          moltype = DNA  length = 21
FEATURE                 Location/Qualifiers
misc_feature            1..21
                        note = Primer
source                  1..21
                        mol_type = other DNA
                        organism = synthetic construct
SEQUENCE: 366
cgttaaaggg gaacgccagg a                                                   21

SEQ ID NO: 367          moltype = DNA  length = 20
FEATURE                 Location/Qualifiers
misc_feature            1..20
                        note = Primer
source                  1..20
                        mol_type = other DNA
                        organism = synthetic construct
SEQUENCE: 367
cagggtggcc tcaaacacaa                                                     20

SEQ ID NO: 368          moltype = DNA  length = 22
FEATURE                 Location/Qualifiers
misc_feature            1..22
                        note = Primer
source                  1..22
                        mol_type = other DNA
                        organism = synthetic construct
SEQUENCE: 368
cggacaggga aatctatggt gc                                                  22

SEQ ID NO: 369          moltype = DNA  length = 22
FEATURE                 Location/Qualifiers
misc_feature            1..22
                        note = Primer
source                  1..22
```

```
                        mol_type = other DNA
                        organism = synthetic construct
SEQUENCE: 369
gcgccaggta aaagagatgt ca                                             22

SEQ ID NO: 370          moltype = DNA   length = 22
FEATURE                 Location/Qualifiers
misc_feature            1..22
                        note = Primer
source                  1..22
                        mol_type = other DNA
                        organism = synthetic construct
SEQUENCE: 370
agctccacca gagaacctct ca                                             22

SEQ ID NO: 371          moltype = DNA   length = 23
FEATURE                 Location/Qualifiers
misc_feature            1..23
                        note = Primer
source                  1..23
                        mol_type = other DNA
                        organism = synthetic construct
SEQUENCE: 371
tgaggagtag cagtgttgga cgg                                            23

SEQ ID NO: 372          moltype = DNA   length = 24
FEATURE                 Location/Qualifiers
misc_feature            1..24
                        note = Primer
source                  1..24
                        mol_type = other DNA
                        organism = synthetic construct
SEQUENCE: 372
tgacccgcag cacagctgtc tttg                                           24

SEQ ID NO: 373          moltype = DNA   length = 23
FEATURE                 Location/Qualifiers
misc_feature            1..23
                        note = Primer
source                  1..23
                        mol_type = other DNA
                        organism = synthetic construct
SEQUENCE: 373
tgaggagtag cagtgttgga cgg                                            23

SEQ ID NO: 374          moltype =     length =
SEQUENCE: 374
000

SEQ ID NO: 375          moltype =     length =
SEQUENCE: 375
000

SEQ ID NO: 376          moltype =     length =
SEQUENCE: 376
000

SEQ ID NO: 377          moltype =     length =
SEQUENCE: 377
000

SEQ ID NO: 378          moltype =     length =
SEQUENCE: 378
000

SEQ ID NO: 379          moltype =     length =
SEQUENCE: 379
000

SEQ ID NO: 380          moltype =     length =
SEQUENCE: 380
000

SEQ ID NO: 381          moltype =     length =
SEQUENCE: 381
000

SEQ ID NO: 382          moltype =     length =
SEQUENCE: 382
```

000

SEQ ID NO: 383        moltype =     length =
SEQUENCE: 383
000

SEQ ID NO: 384        moltype = RNA   length = 15
FEATURE               Location/Qualifiers
misc_feature          1..15
                      note = Guide sequence
source                1..15
                      mol_type = other RNA
                      organism = synthetic construct
SEQUENCE: 384
tatatatata tataa                                                        15

SEQ ID NO: 385        moltype =     length =
SEQUENCE: 385
000

SEQ ID NO: 386        moltype =     length =
SEQUENCE: 386
000

SEQ ID NO: 387        moltype =     length =
SEQUENCE: 387
000

SEQ ID NO: 388        moltype =     length =
SEQUENCE: 388
000

SEQ ID NO: 389        moltype =     length =
SEQUENCE: 389
000

SEQ ID NO: 390        moltype =     length =
SEQUENCE: 390
000

SEQ ID NO: 391        moltype =     length =
SEQUENCE: 391
000

SEQ ID NO: 392        moltype =     length =
SEQUENCE: 392
000

SEQ ID NO: 393        moltype =     length =
SEQUENCE: 393
000

SEQ ID NO: 394        moltype =     length =
SEQUENCE: 394
000

SEQ ID NO: 395        moltype =     length =
SEQUENCE: 395
000

SEQ ID NO: 396        moltype =     length =
SEQUENCE: 396
000

SEQ ID NO: 397        moltype =     length =
SEQUENCE: 397
000

SEQ ID NO: 398        moltype =     length =
SEQUENCE: 398
000

SEQ ID NO: 399        moltype =     length =
SEQUENCE: 399
000

SEQ ID NO: 400        moltype =     length =
SEQUENCE: 400
000

```
SEQ ID NO: 401           moltype =     length =
SEQUENCE: 401
000

SEQ ID NO: 402           moltype =     length =
SEQUENCE: 402
000

SEQ ID NO: 403           moltype =     length =
SEQUENCE: 403
000

SEQ ID NO: 404           moltype =     length =
SEQUENCE: 404
000

SEQ ID NO: 405           moltype =     length =
SEQUENCE: 405
000

SEQ ID NO: 406           moltype =     length =
SEQUENCE: 406
000

SEQ ID NO: 407           moltype =     length =
SEQUENCE: 407
000

SEQ ID NO: 408           moltype =     length =
SEQUENCE: 408
000

SEQ ID NO: 409           moltype = RNA  length = 15
FEATURE                  Location/Qualifiers
misc_feature             1..15
                         note = Guide sequence
source                   1..15
                         mol_type = other RNA
                         organism = synthetic construct
SEQUENCE: 409
tatatataaa aaaaa                                                           15

SEQ ID NO: 410           moltype = RNA  length = 18
FEATURE                  Location/Qualifiers
misc_feature             1..18
                         note = Guide sequence
source                   1..18
                         mol_type = other RNA
                         organism = synthetic construct
SEQUENCE: 410
cataaataaa aaaaatta                                                        18

SEQ ID NO: 411           moltype =     length =
SEQUENCE: 411
000

SEQ ID NO: 412           moltype =     length =
SEQUENCE: 412
000

SEQ ID NO: 413           moltype =     length =
SEQUENCE: 413
000

SEQ ID NO: 414           moltype =     length =
SEQUENCE: 414
000

SEQ ID NO: 415           moltype =     length =
SEQUENCE: 415
000

SEQ ID NO: 416           moltype = RNA  length = 15
FEATURE                  Location/Qualifiers
misc_feature             1..15
                         note = Guide sequence
source                   1..15
                         mol_type = other RNA
```

-continued

| | organism = synthetic construct | |
|---|---|---|
| SEQUENCE: 416 | | |
| ttatatatat atata | | 15 |

SEQ ID NO: 417　　　moltype =　length =
SEQUENCE: 417
000

SEQ ID NO: 418　　　moltype =　length =
SEQUENCE: 418
000

SEQ ID NO: 419　　　moltype =　length =
SEQUENCE: 419
000

SEQ ID NO: 420　　　moltype =　length =
SEQUENCE: 420
000

SEQ ID NO: 421　　　moltype =　length =
SEQUENCE: 421
000

SEQ ID NO: 422　　　moltype =　length =
SEQUENCE: 422
000

SEQ ID NO: 423　　　moltype =　length =
SEQUENCE: 423
000

SEQ ID NO: 424　　　moltype =　length =
SEQUENCE: 424
000

SEQ ID NO: 425　　　moltype =　length =
SEQUENCE: 425
000

SEQ ID NO: 426　　　moltype =　length =
SEQUENCE: 426
000

SEQ ID NO: 427　　　moltype =　length =
SEQUENCE: 427
000

SEQ ID NO: 428　　　moltype =　length =
SEQUENCE: 428
000

SEQ ID NO: 429　　　moltype =　length =
SEQUENCE: 429
000

SEQ ID NO: 430　　　moltype =　length =
SEQUENCE: 430
000

SEQ ID NO: 431　　　moltype =　length =
SEQUENCE: 431
000

SEQ ID NO: 432　　　moltype =　length =
SEQUENCE: 432
000

SEQ ID NO: 433　　　moltype =　length =
SEQUENCE: 433
000

SEQ ID NO: 434　　　moltype =　length =
SEQUENCE: 434
000

SEQ ID NO: 435　　　moltype =　length =
SEQUENCE: 435
000

```
SEQ ID NO: 436            moltype =    length =
SEQUENCE: 436
000

SEQ ID NO: 437            moltype =    length =
SEQUENCE: 437
000

SEQ ID NO: 438            moltype = RNA   length = 15
FEATURE                   Location/Qualifiers
misc_feature              1..15
                          note = Guide sequence
source                    1..15
                          mol_type = other RNA
                          organism = synthetic construct
SEQUENCE: 438
tttttttttat atata                                                        15

SEQ ID NO: 439            moltype = RNA   length = 18
FEATURE                   Location/Qualifiers
misc_feature              1..18
                          note = Guide sequence
source                    1..18
                          mol_type = other RNA
                          organism = synthetic construct
SEQUENCE: 439
taattttttt tatttatg                                                      18

SEQ ID NO: 440            moltype = RNA   length = 20
FEATURE                   Location/Qualifiers
misc_feature              1..20
                          note = Guide Sequence
source                    1..20
                          mol_type = other RNA
                          organism = synthetic construct
SEQUENCE: 440
ggaccagccc ctgaataaac                                                    20

SEQ ID NO: 441            moltype = RNA   length = 20
FEATURE                   Location/Qualifiers
misc_feature              1..20
                          note = Guide Sequence
source                    1..20
                          mol_type = other RNA
                          organism = synthetic construct
SEQUENCE: 441
ggcgtctttc cagtttattc                                                    20

SEQ ID NO: 442            moltype = RNA   length = 20
FEATURE                   Location/Qualifiers
misc_feature              1..20
                          note = Guide Sequence
source                    1..20
                          mol_type = other RNA
                          organism = synthetic construct
SEQUENCE: 442
gcgtctttcc agtttattca                                                    20

SEQ ID NO: 443            moltype = RNA   length = 20
FEATURE                   Location/Qualifiers
misc_feature              1..20
                          note = Guide Sequence
source                    1..20
                          mol_type = other RNA
                          organism = synthetic construct
SEQUENCE: 443
cgtctttcca gtttattcag                                                    20

SEQ ID NO: 444            moltype = RNA   length = 20
FEATURE                   Location/Qualifiers
misc_feature              1..20
                          note = Guide Sequence
source                    1..20
                          mol_type = other RNA
                          organism = synthetic construct
SEQUENCE: 444
ttcaggggct ggtccaatgc                                                    20
```

| | | |
|---|---|---|
| SEQ ID NO: 445　　　　　　　　　　 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 445 | | |
| tcagggctg gtccaatgct | | 20 |
| | | |
| SEQ ID NO: 446 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 446 | | |
| accatgacat atcccagcat | | 20 |
| | | |
| SEQ ID NO: 447 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 447 | | |
| tttccagttt attcagggc | | 20 |
| | | |
| SEQ ID NO: 448 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 448 | | |
| cagttacagg gagcaccacc | | 20 |
| | | |
| SEQ ID NO: 449 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 449 | | |
| ctggtctggc ttcagttaca | | 20 |
| | | |
| SEQ ID NO: 450 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 450 | | |
| cctggtctgg cttcagttac | | 20 |
| | | |
| SEQ ID NO: 451 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 451 | | |
| aactggaaag acgcctggtc | | 20 |
| | | |
| SEQ ID NO: 452 | moltype = RNA　　length = 20 | |
| FEATURE | Location/Qualifiers | |
| misc_feature | 1..20 | |
| | note = Guide Sequence | |
| source | 1..20 | |
| | mol_type = other RNA | |
| | organism = synthetic construct | |
| SEQUENCE: 452 | | |
| gaataaactg gaaagacgcc | | 20 |

```
SEQ ID NO: 453          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 453
tccaatgctg ggatatgtca                                                     20

SEQ ID NO: 454          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 454
aatgctggga tatgtcatgg                                                     20

SEQ ID NO: 455          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 455
atagaggctg agaacctctc                                                     20

SEQ ID NO: 456          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 456
ttgggcatgt ttgagctggt                                                     20

SEQ ID NO: 457          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 457
tttgggcatg tttgagctgg                                                     20

SEQ ID NO: 458          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 458
gagctggtgg gcgaagcata                                                     20

SEQ ID NO: 459          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 459
agctggtggg cgaagcatat                                                     20

SEQ ID NO: 460          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 460
```
tgggcgaagc atatgggcaa                                                    20

SEQ ID NO: 461         moltype = RNA   length = 20
FEATURE                Location/Qualifiers
misc_feature           1..20
                       note = Guide Sequence
source                 1..20
                       mol_type = other RNA
                       organism = synthetic construct
SEQUENCE: 461
ggcctccatc ctaaacaatg                                                    20

SEQ ID NO: 462         moltype = RNA   length = 20
FEATURE                Location/Qualifiers
misc_feature           1..20
                       note = Guide Sequence
source                 1..20
                       mol_type = other RNA
                       organism = synthetic construct
SEQUENCE: 462
gggttgggag gtttgggcgt                                                    20

SEQ ID NO: 463         moltype = RNA   length = 20
FEATURE                Location/Qualifiers
misc_feature           1..20
                       note = Guide Sequence
source                 1..20
                       mol_type = other RNA
                       organism = synthetic construct
SEQUENCE: 463
aggtttgggc gtgggagtcc                                                    20

SEQ ID NO: 464         moltype = RNA   length = 19
FEATURE                Location/Qualifiers
misc_feature           1..19
                       note = Guide Sequence
source                 1..19
                       mol_type = other RNA
                       organism = synthetic construct
SEQUENCE: 464
ttcagagact cagctattt                                                     19

SEQ ID NO: 465         moltype = RNA   length = 19
FEATURE                Location/Qualifiers
misc_feature           1..19
                       note = Guide Sequence
source                 1..19
                       mol_type = other RNA
                       organism = synthetic construct
SEQUENCE: 465
ggccacattg tttaggatg                                                     19

SEQ ID NO: 466         moltype = RNA   length = 19
FEATURE                Location/Qualifiers
misc_feature           1..19
                       note = Guide Sequence
source                 1..19
                       mol_type = other RNA
                       organism = synthetic construct
SEQUENCE: 466
ggctttgggc atgtttgag                                                     19

SEQ ID NO: 467         moltype = RNA   length = 19
FEATURE                Location/Qualifiers
misc_feature           1..19
                       note = Guide Sequence
source                 1..19
                       mol_type = other RNA
                       organism = synthetic construct
SEQUENCE: 467
aacatgccca aagcccagc                                                     19

SEQ ID NO: 468         moltype = RNA   length = 19
FEATURE                Location/Qualifiers
misc_feature           1..19
                       note = Guide Sequence
source                 1..19
                       mol_type = other RNA
                       organism = synthetic construct

```
SEQUENCE: 468
acatgcccaa agcccagcg                                                    19

SEQ ID NO: 469           moltype = RNA  length = 20
FEATURE                  Location/Qualifiers
misc_feature             1..20
                         note = Guide Sequence
source                   1..20
                         mol_type = other RNA
                         organism = synthetic construct
SEQUENCE: 469
cgatgatact cagcaacagg                                                   20

SEQ ID NO: 470           moltype = RNA  length = 20
FEATURE                  Location/Qualifiers
misc_feature             1..20
                         note = Guide Sequence
source                   1..20
                         mol_type = other RNA
                         organism = synthetic construct
SEQUENCE: 470
atggacacgc aactgatctc                                                   20

SEQ ID NO: 471           moltype = RNA  length = 22
FEATURE                  Location/Qualifiers
misc_feature             1..22
                         note = Guide Sequence
source                   1..22
                         mol_type = other RNA
                         organism = synthetic construct
SEQUENCE: 471
gccctctgaa tctccagtca at                                                22

SEQ ID NO: 472           moltype = RNA  length = 22
FEATURE                  Location/Qualifiers
misc_feature             1..22
                         note = Guide Sequence
source                   1..22
                         mol_type = other RNA
                         organism = synthetic construct
SEQUENCE: 472
aatctccagt caattccaac ac                                                22

SEQ ID NO: 473           moltype = RNA  length = 22
FEATURE                  Location/Qualifiers
misc_feature             1..22
                         note = Guide Sequence
source                   1..22
                         mol_type = other RNA
                         organism = synthetic construct
SEQUENCE: 473
aattaggcaa ttcttgtaaa gc                                                22

SEQ ID NO: 474           moltype = RNA  length = 22
FEATURE                  Location/Qualifiers
misc_feature             1..22
                         note = Guide Sequence
source                   1..22
                         mol_type = other RNA
                         organism = synthetic construct
SEQUENCE: 474
ttaggcaatt cttgtaaagc at                                                22

SEQ ID NO: 475           moltype = RNA  length = 22
FEATURE                  Location/Qualifiers
misc_feature             1..22
                         note = Guide Sequence
source                   1..22
                         mol_type = other RNA
                         organism = synthetic construct
SEQUENCE: 475
aaagcatagg cacacatcac cc                                                22

SEQ ID NO: 476           moltype = RNA  length = 22
FEATURE                  Location/Qualifiers
misc_feature             1..22
                         note = Guide Sequence
source                   1..22
                         mol_type = other RNA
```

```
                        organism = synthetic construct
SEQUENCE: 476
gcctggtctg gcttcagtta ca                                                  22

SEQ ID NO: 477          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 477
gtgtccaact ttgtttgctt tc                                                  22

SEQ ID NO: 478          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 478
gtattctgga aagcaaacaa ag                                                  22

SEQ ID NO: 479          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 479
cagtcttggc atcacaggct tc                                                  22

SEQ ID NO: 480          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 480
ggacctcttg gctattacac ag                                                  22

SEQ ID NO: 481          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 481
ggagccagtg ggacctcttg gc                                                  22

SEQ ID NO: 482          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 482
taaatcacag aggcaaagag tt                                                  22

SEQ ID NO: 483          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 483
ttgcatagtg ctagactgtt tt                                                  22

SEQ ID NO: 484          moltype = RNA   length = 22
FEATURE                 Location/Qualifiers
misc_feature            1..22
                        note = Guide Sequence
source                  1..22
```

```
                        mol_type = other RNA
                        organism = synthetic construct
SEQUENCE: 484
gggtcatgtg ttttgaaaac ag                                           22

SEQ ID NO: 485          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 485
cccaaacctc ccaacccaca ac                                           22

SEQ ID NO: 486          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 486
actcagctat ttctggaatg ac                                           22

SEQ ID NO: 487          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 487
tcatcgcctt tgtgagctcc at                                           22

SEQ ID NO: 488          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 488
cagacacagg ctttgctcta gc                                           22

SEQ ID NO: 489          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 489
caaagcctgt gtctggccac ta                                           22

SEQ ID NO: 490          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 490
agcagtttgt gcccactagt gg                                           22

SEQ ID NO: 491          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 491
atgtcaaggt attccagcta ac                                           22

SEQ ID NO: 492          moltype = RNA   length = 22
FEATURE                 Location/Qualifiers
misc_feature            1..22
                        note = Guide Sequence
```

```
source                  1..22
                        mol_type = other RNA
                        organism = synthetic construct
SEQUENCE: 492
gaataactgt atcaaagtta gc                                               22

SEQ ID NO: 493          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 493
ttcctaatta agaggctttg tg                                               22

SEQ ID NO: 494          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 494
gagctagttt gtcagggtct ag                                               22

SEQ ID NO: 495          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 495
gactttggga gctaatatct                                                  20

SEQ ID NO: 496          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 496
cccttcatc ttcccattcg                                                   20

SEQ ID NO: 497          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 497
cctttcatct tcccattcgt                                                  20

SEQ ID NO: 498          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 498
cccacgaatg ggaagatgaa                                                  20

SEQ ID NO: 499          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 499
catcttccca ttcgtgggca                                                  20

SEQ ID NO: 500          moltype = RNA   length = 20
FEATURE                 Location/Qualifiers
misc_feature            1..20
```

```
                        note = Guide Sequence
source                  1..20
                        mol_type = other RNA
                        organism = synthetic construct
SEQUENCE: 500
tctccacctt gcccacgaat                                                    20

SEQ ID NO: 501          moltype = RNA  length = 20
FEATURE                 Location/Qualifiers
misc_feature            1..20
                        note = Guide Sequence
source                  1..20
                        mol_type = other RNA
                        organism = synthetic construct
SEQUENCE: 501
gtctccacct tgcccacgaa                                                    20

SEQ ID NO: 502          moltype = RNA  length = 20
FEATURE                 Location/Qualifiers
misc_feature            1..20
                        note = Guide Sequence
source                  1..20
                        mol_type = other RNA
                        organism = synthetic construct
SEQUENCE: 502
cccaatgctt gcacataaat                                                    20

SEQ ID NO: 503          moltype = RNA  length = 20
FEATURE                 Location/Qualifiers
misc_feature            1..20
                        note = Guide Sequence
source                  1..20
                        mol_type = other RNA
                        organism = synthetic construct
SEQUENCE: 503
ccaatttatg tgcaagcatt                                                    20

SEQ ID NO: 504          moltype = RNA  length = 20
FEATURE                 Location/Qualifiers
misc_feature            1..20
                        note = Guide Sequence
source                  1..20
                        mol_type = other RNA
                        organism = synthetic construct
SEQUENCE: 504
tccaatttat gtgcaagcat                                                    20

SEQ ID NO: 505          moltype = RNA  length = 20
FEATURE                 Location/Qualifiers
misc_feature            1..20
                        note = Guide Sequence
source                  1..20
                        mol_type = other RNA
                        organism = synthetic construct
SEQUENCE: 505
tgtgcgcgtc tgaagaggag                                                    20

SEQ ID NO: 506          moltype = RNA  length = 20
FEATURE                 Location/Qualifiers
misc_feature            1..20
                        note = Guide Sequence
source                  1..20
                        mol_type = other RNA
                        organism = synthetic construct
SEQUENCE: 506
gtgcgcgtct gaagaggagt                                                    20

SEQ ID NO: 507          moltype = RNA  length = 20
FEATURE                 Location/Qualifiers
misc_feature            1..20
                        note = Guide Sequence
source                  1..20
                        mol_type = other RNA
                        organism = synthetic construct
SEQUENCE: 507
tgcgcgtctg aagaggagtg                                                    20

SEQ ID NO: 508          moltype = RNA  length = 20
FEATURE                 Location/Qualifiers
```

```
misc_feature               1..20
                           note = Guide Sequence
source                     1..20
                           mol_type = other RNA
                           organism = synthetic construct
SEQUENCE: 508
tagtccagat gctgttgccg                                                      20

SEQ ID NO: 509             moltype = RNA  length = 20
FEATURE                    Location/Qualifiers
misc_feature               1..20
                           note = Guide Sequence
source                     1..20
                           mol_type = other RNA
                           organism = synthetic construct
SEQUENCE: 509
attaccacgg caacagcatc                                                      20

SEQ ID NO: 510             moltype = RNA  length = 20
FEATURE                    Location/Qualifiers
misc_feature               1..20
                           note = Guide Sequence
source                     1..20
                           mol_type = other RNA
                           organism = synthetic construct
SEQUENCE: 510
gacacgattt agtattacca                                                      20

SEQ ID NO: 511             moltype = RNA  length = 20
FEATURE                    Location/Qualifiers
misc_feature               1..20
                           note = Guide Sequence
source                     1..20
                           mol_type = other RNA
                           organism = synthetic construct
SEQUENCE: 511
ctaaatcgtg tccaaagagg                                                      20

SEQ ID NO: 512             moltype = RNA  length = 20
FEATURE                    Location/Qualifiers
misc_feature               1..20
                           note = Guide Sequence
source                     1..20
                           mol_type = other RNA
                           organism = synthetic construct
SEQUENCE: 512
aggaatctca gcctcctctt                                                      20

SEQ ID NO: 513             moltype = RNA  length = 20
FEATURE                    Location/Qualifiers
misc_feature               1..20
                           note = Guide Sequence
source                     1..20
                           mol_type = other RNA
                           organism = synthetic construct
SEQUENCE: 513
gtggacaagg ttaactaaaa                                                      20

SEQ ID NO: 514             moltype = RNA  length = 20
FEATURE                    Location/Qualifiers
misc_feature               1..20
                           note = Guide Sequence
source                     1..20
                           mol_type = other RNA
                           organism = synthetic construct
SEQUENCE: 514
atagtcaaat catgtggaca                                                      20

SEQ ID NO: 515             moltype = RNA  length = 20
FEATURE                    Location/Qualifiers
misc_feature               1..20
                           note = Guide Sequence
source                     1..20
                           mol_type = other RNA
                           organism = synthetic construct
SEQUENCE: 515
tgctggatag tcaaatcatg                                                      20

SEQ ID NO: 516             moltype = RNA  length = 20
```

-continued

```
FEATURE              Location/Qualifiers
misc_feature         1..20
                     note = Guide Sequence
source               1..20
                     mol_type = other RNA
                     organism = synthetic construct
SEQUENCE: 516
acatgatttg actatccagc                                               20

SEQ ID NO: 517       moltype = RNA   length = 20
FEATURE              Location/Qualifiers
misc_feature         1..20
                     note = Guide Sequence
source               1..20
                     mol_type = other RNA
                     organism = synthetic construct
SEQUENCE: 517
atttgactat ccagcaggct                                               20

SEQ ID NO: 518       moltype = RNA   length = 20
FEATURE              Location/Qualifiers
misc_feature         1..20
                     note = Guide Sequence
source               1..20
                     mol_type = other RNA
                     organism = synthetic construct
SEQUENCE: 518
gtcccgaagt ctctggggcc                                               20

SEQ ID NO: 519       moltype = RNA   length = 20
FEATURE              Location/Qualifiers
misc_feature         1..20
                     note = Guide Sequence
source               1..20
                     mol_type = other RNA
                     organism = synthetic construct
SEQUENCE: 519
aaaacagtcc cgaagtctct                                               20

SEQ ID NO: 520       moltype = RNA   length = 20
FEATURE              Location/Qualifiers
misc_feature         1..20
                     note = Guide Sequence
source               1..20
                     mol_type = other RNA
                     organism = synthetic construct
SEQUENCE: 520
gaaaacagtc ccgaagtctc                                               20

SEQ ID NO: 521       moltype = RNA   length = 20
FEATURE              Location/Qualifiers
misc_feature         1..20
                     note = Guide Sequence
source               1..20
                     mol_type = other RNA
                     organism = synthetic construct
SEQUENCE: 521
tatataccac attcaagtgc                                               20

SEQ ID NO: 522       moltype = RNA   length = 20
FEATURE              Location/Qualifiers
misc_feature         1..20
                     note = Guide Sequence
source               1..20
                     mol_type = other RNA
                     organism = synthetic construct
SEQUENCE: 522
tggatataac gaagttgtgt                                               20

SEQ ID NO: 523       moltype = RNA   length = 20
FEATURE              Location/Qualifiers
misc_feature         1..20
                     note = Guide Sequence
source               1..20
                     mol_type = other RNA
                     organism = synthetic construct
SEQUENCE: 523
atggatataa cgaagttgtg                                               20
```

| | | |
|---|---|---|
| SEQ ID NO: 524<br>FEATURE<br>misc_feature<br>source<br><br>SEQUENCE: 524<br>atatgtttgt tcaccccaac | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |
| SEQ ID NO: 525<br>FEATURE<br>misc_feature<br>source<br><br>SEQUENCE: 525<br>gaaaacttga aatcctgttg | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |
| SEQ ID NO: 526<br>FEATURE<br>misc_feature<br>source<br><br>SEQUENCE: 526<br>tagacattag gagaaacaga | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |
| SEQ ID NO: 527<br>FEATURE<br>misc_feature<br>source<br><br>SEQUENCE: 527<br>ctagcagtga catagacatt | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |
| SEQ ID NO: 528<br>FEATURE<br>misc_feature<br>source<br><br>SEQUENCE: 528<br>agccacctga ctttgatgaa | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |
| SEQ ID NO: 529<br>FEATURE<br>misc_feature<br>source<br><br>SEQUENCE: 529<br>tgagaaatgt tattactata | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |
| SEQ ID NO: 530<br>FEATURE<br>misc_feature<br>source<br><br>SEQUENCE: 530<br>agactgcgag atgagagagt | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |
| SEQ ID NO: 531<br>FEATURE<br>misc_feature<br>source<br><br>SEQUENCE: 531<br>ctcgcagtct gtacttagac | moltype = RNA   length = 20<br>Location/Qualifiers<br>1..20<br>note = Guide Sequence<br>1..20<br>mol_type = other RNA<br>organism = synthetic construct | <br><br><br><br><br><br>20 |

```
SEQ ID NO: 532          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 532
aatgtctctt gagagagcca                                                    20

SEQ ID NO: 533          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 533
atgggaagat gaaagggaag ta                                                 22

SEQ ID NO: 534          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 534
actttgattg ttaaaactta tc                                                 22

SEQ ID NO: 535          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 535
agtcctacct cagcttccca at                                                 22

SEQ ID NO: 536          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 536
caatgcttgc acataaattg ga                                                 22

SEQ ID NO: 537          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 537
acacagagag agacagaatg aa                                                 22

SEQ ID NO: 538          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 538
tcctcttcag acgcgcacac ac                                                 22

SEQ ID NO: 539          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 539
```

```
actcctcttc agacgcgcac ac                                                   22

SEQ ID NO: 540         moltype = RNA   length = 22
FEATURE                Location/Qualifiers
misc_feature           1..22
                       note = Guide Sequence
source                 1..22
                       mol_type = other RNA
                       organism = synthetic construct
SEQUENCE: 540
ccactcctct tcagacgcgc ac                                                   22

SEQ ID NO: 541         moltype = RNA   length = 22
FEATURE                Location/Qualifiers
misc_feature           1..22
                       note = Guide Sequence
source                 1..22
                       mol_type = other RNA
                       organism = synthetic construct
SEQUENCE: 541
ccccactcct cttcagacgc gc                                                   22

SEQ ID NO: 542         moltype = RNA   length = 22
FEATURE                Location/Qualifiers
misc_feature           1..22
                       note = Guide Sequence
source                 1..22
                       mol_type = other RNA
                       organism = synthetic construct
SEQUENCE: 542
ctccccactc ctcttcagac gc                                                   22

SEQ ID NO: 543         moltype = RNA   length = 22
FEATURE                Location/Qualifiers
misc_feature           1..22
                       note = Guide Sequence
source                 1..22
                       mol_type = other RNA
                       organism = synthetic construct
SEQUENCE: 543
tactccccac tcctcttcag ac                                                   22

SEQ ID NO: 544         moltype = RNA   length = 22
FEATURE                Location/Qualifiers
misc_feature           1..22
                       note = Guide Sequence
source                 1..22
                       mol_type = other RNA
                       organism = synthetic construct
SEQUENCE: 544
tatactcccc actcctcttc ag                                                   22

SEQ ID NO: 545         moltype = RNA   length = 22
FEATURE                Location/Qualifiers
misc_feature           1..22
                       note = Guide Sequence
source                 1..22
                       mol_type = other RNA
                       organism = synthetic construct
SEQUENCE: 545
acagcatctg gactatcttg tt                                                   22

SEQ ID NO: 546         moltype = RNA   length = 22
FEATURE                Location/Qualifiers
misc_feature           1..22
                       note = Guide Sequence
source                 1..22
                       mol_type = other RNA
                       organism = synthetic construct
SEQUENCE: 546
atagtccaga tgctgttgcc gt                                                   22

SEQ ID NO: 547         moltype = RNA   length = 22
FEATURE                Location/Qualifiers
misc_feature           1..22
                       note = Guide Sequence
source                 1..22
                       mol_type = other RNA
                       organism = synthetic construct
```

```
SEQUENCE: 547
aaaaggaatc tcagcctcct ct                                             22

SEQ ID NO: 548          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 548
tgtcactgct agtgtgctta at                                             22

SEQ ID NO: 549          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 549
atgtgaattc agtacaagaa tt                                             22

SEQ ID NO: 550          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 550
ttatgtgaat tcagtacaag aa                                             22

SEQ ID NO: 551          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 551
ctttcatttc tgtttatgtg aa                                             22

SEQ ID NO: 552          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 552
ttcacataaa cagaaatgaa ag                                             22

SEQ ID NO: 553          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 553
atgccaactc tctcatctcg ca                                             22

SEQ ID NO: 554          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 554
gagacattct cacatttcca gt                                             22

SEQ ID NO: 555          moltype = RNA   length = 20
FEATURE                 Location/Qualifiers
misc_feature            1..20
                        note = Guide Sequence
source                  1..20
                        mol_type = other RNA
```

```
                        organism = synthetic construct
SEQUENCE: 555
agttacaggg agcaccacca                                                         20

SEQ ID NO: 556          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 556
cagttacagg gagcaccacc                                                         20

SEQ ID NO: 557          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 557
ctggtctggc ttcagttaca                                                         20

SEQ ID NO: 558          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 558
cctggtctgg cttcagttac                                                         20

SEQ ID NO: 559          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 559
cctggtctgg cttcagttac                                                         20

SEQ ID NO: 560          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 560
tctgcagaat tcactgggag                                                         20

SEQ ID NO: 561          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 561
ctctgcagaa ttcactggga                                                         20

SEQ ID NO: 562          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 562
tctctgcaga attcactggg                                                         20

SEQ ID NO: 563          moltype = RNA   length = 20
FEATURE                 Location/Qualifiers
misc_feature            1..20
                        note = Guide Sequence
source                  1..20
```

```
                        mol_type = other RNA
                        organism = synthetic construct
SEQUENCE: 563
taatctctgc agaattcact                                                   20

SEQ ID NO: 564          moltype = RNA   length = 20
FEATURE                 Location/Qualifiers
misc_feature            1..20
                        note = Guide Sequence
source                  1..20
                        mol_type = other RNA
                        organism = synthetic construct
SEQUENCE: 564
ttaatctctg cagaattcac                                                   20

SEQ ID NO: 565          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 565
gcctggtctg gcttcagtta ca                                                22

SEQ ID NO: 566          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 566
gtgtccaact ttgtttgctt tc                                                22

SEQ ID NO: 567          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 567
gtattctgga aagcaaacaa ag                                                22

SEQ ID NO: 568          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 568
cagtcttggc atcacaggct tc                                                22

SEQ ID NO: 569          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 569
ggacctcttg gctattacac ag                                                22

SEQ ID NO: 570          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 570
ggagccagtg ggacctcttg gc                                                22

SEQ ID NO: 571          moltype = RNA   length = 22
FEATURE                 Location/Qualifiers
misc_feature            1..22
                        note = Guide Sequence
```

```
source                  1..22
                        mol_type = other RNA
                        organism = synthetic construct
SEQUENCE: 571
cccagtgaat tctgcagaga tt                                              22

SEQ ID NO: 572          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 572
ggaaggatct gtgtctacag tg                                              22

SEQ ID NO: 573          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 573
ttacctgcac gtatgtaaca ct                                              22

SEQ ID NO: 574          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 574
aaataaaact tacctgcacg ta                                              22

SEQ ID NO: 575          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 575
aagtttattt aaaataaaac tt                                              22

SEQ ID NO: 576          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 576
aaagcatagg cacacatcac cc                                              22

SEQ ID NO: 577          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 577
ttaggcaatt cttgtaaagc at                                              22

SEQ ID NO: 578          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 578
aattaggcaa ttcttgtaaa gc                                              22

SEQ ID NO: 579          moltype = RNA   length = 22
FEATURE                 Location/Qualifiers
misc_feature            1..22
```

```
                        note = Guide Sequence
source                  1..22
                        mol_type = other RNA
                        organism = synthetic construct
SEQUENCE: 579
aatctccagt caattccaac ac                                           22

SEQ ID NO: 580          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 580
gccctctgaa tctccagtca at                                           22

SEQ ID NO: 581          moltype = RNA   length = 22
FEATURE                 Location/Qualifiers
misc_feature            1..22
                        note = Guide Sequence
source                  1..22
                        mol_type = other RNA
                        organism = synthetic construct
SEQUENCE: 581
tatatccttg gttaaaaggt gg                                           22

SEQ ID NO: 582          moltype = DNA   length = 89
FEATURE                 Location/Qualifiers
source                  1..89
                        mol_type = genomic DNA
                        organism = Homo sapiens
SEQUENCE: 582
ggcctccatc ctaaacaatg tggcctttgc ccatatgctt cgcccaccag ctcaaacatg   60
cccaaagccc aaagcccagc gtgggtctt                                    89

SEQ ID NO: 583          moltype = DNA   length = 39
FEATURE                 Location/Qualifiers
misc_feature            1..39
                        note = Modified sequence by targeting target sequences
                         using Enh-Sp5 andEnh-Sp16
source                  1..39
                        mol_type = other DNA
                        organism = synthetic construct
SEQUENCE: 583
ggcctccatc ctaaacaatg tggcctttgc gtgggtctt                         39

SEQ ID NO: 584          moltype = DNA   length = 23
FEATURE                 Location/Qualifiers
source                  1..23
                        mol_type = genomic DNA
                        organism = Homo sapiens
SEQUENCE: 584
cctttgccca tatgcttcgc cca                                          23

SEQ ID NO: 585          moltype = DNA   length = 23
FEATURE                 Location/Qualifiers
source                  1..23
                        mol_type = genomic DNA
                        organism = Homo sapiens
SEQUENCE: 585
acatgcccaa agcccagcgt ggg                                          23

SEQ ID NO: 586          moltype = DNA   length = 89
FEATURE                 Location/Qualifiers
source                  1..89
                        mol_type = genomic DNA
                        organism = Homo sapiens
SEQUENCE: 586
ggtgctccct gtaactgaag ccagaccagg cgtctttcca gtttattcag gggctggtcc   60
aatgctggga tatgtcatgg tggcctgag                                    89

SEQ ID NO: 587          moltype = DNA   length = 41
FEATURE                 Location/Qualifiers
misc_feature            1..41
                        note = Modified sequence by targeting target sequences
                         using TATA-Sp12and TATA-Sp14
source                  1..41
                        mol_type = other DNA
```

```
                        organism = synthetic construct
SEQUENCE: 587
ggtgctccct gtaactgaag ccagactcat ggtggcctga g                            41

SEQ ID NO: 588          moltype = DNA   length = 23
FEATURE                 Location/Qualifiers
source                  1..23
                        mol_type = genomic DNA
                        organism = Homo sapiens
SEQUENCE: 588
ccagaccagg cgtctttcca gtt                                                23

SEQ ID NO: 589          moltype = DNA   length = 23
FEATURE                 Location/Qualifiers
source                  1..23
                        mol_type = genomic DNA
                        organism = Homo sapiens
SEQUENCE: 589
tccaatgctg ggatatgtca tgg                                                23

SEQ ID NO: 590          moltype = DNA   length = 120
FEATURE                 Location/Qualifiers
source                  1..120
                        mol_type = genomic DNA
                        organism = Homo sapiens
SEQUENCE: 590
cctggtggtg ctccctgtaa ctgaagccag accaggcgtc tttccagttt attcaggggc        60
tggtccaatg ctgggatatg tcatggtggc ctgagaggtt ctcagcctct attatttaaa       120

SEQ ID NO: 591          moltype = DNA   length = 120
FEATURE                 Location/Qualifiers
source                  1..120
                        mol_type = genomic DNA
                        organism = Homo sapiens
SEQUENCE: 591
tttaaataat agaggctgag aacctctcag gccaccatga catatcccag cattggacca        60
gcccctgaat aaactggaaa gacgcctggt ctggcttcag ttacagggag caccaccagg       120

SEQ ID NO: 592          moltype = DNA   length = 90
FEATURE                 Location/Qualifiers
source                  1..90
                        mol_type = genomic DNA
                        organism = Homo sapiens
SEQUENCE: 592
actgaagcca gaccaggcgt ctttccagtt tattcagggg ctggtccaat gctgggatat        60
gtcatggtgg cctgagaggt tctcagcctc                                         90

SEQ ID NO: 593          moltype = DNA   length = 89
FEATURE                 Location/Qualifiers
misc_feature            1..89
                        note = Modified sequence by PMP22-TATA RNP
source                  1..89
                        mol_type = other DNA
                        organism = synthetic construct
SEQUENCE: 593
actgaagcca gaccaggcgt ctttccagtt attcaggggc tggtccaatg ctgggatatg        60
tcatggcggc ctgagaggtt ctcagcctc                                          89

SEQ ID NO: 594          moltype = DNA   length = 88
FEATURE                 Location/Qualifiers
misc_feature            1..88
                        note = Modified sequence by PMP22-TATA RNP
source                  1..88
                        mol_type = other DNA
                        organism = synthetic construct
SEQUENCE: 594
actgaagcca gaccaggcgt ctttccagtt ttcaggggct ggtccaatgc tgggatatgt        60
catggtggcc tgagaggttc tcagcctc                                           88

SEQ ID NO: 595          moltype = DNA   length = 91
FEATURE                 Location/Qualifiers
misc_feature            1..91
                        note = Modified sequence by PMP22-TATA RNP
source                  1..91
                        mol_type = other DNA
                        organism = synthetic construct
SEQUENCE: 595
actgaagcca gaccaggcgt ctttccagtt ttattcaggg gctggtccaa tgctgggata        60
tgtcatggcg gcctgagagg ttctcagcct c                                       91
```

```
SEQ ID NO: 596           moltype = DNA   length = 87
FEATURE                  Location/Qualifiers
misc_feature             1..87
                         note = Modified sequence by PMP22-TATA RNP
source                   1..87
                         mol_type = other DNA
                         organism = synthetic construct
SEQUENCE: 596
actgaagcca gaccaggcgt ctttccagtt tcagggctg gtccaatgct gggatatgtc    60
atggcggcct gagaggttct cagcctc                                       87

SEQ ID NO: 597           moltype = DNA   length = 86
FEATURE                  Location/Qualifiers
misc_feature             1..86
                         note = Modified sequence by PMP22-TATA RNP
source                   1..86
                         mol_type = other DNA
                         organism = synthetic construct
SEQUENCE: 597
actgaagcca gaccaggcgt ctttccagtt cagggctgg tccaatgctg ggatatgtca    60
tggcggcctg agaggttctc agcctc                                        86

SEQ ID NO: 598           moltype = DNA   length = 23
FEATURE                  Location/Qualifiers
source                   1..23
                         mol_type = genomic DNA
                         organism = Homo sapiens
SEQUENCE: 598
ggaccagccc ctgaataaac tgg                                           23

SEQ ID NO: 599           moltype = DNA   length = 23
FEATURE                  Location/Qualifiers
source                   1..23
                         mol_type = genomic DNA
                         organism = Homo sapiens
SEQUENCE: 599
ggaccagcca cagaataaac aag                                           23

SEQ ID NO: 600           moltype = DNA   length = 23
FEATURE                  Location/Qualifiers
source                   1..23
                         mol_type = genomic DNA
                         organism = Homo sapiens
SEQUENCE: 600
tgaccagtcc atgaataaac cag                                           23

SEQ ID NO: 601           moltype = DNA   length = 23
FEATURE                  Location/Qualifiers
source                   1..23
                         mol_type = genomic DNA
                         organism = Homo sapiens
SEQUENCE: 601
ggaccagaca ctgaatatac cag                                           23

SEQ ID NO: 602           moltype = DNA   length = 23
FEATURE                  Location/Qualifiers
source                   1..23
                         mol_type = genomic DNA
                         organism = Homo sapiens
SEQUENCE: 602
ggaccagcca cagaataaat tgg                                           23

SEQ ID NO: 603           moltype = DNA   length = 23
FEATURE                  Location/Qualifiers
source                   1..23
                         mol_type = genomic DNA
                         organism = Homo sapiens
SEQUENCE: 603
ggatcagccc cagaataaat tag                                           23

SEQ ID NO: 604           moltype = DNA   length = 23
FEATURE                  Location/Qualifiers
source                   1..23
                         mol_type = genomic DNA
                         organism = Homo sapiens
SEQUENCE: 604
ggagcatccc cagaataaac cag                                           23
```

```
SEQ ID NO: 605          moltype = DNA   length = 23
FEATURE                 Location/Qualifiers
source                  1..23
                        mol_type = genomic DNA
                        organism = Homo sapiens
SEQUENCE: 605
ggatcagcgt ctgaataaac aag                                               23

SEQ ID NO: 606          moltype = DNA   length = 23
FEATURE                 Location/Qualifiers
source                  1..23
                        mol_type = genomic DNA
                        organism = Homo sapiens
SEQUENCE: 606
agaccagccc cagaacaaac aag                                               23

SEQ ID NO: 607          moltype = DNA   length = 23
FEATURE                 Location/Qualifiers
source                  1..23
                        mol_type = genomic DNA
                        organism = Homo sapiens
SEQUENCE: 607
gtacgagccc ctgaataaat agg                                               23

SEQ ID NO: 608          moltype = DNA   length = 23
FEATURE                 Location/Qualifiers
source                  1..23
                        mol_type = genomic DNA
                        organism = Homo sapiens
SEQUENCE: 608
ggaccaaaca ctgaataaac cag                                               23

SEQ ID NO: 609          moltype = DNA   length = 23
FEATURE                 Location/Qualifiers
source                  1..23
                        mol_type = genomic DNA
                        organism = Homo sapiens
SEQUENCE: 609
gcaccagcca ctgaattaac aag                                               23

SEQ ID NO: 610          moltype = DNA   length = 23
FEATURE                 Location/Qualifiers
source                  1..23
                        mol_type = genomic DNA
                        organism = Homo sapiens
SEQUENCE: 610
gtaccagcca ctgaaaaaac agg                                               23

SEQ ID NO: 611          moltype = DNA   length = 23
FEATURE                 Location/Qualifiers
source                  1..23
                        mol_type = genomic DNA
                        organism = Homo sapiens
SEQUENCE: 611
gaaccagccc ctgattagac cag                                               23

SEQ ID NO: 612          moltype = DNA   length = 23
FEATURE                 Location/Qualifiers
source                  1..23
                        mol_type = genomic DNA
                        organism = Homo sapiens
SEQUENCE: 612
gtaccagcca ctgaaaaaac agg                                               23

SEQ ID NO: 613          moltype = DNA   length = 23
FEATURE                 Location/Qualifiers
source                  1..23
                        mol_type = genomic DNA
                        organism = Homo sapiens
SEQUENCE: 613
gtaccagcca ctgaaaaaac agg                                               23

SEQ ID NO: 614          moltype = DNA   length = 23
FEATURE                 Location/Qualifiers
source                  1..23
                        mol_type = genomic DNA
                        organism = Homo sapiens
SEQUENCE: 614
gcaccaggcc ttgaataaac aag                                               23
```

```
SEQ ID NO: 615          moltype = DNA   length = 23
FEATURE                 Location/Qualifiers
source                  1..23
                        mol_type = genomic DNA
                        organism = Homo sapiens
SEQUENCE: 615
ggcccagcca ctgagtaaac tag                                              23

SEQ ID NO: 616          moltype = DNA   length = 23
FEATURE                 Location/Qualifiers
source                  1..23
                        mol_type = genomic DNA
                        organism = Homo sapiens
SEQUENCE: 616
ggaattgccc ctgaataaac aag                                              23

SEQ ID NO: 617          moltype = DNA   length = 23
FEATURE                 Location/Qualifiers
source                  1..23
                        mol_type = genomic DNA
                        organism = Homo sapiens
SEQUENCE: 617
gggaacagcc ctgaataaac ctg                                              23

SEQ ID NO: 618          moltype = DNA   length = 23
FEATURE                 Location/Qualifiers
source                  1..23
                        mol_type = genomic DNA
                        organism = Homo sapiens
SEQUENCE: 618
aggaccagct ctgaataacc agg                                              23

SEQ ID NO: 619          moltype = DNA   length = 23
FEATURE                 Location/Qualifiers
source                  1..23
                        mol_type = genomic DNA
                        organism = Homo sapiens
SEQUENCE: 619
ggaacagccc tgaataaacc tgg                                              23

SEQ ID NO: 620          moltype = DNA   length = 23
FEATURE                 Location/Qualifiers
source                  1..23
                        mol_type = genomic DNA
                        organism = Homo sapiens
SEQUENCE: 620
gagttcagcc cctgaataac agg                                              23

SEQ ID NO: 621          moltype = DNA   length = 23
FEATURE                 Location/Qualifiers
source                  1..23
                        mol_type = genomic DNA
                        organism = Homo sapiens
SEQUENCE: 621
gggaccagcc ccagaataaa ggg                                              23

SEQ ID NO: 622          moltype = DNA   length = 23
FEATURE                 Location/Qualifiers
source                  1..23
                        mol_type = genomic DNA
                        organism = Homo sapiens
SEQUENCE: 622
aagccaaccc ctgaataaac agg                                              23

SEQ ID NO: 623          moltype = DNA   length = 23
FEATURE                 Location/Qualifiers
source                  1..23
                        mol_type = genomic DNA
                        organism = Homo sapiens
SEQUENCE: 623
cacacagccc ctcaataaac tgg                                              23

SEQ ID NO: 624          moltype = DNA   length = 23
FEATURE                 Location/Qualifiers
source                  1..23
                        mol_type = genomic DNA
                        organism = Homo sapiens
SEQUENCE: 624
```
gaggcagccc ctgtataaac tgg                                                    23

SEQ ID NO: 625           moltype = DNA   length = 23
FEATURE                  Location/Qualifiers
source                   1..23
                         mol_type = genomic DNA
                         organism = Homo sapiens
SEQUENCE: 625
gaccagcccc ctgaataaca tgg                                                    23

SEQ ID NO: 626           moltype = DNA   length = 23
FEATURE                  Location/Qualifiers
source                   1..23
                         mol_type = genomic DNA
                         organism = Mus musculus
SEQUENCE: 626
gtaccagccc ctgacaaaac agg                                                    23

SEQ ID NO: 627           moltype = DNA   length = 23
FEATURE                  Location/Qualifiers
source                   1..23
                         mol_type = genomic DNA
                         organism = Mus musculus
SEQUENCE: 627
ggagcagccc cggaatgaac agg                                                    23

SEQ ID NO: 628           moltype = DNA   length = 23
FEATURE                  Location/Qualifiers
source                   1..23
                         mol_type = genomic DNA
                         organism = Mus musculus
SEQUENCE: 628
ggaccagccc ctgtataccc tgg                                                    23

SEQ ID NO: 629           moltype = DNA   length = 23
FEATURE                  Location/Qualifiers
source                   1..23
                         mol_type = genomic DNA
                         organism = Mus musculus
SEQUENCE: 629
ggaccagccc ctgtataccc tgg                                                    23

SEQ ID NO: 630           moltype = DNA   length = 23
FEATURE                  Location/Qualifiers
source                   1..23
                         mol_type = genomic DNA
                         organism = Mus musculus
SEQUENCE: 630
ggaccagccc ctgtataccc tgg                                                    23

SEQ ID NO: 631           moltype = DNA   length = 23
FEATURE                  Location/Qualifiers
source                   1..23
                         mol_type = genomic DNA
                         organism = Mus musculus
SEQUENCE: 631
ggccctgccc ctaaataaac agg                                                    23

SEQ ID NO: 632           moltype = DNA   length = 23
FEATURE                  Location/Qualifiers
source                   1..23
                         mol_type = genomic DNA
                         organism = Mus musculus
SEQUENCE: 632
ggatcagccc cagaataacc tgg                                                    23

SEQ ID NO: 633           moltype = DNA   length = 23
FEATURE                  Location/Qualifiers
source                   1..23
                         mol_type = genomic DNA
                         organism = Mus musculus
SEQUENCE: 633
ggactagccc ctgagtacac tgg                                                    23

ARTIFICIAL GENOME MANIPULATION FOR GENE EXPRESSION REGULATION

CROSS-REFERENCE TO RELATED APPLICATIONS

This application is a continuation application of U.S. patent application Ser. No. 16/776,707, filed on 30 Jan. 2020, which is a continuation-in-part of PCT Application No. PCT/KR2018/011424, filed on Sep. 27, 2018, which claims benefit and priority to U.S. Application Nos. 62/564,478, filed on Sep. 28, 2017 and 62/565,868, filed on Sep. 29, 2017 and also claims priority to U.S. Application No. 62/799,169, filed on Jan. 31, 2019. The entire disclosures of the applications identified in this paragraph are incorporated herein by references.

FIELD

The present invention relates to an expression control composition for controlling the expression of a duplicate gene and a method using the same. More particularly, the present invention relates to an expression control composition which includes a guide nucleic acid capable of targeting the transcriptional regulatory region of a duplicate gene and a method of regulating the expression of a duplicate gene by artificially manipulating and/or modifying the transcriptional regulatory region of the duplicate gene using the expression control composition. In addition, the present invention relates to a method of treating or improving a disease caused by gene duplication using the expression control composition for regulating the expression of a duplicate gene.

BACKGROUND

Gene duplication is one of the errors generated in the genetic recombination of a chromosome, and a replication phenomenon of duplicating a partial region of the chromosome. Gene duplication is a type of mutation that is passed on to the next generation. Gene duplication, along with gene deletion occurring due to non-replication of a partial region of the chromosome, affects gene expression.

Gene duplication also causes a hereditary disease. Representatively, Charcot-Marie-Tooth (CMT) type 1A results from gene duplication occurring in a specific region of a chromosome, and the overexpression of a gene involved in the peripheral nerve development of hands and feet occurs due to gene duplication, and thus malformity of hands and feet is caused.

As such, it is important for a gene to be expressed at a suitable position and the right time for normal performance of biological processes such as cell proliferation, death, aging and differentiation. When a gene is improperly expressed at an inappropriate time and position, particularly, the abnormal gene expression caused by gene duplication may lead to a disease, and therefore, it is necessary to understand the mechanism of a molecule for controlling the expression of each gene, and it is important to identify a transcription regulatory factor associated with each gene. There are various transcription regulatory factors that can precisely control gene expression, for example, a promoter, a distal control element, and a transcription factor, an activator and coactivators, which are involved in the control of gene expression.

Gene expression may be controlled by the change in a transcription regulatory factor, and an abnormal change in transcription regulatory factor may cause the abnormal expression of a gene, thereby inducing a disease. Accordingly, the change in transcription regulatory factor may cause various diseases, or improve and treat diseases.

However, the current method of controlling a transcription regulatory factor only controls transient gene expression, and continuous gene expression regulation is difficult. For this reason, there is no fundamental treatment method for treating a disease caused by gene expression abnormalities or difficulties. Therefore, there is a demand for a method exhibiting a more continuous therapeutic effect by genetic editing or modification of a transcription regulatory factor.

NON-PATENT DOCUMENT

1. Hamdan, H., Kockara, N. T., Jolly, L. A., Haun, S., and Wight, P. A. (2015). Control of human PLP1 expression through transcriptional regulatory elements and alternatively spliced exons in intron 1. ASN Neuro 7.
2. Hamdan, H., Patyal, P., Kockara, N. T., and Wight, P. A. (2018). The wmN1 enhancer region in intron 1 is required for expression of human PLP1. Glia.
3. Meng, F., Zolova, O., Kokorina, N. A., Dobretsova, A., and Wight, P. A. (2005). Characterization of an intronic enhancer that regulates myelin proteolipid protein (Plp) gene expression in oligodendrocytes. J Neurosci Res 82, 346-356.
4. Tuason, M. C., Rastikerdar, A., Kuhlmann, T., Goujet-Zalc, C., Zalc, B., Dib, S., Friedman, H., and Peterson, A. (2008). Separate proteolipid protein/DM20 enhancers serve different lineages and stages of development. J Neurosci 28, 6895-6903.
5. Wight, P. A. (2017). Effects of Intron 1 Sequences on Human PLP1 Expression: Implications for PLP1-Related Disorders. ASN Neuro 9, 1759091417720583.

SUMMARY

The present invention relates to an expression control composition for controlling the expression of a duplicate gene present in the genome of a cell. More specifically, the present invention relates to an expression control composition including a guide nucleic acid capable of targeting the transcriptional regulatory region of a duplicate gene, and a method of controlling the expression of a duplicate gene by artificially manipulating and/or modifying the transcriptional regulatory region of the duplicate gene using the expression control composition. In addition, the present invention relates to a method of treating or improving a disease caused by gene duplication using the expression control composition for controlling the expression of a duplicate gene.

The present invention provides an expression control composition for controlling the expression of a duplicate gene present in the genome of a cell.

In one aspect, the expression control composition may comprise the following: a guide nucleic acid capable of targeting a target sequence present in a transcriptional regulatory region of a duplicate gene or a nucleic acid encoding the same; and one or more editor protein or a nucleic acid encoding the same.

The guide nucleic acid may include a guide domain capable of targeting the target sequence present in the transcriptional regulatory region of the duplicated gene.

Here, the guide domain may include a guide sequence capable of forming a complementary binding with a guide nucleic acid-binding sequence of the target sequence present in the transcriptional regulatory region of the duplicated gene.

Here, the guide domain may form a complementary binding with the guide nucleic acid-binding sequence of the target sequence in the transcriptional regulatory region of the duplicated gene.

Here, the complementary binding may include mismatching bindings of 0 to 5.

The guide nucleic acid may include one or more domains selected from the group consisting of a first complementary domain, a second complementary domain, a proximal domain and a tail domain.

The editor protein may be a CRISPR enzyme.

The guide nucleic acid and editor protein may form a guide nucleic acid-editor protein complex.

Here, the guide nucleic acid-editor protein complex may be formed by interacting with a partial nucleic acid of the guide nucleic acid and a partial amino acid of the editor protein.

The transcriptional regulatory region may be one or more regions selected from the group consisting of a promoter region, an enhancer region, a silencer region, an insulator region and a locus control region (LCR).

The target sequence may be a 10 to 25-nt (nucleotide) contiguous sequence located in the transcriptional regulatory region of the duplicate gene.

The target sequence may be a 10 to 25-nt contiguous sequence located in or adjacent to a promoter region of the duplicate gene.

Here, the target sequence may be a 10 to 25-nt contiguous sequence located in or adjacent to a core promoter region of the duplicate gene.

Here, the target sequence may be a 10 to 25-nt contiguous sequence including a TATA box region of the core promoter region of the duplicate gene or a 10 to 25-nt contiguous sequence located adjacent to the TATA box region.

Here, the target sequence may be a 10 to 25-nt contiguous sequence including all or a part of the 5'-TATA-3' (SEQ ID NO: 261) sequence present in the core promoter region of the duplicate gene.

Here, the target sequence may be a 10 to 25-nt contiguous sequence including all or a part of the 5'-TATAWAW-3' (W=A or T) (SEQ ID NO: 262) sequence present in the core promoter region of the duplicate gene.

Here, the target sequence may be a 10 to 25-nt contiguous sequence including all or a part of the 5'-TATAWAWR-3' (W=A or T, R=A or G) (SEQ ID NO: 263) sequence present in the core promoter region of the duplicate gene.

Here, the target sequence may be a 10 to 25-nt contiguous sequence including all or a part of a sequence selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence.

Here, the target sequence may be a 10 to 25-nt contiguous sequence located to 5' end or 3' end of a sequence selected from the group consisting of the 5'-TATA-3' (SEQ ID NO: 261) sequence, the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence.

The target sequence may be a 10 to 25-nt contiguous sequence located in an enhancer region of the duplicate gene.

The target sequence may be a 10 to 25-nt contiguous sequence located adjacent to an enhancer region of the duplicate gene.

The target sequence may be a 10 to 25-nt contiguous sequence located adjacent to 5' end and/or 3' end of PAM (proto-spacer-adjacent motif) sequence in a nucleic acid sequence of the transcriptional regulatory region of the duplicate gene.

Here, the PAM sequence may be determined according to the CRISPR enzyme.

The CRISPR enzyme may be a Cas9 protein or a Cpf1 protein.

Here, the Cas9 protein may be one or more Cas9 proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein and a *Neisseria meningitidis*-derived Cas9 protein.

The duplicate gene may be one or more genes selected from the group consisting of a PMP22 gene, a PLP1 gene, a MECP2 gene, a SOX3 gene, a RAI1 gene, a TBX1 gene, an ELN gene, a JAGGED1 gene, a NSD1 gene, a MMP23 gene, a LMB1 gene, a SNCA gene and an APP gene.

The duplicate gene may be an oncogene.

Here, the oncogene may be one or more genes selected from the group consisting of a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The cell may be a eukaryotic cell.

The eukaryotic cell may be a mammalian cell.

The guide nucleic acid and editor protein may be present in one or more vectors in a form of a nucleic acid sequence, respectively.

Here, the vector may be a plasmid or a viral vector.

Here, the viral vector may be one or more viral vectors selected from the group consisting of a retrovirus, a lentivirus, an adenovirus, an adeno-associated virus (AAV), a vaccinia virus, a poxvirus and a herpes simplex virus.

The expression control composition may include the guide nucleic acid and the editor protein in a form of the guide nucleic acid-editor protein complex.

The expression control composition may further comprise a donor.

In another aspect, the expression control composition may include the following:
  i) a first guide nucleic acid capable of targeting a target sequence located upstream of the transcriptional regulatory region of a duplicate gene or a nucleic acid sequence encoding the same;
  ii) a second guide nucleic acid capable of targeting a target sequence located downstream of the transcriptional regulatory region of a duplicate gene or a nucleic acid sequence encoding the same; and
  iii) one or more editor proteins or nucleic acid sequence(s) encoding the same.

The first guide nucleic acid may include a first guide domain capable of targeting a target sequence located upstream of the transcriptional regulatory region of a duplicate gene.

Here, the first guide domain may include a guide sequence capable of complementarily binding to a guide nucleic acid-binding sequence of the target sequence located upstream of the transcriptional regulatory region of a duplicate gene.

Here, the first guide domain may complementarily bind with the guide nucleic acid-binding sequence of the target sequence located upstream of the transcriptional regulatory region of a duplicate gene.

Here, the complementary binding may include 0 to 5 mismatches.

The second guide nucleic acid may include a second guide domain capable of targeting a target sequence located downstream of the transcriptional regulatory region of a duplicate gene.

Here, the second guide domain may include a guide sequence capable of complementarily binding to a guide nucleic acid-binding sequence of the target sequence located downstream of the transcriptional regulatory region of a duplicate gene.

Here, the second guide domain may complementarily bind with the guide nucleic acid-binding sequence of the target sequence located downstream of the transcriptional regulatory region of a duplicate gene.

Here, the complementary binding may include 0 to 5 mismatches.

The first guide nucleic acid and/or the second guide nucleic acid may include one or more domains selected from the group consisting of a first complementary domain, a linker domain, a second complementary domain, a proximal domain and a tail domain.

The first guide nucleic acid and/or second guide nucleic acid may target the transcriptional regulatory region of the same duplicate gene.

The editor protein may be a CRISPR enzyme.

The first guide nucleic acid and the editor protein may form a first guide nucleic acid-editor protein complex.

Here, the first guide nucleic acid-editor protein complex may be formed by interactions of a partial nucleic acid of the first guide nucleic acid and partial amino acids of the editor protein.

The second guide nucleic acid and the editor protein may form a second guide nucleic acid-editor protein complex.

Here, the second guide nucleic acid-editor protein complex may be formed by interactions of a partial nucleic acid of the second guide nucleic acid and partial amino acids of the editor protein.

The transcriptional regulatory region may be one or more regions selected form the group consisting of a promoter region, an enhancer region, a silencer region, an insulator region and a locus control region (LCR).

The target sequence may be a 10 to 25-nt contiguous sequence located upstream of the transcriptional regulatory region of a duplicate gene.

The target sequence may be a 10 to 25-nt contiguous sequence located upstream of the promoter region of a duplicate gene or a 10 to 25-nt contiguous sequence adjacent to the promoter region thereof.

The target sequence may be a 10 to 25-nt contiguous sequence located upstream of the enhancer region of a duplicate gene.

The target sequence may be a 10 to 25-nt contiguous sequence adjacent to the 5' end and/or 3' end of a protospacer-adjacent motif (PAM) sequence of a nucleic acid sequence located upstream of the transcriptional regulatory region of a duplicate gene.

The target sequence may be a 10 to 25-nt contiguous sequence located downstream of the transcriptional regulatory region of a duplicate gene.

The target sequence may be a 10 to 25-nt contiguous sequence located downstream of the promoter region of a duplicate gene or a 10 to 25-nt contiguous sequence adjacent to the promoter region thereof.

The target sequence may be a 10 to 25-nt contiguous sequence located downstream of the enhancer region of a duplicate gene.

The target sequence may be a 10 to 25-nt contiguous sequence adjacent to the 5' end and/or 3' end of a PAM sequence of the nucleic acid sequence located downstream of the transcriptional regulatory region of a duplicate gene.

Here, the PAM sequence may be determined according to a CRISPR enzyme.

The CRISPR enzyme may be a Cas9 or Cpf1 protein.

Here, the Cas9 protein may be one or more Cas9 proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein and a *Neisseria meningitidis*-derived Cas9 protein.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

The cell may be a eukaryotic cell.

The eukaryotic cell may be a mammalian cell.

Each of the first guide nucleic acid, the second guide nucleic acid and the editor protein may be present in one or more vectors in the form of a nucleic acid sequence.

Here, the vector may be a plasmid or viral vector.

Here, the viral vector may be one or more viral vectors selected from the group consisting of a retrovirus, a lentivirus, an adenovirus, an adeno-associated virus (AAV), a vaccinia virus, a poxvirus and a herpes simplex virus.

The expression control composition may include guide nucleic acids and editor proteins in the forms of a first guide nucleic acid-editor protein complex and a second guide nucleic acid-editor protein complex.

The expression control composition may further include a donor.

In another aspect, the expression control composition may include a guide nucleic acid for targeting a TATA-box or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a 10 to 25-nt contiguous sequence including the entire or a part of the 5'-UAUA-3' (SEQ ID NO: 374) sequence.

The guide sequence complementarily binding to the target sequence may be a 10 to 25-nt contiguous sequence including the entire or a part of the 5'-UAUAWAW-3' (W=A or U) (SEQ ID NO: 375) sequence, or may be a 10 to 25-nt contiguous sequence including the entire or a part of the 5'-WUWUAUA-3' (W=A or U) (SEQ ID NO: 376) sequence.

The guide sequence complementarily binding to the target sequence may be a 10 to 25-nt contiguous sequence including the entire or a part of the 5'-UAUAWAWR-3' (W=A or U, R=A or G) (SEQ ID NO: 377) sequence, or may be a 10 to 25-nt contiguous sequence including the entire or a part of the 5'-RWUWUAUA-3' (W=A or U, R=A or G) (SEQ ID NO: 378) sequence.

The guide sequence complementarily binding to the target sequence may be a 10 to 25-nt contiguous sequence including the entirety or a part of one or more sequences selected from the group consisting of the 5'-CAUAAAA-3' (SEQ ID NO: 379) sequence, the 5'-UAUAA-3' (SEQ ID NO: 380) sequence, the 5'-UAUAAAA-3' (SEQ ID NO: 381) sequence, the 5'-CAUAAAUA-3' (SEQ ID NO: 382) sequence, the 5'-UAUAUAA-3' (SEQ ID NO: 383) sequence, the 5'-UAUAUAUAUAUAA-3' (SEQ ID NO: 384) sequence, the 5'-UAUAUUAUA-3' (SEQ ID NO: 385) sequence, the 5'-UAUAAA-3' (SEQ ID NO: 386) sequence, the 5'-UAUAAAAUA-3' (SEQ ID NO: 387) sequence, the 5'-UAUAUA-3' (SEQ ID NO: 388) sequence, the 5'-GAUUAAAAA-3' (SEQ ID NO: 389) sequence, the 5'-UAUAAAAA-3' (SEQ ID NO: 390) sequence, the 5'-UUAUAA-3' (SEQ ID NO: 391) sequence, the 5'-UUUUAAAA-3' (SEQ ID NO: 392) sequence, the 5'-UC-UUUAAAA-3' (SEQ ID NO: 393) sequence, the 5'-GACAUUUAA-3' (SEQ ID NO: 394) sequence, the 5'-UGAUAUCAA-3' (SEQ ID NO: 395) sequence, the 5'-UAUAAAUA-3' (SEQ ID NO: 396) sequence, the 5'-UAUAAGA-3' (SEQ ID NO: 397) sequence, the 5'-AAUAAA-3' (SEQ ID NO: 398) sequence, the 5'-UUUAUA-3' (SEQ ID NO: 399) sequence, the 5'-CAUAAAAA-3' (SEQ ID NO: 400) sequence, the 5'-UAUACA-3' (SEQ ID NO: 401) sequence, the 5'-UUUAAGA-3' (SEQ ID NO: 402) sequence, the 5'-GAUAAAG-3' (SEQ ID NO: 403) sequence, the 5'-UAUAACA-3' (SEQ ID NO: 404) sequence, the 5'-UCUUAUCUU-3' (SEQ ID NO: 405) sequence, the 5'-UUGUACUUU-3' (SEQ ID NO: 406) sequence, the 5'-CAUAUAA-3' (SEQ ID NO: 407) sequence, the 5'-UAUAAAU-3' (SEQ ID NO: 408) sequence, the 5'-UAUAUAUAAAAAAAA-3' (SEQ ID NO: 409) sequence and 5'-CAUAAAUAAAAAAAAUUA-3' (SEQ ID NO: 410) sequence.

The guide sequence complementarily binding to the target sequence may be a 10 to 25-nt contiguous sequence including the entirety or a part of one or more sequences selected from the group consisting of the 5'-UUUUAUG-3' (SEQ ID NO: 411) sequence, the 5'-UUAUA-3' (SEQ ID NO: 412) sequence, the 5'-UUUUAUA-3' (SEQ ID NO: 413) sequence, the 5'-UAUUUAUG-3' (SEQ ID NO: 414) sequence, the 5'-UUAUAUA-3' (SEQ ID NO: 415) sequence, the 5'-UUAUAUAUAUAUAUA-3' (SEQ ID NO: 416) sequence, the 5'-UAUAAUAUA-3' (SEQ ID NO: 417) sequence, the 5'-UUUAUA-3' (SEQ ID NO: 418) sequence, the 5'-UAUUUUAUA-3' (SEQ ID NO: 419) sequence, the 5'-UUUUUAAUC-3' (SEQ ID NO: 420) sequence, the 5'-UUUUUAUA-3' (SEQ ID NO: 421) sequence, the 5'-UUUUAAAGA-3' (SEQ ID NO: 422) sequence, the 5'-UUAAAUGUC-3' (SEQ ID NO: 423) sequence, the 5'-UUGAUAUCA-3' (SEQ ID NO: 424) sequence, the 5'-UAUUUAUA-3' (SEQ ID NO: 425) sequence, the 5'-UCUUAUA-3' (SEQ ID NO: 426) sequence, the 5'-UUUAUU-3' (SEQ ID NO: 427) sequence, the 5'-UAUAAA-3' (SEQ ID NO: 428) sequence, the 5'-UUUUUAUG-3' (SEQ ID NO: 429) sequence, the 5'-UGUAUA-3' (SEQ ID NO: 430) sequence, the 5'-UCUUAAA-3' (SEQ ID NO: 431) sequence, the 5'-CUUUAUC-3' (SEQ ID NO: 432) sequence, the 5'-UGUUAUA-3' (SEQ ID NO: 433) sequence, the 5'-AAGAUAAGA-3' (SEQ ID NO: 434) sequence, the 5'-AAAGUACAA-3' (SEQ ID NO: 435) sequence, the 5'-UUAUAUG-3' (SEQ ID NO: 436) sequence, the 5'-AUUUAUA-3' (SEQ ID NO: 437) sequence, the 5'-UUUUUUUUAUAUAUA-3' (SEQ ID NO: 438) sequence and 5'-UAAUUUUUUUUAUUUAUG-3' (SEQ ID NO: 439) sequence.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The nucleic acid encoding the guide nucleic acid may be included in a vector.

Here, the vector may be a plasmid or a viral vector.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

In another aspect, the expression control composition may include the following: a guide nucleic acid for targeting a TATA-box or a nucleic acid encoding the same; and a CRISPR enzyme or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a nucleotide sequence including at least one sequence selected from the group consisting of SEQ ID NOs: 374 to 439.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The CRISPR enzyme may be a Cas9 protein or a Cpf1 protein.

Here, the Cas9 protein may be at least one selected from the group consisting of a *Streptococcus thermophiles*-derived Cas9 protein, a *Campylobacter jejuni*-derived Cas9 protein and a *Streptococcus pyogenes*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The present invention provides a method for controlling the expression of a duplicate gene present in the genome of a eukaryotic cell.

In one aspect, the method for controlling the expression of a duplicate gene present in the genome of a eukaryotic cell may comprise introducing an expression control composition into the eukaryotic cell.

The expression control composition may comprise the following:
  a guide nucleic acid capable of targeting a target sequence present in a transcriptional regulatory region of a duplicate gene or a nucleic acid encoding the same; and
  one or more editor protein or a nucleic acid encoding the same.

The eukaryotic cell may be a mammalian cell.

The guide nucleic acid may include a guide domain capable of targeting the target sequence present in the transcriptional regulatory region of the duplicated gene.

Here, the guide domain may include a nucleotide sequence capable of forming a complementary binding with a guide nucleic acid-binding sequence of the target sequence present in the transcriptional regulatory region of the duplicated gene.

Here, the guide domain may form a complementary binding with the guide nucleic acid-binding sequence of the target sequence in the transcriptional regulatory region of the duplicated gene.

Here, the complementary binding may include mismatching bindings of 0 to 5.

The guide nucleic acid may include one or more domains selected from the group consisting of a first complementary domain, a second complementary domain, a proximal domain and a tail domain.

The editor protein may be a CRISPR enzyme.

The guide nucleic acid and editor protein may form a guide nucleic acid-editor protein complex.

Here, the guide nucleic acid-editor protein complex may be formed by interacting with a partial nucleic acid of the guide nucleic acid and a partial amino acid of the editor protein.

The expression control composition may include the guide nucleic acid and the editor protein in a form of the guide nucleic acid-editor protein complex.

The expression control composition may include one or more vector in which the guide nucleic acid and the editor protein is included in a form of nucleic acid respectively.

The introducing may be performed by one or more methods selected from electroporation, liposomes, plasmids, viral vectors, nanoparticles and a protein translocation domain (PTD) fusion protein method.

In another aspect, the method of controlling the expression of a duplicate gene present in the genome of a eukaryotic cell may include introducing an expression control composition into a eukaryotic cell.

The expression control composition may include the following:
  i) a first guide nucleic acid capable of targeting a target sequence located upstream of the transcriptional regulatory region of a duplicate gene or a nucleic acid sequence encoding the same;
  ii) a second guide nucleic acid capable of targeting a target sequence located downstream of the transcriptional regulatory region of a duplicate gene or a nucleic acid sequence encoding the same; and
  iii) one or more editor proteins or nucleic acid sequence(s) encoding the same.

The eukaryotic cell may be a mammalian cell.

The first guide nucleic acid may include a first guide domain capable of targeting a target sequence located upstream of the transcriptional regulatory region of a duplicate gene.

Here, the first guide domain may include a nucleotide sequence capable of complementarily binding to a guide nucleic acid-binding sequence of the target sequence located upstream of the transcriptional regulatory region of the duplicate gene.

Here, the first guide domain may complementarily bind with the guide nucleic acid-binding sequence of the target sequence located upstream of the transcriptional regulatory region of the duplicate gene.

Here, the complementary binding may include 0 to 5 mismatches.

The second guide nucleic acid may include a second guide domain capable of targeting a target sequence located downstream of the transcriptional regulatory region of a duplicate gene.

Here, the second guide domain may include a nucleotide sequence capable of complementarily binding to a guide nucleic acid-binding sequence of the target sequence located downstream of the transcriptional regulatory region of a duplicate gene.

Here, the second guide domain may complementarily bind with the guide nucleic acid-binding sequence of the target sequence located downstream of the transcriptional regulatory region of a duplicate gene.

Here, the complementary binding may include 0 to 5 mismatches.

The first guide nucleic acid and/or the second guide nucleic acid may include one or more domains selected from the group consisting of a first complementary domain, a linker domain, a second complementary domain, a proximal domain and a tail domain.

The editor protein may be a CRISPR enzyme.

The first guide nucleic acid and the editor protein may form a first guide nucleic acid-editor protein complex.

Here, the first guide nucleic acid-editor protein complex may be formed by interactions of a partial nucleic acid of the first guide nucleic acid and partial amino acids of the editor protein.

The second guide nucleic acid and the editor protein may form a second guide nucleic acid-editor protein complex.

Here, the second guide nucleic acid-editor protein complex may be formed by interactions of a partial nucleic acid of the second guide nucleic acid and partial amino acids of the editor protein.

The expression control composition may include the first guide nucleic acid, the second guide nucleic acid and the editor protein in the forms of a first guide nucleic acid-editor protein complex and a second guide nucleic acid-editor protein complex.

The expression control composition may include one or more vectors including the first guide nucleic acid, the second guide nucleic acid and the editor protein as respective nucleic acid sequences.

The introduction may be performed using one or more methods selected from electroporation, liposomes, plasmids, viral vectors, nanoparticles and a protein translocation domain (PTD) fusion protein.

In another aspect, the method of controlling the expression of a duplicate gene present in the genome of a eukaryotic cell may include introducing an expression control composition into a eukaryotic cell.

The expression control composition may include the following: a guide nucleic acid for targeting a TATA-box or a nucleic acid encoding the same; and a CRISPR enzyme or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a nucleotide sequence including at least one sequence selected from the group consisting of SEQ ID NOs: 374 to 439.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The CRISPR enzyme may be a Cas9 protein or a Cpf1 protein.

Here, the Cas9 protein may be at least one selected from the group consisting of a *Streptococcus pyogenes*-derived Cas9 protein, a *Campylobacter jejuni*-derived Cas9 protein and a *Streptococcus thermophiles*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The introducing of the expression control composition may be performed by one or more methods selected from electroporation, liposomes, plasmids, viral vectors, nanoparticles and a protein translocation domain (PTD) fusion protein method.

In still another aspect, the method of controlling the expression of a duplicate gene present in the genome of a eukaryotic cell may include introducing an expression control composition into a eukaryotic cell.

The expression control composition may include the following:
a guide nucleic acid for targeting a transcriptional regulatory region of the duplicate gene or a nucleic acid encoding the same; and
a CRISPR enzyme or a nucleic acid encoding the same.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The transcriptional regulatory region may be a promoter or an enhancer.

The guide nucleic acid may comprise a guide sequence complementarily binding with a target sequence present in the transcriptional regulatory region.

The guide sequence may be a sequence of 10 to 25 contiguous nucleotides.

The guide sequence complementarily binding to the target sequence may be a nucleotide sequence including at least one sequence selected from the group consisting of SEQ ID NOs: 440 to 581.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The CRISPR enzyme may be a Cas9 protein or a Cpf1 protein.

Here, the Cas9 protein may be at least one selected from the group consisting of a *Streptococcus pyogenes*-derived Cas9 protein, a *Campylobacter jejuni*-derived Cas9 protein and a *Streptococcus thermophilus*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The introducing of the expression control composition may be performed by one or more methods selected from electroporation, liposomes, plasmids, viral vectors, nanoparticles and a protein translocation domain (PTD) fusion protein method.

The present invention provides a method for treating a gene duplication disease.

In one aspect, the method for treating a gene duplication disease may comprise administration of an expression control composition into a subject to be treated.

The expression control composition may comprise the following:
  a guide nucleic acid capable of targeting a target sequence present in a transcriptional regulatory region of a duplicate gene or a nucleic acid encoding the same; and
  one or more editor protein or a nucleic acid encoding the same.

The guide nucleic acid may include a guide domain capable of targeting the target sequence present in the transcriptional regulatory region of the duplicated gene.

Here, the guide domain may include a nucleotide sequence capable of forming a complementary binding with a guide nucleic acid-binding sequence of the target sequence present in the transcriptional regulatory region of the duplicated gene.

Here, the guide domain may form a complementary binding with the guide nucleic acid-binding sequence of the target sequence in the transcriptional regulatory region of the duplicated gene.

Here, the complementary binding may include mismatching bindings of 0 to 5.

The guide nucleic acid may include one or more domains selected from the group consisting of a first complementary domain, a second complementary domain, a proximal domain and a tail domain.

The editor protein may be a CRISPR enzyme.

The guide nucleic acid and editor protein may form a guide nucleic acid-editor protein complex.

Here, the guide nucleic acid-editor protein complex may be formed by interacting with a partial nucleic acid of the guide nucleic acid and a partial amino acid of the editor protein.

The gene duplication disease may be Charcot-Marie-Tooth 1A (CMT1A), Dejerine-Sottas disease (DSD), Congenital Hypomyelination Neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), Velocardiofacial syndrome (VCFS), Williams Beuren syndrome (WBS), Alagille syndrome (AS), Growth retardation syndrome, Premature closure cranial sutures, Autosomal dominant leukodystrophy (ADLD), Parkinson disease or Alzheimer disease.

The gene duplication disease may be a cancer caused by an oncogene duplication.

Here, the cancer caused by an oncogene duplication may be Breast cancer, Cervical cancer, Colorectal cancer, Esophageal cancer, Gastric cancer, Glioblastoma, Head and neck cancer, Hepatocellular cancer, Neuroblastoma, Ovarian cancer, Sarcoma or Small cell lung cancer.

The subject to be treated may be a mammal including a human, a monkey, a mouse and a rat.

The administration may be performed by injection, transfusion, implantation or transplantation.

In another aspect, the method of treating a gene duplication disease may include administering an expression control composition into a subject to be treat.

The expression control composition may include the following:
  i) a first guide nucleic acid capable of targeting a target sequence located upstream of the transcriptional regulatory region of a duplicate gene or a nucleic acid sequence encoding the same;
  ii) a second guide nucleic acid capable of targeting a target sequence located downstream of the transcriptional regulatory region of a duplicate gene or a nucleic acid sequence encoding the same; and
  iii) one or more editor proteins or nucleic acid sequence(s) encoding the same.

The first guide nucleic acid may include a first guide domain capable of targeting a target sequence located upstream of the transcriptional regulatory region of a duplicate gene.

Here, the first guide domain may include a nucleotide sequence capable of complementarily binding to a guide nucleic acid-binding sequence of the target sequence located upstream of the transcriptional regulatory region of a duplicate gene.

Here, the first guide domain may complementarily bind with the guide nucleic acid-binding sequence of the target sequence located upstream of the transcriptional regulatory region of a duplicate gene.

Here, the complementary binding may include 0 to 5 mismatches.

The second guide nucleic acid may include a second guide domain capable of targeting a target sequence located downstream of the transcriptional regulatory region of a duplicate gene.

Here, the second guide domain may include a nucleotide sequence capable of complementarily binding to a guide nucleic acid-binding sequence of the target sequence located downstream of the transcriptional regulatory region of a duplicate gene.

Here, the second guide domain may complementarily bind with the guide nucleic acid-binding sequence of the target sequence located downstream of the transcriptional regulatory region of a duplicate gene.

Here, the complementary binding may include 0 to 5 mismatches.

The first guide nucleic acid and/or the second guide nucleic acid may include one or more domains selected from the group consisting of a first complementary domain, a linker domain, a second complementary domain, a proximal domain and a tail domain.

The editor protein may be a CRISPR enzyme.

The first guide nucleic acid, the second guide nucleic acid and the editor protein may form a first guide nucleic acid-editor protein complex and a second guide nucleic acid-editor protein complex.

Here, the first guide nucleic acid-editor protein complex may be formed by interactions of a partial nucleic acid of the first guide nucleic acid and partial amino acids of the editor protein.

Here, the second guide nucleic acid-editor protein complex may be formed by interactions of a partial nucleic acid of the second guide nucleic acid and partial amino acids of the editor protein.

The gene duplication disease may be Charcot-Marie-Tooth Type 1A (CMT1A), Dejerine-Sottas disease (DSD), congenital hypomyelination neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), velocardiofacial syndrome (VCFS), Williams Beuren syndrome (WBS), Alagille syndrome (AS), growth retardation syndrome, premature closure cranial sutures, autosomal dominant leukodystrophy (ADLD), Parkinson's disease or Alzheimer's disease.

The subject to be treat may be a mammal including a human, a monkey, a mouse and a rat.

The administration may be performed by injection, transfusion, implantation or transplantation.

In another aspect, the method of treating a gene duplication disease may include administering an expression control composition into a subject to be treat.

The expression control composition may include the following: a guide nucleic acid for targeting a TATA-box or a nucleic acid encoding the same; and a CRISPR enzyme or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a nucleotide sequence including at least one sequence selected from the group consisting of SEQ ID NOs: 374 to 439.

The guide nucleic acid may be a single guide RNA.

The CRISPR enzyme may be a Cas9 protein or a Cpf1 protein.

Here, the Cas9 protein may be at least one selected from the group consisting of a *Streptococcus pyogenes*-derived Cas9 protein, a *Campylobacter jejuni*-derived Cas9 protein and a *Streptococcus thermophilus*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The gene duplication disease may be Charcot-Marie-Tooth 1A (CMT1A), Dejerine-Sottas disease (DSD), Congenital Hypomyelination Neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), Velocardiofacial syndrome (VCFS), Williams Beuren syndrome (WBS), Alagille syndrome (AS), Growth retardation syndrome, Premature closure cranial sutures, Autosomal dominant leukodystrophy (ADLD), Parkinson disease or Alzheimer disease.

The gene duplication disease may be a cancer caused by an oncogene duplication.

Here, the cancer caused by an oncogene duplication may be Breast cancer, Cervical cancer, Colorectal cancer, Esophageal cancer, Gastric cancer, Glioblastoma, Head and neck cancer, Hepatocellular cancer, Neuroblastoma, Ovarian cancer, Sarcoma or Small cell lung cancer.

The subject to be treated may be a mammal including a human, a monkey, a mouse and a rat.

The administration may be performed by injection, transfusion, implantation or transplantation.

The present invention can control the expression of a duplication gene by an expression control composition. More specifically, the expression of the duplication gene can be controlled by artificially manipulating and/or modifying the transcriptional regulatory region of a duplicate gene by using the expression control composition including a guide nucleic acid capable of targeting the transcriptional regulatory region of the duplicate gene. A disease caused by gene duplication can also be improved or treated using the expression control composition for controlling the expression of the duplicate gene.

BRIEF DESCRIPTION OF THE DRAWINGS

FIG. 1 illustrates an indel frequency (%) of TATA-box due to SpCas9-sgRNA-mediated gene manipulation.

FIG. 2 illustrates an indel frequency (%) of enhancer due to SpCas9-sgRNA-mediated gene manipulation.

FIG. 3 illustrates an indel frequency (%) of TATA-box due to CjCas9-sgRNA-mediated gene manipulation.

FIG. 4 illustrates an indel frequency (%) of enhancer due to CjCas9-sgRNA-mediated gene manipulation.

FIG. 5 illustrates gene manipulation effects by SpCas9-sgRNA targeting regulatory elements of a human PMP22 gene in Schwann-like cells.

FIG. 6 illustrates Frameshift mutation ratios induced by the SpCas9-sgRNAs targeting CDS of human PMP22.

Figure 13A:
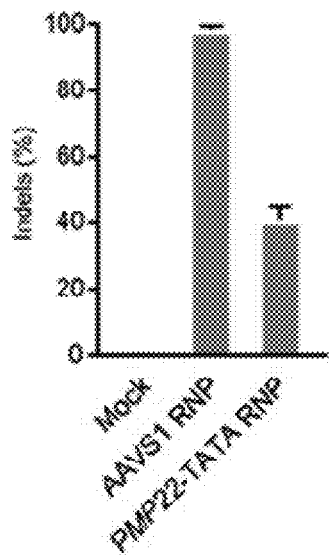
Figure 13B:
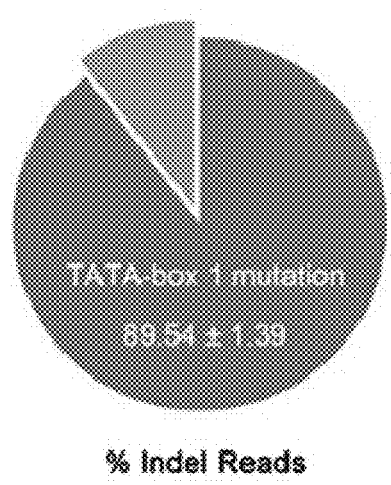
Figure 13C:
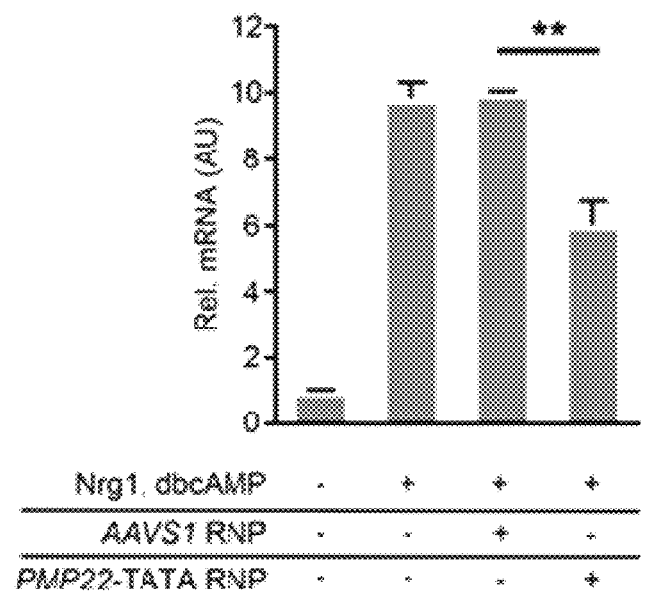

FIGS. 13A, 13B and 13C are graphs illustrating effective and specific expression decreases of PMP22 through CRISPR-Cas9 targeting a TATA-box site of a human PMP22 gene in vitro, and the leftmost graph (a), the middle graph (b), and the rightmost graph (c) illustrate indel frequency measurement results using targeted deep sequencing in human primary Schwann cells, TATA-box 1 mutation frequency measurement results (n=3) among the total indel frequencies, and relative mRNA expression comparison results of PMP22, which are measured by qRT-PCR with or without a treatment of a myelination signal factor and an RNP complex in human primary Schwann cells (n=3, One-way ANOVA and Tukey post-hoc tests: *p<0.05), respectively.

Figure 14:
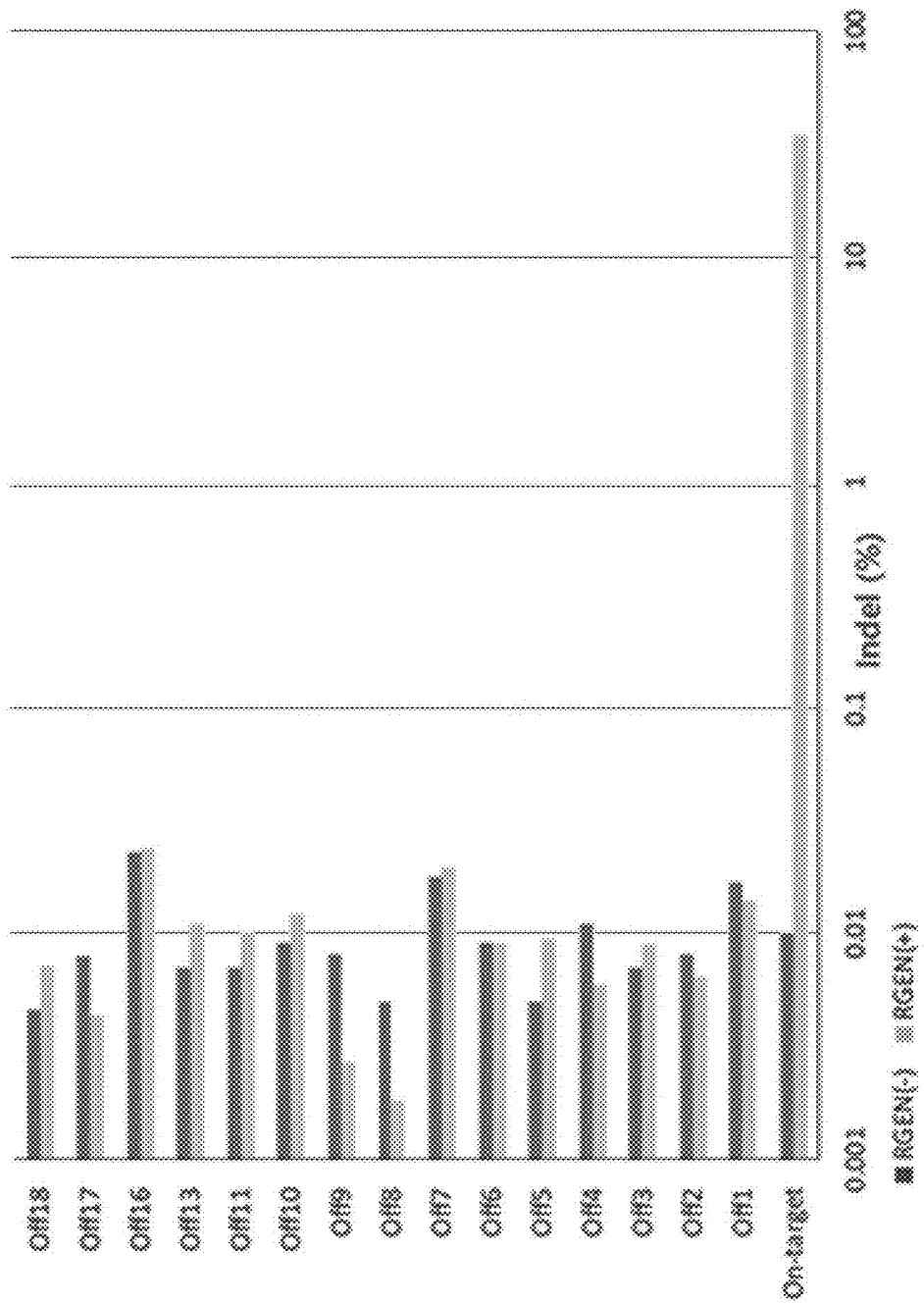

FIG. 14 illustrates indel frequencies by PMP22-TATA RNP in off-targets and on-targets found through an in silico off-target analysis by target deep sequencing in human primary Schwann cells.

FIG. 15 illustrates indel patterns with a high frequency by PMP22-TATA RNP in off-targets and on-targets found through an in silico off-target analysis by target deep sequencing in human primary Schwann cells. The local sequence of WT is a SEQ ID NO: 592, and the local sequences including indels are SEQ ID NOs: 593 to 597 (Indel-1 to -4 order).

FIG. 16 shows off-target sites found through an in silico off-target analysis. The on-target sequence is a SEQ ID NO: 598, and the off-target sequences are SEQ ID NOs: 599 to 616 (Off1 to Off18 order).

Figure 17:
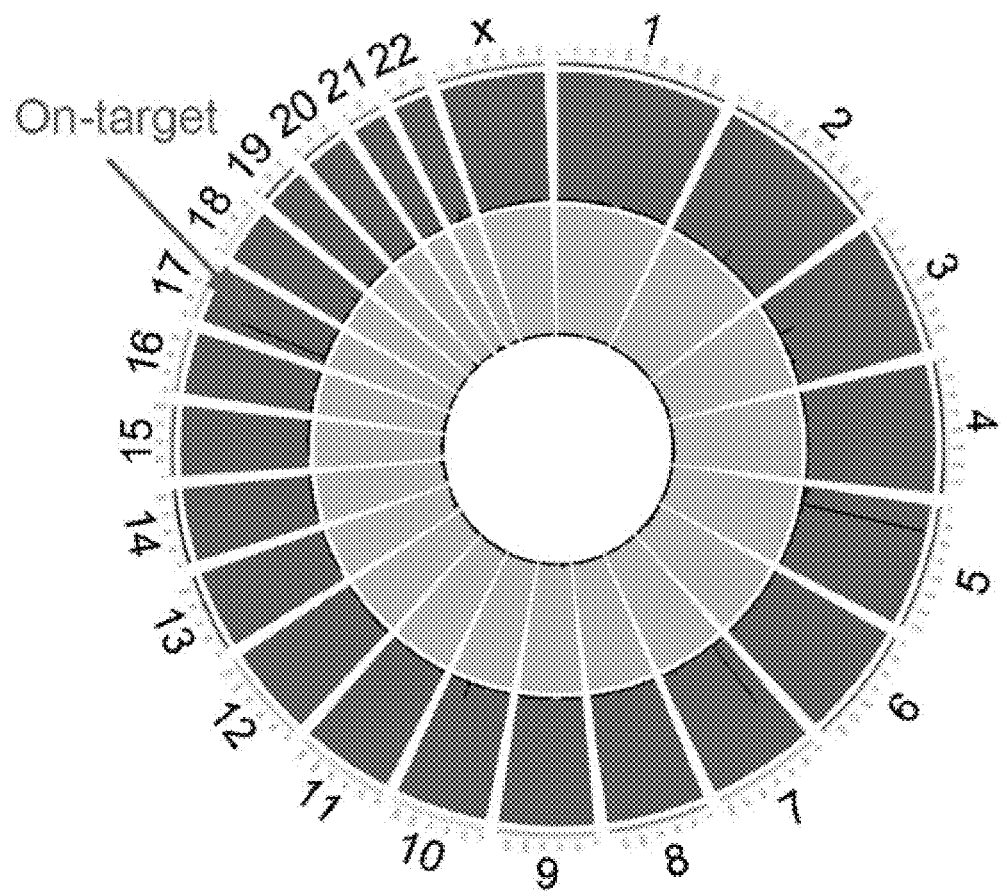

FIG. 17 is a Genome-wide Circos plot illustrating on-target site for PMP22-TATA RNP in a human's entire genome.

FIG. 18 illustrates off-target sites appearing by the Dig-enome-seq among off-target sites found through an in silico off-target analysis. The on-target sequence is a SEQ ID NO: 598, and the off-target sequences are SEQ ID NOs: 617 to 625 (Off1 to Off9 order).

Figure 19:
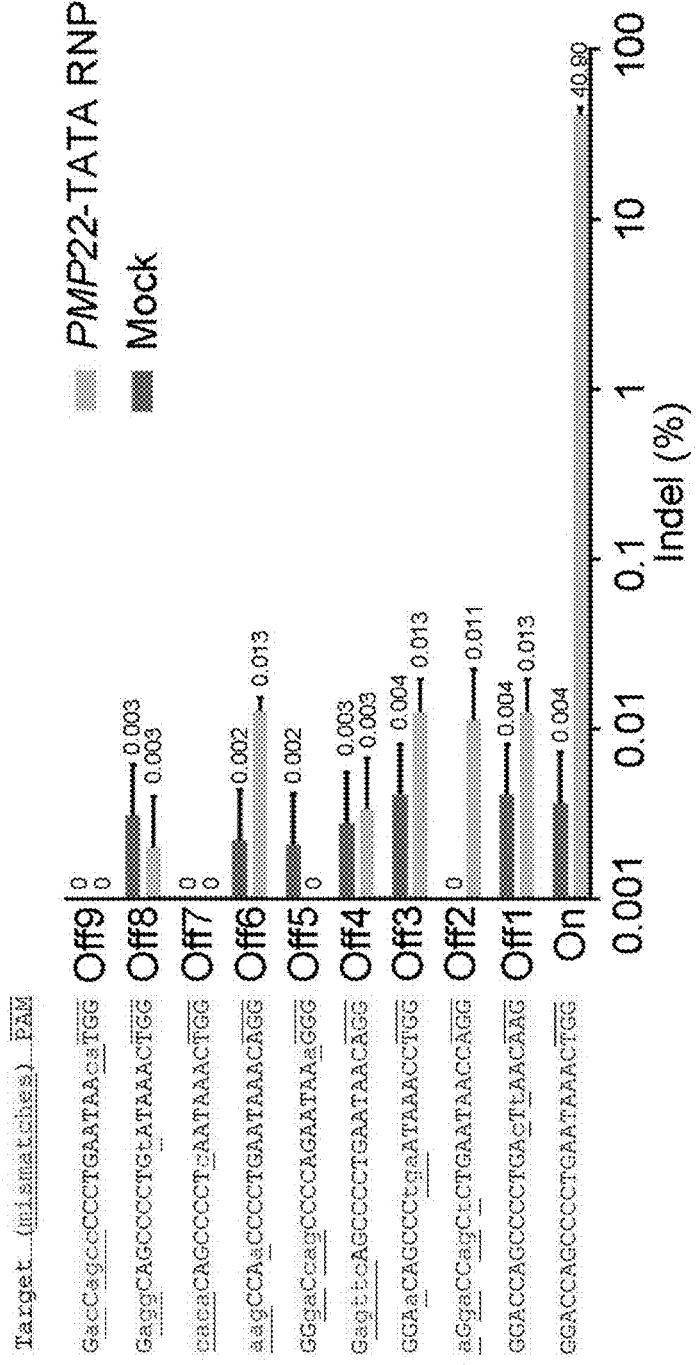

FIG. 19 is a graph illustrating indel frequencies in off-target sites by PMP22-TATA RNP. The on-target sequence is a SEQ ID NO: 598, and the off-target sequences are SEQ ID NOs: 617 to 625 (Off1 to Off9 order).

Figure 20:
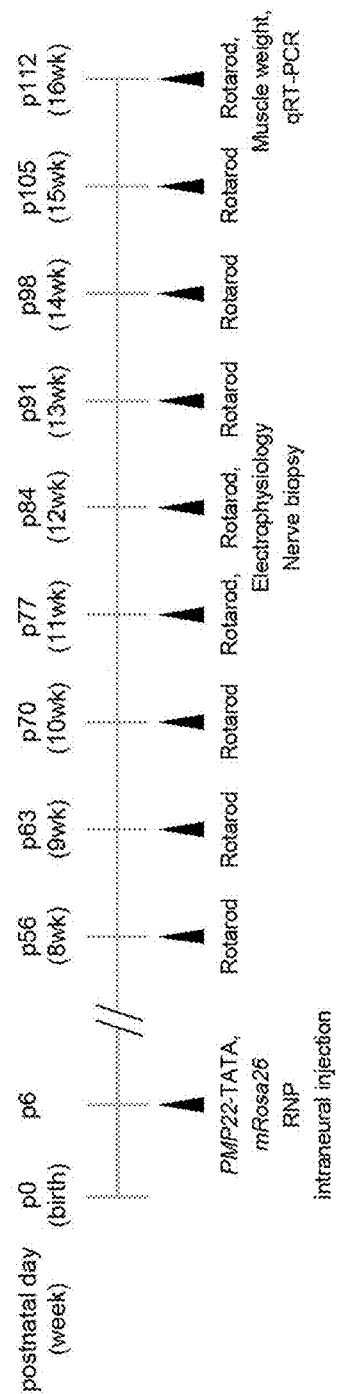

FIG. 20 schematically illustrates a therapeutic approach using PMP22-TATA RNA therapy in C22 mice.

Figure 21A:
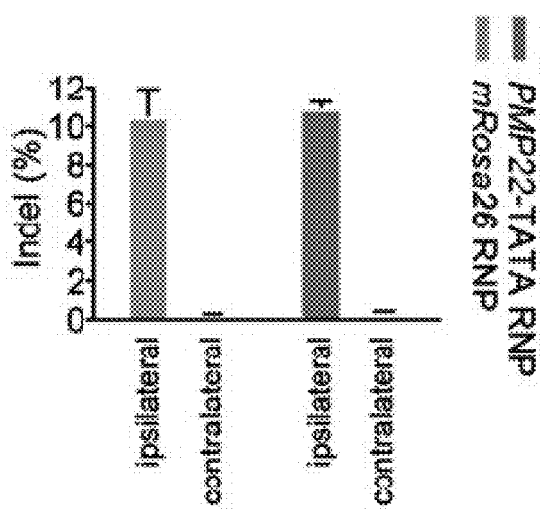
Figure 21B:
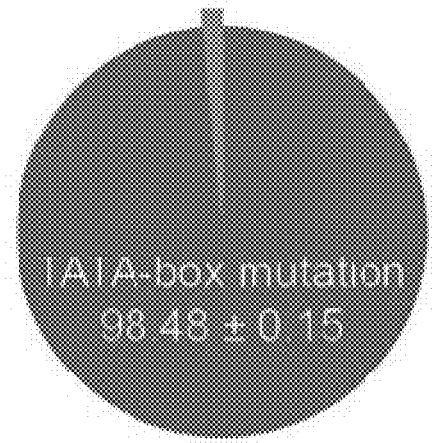
Figure 21C:
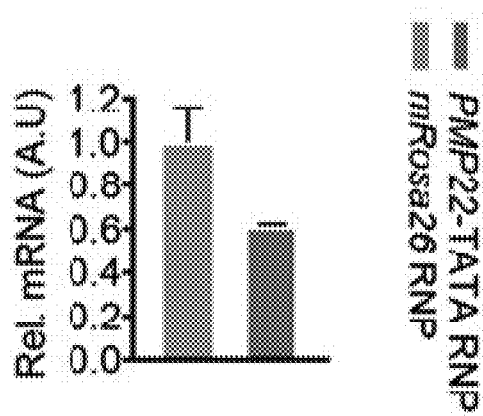

FIGS. 21A, 21B and 21C are a set of results illustrating the alleviation of a disease phenotype through expression inhibition of PMP22 by CRISPR/Cas9 in CMT1A mice, and (a) is a graph illustrating indel frequencies using targeted deep sequencing in a sciatic nerve treated with mRosa26 or a PMP22-TATA RNP complex (n=3), (b) is a TATA-box 1 mutation frequency measurement result (n=3) among the total indel frequencies, and (c) is a graph comparing the relative amounts of mRNA expressed of PMP22 using qRT-PCR from the sciatic nerve treated with mRosa26 or a PMP22-TATA RNP complex.

FIG. 22 illustrates off-target sites of PMP22-TATA sgRNA in a mouse genome by an in silico analysis. The on-target sequence is a SEQ ID NO: 598, and the off-target sequences are SEQ ID NOs: 626 to 633 (Off1 to Off8 order).

Figure 23:
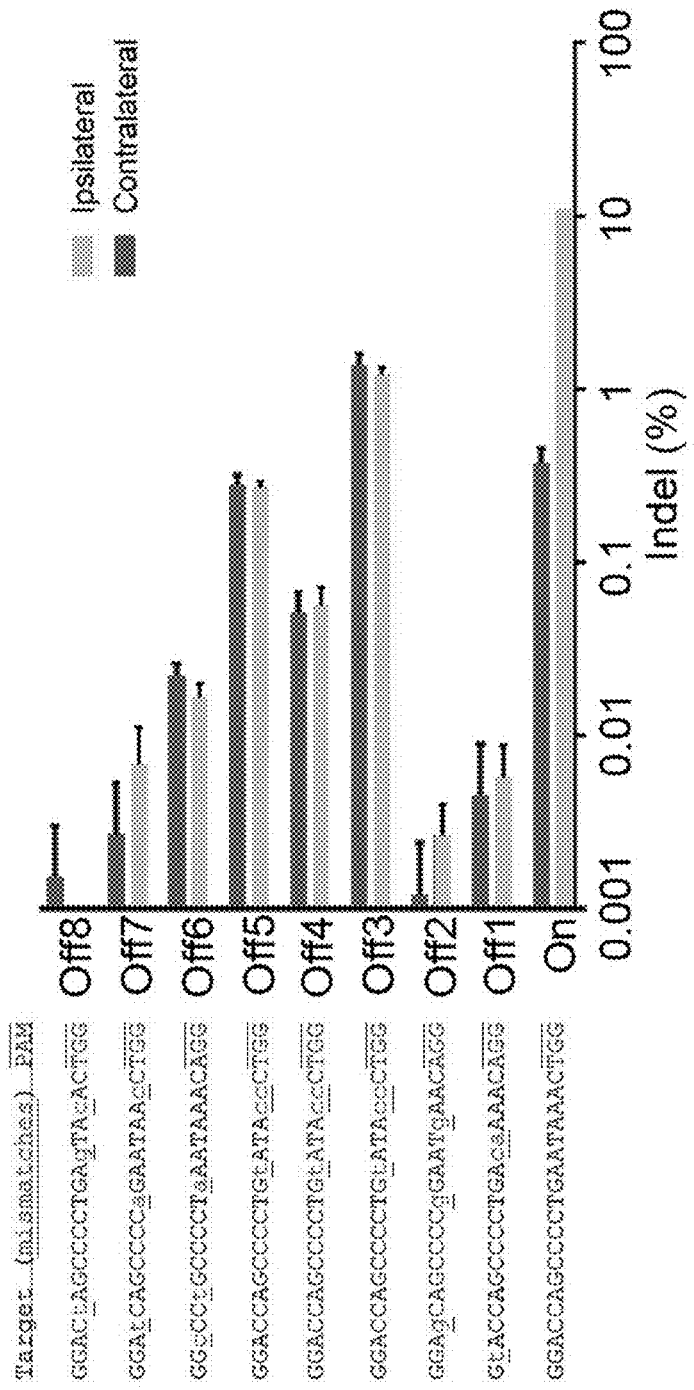

FIG. 23 is a graph illustrating an indel frequency at each off-target site of PMP22-TATA sgRNA in a mouse genome by an in silico analysis. The on-target sequence is a SEQ ID NO: 598, and the off-target sequences are SEQ ID NOs: 626 to 633 (Off1 to Off8 order).

Figure 24:
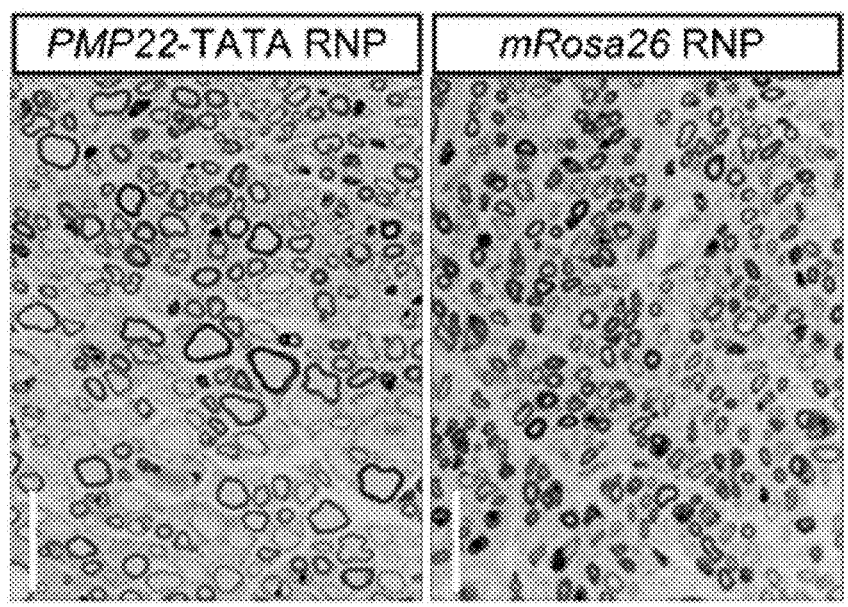

FIG. 24 is a set of images of a semithin section of the sciatic nerve tissue treated with mRosa26 or a PMP22-TATA RNP complex, shows the alleviation of a disease phenotype through expression inhibition of PMP22 by CRISPR/Cas9 in CMT1A mice.

Figure 25A:
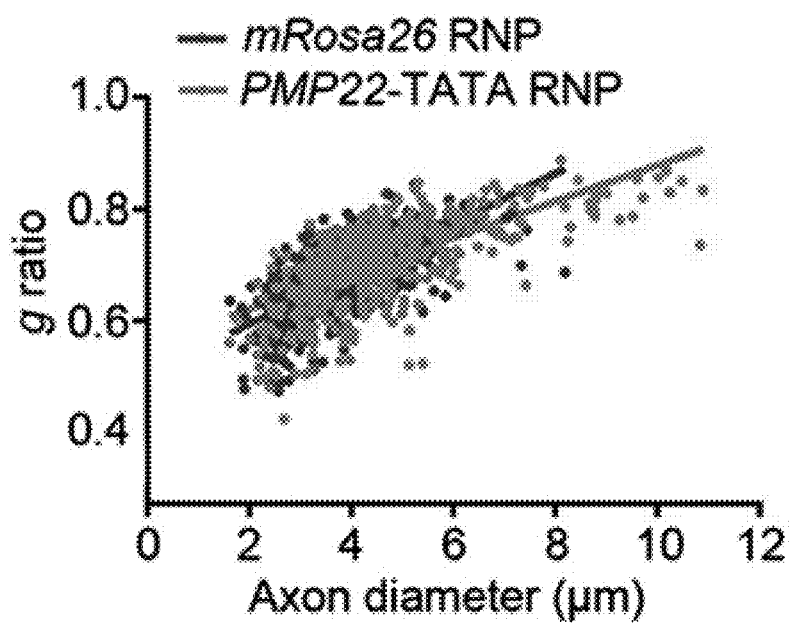
Figure 25B:
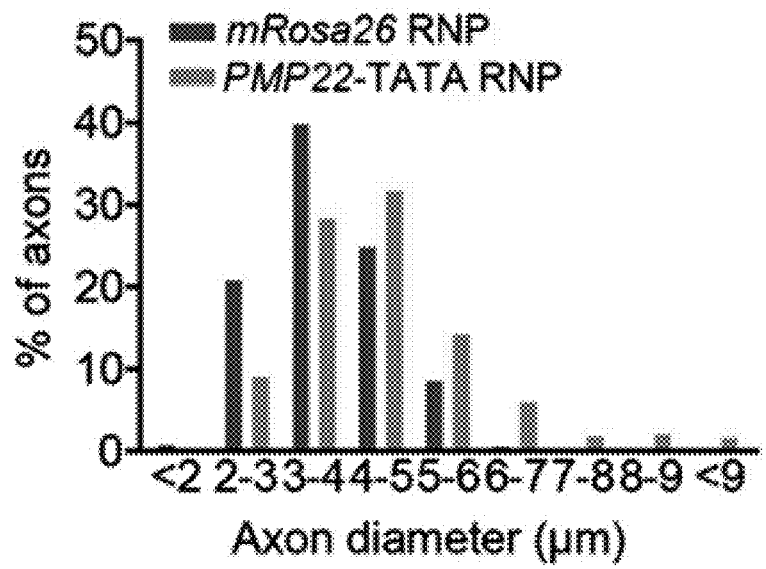

FIGS. 25A and 25B are a set of results illustrating the alleviation of a disease phenotype through expression inhibition of PMP22 by CRISPR/Cas9 in CMT1A mice, and the upper graph (a) and the low graph (b) are a scatter plot illustrating that the g-ratio is increased in mice treated with PMP22-TATA RNP and a graph illustrating that the diameter of the myelinated axon is increased in mice treated with PMP22-TATA RNP, respectively.

Figure 26A:
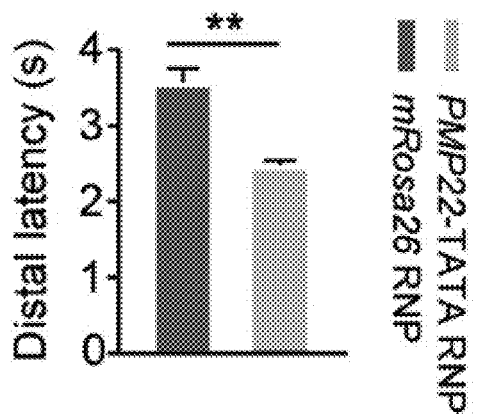
Figure 26B:
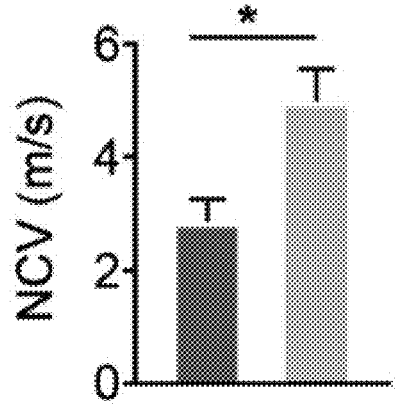
Figure 26C:
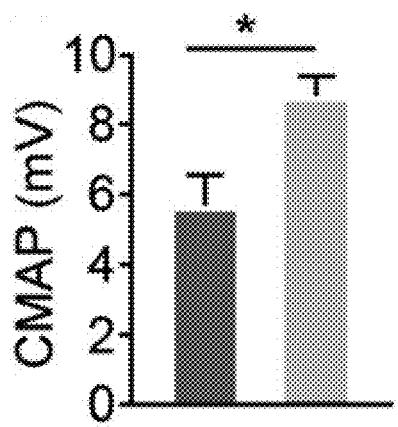

FIGS. 26A, 26B and 26C are a set of results illustrating electrophysiological changes through expression inhibition of PMP22 by CRISPR/Cas9 in CMT1A mice, and (a) is a graph illustrating the change in distal latency (DL), (b) is a graph illustrating the change in motor nerve conduction velocity (NCV), and (c) is a graph illustrating the change in compound muscle action potential (CMAP) (n=7 for mRosa26 RNP; n=10 for PMP22-TATA).

Figure 27A:
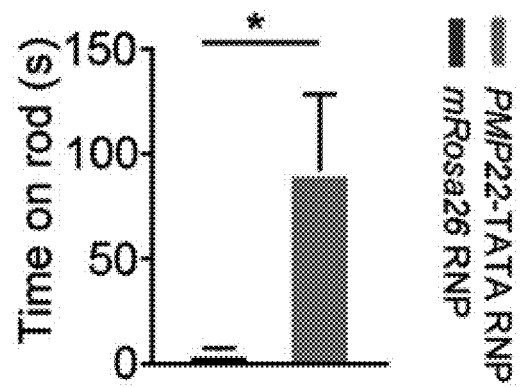
Figure 27B:
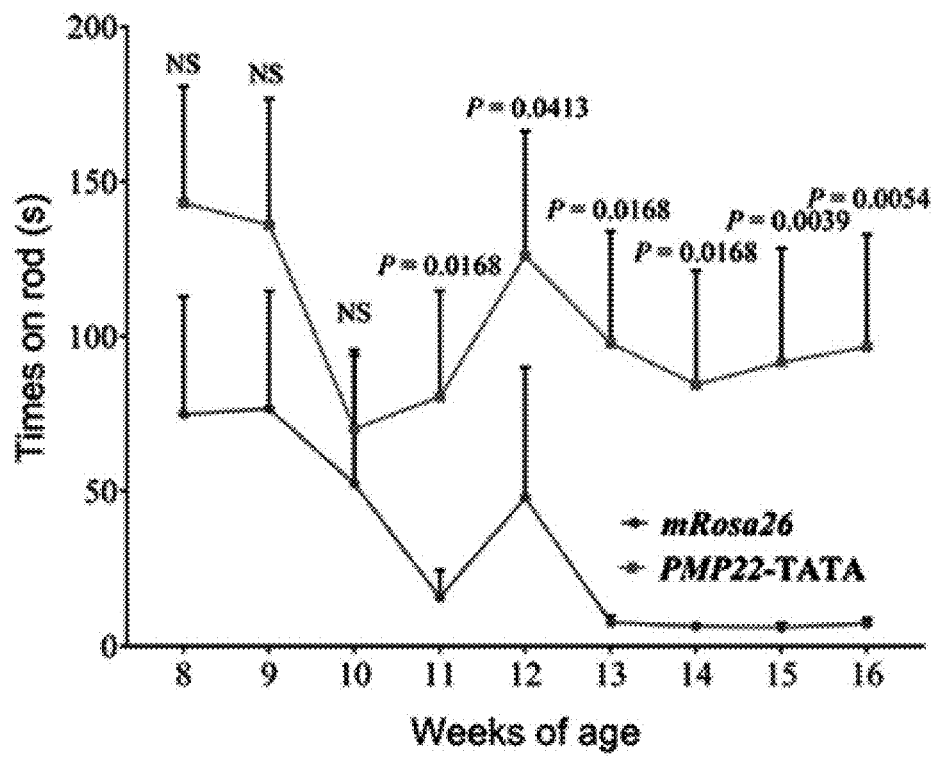

FIGS. 27A and 27B are a set of analysis results of locomotor behavior due to the expression inhibition of PMP22 by CRISPR/Cas9 in CMT1A mice, and the upper graph (a) and the lower graph (b) are a rotarod test result (n=7 for mRosa26 RNP, n=11 for PMP22-TATA) and a rotarod test result measured weekly until the mice became 8 weeks old to 16 weeks old (n=7 for mRosa26 RNP, n=11 for PMP22-TATA), respectively.

Figure 28A:
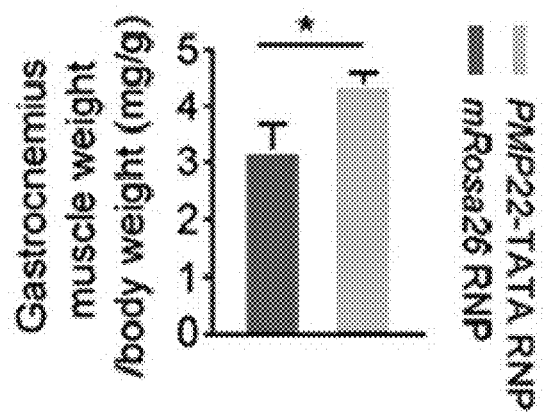
Figure 28B:
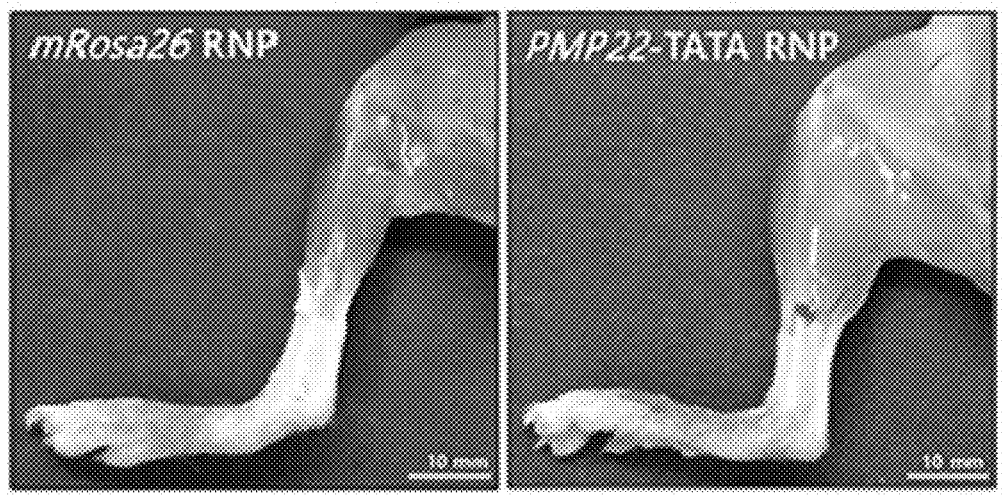

FIGS. 28A and 28B are a set of analysis results of locomotor behavior due to the expression inhibition of PMP22 by CRISPR/Cas9 in CMT1A mice, and the upper graph (a) and the lower image (b) are a graph illustrating the ratio of gastrocnemius muscle weight/body weight of a C22 mouse treated with mRosa26 or a PMP22-TATA RNP complex and a set of gastrocnemius muscle images of a C22 mouse treated with mRosa26 or a PMP22-TATA RNP complex, respectively.

Figure 29:
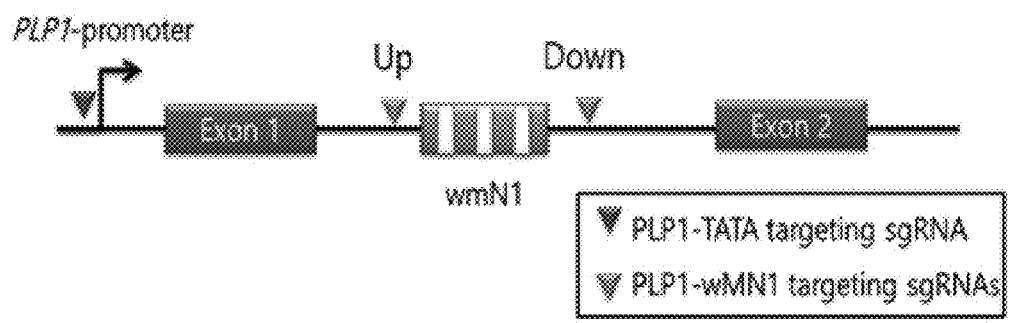

FIG. 29 is a schematic diagram illustrating a PMD therapeutic strategy, in which sgRNA targeting a TATA box region and an enhancer region of a PLP1 gene was designed. In the case of sgRNAs targeting the enhancer region, a strategy of removing an enhancer using two sgRNAs is shown. Here, sgRNA targeting the upstream of the enhancer region was represented as Up, and sgRNA targeting the downstream thereof was represented as down, and Up and Down are also represented according to locations in Tables 5 and 6.

Figure 30:
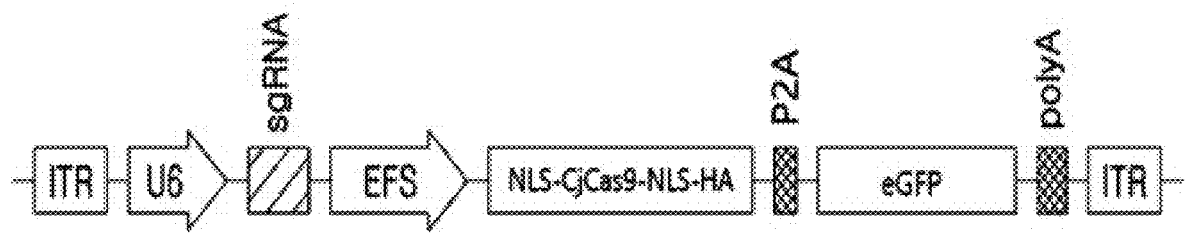

FIG. 30 illustrates a CjCas9 plasmid used in an exemplary embodiment.

Figure 31A:
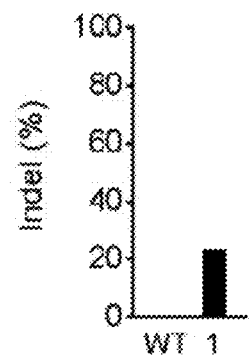
Figure 31B:
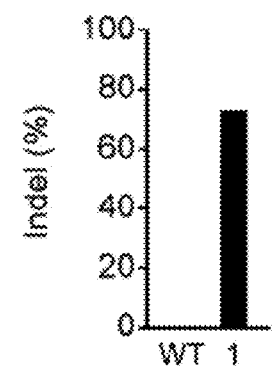

FIGS. 31A and 31B are a set of graphs showing screening results of SpCas9-sgRNAs targeting the TATA box region of mPlp1. (a) shows the indel frequency (%) confirmed in NIH-3T3 cells, and (b) shows the indel frequency (%) confirmed in N20.1 cells. Here, the used sgRNA are sgRNA targeting mPlp1-TATA-Sp-01, and distinguished by the numbers represented in target sequences on the graphs.

Figure 32A:
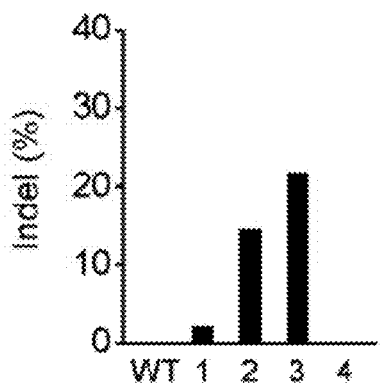
Figure 32B:
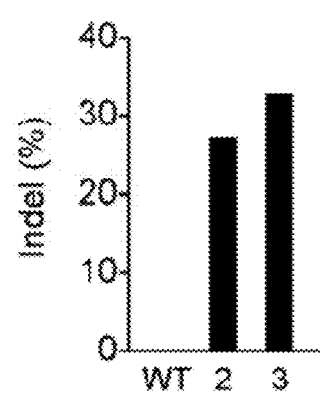

FIGS. 32A and 32B are a set of graphs showing screening results of CjCas9-sgRNAs targeting the TATA box region of mPlp1. (a) shows the indel frequency (%) confirmed in NIH-3T3 cells, and (b) shows the indel frequency (%) confirmed in N20.1 cells. Here, the used sgRNAs were mPlp1-TATA-Cj-01 to mPlp1-TATA-Cj-04, and distinguished by the numbers represented in target sequences on the graphs.

Figure 33A:
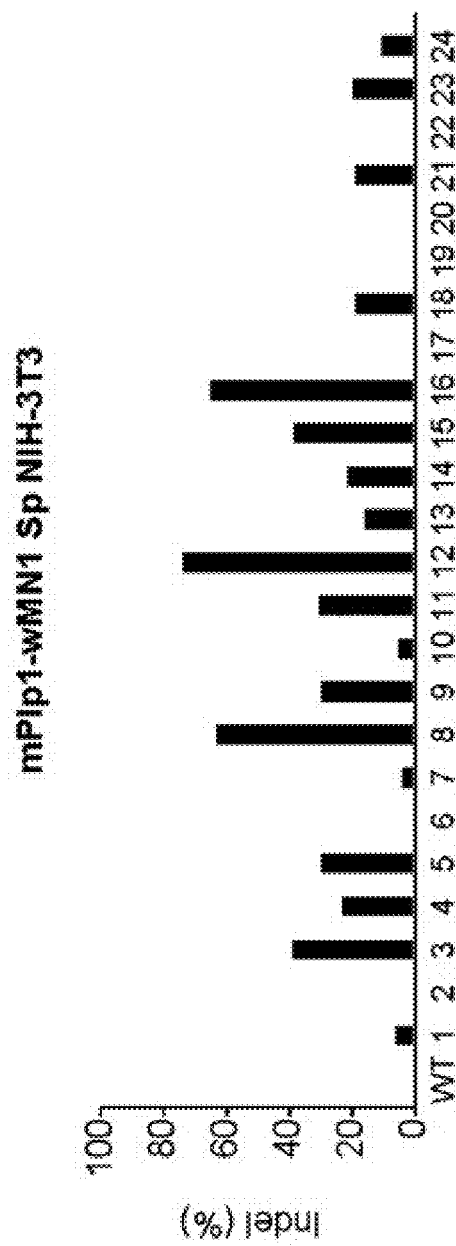
Figure 33B:
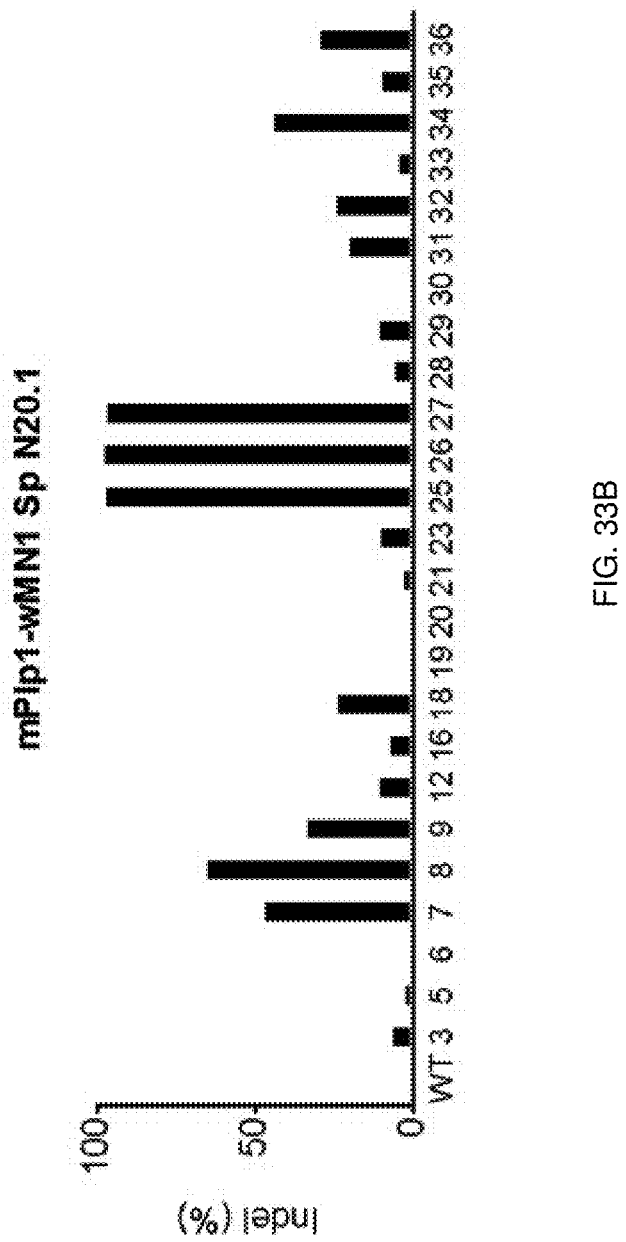

FIGS. 33A and 33B are a set of graphs showing screening results of SpCas9-sgRNAs targeting an enhancer (wMN1 enhancer) region of mPlp1. (a) shows the indel frequency (%) confirmed in NIH-3T3 cells, and (b) shows the indel frequency (%) confirmed in N20.1 cells. Here, the used sgRNAs were mPlp1-wMN1-Sp-01 to mPlp1-wMN1-Sp-36, and distinguished by the numbers represented in target sequences on the graphs.

Figure 34A:
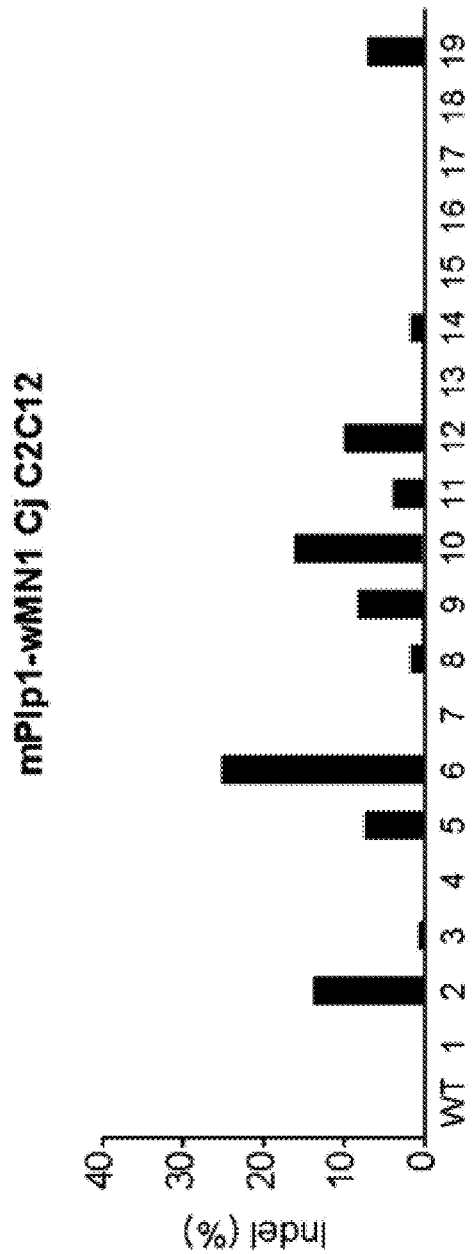
Figure 34B:
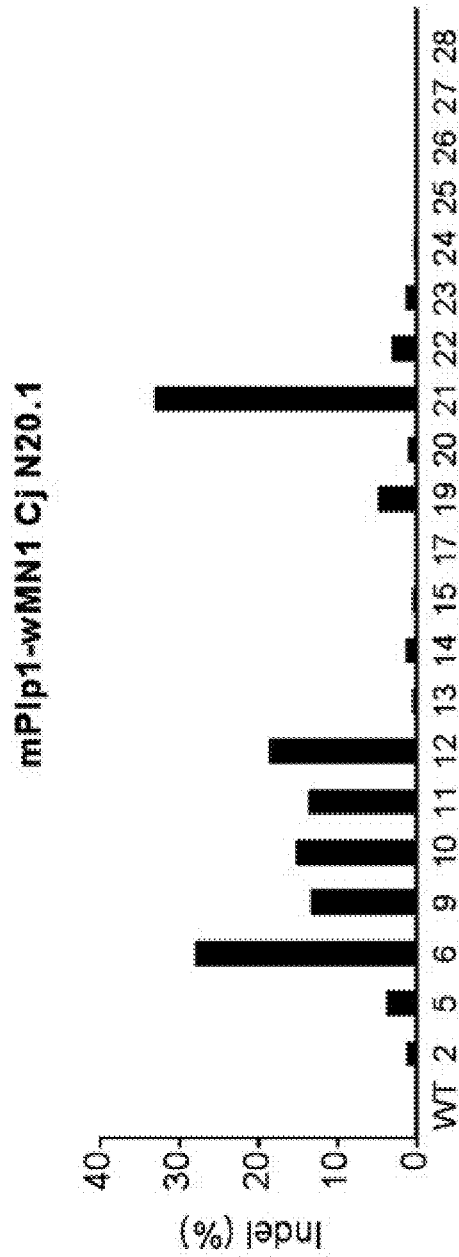

FIGS. 34A and 34B are a graph showing a screening result of CjCas9-sgRNAs targeting an enhancer (wMN1 enhancer) region of mPlp1. (a) shows the indel frequency (%) confirmed in NIH-3T3 cells, and (b) shows the indel frequency (%) confirmed in N20.1 cells. Here, the used sgRNAs were mPlp1-wMN1-Cj-01 to mPlp1-wMN1-Cj-28, and distinguished by the numbers represented in target sequences on the graph.

Figure 35A:
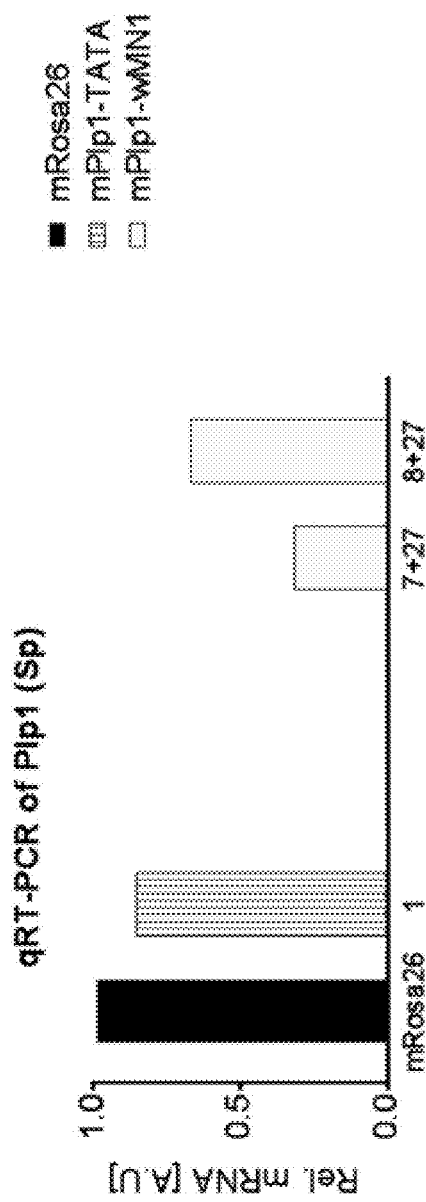
Figure 35B:
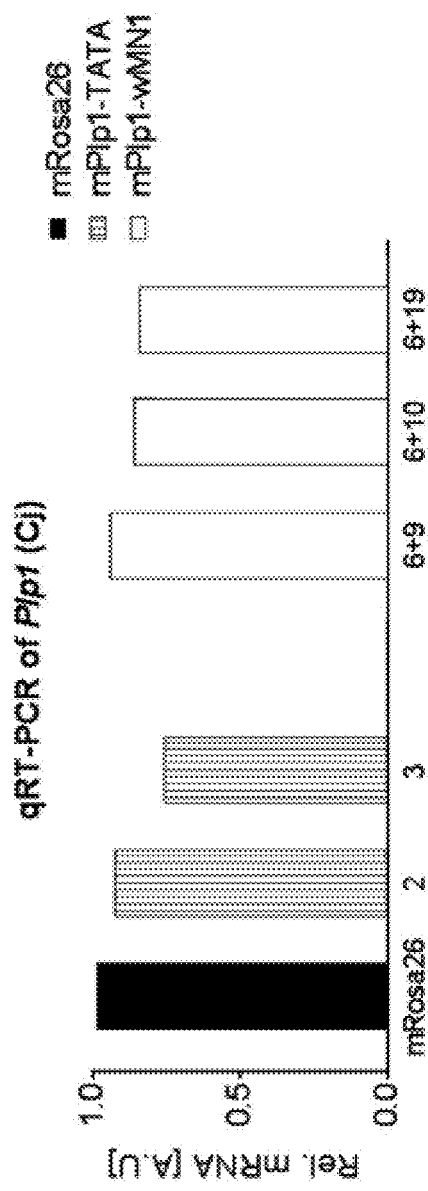

FIGS. 35A and 35B are a set of graphs showing the mRNA expression levels of Plp according to SpCas9-sgRNA and CjCas9-sgRNA targeting the TATA box and enhancer (wMN1 enhancer) regions of mPlp1. (a) shows the mRNA expression level of Plp according to SpCas9-sgRNA, and here, mPlp1-TATA-Sp-01 targeting the TATA box region and mPlp1-wMN1-Sp-07+mPlp1-wMN1-Sp-27 and mPlp1-wMN1-Sp-08+mPlp1-wMN1-Sp-27 targeting the enhancer were used as sgRNAs. (b) shows the mRNA expression level of Plp according to CjCas9-sgRNA, and here, mPlp1-TATA-Cj-02 and mPlp1-TATA-Cj-03 targeting the TATA box region; and mPlp1-wMN1-Cj-06+mPlp1-wMN1-Cj-09, mPlp1-wMN1-Cj-06+mPlp1-wMN1-Cj-10 and mPlp1-wMN1-Cj-06+mPlp1-wMN1-Cj-19 targeting the enhancer were used as sgRNAs. The mRosa26 was used as a control.

Figure 36:
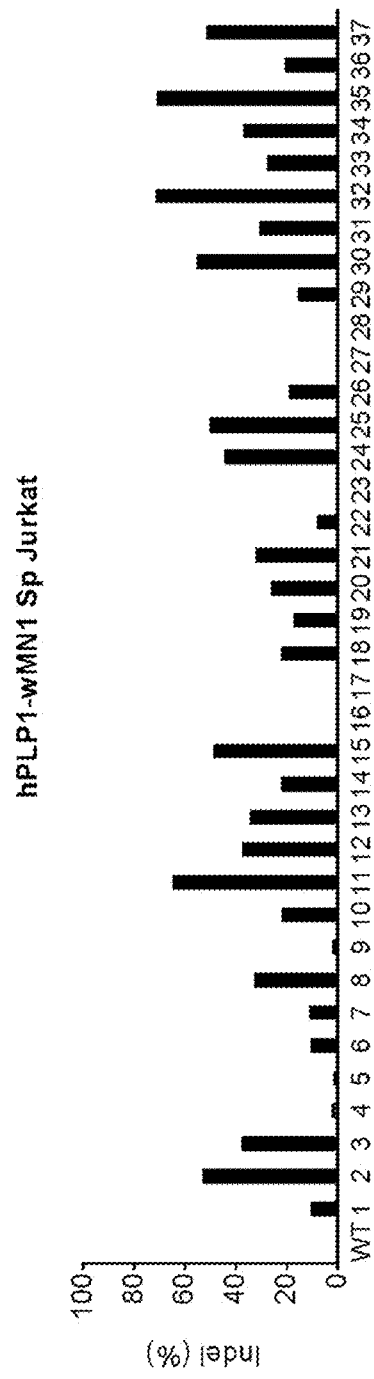

FIG. 36 is a graph showing a screening result of SpCas9-sgRNAs targeting the enhancer (wMN1 enhancer) region of hPLP1, showing indel frequencies (%) confirmed in Jurkat cells, and the used sgRNAs were hPLP1-wMN1-Sp-01 to hPLP1-wMN1-Sp-36, and distinguished by the numbers represented in target sequences on the graph.

Figure 37:
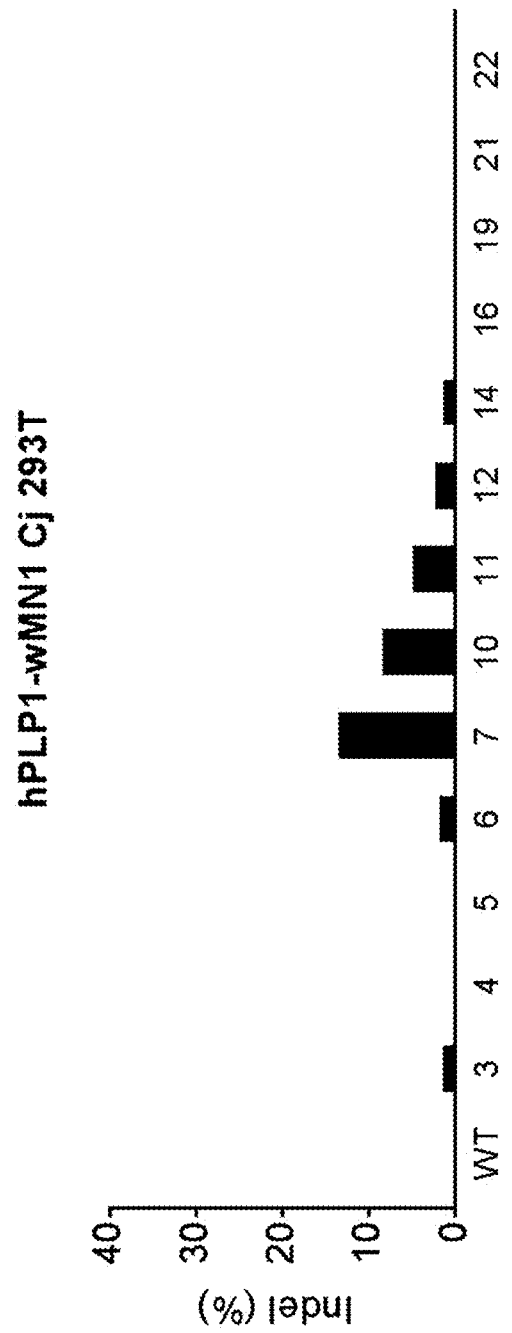

FIG. 37 is a graph showing a screening result of CjCas9-sgRNAs targeting the enhancer (wMN1 enhancer) region of hPLP1, showing indel frequencies (%) confirmed in 293T cells, and the used sgRNAs were hPLP1-wMN1-Cj-01 to hPLP1-wMN1-Cj-36, and distinguished by the numbers represented in target sequences on the graph.

Figure 38A:
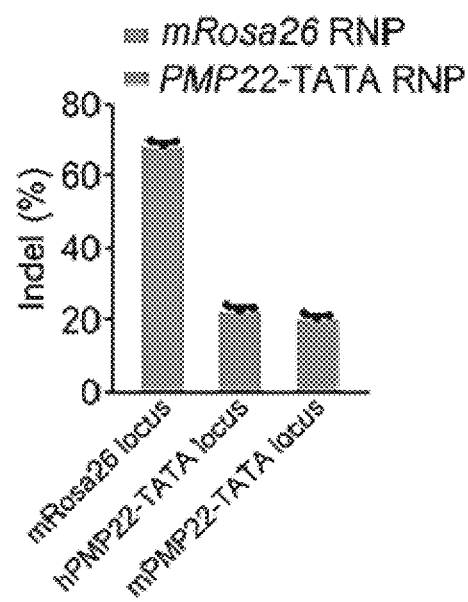
Figures 38B, 38C:
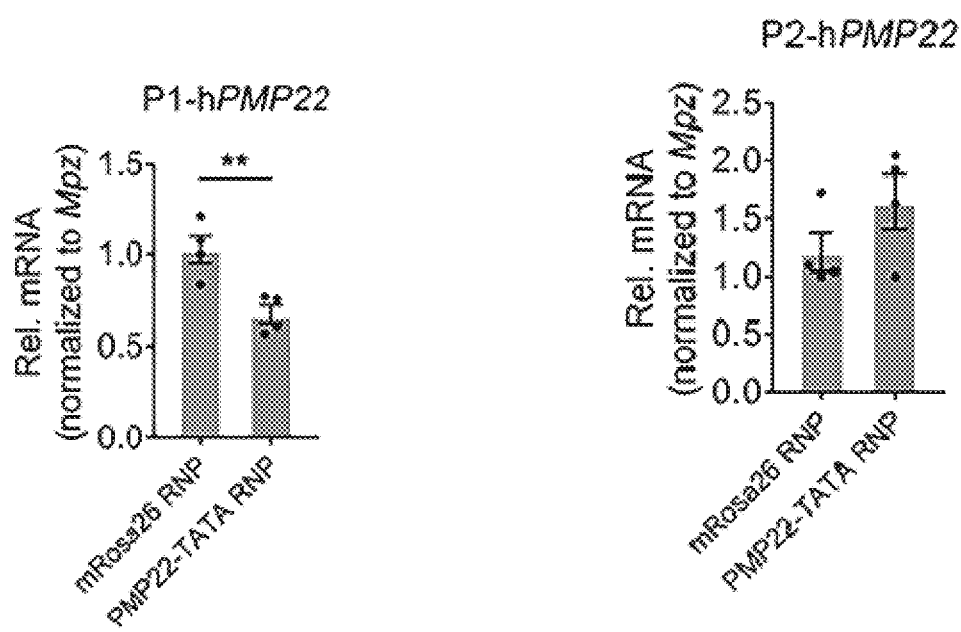

FIGS. 38A, 38B and 38C are a graph of comparing mRNA expression of human PMP22 by SpCas9-sgRNA-mediated gene manipulation, where (a) is a graph showing indel frequencies measurement results by SpCas9-sgRNA at TATA locus of human PMP22 gene and mouse PMP22 gene, (b) is a graph showing the mRNA expression of human PMP22 by SpCas9-sgRNA targeting a P1 promoter of a human PMP22 gene, and (c) is a graph showing the mRNA expression of human PMP22 bySpCas9-sgRNA targeting a P2 promoter of a human PMP22 gene.

Figure 39:
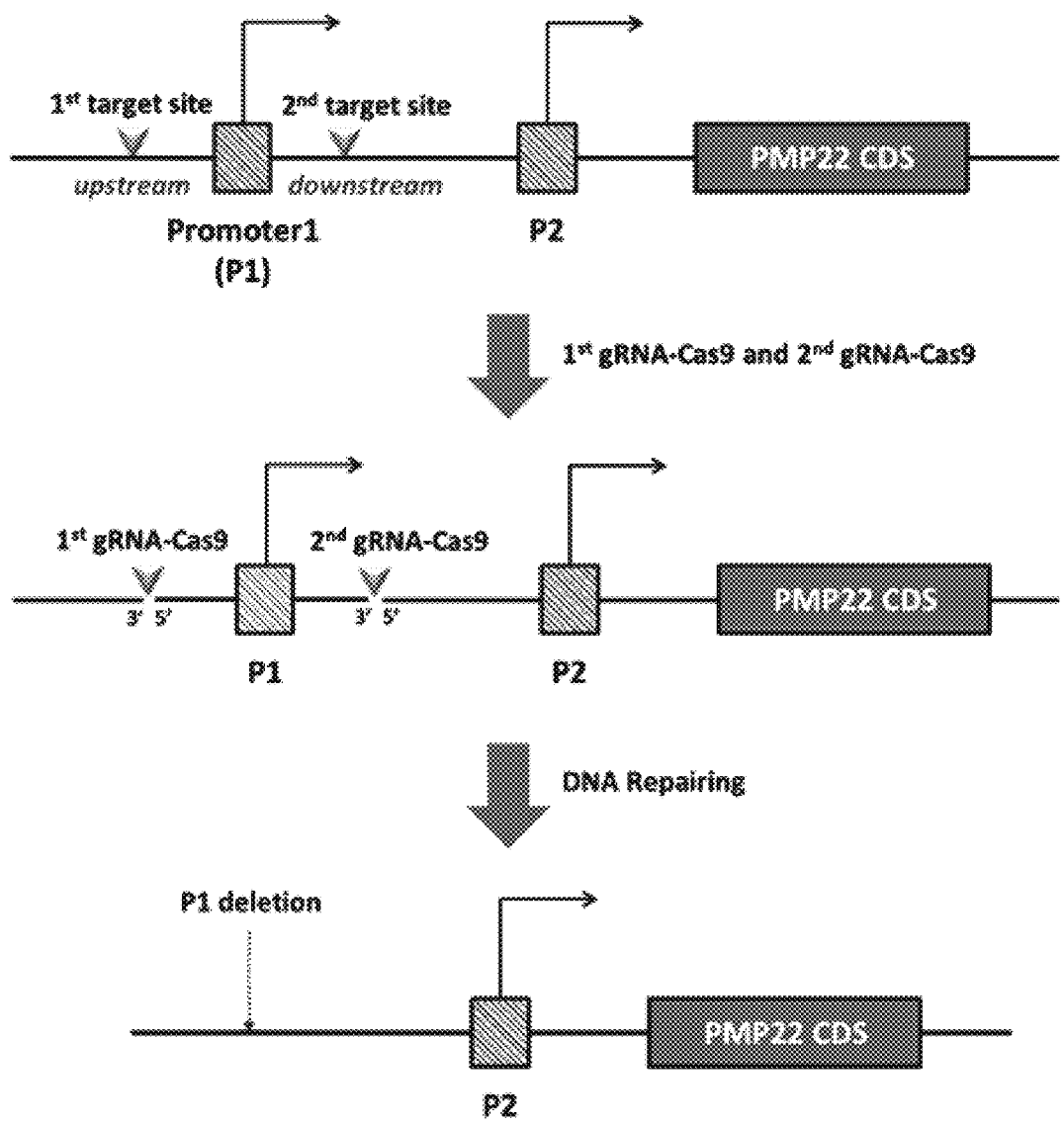

FIG. 39 illustrates the deletion of the transcriptional regulatory region of a duplicate gene using Cas9-sgRNA.

Figure 40:
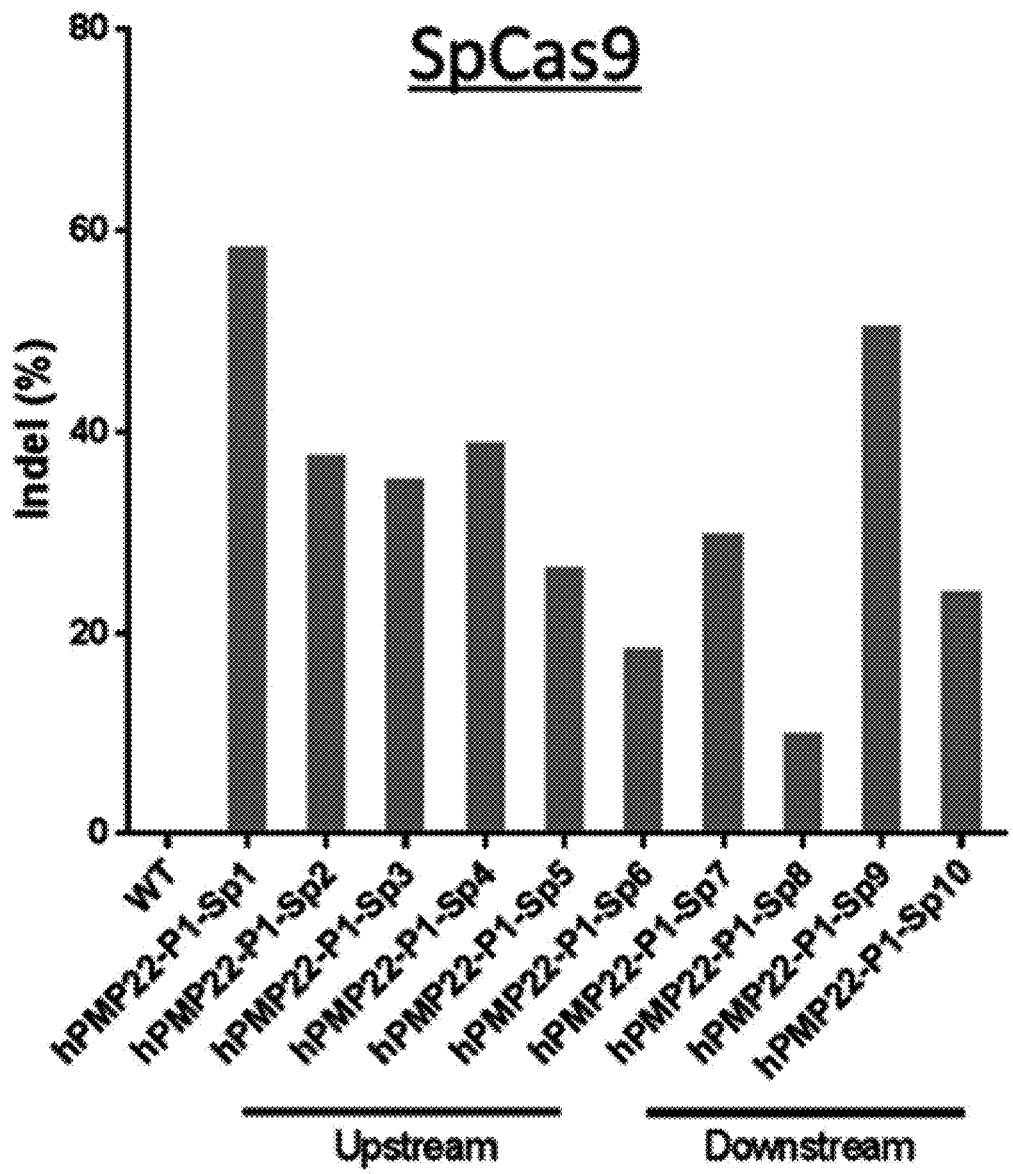

FIG. 40 illustrates indel frequencies (%) according to SpCas9-sgRNA-mediated gene manipulation, which are obtained by dividing a target site of sgRNA upstream and downstream.

Figure 41:
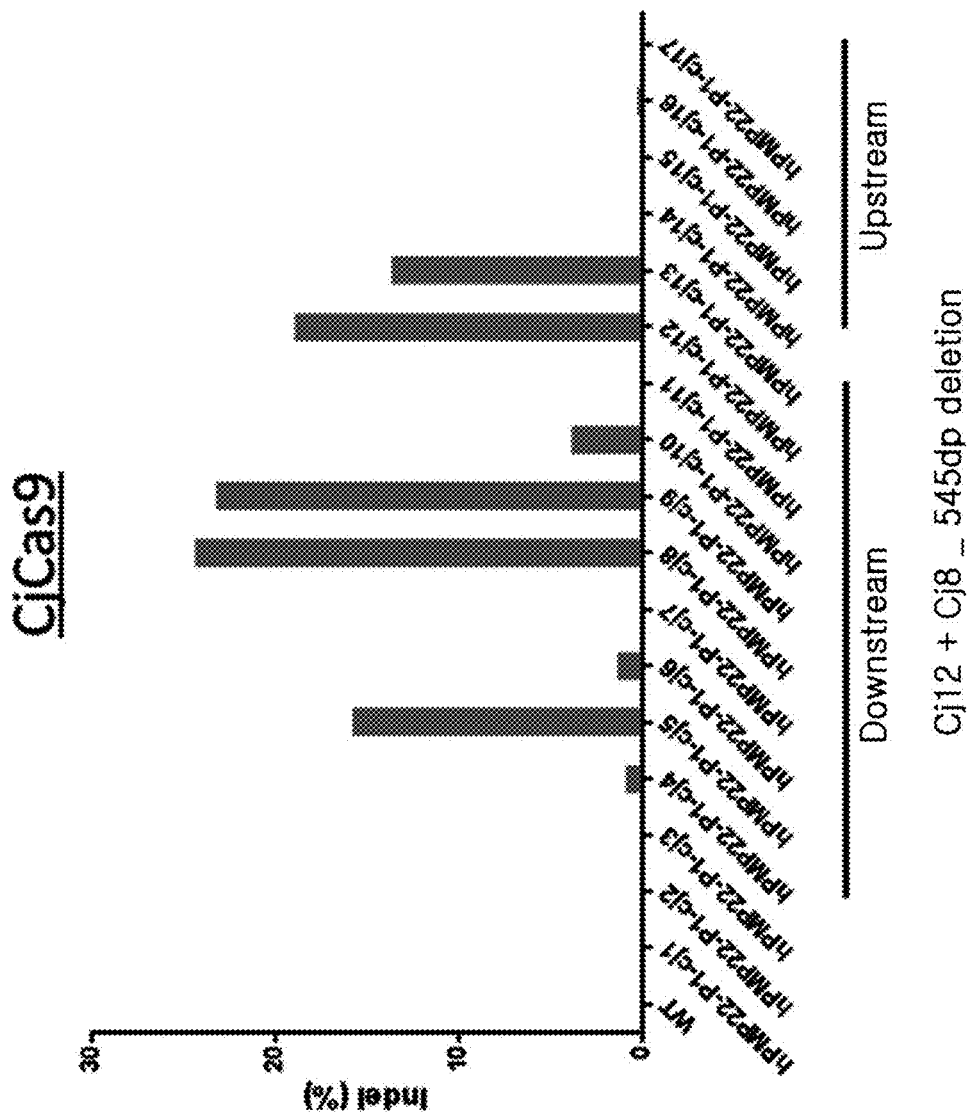

FIG. 41 illustrates indel frequencies (%) according to CjCas9-sgRNA-mediated gene manipulation, which are obtained by dividing a target site of sgRNA upstream and downstream.

Figure 42:
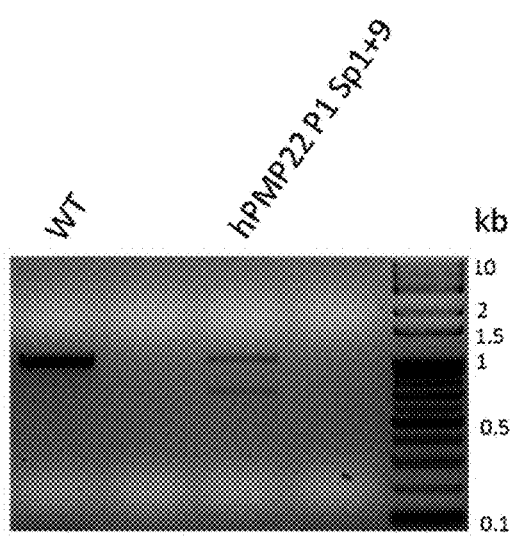

FIG. 42 illustrates the deletion of a PMP22 promoter1 using SpCas9-first sgRNA and SpCas9-second sgRNA.

Figure 43:
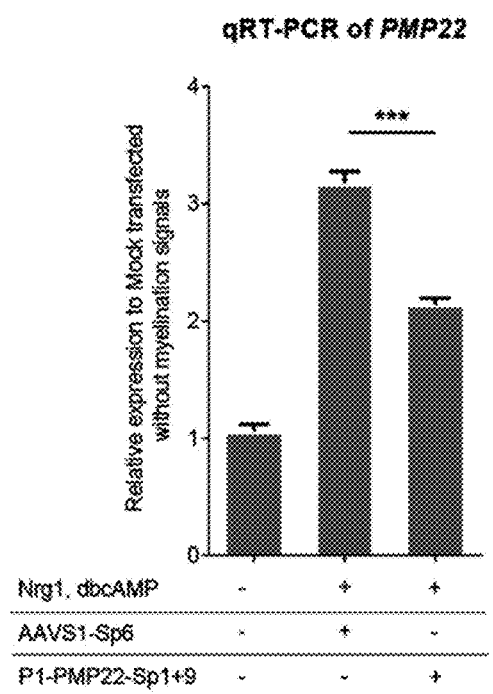

FIG. 43 illustrates the effect of reducing the PMP22 expression level by the deletion of PMP22 promoter1 using SpCas9-first sgRNA and SpCas9-second sgRNA.

DETAILED DESCRIPTION

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limitive.

One aspect disclosed in the specification relates to an expression control composition.

The expression control composition is a composition for controlling the expression of a duplicate gene by gene duplication.

The "gene duplication" means that two or more identical genes are present in a genome. The gene duplication also include having two or more parts of the same gene in a genome. For example, the gene duplication may mean to be present two or more full-length A genes in a genome, or one full-length A gene and one or more parts, for example, exon 1, of the A gene in a genome. For example, the gene duplication may mean to be present two full-length B genes and one or more parts, for example, exon 1 and exon 2, of the B gene in a genome. The type of gene duplication may vary, and the gene duplication includes duplications (that is, two or more) of a full-length gene and/or a partial sequence of the gene in a genome.

In addition, the gene duplication includes a replication phenomenon of duplicating a partial region of a chromosome, which occurs during the genetic recombination of the chromosome. Such gene duplication is a type of gene mutation, and is passed on to the next generation. The gene duplication affects gene expression along with gene deletion which occurs because a partial region of a gene is not replicated.

Here, an object of gene duplication, that is, a gene that is present in a number of two or more is referred to as a "duplicate gene (duplication gene)".

The duplicate gene may be a gene increased in total copy number in a genome due to gene duplication.

The duplicate gene may be a mutant gene in which only a partial region is duplicated due to gene duplication. Here, the mutant gene may be a gene in which one or more nucleotide sequences in the whole sequence of the gene are duplicated. Alternatively, the mutant gene may be a gene in which a partial nucleic acid fragment of the gene is duplicated due to gene duplication. Here, the nucleic acid fragment may have a nucleotide sequence of 50 bp or more.

The gene duplication includes whole genome duplication.

The gene duplication includes target gene duplication. Here, the target gene duplication is a type of gene duplication in which, in the differentiation and adaptation of a new species to environmental changes, a related gene is amplified or disappears to be suitable for a specific environment, and most replications are done by transposons.

The gene duplication includes ectopic recombination. Here, the ectopic recombination occurs according to the degree of repeat sequences between two chromosomes because of replication resulting from unequal crossover during meiosis of homologous chromosomes. Duplication at the crossover point and reciprocal deletion arise. The ectopic recombination is mediated by a typical repetitive genetic element such as a transposable element, and results in replication caused by recombination.

The gene duplication includes replication slippage. Here, the replication slippage is replication of a short genetic sequence due to an error during DNA replication, and occurs when a DNA polymerase is incorrectly attached to a denatured DNA strand, and the DNA strand is replicated again. The replication slippage is also frequently mediated by a repetitive genetic element.

The gene duplication includes retrotransposition. Here, the retrotransposition is replication mediated by a retrovirus or retroelement invading cells, in which reverse transcription of a gene is performed to form a retrogene, and due to the recombination of retrogenes, gene replication is performed. The retrotransposition is mediated by a genetic element such as a retrotransposable element.

The gene duplication may increase the expression of mRNA transcribed from a duplicate gene. Here, the expression of the transcribed mRNA may be increased compared to a state in which gene duplication does not occur.

The gene duplication may increase the expression of a protein encoded by a duplicate gene. Here, the expression of the protein may be increased compared to a state in which gene duplication does not occur.

The gene duplication may cause a dysfunction of a protein encoded by a duplicate gene.

Here, the dysfunction may be an overfunction, a suppressed function and a third function of the protein.

The gene duplication may cause a gene duplication disease.

The "gene duplication disease" is a disease caused by gene duplication, and includes all diseases or disorders causing a genetic abnormality by abnormal amplification of a duplicate gene, and inducing pathological characteristics by a protein overexpressed or abnormally produced thereby. Here, the "pathological characteristics" refers to changes at a cellular level of an organism, and tissue, organ and individual levels due to a disease.

The gene duplication disease may be Charcot-Marie-Tooth Type 1A (CMT1A), Dejerine-Sottas disease (DSD), congenital hypomyelination neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), velocardiofacial syndrome (VCFS), Williams Beuren syndrome (WBS), Alagille syndrome (AS), growth retardation syndrome, premature closure cranial sutures, autosomal dominant leukodystrophy (ADLD), Parkinson's disease or Alzheimer's disease.

The gene duplication disease may be a cancer caused by oncogene duplication.

Here, the cancer may be breast cancer, cervical cancer, colorectal cancer, esophageal cancer, gastric cancer, glioblastoma, head and neck cancer, hepatocellular cancer, neuroblastoma, ovarian cancer, sarcoma or small cell lung cancer.

The gene duplication disease may be a disease caused by duplication of a PMP22 gene, a PLP1 gene, an MECP2 gene, a SOX3 gene, a RAI1 gene, a TBX1 gene, an ELN gene, a JAGGED1 gene, a NSD1 gene, a MMP23 gene, a LMB1 gene, a SNCA gene or an APP gene.

The gene duplication disease may be a disease caused by duplication of an MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene or an AKT2 gene.

The gene duplication disease may be a disease caused by an abnormal increase in the expression of transcribed mRNA of a duplicate gene.

The gene duplication disease may be a disease caused by an abnormal increase in the expression of a protein encoded by a duplicate gene.

The expression control composition may be used in the control of the expression of mRNA produced by transcription of a duplicate gene.

The expression control composition may be used in the control of the expression of a protein encoded by a duplicate gene.

The expression control composition may be used for artificial modification or manipulation of a duplicate gene.

Here, the "artificially modification or manipulation (artificially modified, manipulated or engineered)" refers to an artificially modified state, rather than a naturally-occurring state. Hereinafter, an unnaturally, artificially modified or manipulated duplicate gene may be used interchangeably with an artificial duplicate gene.

The "expression control system" is the term including all phenomena occurring due to the control of the expression of an artificially manipulated duplicate gene, and all materials, compositions, methods and uses directly or indirectly involved in the expression control system.

The expression control composition may be used for artificial manipulation or modification of the transcriptional regulatory region of the duplicate gene.

Here, the "transcriptional regulatory region (transcription control region)" is a region controlling an overall process of synthesizing RNA based on DNA of a gene, and includes all regions which interact with a transcription factor in a DNA sequence of a gene and/or a proximal DNA sequence of a gene. Here, the transcription factor is a protein that, when activated, binds to a specific region of DNA, that is, a response element close to a gene, thereby promoting or inhibiting gene expression, and the response element is included in the transcriptional regulatory region. The types and positions of the transcriptional regulatory region may vary according to a gene, and even in the same species, there may be a difference in nucleic acid sequences between individuals.

The transcriptional regulatory region may be a promoter, an enhancer, a silencer, an insulator and/or a locus control region (LCR).

The promoter may be a core promoter, a proximal promoter and/or a distal promoter.

Here, the core promoter may include a transcription start site (TSS), an RNA polymerase-binding site, a transcription factor-binding site and/or a TATA box.

The TATA box may be a region located 25 base pairs upstream of an initiation site used to initiate the transcription of Rpb4/Rbp7.

The TATA box may be a region located 30 base pairs upstream of the TSS.

The TATA box may be a region located 40 to 100 base pairs upstream of the TSS.

For example, the TATA box may be a region including a 5'-TATA(A/T)A(A/T)-3' sequence present in a promoter and/or a core promoter. Alternatively, the TATA box may be a region including a 5'-TATA(A/T)A(A/T)(A/G)-3' sequence present in a promoter and/or a core promoter.

For example, the TATA box may be a region including one or more sequences selected form the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence, which are present in a promoter and/or a core promoter.

For example, the TATA box may be a region in which a TATA-binding protein (TBP) present in a promoter and/or a core promoter binds.

Here, the proximal promoter may include a region 1 to 300-bp upstream of the TSS, a CpG site and/or a specific transcription factor-binding site.

The enhancer may include an enhancer-box (E-box).

The insulator may be a region that inhibits an interaction between an enhancer and a promoter or prevents the expansion of suppressed chromatin.

The locus control region (LCR) may be a region in which numerous cis-acting factors such as an enhancer, a silencer, an insulator, MAR, and SAR are present.

As one aspect disclosed in the specification, the expression control composition may include a guide nucleic acid.

The expression control composition may include a guide nucleic acid targeting a duplicate gene or a nucleic acid sequence encoding the same.

The "guide nucleic acid" refers to a nucleotide sequence that recognizes a target nucleic acid, gene or chromosome, and interacts with an editor protein. Here, the guide nucleic acid may complementarily bind to a partial nucleotide sequence in the target nucleic acid, gene or chromosome. In addition, a partial nucleotide sequence of the guide nucleic acid may interact with some amino acids of the editor protein, thereby forming a guide nucleic acid-editor protein complex.

The guide nucleic acid may perform a function to induce a guide nucleic acid-editor protein complex to be located in a target region of a target nucleic acid, gene or chromosome.

The guide nucleic acid may be present in the form of DNA, RNA or a DNA/RNA hybrid, and may have a nucleic acid sequence of 5 to 150 nt.

The guide nucleic acid may have one continuous nucleic acid sequence.

For example, the one continuous nucleic acid sequence may be $(N)_m$, where N represents A, T, C or G, or A, U, C or G, and m is an integer of 1 to 150.

The guide nucleic acid may have two or more continuous nucleic acid sequences.

For example, the two or more continuous nucleic acid sequences may be $(N)_m$ and $(N)_o$, where N represents A, T, C or G, or A, U, C or G, m and o are an integer of 1 to 150, and m and o may be the same as or different from each other.

The guide nucleic acid may include one or more domains.

The domains may be, but are not limited to, a guide domain, a first complementary domain, a linker domain, a second complementary domain, a proximal domain, or a tail domain.

Here, one guide nucleic acid may have two or more functional domains. Here, the two or more functional domains may be different from each other. For one example, one guide nucleic acid may have a guide domain and a first complementary domain. For another example, one guide nucleic acid may have a second complementary domain, a proximal domain and a tail domain. For still another example, one guide nucleic acid may have a guide domain, a first complementary domain, a second complementary domain, a proximal domain and a tail domain. Alternatively, the two or more functional domains included in one guide nucleic acid may be the same as each other. For one example, one guide nucleic acid may have two or more proximal domains. For another example, one guide nucleic acid may have two or more tail domains. However, the description that the functional domains included in one guide nucleic acid are the same domains does not mean that the sequences of the two functional domains are the same. Even if the sequences are different, the two functional domain can be the same domain when perform functionally the same function.

The functional domain will be described in detail below.

i) Guide Domain

The term "guide domain" is a domain capable of complementary binding with partial sequence of either strand of a double strand of a nucleic acid in a transcriptional regulatory region of a target gene, and acts for specific interaction with a nucleic acid in a transcriptional regulatory region of a target gene. For example, the guide domain may perform a function to induce a guide nucleic acid-editor protein complex to be located to a specific nucleotide sequence in a nucleic acid of a transcriptional regulatory region of a target gene.

The guide domain may be a sequence of 10 to 35 nucleotides.

In an example, the guide domain may be a sequence of 10 to 35, 15 to 35, 20 to 35, 25 to 35 or 30 to 35 nucleotides.

In another example, the guide domain may be a sequence of 10 to 15, 15 to 20, 20 to 25, 25 to 30 or 30 to 35 nucleotides.

The guide domain may have a guide sequence.

The term "guide sequence" is a nucleotide sequence complementary to partial sequence of either strand of a double strand of a nucleic acid in a transcriptional regulatory region of a target gene. Here, the guide sequence may be a nucleotide sequence having at least 50%, 55%, 60%, 65%, 70%, 75%, 80%, 85%, 90%, 95% or more complementarity or complete complementarity.

The guide sequence may be a sequence of 10 to 25 nucleotides.

In an example, the guide sequence may be a sequence of 10 to 25, 15 to 25 or 20 to 25 nucleotides.

In another example, the guide sequence may be a sequence of 10 to 15, 15 to 20 or 20 to 25 nucleotides.

In addition, the guide domain may further include an additional nucleotide sequence.

The additional nucleotide sequence may be utilized to improve or degrade the function of the guide domain.

The additional nucleotide sequence may be utilized to improve or degrade the function of the guide sequence.

The additional nucleotide sequence may be a sequence of 1 to 10 nucleotides.

In one example, the additional nucleotide sequence may be a sequence of 2 to 10, 4 to 10, 6 to 10 or 8 to 10 nucleotides.

In another example, the additional nucleotide sequence may be a sequence of 1 to 3, 3 to 6 or 7 to 10 nucleotides.

In one embodiment, the additional nucleotide sequence may be a sequence of 1, 2, 3, 4, 5, 6, 7, 8, 9 or 10 nucleotides.

For example, the additional nucleotide sequence may be one nucleotide sequence G (guanine), or two nucleotide sequence GG.

The additional nucleotide sequence may be located at the 5' end of the guide sequence.

The additional nucleotide sequence may be located at the 3' end of the guide sequence.

ii) First Complementary Domain

The term "first complementary domain" is a domain including a nucleotide sequence complementary to a second complementary domain to be described in below, and has enough complementarity so as to form a double strand with the second complementary domain. For example, the first complementary domain may be a nucleotide sequence having at least 50%, 55%, 60%, 65%, 70%, 75%, 80%, 85%, 90%, 95% or more complementarity or complete complementarity to a second complementary domain.

The first complementary domain may form a double strand with a second complementary domain by a complementary binding. Here, the formed double strand may act to form a guide nucleic acid-editor protein complex by interacting with some amino acids of the editor protein.

The first complementary domain may be a sequence of 5 to 35 nucleotides.

In an example, the first complementary domain may be a sequence of 5 to 35, 10 to 35, 15 to 35, 20 to 35, 25 to 35, or 30 to 35 nucleotides.

In another example, the first complementary domain may be a sequence of 1 to 5, 5 to 10, 10 to 15, 15 to 20, 20 to 25, 25 to 30 or 30 to 35 nucleotides.

iii) Linker Domain

The term "linker domain" is a nucleotide sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a sequence of 1 to 30 nucleotides.

In one example, the linker domain may be a sequence of 1 to 5, 5 to 10, 10 to 15, 15 to 20, 20 to 25, or 25 to 30 nucleotides.

In another example, the linker domain may be a sequence of 1 to 30, 5 to 30, 10 to 30, 15 to 30, 20 to 30, or 25 to 30 nucleotides.

iv) Second Complementary Domain

The term "second complementary domain" is a domain including a nucleotide sequence complementary to the first complementary domain described above, and has enough complementarity so as to form a double strand with the first complementary domain. For example, the second complementary domain may be a nucleotide sequence having at least 50%, 55%, 60%, 65%, 70%, 75%, 80%, 85%, 90%, 95% or more complementarity or complete complementarity to a first complementary domain.

The second complementary domain may form a double strand with a first complementary domain by a complementary binding. Here, the formed double strand may act to form a guide nucleic acid-editor protein complex by interacting with some amino acids of the editor protein. The second complementary domain may have a nucleotide sequence complementary to a first complementary domain, and a nucleotide sequence having no complementarity to the first complementary domain, for example, a nucleotide sequence not forming a double strand with the first complementary domain, and may have a longer base sequence than the first complementary domain.

The second complementary domain may be a sequence of 5 to 35 nucleotides.

In an example, the second complementary domain may be a sequence of 5 to 35, 10 to 35, 15 to 35, 20 to 35, 25 to 35, or 30 to 35 nucleotides.

In another example, the second complementary domain may be a sequence of 1 to 5, 5 to 10, 10 to 15, 15 to 20, 20 to 25, 25 to 30 or 30 to 35 nucleotides.

v) Proximal Domain

The term "proximal domain" is a nucleotide sequence located adjacent to a second complementary domain.

The proximal domain may have a complementary nucleotide sequence therein, and may be formed in a double strand due to a complementary nucleotide sequence.

The proximal domain may be a sequence of 1 to 20 nucleotides.

In one example, the proximal domain may be a sequence of 1 to 20, 5 to 20, 10 to 20 or 15 to 20 nucleotide.

In another example, the proximal domain may be a sequence of 1 to 5, 5 to 10, 10 to 15 or 15 to 20 nucleotides.

vi) Tail Domain

The term "tail domain" is a nucleotide sequence located at one or more ends of the both ends of the guide nucleic acid.

The tail domain may have a complementary nucleotide sequence therein, and may be formed in a double strand due to a complementary nucleotide sequence.

The tail domain may be a sequence of 1 to 50 nucleotides.

In an example, the tail domain may be a sequence of 5 to 50, 10 to 50, 15 to 50, 20 to 50, 25 to 50, 30 to 50, 35 to 50, 40 to 50, or 45 to 50 nucleotides.

In another example, the tail domain may be a sequence of 1 to 5, 5 to 10, 10 to 15, 15 to 20, 20 to 25, 25 to 30, 30 to 35, 35 to 40, 40 to 45, or 45 to 50 nucleotides.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP).

The guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

In one exemplary embodiment disclosed in the specification, the guide nucleic acid may be a gRNA.

The term "gRNA" refers to a RNA capable of specifically targeting a gRNA-CRISPR enzyme complex, that is, a CRISPR complex, with respect to a nucleic acid in a transcriptional regulatory region of a target gene. In addition, the gRNA is a RNA specific to the nucleic acid in the transcriptional regulatory region of the target gene, which may bind to a CRISPR enzyme and guide the CRISPR enzyme to the transcriptional regulatory region of the target gene.

The gRNA may include multiple domains. Due to each domain, interactions may occur in a three-dimensional structure or active form of a gRNA strand, or between these strands.

The gRNA may be called single-stranded gRNA (single RNA molecule, single gRNA or sgRNA); or double-stranded gRNA (including more than one, generally, two discrete RNA molecules).

In one exemplary embodiment, the single-stranded gRNA may include a guide domain, that is, a domain including a guide sequence capable of forming a complementary bond with a nucleic acid in a transcriptional regulatory region of a target gene; a first complementary domain; a linker domain; a second complementary domain, which is a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a nucleic acid in a transcriptional regulatory region of a target gene and a first complementary domain; and a second strand which includes a second complementary domain, which is a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a nucleic acid in a transcriptional regulatory region of a target gene; a first complementary domain; a second complementary domain, and a domain having a sequence complementary to the first complementary domain sequence, thereby forming a double-stranded nucleic acid with the first complementary domain in the 5' to 3' direction.

Here, the first complementary domain may have homology with a natural first complementary domain, or may be derived from a natural first complementary domain. In addition, the first complementary domain may have a difference in the nucleotide sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Staphylococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUUAGAGCUA-3' (SEQ ID NO: 296) or a nucleotide sequence having partial, that is, at least 50% or more, or complete homology with 5'-GUUUUAGAGCUA-3' (SEQ ID NO: 296). Here, the first complementary domain may further include $(X)_n$, resulting in 5'-GUUUUAGAGCUA$(X)_n$-3' (SEQ ID NO: 296). The X may be selected from the group consisting of bases A, T, U and G, and the n may represent the number of nucleotides, which is an integer of 5 to 15. Here, the $(X)_n$ may be n repeats of the same nucleotide, or a mixture of n nucleotides of A, T, U and G.

In another embodiment, when the first complementary domain is the first complementary domain of *Campylobacter jejuni* or a first complementary domain derived therefrom, the first complementary domain may be 5'-GUUUUAGUCCCUUUUUAAAUUUCUU-3' (SEQ ID NO: 297), or a nucleotide sequence having partial, that is, at least 50% or more, or complete homology with 5'-GUUUUAGUCCCUUUUUAAAUUUCUU-3' (SEQ ID NO: 297). Here, the first complementary domain may further include $(X)_n$, resulting in 5'-GUUUUAGUCCCUUUUUAAAUUUCUU$(X)_n$-3' (SEQ ID NO: 297). The X may be selected from the group consisting of nucleotides A, T, U and G, and the n may represent the number of nucleotides, which is an integer of 5 to 15. Here, the $(X)_n$ may represent n repeats of the same nucleotide, or a mixture of n nucleotides of A, T, U and G.

In another embodiment, the first complementary domain may have partial, that is, at least 50% or more, or complete homology with a first complementary domain of *Parcubacteria bacterium* (GWC2011_GWC2_44_17), *Lachnospiraceae bacterium* (MC2017), *Butyrivibrio proteoclasiicus*, *Peregrinibacteria bacterium* (GW2011_GWA_33_10), *Acidaminococcus* sp. (BV3L6), *Porphyromonas macacae*, *Lachnospiraceae bacterium* (ND2006), *Porphyromonas crevioricanis*, *Prevotella disiens*, *Moraxella bovoculi* (237), *Smiihella* sp. (SC_K08D17), *Leptospira inadai*, *Lachnospiraceae bacterium* (MA2020), *Francisella novicida* (U112), *Candidatus Methanoplasma termitum* or *Eubacterium eligens*, or a first complementary domain derived therefrom.

For example, when the first complementary domain is the first complementary domain of *Parcubacteria bacterium* or a first complementary domain derived therefrom, the first complementary domain may be 5'-UUUGUAGAU-3' (SEQ ID NO: 298), or a nucleotide sequence having partial, that is, at least 50% or more homology with 5'-UUUGUAGAU-3' (SEQ ID NO: 298). Here, the first complementary domain may further include $(X)_n$, resulting in 5'-$(X)_n$UUUGUAGAU-3' (SEQ ID NO: 298). The X may be selected from the group consisting of nucleotides A, T, U and G, and the n may represent the number of nucleotides, which is an integer of 1 to 5. Here, the $(X)_n$ may represent n repeats of the same nucleotide, or a mixture of n nucleotides of A, T, U and G.

Here, the linker domain may be a nucleotide sequence connecting a first complementary domain with a second complementary domain.

The linker domain may form a covalent or non-covalent bonding with a first complementary domain and a second complementary domain, respectively.

The linker domain may connect the first complementary domain with the second complementary domain covalently or non-covalently.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding.

The linker domain may be used to produce single-stranded gRNA by being connected with crRNA and tracrRNA of double-stranded gRNA or connecting the crRNA with the tracrRNA by covalent or non-covalent bonding.

Here, the second complementary domain may have homology with a natural second complementary domain, or may be derived from the natural second complementary domain. In addition, the second complementary domain may have a difference in nucleotide sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus pyogenes*, *Campylobacter jejuni*, *Streptococcus thermophilus*, *Staphylococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3' (SEQ ID NO: 299), or a nucleotide sequence having partial, that is, at least 50% or more homology with 5'-UAGCAAGUUAAAAU-3' (SEQ ID NO: 299) (a nucleotide sequence forming a double strand with the first complementary domain is underlined). Here, the second complementary domain may further include $(X)_n$ and/or $(X)_m$, resulting in 5'-$(X)_n$ UAGCAAGUUAAAAU$(X)_m$-3' (SEQ ID NO: 299). The X may be selected from the group consisting of nucleotides A, T, U and G, and each of the n and m may represent the number of nucleotides, in which the n may be an integer of 1 to 15, and the m may be an integer of 1 to 6. Here, the $(X)_n$ may represent n repeats of the same nucleotide, or a mixture of n nucleotides of A, T, U and G. In addition, $(X)_m$ may represent m repeats of the same nucleotide, or a mixture of m nucleotides of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3' (SEQ ID NO: 300), or a nucleotide sequence having partial, that is, at least 50% or more homology with 5'-AAGAAAUUUAAAAAGGGACUAAAAU-3' (SEQ ID NO: 300) (a nucleotide sequence forming a double strand with the first complementary domain is underlined). Here, the second complementary domain may further include $(X)_n$ and/or $(X)_m$, resulting in 5'-$(X)_n$AAGAAAUUUAAAAAGGGACUAAAAU$(X)_m$-3' (SEQ ID NO: 300). The X may be selected from the group consisting of nucleotides A, T, U and G, and each of the n and m may represent the number of nucleotides, in which the n may be an integer of 1 to 15, and the m may be an integer of 1 to 6. Here, $(X)_n$ may represent n repeats of the same nucleotide, or a mixture of n nucleotides of A, T, U and G. In addition, $(X)_m$ may represent m repeats of the same nucleotide, or a mixture of m nucleotides of A, T, U and G.

In another embodiment, the second complementary domain may have partial, that is, at least 50% or more, or complete homology with a second complementary domain of *Parcubacteria bacterium* (GWC2011_GWC2_44_17), *Lachnospiraceae bacterium* (MC2017), *Butyrivibrio proteoclasiicus*, *Peregrinibacteria bacterium* (GW2011_GWA_33_10), *Acidaminococcus* sp. (BV3L6), *Porphyromonas macacae*, *Lachnospiraceae bacterium* (ND2006), *Porphyromonas crevioricanis*, *Prevotella disiens*, *Moraxella bovoculi* (237), *Smiihella* sp. (SC_KO8D17), *Leptospira inadai*, *Lachnospiraceae bacte-*

*rium* (MA2020), *Francisella novicida* (U112), *Candidatus Methanoplasma termitum* or *Eubacterium eligens*, or a second complementary domain derived therefrom.

For example, when the second complementary domain is a second complementary domain of *Parcubacteria bacterium* or a second complementary domain derived therefrom, the second complementary domain may be 5'-AAAUUUC-UACU-3' (SEQ ID NO: 301), or a nucleotide sequence having partial, that is, at least 50% or more homology with 5'-AAAUUUCUACU-3' (SEQ ID NO: 301) (a nucleotide sequence forming a double strand with the first complementary domain is underlined). Here, the second complementary domain may further include $(X)_n$ and/or $(X)_m$, resulting in 5'-$(X)_n$AAAUUUCUACU$(X)_m$-3' (SEQ ID NO: 301). The X may be selected from the group consisting of nucleotides A, T, U and G, and each of the n and m may represent the number of nucleotides, in which the n may be an integer of 1 to 10, and the m may be an integer of 1 to 6. Here, the $(X)_n$ may represent n repeats of the same nucleotide, or a mixture of n nucleotides of A, T, U and G. In addition, the $(X)_m$ may represent m repeats of the same nucleotide, or a mixture of m nucleotides of A, T, U and G.

Here, the first complementary domain and the second complementary domain may complementarily bind to each other.

The first complementary domain and the second complementary domain may form a double strand by the complementary binding.

The formed double strand may interact with a CRISPR enzyme.

Optionally, the first complementary domain may include an additional nucleotide sequence that does not complementarily bind to a second complementary domain of a second strand.

Here, the additional nucleotide sequence may be a sequence of 1 to 15 nucleotides. For example, the additional nucleotide sequence may be a sequence of 1 to 5, 5 to 10 or 10 to 15 nucleotides.

Here, the proximal domain may be a domain located at the 3'end direction of the second complementary domain.

The proximal domain may have homology with a natural proximal domain, or may be derived from the natural proximal domain. In addition, the proximal domain may have a difference in nucleotide sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes, Campylobacter jejuni, Streptococcus thermophilus, Staphylococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGC-UAGUCCG-3' (SEQ ID NO: 302), or a nucleotide sequence having partial, that is, at least 50% or more homology with 5'-AAGGCUAGUCCG-3' (SEQ ID NO: 302). Here, the proximal domain may further include $(X)_n$, resulting in 5'-AAGGCUAGUCCG$(X)_n$-3' (SEQ ID NO: 302). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides of A, T, U and G.

In yet another example, when the proximal domain is a proximal domain of *Campylobacter jejuni* or a proximal domain derived therefrom, the proximal domain may be 5'-AAAGAGUUUGC-3' (SEQ ID NO: 303), or a nucleotide sequence having at least 50% or more homology with 5'-AAAGAGUUUGC-3' (SEQ ID NO: 303). Here, the proximal domain may further include $(X)_n$, resulting in 5'-AAAGAGUUUGC$(X)_n$-3' (SEQ ID NO: 303). The X may be selected from the group consisting of nucleotides A, T, U and G, and the n may represent the number of nucleotides, which is an integer of 1 to 40. Here, the $(X)_n$ may represent n repeats of the same nucleotide, or a mixture of n nucleotides of A, T, U and G.

Here, the tail domain is a domain which is able to be selectively added to the 3' end of single-stranded gRNA or the first or second strand of double-stranded gRNA.

The tail domain may have homology with a natural tail domain, or may be derived from the natural tail domain. In addition, the tail domain may have a difference in nucleotide sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes, Campylobacter jejuni, Streptococcus thermophilus, Staphylococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3' (SEQ ID NO: 304), or a nucleotide sequence having partial, that is, at least 50% or more homology with 5'-UUAUCAAC-UUGAAAAAGUGGCACCGAGUCGGUGC-3' (SEQ ID NO: 304). Here, the tail domain may further include $(X)_n$, resulting in 5'-UUAUCAAC-UUGAAAAAGUGGCACCGAGUCGGUGC$(X)_n$-3' (SEQ ID NO: 304). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3' (SEQ ID NO: 305), or a nucleotide sequence having partial, that is, at least 50% or more homology with 5'-GGGACUCUGCGGGGUUA-CAAUCCCCUAAAACCGCUUUU-3' (SEQ ID NO: 305). Here, the tail domain may further include $(X)_n$, resulting in 5'-GGGACUCUGCGGGGUUACAAUCCCC-UAAAACCGCUUUU$(X)_n$-3' (SEQ ID NO: 305). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides of A, T, U and G.

In another embodiment, the tail domain may include a 1 to 10-nt sequence at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

The gRNA may include a plurality of domains as described above, and therefore, the length of the nucleic acid sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or double-stranded gRNA (including more than one, generally two discrete RNA molecules).

Double-Stranded qRNA

The double-stranded gRNA consists of a first strand and a second strand.

Here, the first strand may consist of

5'-[guide domain]-[first complementary domain]-3', and the second strand may consist of 5'-[second complementary domain]-[proximal domain]-3' or 5'-[second complementary domain]-[proximal domain]-[tail domain]-3'.

Here, the first strand may be referred to as crRNA, and the second strand may be referred to as tracrRNA.

Here, the first strand and the second strand may optionally include an additional nucleotide sequence.

In one example, the first strand may be

5'-(N$_{target}$)-(Q)$_m$-3'; or

5'-(X)$_a$—(N$_{target}$)—(X)$_b$-(Q)$_m$-(X)$_c$-3'.

Here, the N$_{target}$ is a nucleotide sequence complementary to partial sequence of either strand of a double strand of a nucleic acid in a transcriptional regulatory region of a target gene, and a nucleotide sequence region which may be changed according to a target sequence on a nucleic acid in a transcriptional regulatory region of a target gene.

Here, the (Q)$_m$ is a nucleotide sequence including a first complementary domain, which is able to form a complementary bond with the second complementary domain of the second strand. The (Q)$_m$ may be a sequence having partial or complete homology with the first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Streptococcus pyogenes* or a *Streptococcus pyogenes*-derived first complementary domain, the (Q)$_m$ may be 5'-GUUUUAGAGCUA-3' (SEQ ID NO: 296), or a nucleotide sequence having at least 50% or more homology with 5'-GUUUUAGAGCUA-3' (SEQ ID NO: 296).

In another example, when the first complementary domain has partial or complete homology with a first complementary domain of *Campylobacter jejuni* or a *Campylobacter jejuni*-derived first complementary domain, the (Q)$_m$ may be 5'-GUUUUAGUCCC-UUUUUAAAUUUCUU-3' (SEQ ID NO: 297), or a nucleotide sequence having at least 50% or more homology with 5'-GUUUUAGUCCCUUUUUAAAUUUCUU-3' (SEQ ID NO: 297).

In still another example, when the first complementary domain has partial or complete homology with a first complementary domain of *Streptococcus thermophilus* or a *Streptococcus thermophilus*-derived first complementary domain, the (Q)$_m$ may be 5'-GUUUUAGAGCUGUGUU-GUUUCG-3' (SEQ ID NO: 306), or a nucleotide sequence having at least 50% or more homology with 5'-GUUUUA-GAGCUGUGUUGUUUCG-3' (SEQ ID NO: 306).

In addition, each of the (X)$_a$, (X)$_b$ and (X)$_c$ is selectively an additional nucleotide sequence, where the X may be each independently selected from the group consisting of A, U, C and G, and each of the a, b and c may be the number of nucleotides, which is 0 or an integer of 1 to 20.

In one exemplary embodiment, the second strand may be 5'-(Z)$_h$—(P)$_k$-3'; or 5'-(X)$_d$—(Z)$_h$—(X)$_e$—(P)$_k$—(X)$_f$-3'.

In another embodiment, the second strand may be 5'-(Z)$_h$—(P)$_k$—(F)$_i$-3'; or 5'-(X)$_d$—(Z)$_h$—(X)$_e$—(P)$_k$—(X)$_f$—(F)$_i$-3'.

Here, the (Z)$_h$ is a nucleotide sequence including a second complementary domain, which is able to form a complementary bond with the first complementary domain of the first strand. The (Z)$_h$ may be a sequence having partial or complete homology with the second complementary domain of a species existing in nature, and the nucleotide sequence of the second complementary domain may be modified according to the species of origin. The Z may be each independently selected from the group consisting of A, U, C and G, and the h may be the number of nucleotides, which is an integer of 5 to 50.

For example, when the second complementary domain has partial or complete homology with a second complementary domain of *Streptococcus pyogenes* or a second complementary domain derived therefrom, the (Z)$_h$ may be 5'-UAGCAAGUUAAAAU-3' (SEQ ID NO: 299), or a nucleotide sequence having at least 50% or more homology with 5'-UAGCAAGUUAAAAU-3' (SEQ ID NO: 299).

In another example, when the second complementary domain has partial or complete homology with a second complementary domain of *Campylobacter jejuni* or a second complementary domain derived therefrom, the (Z)$_h$ may be 5'-AAGAAAUUUAAAAAGGGACUAAAAU-3' (SEQ ID NO: 300), or a nucleotide sequence having at least 50% or more homology with 5'-AAGAAAUUUAAAAAGGGAC-UAAAAU-3' (SEQ ID NO: 300).

In still another example, when the second complementary domain has partial or complete homology with a second complementary domain of *Streptococcus thermophilus* or a second complementary domain derived therefrom, the (Z)$_h$ may be 5'-CGAAACAACACAGCGAGUUAAAAU-3' (SEQ ID NO: 307), or a nucleotide sequence having at least 50% or more homology with 5'-CGAAACAACACAGCGAGUUAAAAU-3' (SEQ ID NO: 307).

The (P)$_k$ is a nucleotide sequence including a proximal domain, which may have partial or complete homology with a proximal domain of a species existing in nature, and the nucleotide sequence of the proximal domain may be modified according to the species of origin. The P may be each independently selected from the group consisting of A, U, C and G, and the k may be the number of nucleotides, which is an integer of 1 to 20.

For example, when the proximal domain has partial or complete homology with a proximal domain of *Streptococcus pyogenes* or a proximal domain derived therefrom, the (P)$_k$ may be 5'-AAGGCUAGUCCG-3' (SEQ ID NO: 302), or a nucleotide sequence having at least 50% or more homology with 5'-AAGGCUAGUCCG-3' (SEQ ID NO: 302).

In another example, when the proximal domain has partial or complete homology with a proximal domain of *Campy-*

*lobacter jejuni* or a proximal domain derived therefrom, the $(P)_k$ may be 5'-AAAGAGUUUGC-3' (SEQ ID NO: 303), or a nucleotide sequence having at least 50% or more homology with 5'-AAAGAGUUUGC-3' (SEQ ID NO: 303).

In still another example, when the proximal domain has partial or complete homology with a proximal domain of *Streptococcus thermophilus* or a proximal domain derived therefrom, the $(P)_k$ may be 5'-AAGGCUUAGUCCG-3' (SEQ ID NO: 308), or a nucleotide sequence having at least 50% or more homology with 5'-AAGGCUUAGUCCG-3' (SEQ ID NO: 308).

The $(F)_i$ may be a nucleotide sequence including a tail domain, and having partial or complete homology with a tail domain of a species existing in nature, and the nucleotide sequence of the tail domain may be modified according to the species of origin. The F may be each independently selected from the group consisting of A, U, C and G, and the i may be the number of nucleotides, which is an integer of 1 to 50.

For example, when the tail domain has partial or complete homology with a tail domain of *Streptococcus pyogenes* or a tail domain derived therefrom, the $(F)_i$ may be 5'-UUAU-CAACUUGAAAAAGUGGCACCGAGUCGGUGC-3' (SEQ ID NO: 304), or a nucleotide sequence having at least 50% or more homology with 5'-UUAUCAAC-UUGAAAAAGUGGCACCGAGUCGGUGC-3' (SEQ ID NO: 304).

In another example, when the tail domain has partial or complete homology with a tail domain of *Campylobacter jejuni* or a tail domain derived therefrom, the $(F)_i$ may be 5'-GGGACUCUGCGGGGUUACAAUCCCC-UAAAACCGCUUUU-3' (SEQ ID NO: 305), or a nucleotide sequence having at least 50% or more homology with 5'-GGGACUCUGCGGGGUUACAAUCCCC-UAAAACCGCUUUU-3' (SEQ ID NO: 305).

In still another example, when the tail domain has partial or complete homology with a tail domain of *Streptococcus thermophilus* or a tail domain derived therefrom, the $(F)_i$ may be 5'-UACUCAACUUGAAAAG-GUGGCACCGAUUCGGUGUUUUU-3' (SEQ ID NO: 309), or a nucleotide sequence having at least 50% or more homology with 5'-UACUCAACUUGAAAAG-GUGGCACCGAUUCGGUGUUUUU-3' (SEQ ID NO: 309).

In addition, the $(F)_i$ may include a sequence of 1 to 10 nucleotides at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

In addition, the $(X)_d$, $(X)_e$ and $(X)_f$ may be nucleotide sequences selectively added, where the X may be each independently selected from the group consisting of A, U, C and G, and each of the d, e and f may be the number of nucleotides, which is 0 or an integer of 1 to 20.

Single-Stranded gRNA

Single-stranded gRNA may be classified into a first single-stranded gRNA and a second single-stranded gRNA.

First Single-Stranded gRNA

First single-stranded gRNA is single-stranded gRNA in which a first strand or a second strand of the double-stranded gRNA is linked by a linker domain.

Specifically, the single-stranded gRNA may consist of

5'-[guide domain]-[first complementary domain]-[linker domain]-[second complementary domain]-3', 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3'.

The first single-stranded gRNA may selectively include an additional nucleotide sequence.

In one exemplary embodiment, the first single-stranded gRNA may be

5'-$(N_{target})$-$(Q)_m$-$(L)_j$-$(Z)_h$-3';
5'-$(N_{target})$-$(Q)_m$-$(L)_j$-$(Z)_h$—$(P)_k$-3'; or
5'-$(N_{target})$-$(Q)_m$-$(L)_j$-$(Z)_h$—$(P)_k$—$(F)_i$-3'.

In another embodiment, the single-stranded gRNA may be

5'-$(X)_a$—$(N_{target})$—$(X)_b$-$(Q)_m$-$(X)_c$-$(L)_j$-$(X)_d$—$(Z)_h$—$(X)_e$-3';

5'-$(X)_a$—$(N_{target})$—$(X)_b$-$(Q)_m$-$(X)_c$-$(L)_j$-$(X)_d$—$(Z)_h$—$(X)_e$—$(P)_k$—$(X)_f$-3'; or 5'-$(X)_a$—$(N_{target})$—$(X)_b$-$(Q)_m$-$(X)_c$-$(L)_j$-$(X)_d$—$(Z)_h$—$(X)_e$—$(P)_k$—$(X)_f$—$(F)_i$-3'.

Here, the $N_{target}$ is a nucleotide sequence complementary to partial sequence of either strand of a double strand of a nucleic acid in a transcriptional regulatory region of a target gene, and a nucleotide sequence region capable of being changed according to a target sequence on a transcriptional regulatory region of a target gene.

The $(Q)_m$ includes a nucleotide sequence including the first complementary domain, which is able to form a complementary bond with a second complementary domain. The $(Q)_m$ may be a sequence having partial or complete homology with a first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Streptococcus pyogenes* or a first complementary domain derived therefrom, the $(Q)_m$ may be 5'-GUUUUA-GAGCUA-3' (SEQ ID NO: 296), or a nucleotide sequence having at least 50% or more homology with 5'-GUUUUA-GAGCUA-3' (SEQ ID NO: 296).

In another example, when the first complementary domain has partial or complete homology with a first complementary domain of *Campylobacter jejuni* or a first complementary domain derived therefrom, the $(Q)_m$ may be 5'-GUUUUAGUCCCUUUUUAAAUUUCUU-3' (SEQ ID NO: 297), or a nucleotide sequence having at least 50% or more homology with 5'-GUUUUAGUCCC-UUUUUAAAUUUCUU-3' (SEQ ID NO: 297).

In still another example, when the first complementary domain has partial or complete homology with a first complementary domain of *Streptococcus thermophilus* or a first complementary domain derived therefrom, the $(Q)_m$ may be 5'-GUUUUAGAGCUGUGUUGUUUCG-3' (SEQ ID NO: 306), or a nucleotide sequence having at least 50% or more homology with 5'-GUUUUAGAGCUGUGUU-GUUUCG-3' (SEQ ID NO: 306).

In addition, the (L)$_j$ is a nucleotide sequence including the linker domain, and connecting the first complementary domain with the second complementary domain, thereby producing single-stranded gRNA. Here, the L may be each independently selected from the group consisting of A, U, C and G, and the j may be the number of nucleotides, which is an integer of 1 to 30.

The (Z)$_h$ is a nucleotide sequence including the second complementary domain, and includes a nucleotide sequence capable of complementary binding with the first complementary domain. The (Z)$_h$ may be a sequence having partial or complete homology with the second complementary domain of a species existing in nature, and the nucleotide sequence of the second complementary domain may be changed according to the species of origin. The Z may be each independently selected from the group consisting of A, U, C and G, and the h is the number of nucleotides, which may be an integer of 5 to 50.

For example, when the second complementary domain has partial or complete homology with a second complementary domain of *Streptococcus pyogenes* or a second complementary domain derived therefrom, the (Z)$_h$ may be 5'-UAGCAAGUUAAAAU-3' (SEQ ID NO: 299), or a nucleotide sequence having at least 50% or more homology with 5'-UAGCAAGUUAAAAU-3' (SEQ ID NO: 299).

In another example, when the second complementary domain has partial or complete homology with a second complementary domain of *Campylobacter jejuni* or a second complementary domain derived therefrom, the (Z)$_h$ may be 5'-AAGAAAUUUAAAAAGGGACUAAAAU-3' (SEQ ID NO: 300), or a nucleotide sequence having at least 50% or more homology with 5'-AAGAAAUUUAAAAAGGGAC-UAAAAU-3' (SEQ ID NO: 300).

In still another example, when the second complementary domain has partial or complete homology with a second complementary domain of *Streptococcus thermophilus* or a second complementary domain derived therefrom, the (Z)$_h$ may be 5'-CGAAACAACACAGCGAGUUAAAAU-3' (SEQ ID NO: 307), or a nucleotide sequence having at least 50% or more homology with 5'-CGAAACAACACAGCGAGUUAAAAU-3' (SEQ ID NO: 307).

The (P)$_k$ is a nucleotide sequence including a proximal domain, which may have partial or complete homology with a proximal domain of a species existing in nature, and the nucleotide sequence of the proximal domain may be modified according to the species of origin. The P may be each independently selected from the group consisting of A, U, C and G, and the k may be the number of nucleotides, which is an integer of 1 to 20.

For example, when the proximal domain has partial or complete homology with a proximal domain of *Streptococcus pyogenes* or a proximal domain derived therefrom, the (P)$_k$ may be 5'-AAGGCUAGUCCG-3' (SEQ ID NO: 302), or a nucleotide sequence having at least 50% or more homology with 5'-AAGGCUAGUCCG-3' (SEQ ID NO: 302).

In another example, when the proximal domain has partial or complete homology with a proximal domain of *Campylobacter jejuni* or a proximal domain derived therefrom, the (P)$_k$ may be 5'-AAAGAGUUUGC-3' (SEQ ID NO: 303), or a nucleotide sequence having at least 50% or more homology with 5'-AAAGAGUUUGC-3' (SEQ ID NO: 303).

In still another example, when the proximal domain has partial or complete homology with a proximal domain of *Streptococcus thermophilus* or a proximal domain derived therefrom, the (P)$_k$ may be 5'-AAGGCUUAGUCCG-3' (SEQ ID NO: 308), or a nucleotide sequence having at least 50% or more homology with 5'-AAGGCUUAGUCCG-3' (SEQ ID NO: 308).

The (F)$_i$ may be a nucleotide sequence including a tail domain, and having partial or complete homology with a tail domain of a species existing in nature, and the nucleotide sequence of the tail domain may be modified according to the species of origin. The F may be each independently selected from the group consisting of A, U, C and G, and the i may be the number of nucleotides, which is an integer of 1 to 50.

For example, when the tail domain has partial or complete homology with a tail domain of *Streptococcus pyogenes* or a tail domain derived therefrom, the (F)$_i$ may be 5'-UUAU-CAACUUGAAAAAGUGGCACCGAGUCGGUGC-3' (SEQ ID NO: 304), or a nucleotide sequence having at least 50% or more homology with 5'-UUAUCAAC-UUGAAAAAGUGGCACCGAGUCGGUGC-3' (SEQ ID NO: 304).

In another example, when the tail domain has partial or complete homology with a tail domain of *Campylobacter jejuni* or a tail domain derived therefrom, the (F)$_i$ may be 5'-GGGACUCUGCGGGGUUACAAUCCCC-UAAAACCGCUUUU-3' (SEQ ID NO: 305), or a nucleotide sequence having at least 50% or more homology with 5'-GGGACUCUGCGGGGUUACAAUCCCC-UAAAACCGCUUUU-3' (SEQ ID NO: 305).

In still another example, when the tail domain has partial or complete homology with a tail domain of *Streptococcus thermophilus* or a tail domain derived therefrom, the (F)$_i$ may be 5'-UACUCAACUUGAAAAG-GUGGCACCGAUUCGGUGUUUU-3' (SEQ ID NO: 309), or a nucleotide sequence having at least 50% or more homology with 5'-UACUCAACUUGAAAAG-GUGGCACCGAUUCGGUGUUUU-3' (SEQ ID NO: 309).

In addition, the (F)$_i$ may include a sequence of 1 to 10 nucleotides at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

In addition, the (X)$_a$, (X)$_b$, (X)$_c$, (X)$_d$, (X)$_e$ and (X)$_f$ may be nucleotide sequences selectively added, where the X may be each independently selected from the group consisting of A, U, C and G, and each of the a, b, c, d, e and f may be the number of nucleotides, which is 0 or an integer of 1 to 20.

Second Single-Stranded gRNA

Second single-stranded gRNA may be single-stranded gRNA consisting of a guide domain, a first complementary domain and a second complementary domain.

Here, the second single-stranded gRNA may consist of:

5'-[second complementary domain]-[first complementary domain]-[guide domain]-3'; or 5'-[second complementary domain]-[linker domain]-[first complementary domain]-[guide domain]-3'.

The second single-stranded gRNA may selectively include an additional nucleotide sequence.

In one exemplary embodiment, the second single-stranded gRNA may be

5'-$(Z)_h$-$(Q)_m$-$(N_{target})$-3'; or
5'-$(X)_a$—$(Z)_h$—$(X)_b$-$(Q)_m$-$(X)_c$—$(N_{target})$-3'.

In another embodiment, the single-stranded gRNA may be

5'-$(Z)_h$-$(L)_j$-$(Q)_m$-$(N_{target})$-3'; or
5'-$(X)_a$—$(Z)_h$-$(L)_j$-$(Q)_m$-$(X)_c$—$(N_{target})$-3'.

Here, the $N_{target}$ is a nucleotide sequence complementary to partial sequence of either strand of a double strand of a nucleic acid in a transcriptional regulatory region of a target gene, and a nucleotide sequence region capable of being changed according to a target sequence on a transcriptional regulatory region of a target gene. The $(Q)_m$ is a nucleotide sequence including the first complementary domain, and includes a nucleotide sequence capable of complementary binding with a second complementary domain. The $(Q)_m$ may be a sequence having partial or complete homology with the first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Parcubacteria bacterium* or a first complementary domain derived therefrom, the $(Q)_m$ may be 5'-UUUGUAGAU-3' (SEQ ID NO: 298), or a nucleotide sequence having at least 50% or more homology with 5'-UUUGUAGAU-3' (SEQ ID NO: 298).

The $(Z)_h$ is a nucleotide sequence including a second complementary domain, and includes a nucleotide sequence capable of complementary binding with a second complementary domain. The $(Z)_h$ may be a sequence having partial or complete homology with the second complementary domain of a species existing in nature, and the nucleotide sequence of the second complementary domain may be modified according to the species of origin. The Z may be each independently selected from the group consisting of A, U, C and G, and the h may be the number of nucleotides, which is an integer of 5 to 50.

For example, when the second complementary domain has partial or complete homology with a second complementary domain of *Parcubacteria bacterium* or a *Parcubacteria bacterium*-derived second complementary domain, the $(Z)_h$ may be 5'-AAAUUUCUACU-3' (SEQ ID NO: 301), or a nucleotide sequence having at least 50% or more homology with 5'-AAAUUUCUACU-3' (SEQ ID NO: 301).

In addition, the $(L)_j$ is a nucleotide sequence including the linker domain, which connects the first complementary domain with the second complementary domain. Here, the L may be each independently selected from the group consisting of A, U, C and G, and the j may be the number of nucleotides, which is an integer of 1 to 30.

In addition, each of the $(X)_a$, $(X)_b$ and $(X)_c$ is selectively an additional nucleotide sequence, where the X may be each independently selected from the group consisting of A, U, C and G, and the a, b and c may be the number of nucleotides, which is 0 or an integer of 1 to 20.

In one exemplary embodiment of the specification, the guide nucleic acid may be gRNA complementarily binding to a target sequence in the transcriptional regulatory region of a duplicate gene.

The "target sequence" refers to a nucleotide sequence present in the transcriptional regulatory region of a target gene or nucleotide sequence(s) located upstream and/or downstream of the transcriptional regulatory region of a target gene, and particularly, a partial nucleotide sequence in a target region in the transcriptional regulatory region of a target gene or a partial nucleotide sequence in a target region located upstream and/or downstream of the transcriptional regulatory region of a target gene, and here, the "target region" may be a region that can be modified by a guide nucleic acid-editor protein in the transcriptional regulatory region of a target gene or a region that can be modified by a guide nucleic acid-editor protein located upstream and/or downstream of the transcriptional regulatory region of a target gene.

Hereinafter, the target sequence may be used to refer to both of two types of nucleotide sequence information. For example, in the case of a target gene, the target sequence may refer to the nucleotide sequence information of a transcribed strand of target gene DNA, or the nucleotide sequence information of a non-transcribed strand.

For example, the target sequence may refer to a partial nucleotide sequence (transcribed strand), that is, 5'-ATCATTGGCAGACTAGTTCG-3' (SEQ ID NO: 310), in the target region of target gene A, and a nucleotide sequence complementary thereto (non-transcribed strand), that is, 5'-CGAACTAGTCTGCCAATGAT-3' (SEQ ID NO: 311).

The target sequence may be a 5 to 50-nt sequence.

In one exemplary embodiment, the target sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The target sequence includes a guide nucleic acid-binding sequence or a guide nucleic acid-non binding sequence.

The "guide nucleic acid-binding sequence" is a nucleotide sequence having partial or complete complementarity with a guide sequence included in the guide domain of the guide nucleic acid, and may be complementarily bonded with the guide sequence included in the guide domain of the guide nucleic acid. The target sequence and guide nucleic acid-binding sequence may be a nucleotide sequence that may vary according to a target to be genetically engineered or edited depending on the transcriptional regulatory region of the target gene, and may be designed in various ways according to a nucleic acid sequence in the transcriptional regulatory region of the target gene.

The "guide nucleic acid-non binding sequence" is a nucleotide sequence having partial or complete homology with a guide sequence included in the guide domain of the guide nucleic acid, and may not be complementarily bonded with the guide sequence included in the guide domain of the guide nucleic acid. In addition, the guide nucleic acid-non binding sequence may be a nucleotide sequence having complementarity with the guide nucleic acid-binding sequence, and may be complementarily bonded with the guide nucleic acid-binding sequence.

The guide nucleic acid-binding sequence may be a partial nucleotide sequence of the target sequence, and one nucleotide sequence of two nucleotide sequences having different sequence order to each other included in the target sequence, that is, one of the two nucleotide sequences capable of complementary binding to each other. Here, the guide nucleic acid-non binding sequence may be a nucleotide sequence other than the guide nucleic acid-binding sequence of the target sequence.

For example, when a partial nucleotide sequence, that is, 5'-ATCATTGGCAGACTAGTTCG-3' (SEQ ID NO: 310), of a target region in the transcriptional regulatory region of the target gene A, and a nucleotide sequence, that is, 5'-CGAACTAGTCTGCCAATGAT-3' (SEQ ID NO: 311), which is complementary thereto, are used as target sequences, the guide nucleic acid-binding sequence may be one of the two target sequences, that is, 5'-ATCATTGGCAGACTAGTTCG-3' (SEQ ID NO: 310) or 5'-CGAACTAGTCTGCCAATGAT-3' (SEQ ID NO: 311). Here, when the guide nucleic acid-binding sequence is 5'-ATCATTGGCAGACTAGTTCG-3' (SEQ ID NO: 310), the guide nucleic acid-non binding sequence may be 5'-CGAACTAGTCTGCCAATGAT-3' (SEQ ID NO: 311), or when the guide nucleic acid-binding sequence is 5'-CGAACTAGTCTGCCAATGAT-3' (SEQ ID NO: 311), the guide nucleic acid-non binding sequence may be 5'-ATCATTGGCAGACTAGTTCG-3' (SEQ ID NO: 310).

The guide nucleic acid-binding sequence may be one of the target sequences, that is, a nucleotide sequence which is the same as a transcribed strand and a nucleotide sequence which is the same as a non-transcribed strand. Here, the guide nucleic acid-non binding sequence may be a nucleotide sequence other than the guide nucleic acid-binding sequence of the target sequences, that is, one selected from a nucleotide sequence which is the same as a transcribed strand and a nucleotide sequence which is the same as a non-transcribed strand.

The guide nucleic acid-binding sequence may have the same length as the target sequence.

The guide nucleic acid-non binding sequence may have the same length as the target sequence or the guide nucleic acid-binding sequence.

The guide nucleic acid-binding sequence may be a 5 to 50-nt sequence.

In one exemplary embodiment, the guide nucleic acid-binding sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The guide nucleic acid-non binding sequence may be a 5 to 50-nt sequence.

In one exemplary embodiment, the guide nucleic acid-nonbinding sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The guide nucleic acid-binding sequence may partially or completely complementarily bind to the guide sequence included in the guide domain of the guide nucleic acid, and the length of the guide nucleic acid-binding sequence may be the same as that of the guide sequence.

The guide nucleic acid-binding sequence may be a nucleotide sequence complementary to the guide sequence included in the guide domain of the guide nucleic acid, and for example, a nucleotide sequence which has at least 70%, 75%, 80%, 85%, 90%, 95% or more complementarity or complete complementarity.

As an example, the guide nucleic acid-binding sequence may have or include a 1 to 8-nt sequence which is not complementary to the guide sequence included in the guide domain of the guide nucleic acid.

The guide nucleic acid-non binding sequence may have partial or complete homology with the guide sequence included in the guide domain of the guide nucleic acid, and the length of the guide nucleic acid-non binding sequence may be the same as that of the guide sequence.

The guide nucleic acid-non binding sequence may be a nucleotide sequence having homology with the guide sequence included in the guide domain of the guide nucleic acid, and for example, a nucleotide sequence which has at least 70%, 75%, 80%, 85%, 90%, 95% or more homology or complete homology.

In one example, the guide nucleic acid-non binding sequence may have or include a 1 to 8-nt sequence which is not homologous to the guide sequence included in the guide domain of the guide nucleic acid.

The guide nucleic acid-non binding sequence may complementarily bind with the guide nucleic acid-binding sequence, and the guide nucleic acid-non binding sequence may have the same length as the guide nucleic acid-binding sequence.

The guide nucleic acid-non binding sequence may be a nucleotide sequence complementary to the guide nucleic acid-binding sequence, and for example, a nucleotide sequence having at least 90%, 95% or more complementarity or complete complementarity.

In one example, the guide nucleic acid-non binding sequence may have or include a 1 to 2-nt sequence which is not complementary to the guide nucleic acid-binding sequence.

In addition, the guide nucleic acid-binding sequence may be a nucleotide sequence located near a nucleotide sequence recognized by an editor protein.

In one example, the guide nucleic acid-binding sequence may be a consecutive 5 to 50-nt sequence located adjacent to the 5' end and/or 3' end of a nucleotide sequence recognized by an editor protein.

In addition, the guide nucleic acid-non binding sequence may be a nucleotide sequence located near a nucleotide sequence recognized by an editor protein.

In one example, the guide nucleic acid-non binding sequence may be a 5 to 50-nt contiguous sequence located adjacent to the 5' end and/or 3' end of a nucleotide sequence recognized by an editor protein.

The "targeting" refers to complementary binding with the guide nucleic acid-binding sequence of the target sequence present in the transcriptional regulatory region of a target gene. Here, the complementary binding may be 100% completely complementary binding, or 70% or more and less than 100%, incomplete complementary binding. Therefore, the "targeting gRNA" refers to gRNA complementarily binding to the guide nucleic acid-binding sequence of the target sequence present in the transcriptional regulatory region of a target gene.

The target gene disclosed in the specification may be a duplicate gene.

The target gene disclosed in the specification may be a PMP22 gene, a PLP1 gene, an MECP2 gene, a SOX3 gene, a RAI1 gene, a TBX1 gene, an ELN gene, a JAGGED1 gene, an NSD1 gene, an MMP23 gene, an LMB1 gene, a SNCA gene and/or an APP gene.

The target gene disclosed in the specification may be an oncogene.

Here, the oncogene may be an MYC gene, an ERBB2 (HER2) gene, a CCND1(Cyclin D1) gene, an FGFR1 gene, an FGFR2 gene, a HRAS gene, a KRAS gene, an MYB gene, an MDM2 gene, a CCNE(Cyclin E) gene, an MET gene, a CDK4 gene, an ERBB1 gene, an MYCN gene and/or an AKT2 gene.

In an exemplary embodiment, the target sequence disclosed in the specification may be a 10 to 35-nt contiguous sequence located in the promoter region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in the core promoter region of a duplicate gene.

For example, the target sequence may be a 10 to 25-nt contiguous sequence located in a region including or near TTS of a duplicate gene.

For example, the target sequence may be a 10 to 25-nt contiguous sequence located in a region including or near the RNA polymerase-binding region of a duplicate gene.

For example, the target sequence may be a 10 to 25-nt contiguous sequence located in a region including or near the transcription factor-binding region of a duplicate gene.

For example, the target sequence may be a 10 to 25-nt contiguous sequence located in a region including or near the TATA box of a duplicate gene.

For example, the target sequence may be a 10 to 25-nt contiguous sequence including all or a part of the 5'-TATA-3' (SEQ ID NO: 261) sequence present in the core promoter region of the duplicate gene.

Here, the guide sequence complementarily binding to the target sequence may be a 10 to 25-nt contiguous sequence including the entire or a part of the 5'-UAUA-3' (SEQ ID NO: 374) sequence.

For example, the target sequence may be a 10 to 25-nt contiguous sequence including all or a part of the 5'-TATAWAW-3' (W=A or T) (SEQ ID NO: 262) sequence present in the core promoter region of the duplicate gene.

Here, the guide sequence complementarily binding to the target sequence may be a 10 to 25-nt contiguous sequence including the entire or a part of the 5'-UAUAWAW-3' (W=A or U) (SEQ ID NO: 375) sequence, or may be a 10 to 25-nt contiguous sequence including the entire or a part of the 5'-WUWUAUA-3' (W=A or U) (SEQ ID NO: 376) sequence.

For example, the target sequence may be a 10 to 25-nt contiguous sequence including all or a part of the 5'-TATAWAWR-3' (W=A or T, R=A or G) (SEQ ID NO: 263) sequence present in the core promoter region of the duplicate gene.

Here, the guide sequence complementarily binding to the target sequence may be a 10 to 25-nt contiguous sequence including the entire or a part of the 5'-UAUAWAWR-3' (W=A or U, R=A or G) (SEQ ID NO: 377) sequence, or may be a 10 to 25-nt contiguous sequence including the entire or a part of the 5'-RWUWUAUA-3' (W=A or U, R=A or G) (SEQ ID NO: 378) sequence.

For example, the target sequence may be a 10 to 25-nt contiguous sequence including the entirety or a part of one or more sequences selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence, which are present in the core promoter region of a duplicate gene.

Here, the guide sequence complementarily binding to the target sequence may be a 10 to 25-nt contiguous sequence including the entirety or a part of one or more sequences selected from the group consisting of the 5'-CAUAAAA-3' (SEQ ID NO: 379) sequence, the 5'-UAUAA-3' (SEQ ID NO: 380) sequence, the 5'-UAUAAAA-3' (SEQ ID NO: 381) sequence, the 5'-CAUAAAUA-3' (SEQ ID NO: 382) sequence, the 5'-UAUAUAA-3' (SEQ ID NO: 383) sequence, the 5'-UAUAUAUAUAUAUAA-3' (SEQ ID NO: 384) sequence, the 5'-UAUAUUAUA-3' (SEQ ID NO: 385) sequence, the 5'-UAUAAA-3' (SEQ ID NO: 386) sequence, the 5'-UAUAAAAUA-3' (SEQ ID NO: 387) sequence, the 5'-UAUAUA-3' (SEQ ID NO: 388) sequence, the 5'-GAUUAAAAA-3' (SEQ ID NO: 389) sequence, the 5'-UAUAAAAA-3' (SEQ ID NO: 390) sequence, the 5'-UUAUAA-3' (SEQ ID NO: 391) sequence, the 5'-UUUUAAAA-3' (SEQ ID NO: 392) sequence, the 5'-UCUUUAAAA-3' (SEQ ID NO: 393) sequence, the 5'-GACAUUUAA-3' (SEQ ID NO: 394) sequence, the 5'-UGAUAUCAA-3' (SEQ ID NO: 395) sequence, the 5'-UAUAAAUA-3' (SEQ ID NO: 396) sequence, the 5'-UAUAAGA-3' (SEQ ID NO: 397) sequence, the 5'-AAUAAA-3' (SEQ ID NO: 398) sequence, the 5'-UUUAUA-3' (SEQ ID NO: 399) sequence, the 5'-CAUAAAAA-3' (SEQ ID NO: 400) sequence, the 5'-UAUACA-3' (SEQ ID NO: 401) sequence, the 5'-UUUAAGA-3' (SEQ ID NO: 402) sequence, the 5'-GAUAAAG-3' (SEQ ID NO: 403) sequence, the 5'-UAUAACA-3' (SEQ ID NO: 404) sequence, the 5'-UCUUAUCUU-3' (SEQ ID NO: 405) sequence, the 5'-UUGUACUUU-3' (SEQ ID NO: 406) sequence, the 5'-CAUAUAA-3' (SEQ ID NO: 407) sequence, the 5'-UAUAAAU-3' (SEQ ID NO: 408) sequence, the 5'-UAUAUAUAAAAAAAA-3' (SEQ ID NO: 409) sequence and 5'-CAUAAAUAAAAAAAAUUA-3' (SEQ ID NO: 410) sequence.

Alternatively, the guide sequence complementarily binding to the target sequence may be a 10 to 25-nt contiguous sequence including the entirety or a part of one or more sequences selected from the group consisting of the 5'-UUUUAUG-3' (SEQ ID NO: 411) sequence, the 5'-UUAUA-3' (SEQ ID NO: 412) sequence, the 5'-UUUUAUA-3' (SEQ ID NO: 413) sequence, the 5'-UAUUUAUG-3' (SEQ ID NO: 414) sequence, the 5'-UUAUAUA-3' (SEQ ID NO: 415) sequence, the 5'-UUAUAUAUAUAUAUA-3' (SEQ ID NO: 416) sequence, the 5'-UAUAAUAUA-3' (SEQ ID NO: 417) sequence, the 5'-UUUAUA-3' (SEQ ID NO: 418) sequence, the 5'-UAUUUAUA-3' (SEQ ID NO: 419) sequence, the 5'-UUUUUAAUC-3' (SEQ ID NO: 420) sequence, the 5'-UUUUUAUA-3' (SEQ ID NO: 421) sequence, the 5'-UUUUAAAGA-3' (SEQ ID NO: 422) sequence, the 5'-UUAAAUGUC-3' (SEQ ID NO: 423) sequence, the 5'-UUGAUAUCA-3' (SEQ ID NO: 424) sequence, the 5'-UAUUUAUA-3' (SEQ ID NO: 425) sequence, the 5'-UCUUAUA-3' (SEQ ID NO: 426) sequence, the 5'-UUUAUU-3' (SEQ ID NO: 427) sequence, the 5'-UAUAAA-3' (SEQ ID NO: 428) sequence, the 5'-UUUUUAUG-3' (SEQ ID NO: 429) sequence, the 5'-UGUAUA-3' (SEQ ID NO: 430) sequence, the 5'-UCUUAAA-3' (SEQ ID NO: 431) sequence, the 5'-CUUUAUC-3' (SEQ ID NO: 432) sequence, the 5'-UGUUAUA-3' (SEQ ID NO: 433) sequence, the 5'-AAGAUAAGA-3' (SEQ ID NO: 434) sequence, the 5'-AAAGUACAA-3' (SEQ ID NO: 435) sequence, the 5'-UUAUAUG-3' (SEQ ID NO: 436) sequence, the 5'-AUUUAUA-3' (SEQ ID NO: 437) sequence, the 5'-UUUUUUUUAUAUAUA-3' (SEQ ID NO: 438) sequence and 5'-UAAUUUUUUUUAUUUAUG-3' (SEQ ID NO: 439) sequence.

For example, the target sequence may be a 10 to 25-nt contiguous sequence, which includes the entire or a part of a TATA-binding protein (TBP)-binding nucleic acid sequence, which is present in the core promoter region of a duplicate gene.

In another example, the target sequence may be a 10 to 25-nt contiguous sequence located in the proximal promoter region of a duplicate gene.

For example, the target sequence may be a 10 to 25-nt contiguous sequence located in a 1 to 300 bp upstream region of the TSS of a duplicate gene.

In still another example, the target sequence may be a 10 to 25-nt contiguous sequence located in the distal promoter region of a duplicate gene.

The target sequence disclosed in the specification may be a 10 to 35-nt contiguous sequence located in the enhancer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1(Cyclin D1) gene, an FGFR1 gene, an FGFR2 gene, a HRAS gene, a KRAS gene, an MYB gene, an MDM2 gene, a CCNE(Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

For example, the target sequence may be a 10 to 25-nt contiguous sequence located in a region including or near the enhancer-box (E-box) of a duplicate gene.

For example, the target sequence may be a 10 to 35-nt contiguous sequence located in the enhancer region present in an intron of a duplicate gene.

The target sequence disclosed in the specification may be a 10 to 35-nt contiguous sequence located in the insulator region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected form the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located in the silencer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located in the locus control region (LCR) of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located upstream of the promoter region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located upstream of the core promoter region of a duplicate gene.

For example, the target sequence may be a 10 to 25-nt contiguous sequence including TSS of a duplicate gene or located upstream of the region close to the TSS.

For example, the target sequence may be a 10 to 25-nt contiguous sequence including an RNA polymerase-binding site of a duplicate gene or located upstream of the region close to the RNA polymerase-binding site.

For example, the target sequence may be a 10 to 25-nt contiguous sequence including a transcription factor-binding site of a duplicate gene or located upstream of the region close to the transcription factor-binding site.

For example, the target sequence may be a 10 to 25-nt contiguous sequence including a TATA box of a duplicate gene or located upstream of the region close to the TATA box.

For example, the target sequence may be a 10 to 25-nt contiguous sequence located upstream of a region including the 5'-TATA-3' (SEQ ID NO: 261) sequence present in the core promoter region of the duplicate gene.

For example, the target sequence may be a 10 to 25-nt contiguous sequence located upstream of a region including the 5'-TATAWAW-3' (W=A or T) (SEQ ID NO: 262) sequence present in the core promoter region of a duplicate gene.

For example, the target sequence may be a 10 to 25-nt contiguous sequence located upstream of a region including the 5'-TATAWAWR-3' (W=A or T, R=A or G) (SEQ ID NO: 263) sequence present in the core promoter region of a duplicate gene.

For example, the target sequence may be a 10 to 25-nt contiguous sequence located upstream of a region including one or more sequences selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence, which are present in the core promoter region of a duplicate gene.

For example, the target sequence may be a 10 to 25-nt contiguous sequence located upstream of a region including a nucleic acid sequence binding to a TATA-binding protein (TBP) present in the core promoter region of a duplicate gene.

In another example, the target sequence may be a 10 to 25-nt contiguous sequence located upstream of the proximal promoter region of a duplicate gene.

For example, the target sequence may be a 10 to 25-nt contiguous sequence located upstream of the 1 to 300 bp upstream region of TSS of a duplicate gene.

In still another example, the target sequence may be a 10 to 25-nt contiguous sequence located upstream of the distal promoter region of a duplicate gene.

The target sequence disclosed in the specification may be a 10 to 35-nt contiguous sequence located downstream of the promoter region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located downstream of the core promoter region of a duplicate gene.

For example, the target sequence may be a 10 to 25-nt contiguous sequence including TSS of a duplicate gene or located downstream of the region close to the TSS.

For example, the target sequence may be a 10 to 25-nt contiguous sequence including an RNA polymerase-binding site of a duplicate gene or located downstream of the region close to the RNA polymerase-binding site.

For example, the target sequence may be a 10 to 25-nt contiguous sequence including a transcription factor-binding site of a duplicate gene or located downstream of the region close to the transcription factor-binding site.

For example, the target sequence may be a 10 to 25-nt contiguous sequence including a TATA box of a duplicate gene or located downstream of the region close to the TATA box.

For example, the target sequence may be a 10 to 25-nt contiguous sequence located downstream of a region including the 5'-TATA-3' (SEQ ID NO: 261) sequence present in the core promoter region of the duplicate gene.

For example, the target sequence may be a 10 to 25-nt contiguous sequence located downstream of a region including the 5'-TATAWAW-3' (W=A or T) (SEQ ID NO: 262) sequence present in the core promoter region of a duplicate gene.

For example, the target sequence may be a 10 to 25-nt contiguous sequence located downstream of a region including the 5'-TATAWAWR-3' (W=A or T, R=A or G) (SEQ ID NO: 263) sequence present in the core promoter region of a duplicate gene.

For example, the target sequence may be a 10 to 25-nt contiguous sequence located downstream of a region including one or more sequences selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence, which are present in the core promoter region of a duplicate gene.

For example, the target sequence may be a 10 to 25-nt contiguous sequence located downstream of a region including a nucleic acid sequence binding to a TATA-binding protein (TBP) present in the core promoter region of a duplicate gene.

In another example, the target sequence may be a 10 to 25-nt contiguous sequence located downstream of the proximal promoter region of a duplicate gene.

For example, the target sequence may be a 10 to 25-nt contiguous sequence located downstream of the 1 to 300 bp downstream region of TSS of a duplicate gene.

In still another example, the target sequence may be a 10 to 25-nt contiguous sequence located downstream of the distal promoter region of a duplicate gene.

The target sequence disclosed in the specification may be a 10 to 35-nt contiguous sequence located upstream of an enhancer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

For example, the target sequence may be a 10 to 25-nt contiguous sequence including an enhancer-box (E-box) of a duplicate gene or located upstream of the region closed to the enhancer-box.

For example, the target sequence may be a 10 to 35-nt contiguous sequence located upstream of an enhancer region present in an intron of a duplicate gene.

The target sequence disclosed in the specification may be a 10 to 35-nt contiguous sequence located downstream of an enhancer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

For example, the target sequence may be a 10 to 25-nt contiguous sequence including an enhancer-box (E-box) of a duplicate gene or located downstream of the region closed to the enhancer-box.

For example, the target sequence may be a 10 to 35-nt contiguous sequence located downstream of an enhancer region present in an intron of a duplicate gene.

The target sequence disclosed in the specification may be a 10 to 35-nt contiguous sequence located upstream of an insulator region pf a duplicate gene.

The target sequence disclosed in the specification may be a 10 to 35-nt contiguous sequence located downstream of an insulator region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located upstream of a silencer region of a duplicate gene.

The target sequence disclosed in the specification may be a 10 to 35-nt contiguous sequence located downstream of a silencer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located upstream of a locus control region (LCR) of a duplicate gene.

The target sequence disclosed in the specification may be a 10 to 35-nt contiguous sequence located downstream of a LCR of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence, which is adjacent to the 5' end and/or 3' end of a proto-spacer-adjacent motif (PAM) sequence located in the transcriptional regulatory region of a duplicate gene.

The target sequence disclosed in the specification may be a 10 to 35-nt contiguous sequence adjacent to the 5' end and/or 3' end of a PAM sequence located upstream of the transcriptional regulatory region of a duplicate gene.

The target sequence disclosed in the specification may be a 10 to 35-nt contiguous sequence adjacent to the 5' end and/or 3' end of a PAM sequence located downstream of the transcriptional regulatory region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

Here, the transcriptional regulatory region of a duplicate gene may be the promoter, enhancer, silencer, insulator or locus control region (LCR) of a duplicate gene.

The "proto-spacer-adjacent motif (PAM) sequence" is a nucleotide sequence that can be recognized by an editor protein. Here, the PAM sequence may have different nucleotide sequences according to the type of the editor protein and an editor protein-derived species.

Here, the PAM sequence may be, for example, one or more sequences of the following sequences (described in a 5' to 3' direction).

NGG (N is A, T, C or G);
NNNNRYAC (N is each independently A, T, C or G, R is A or G, and Y is C or T);
NNAGAAW (N is each independently A, T, C or G, and W is A or T);
NNNNGATT (N is each independently A, T, C or G);
NNGRR(T) (N is each independently A, T, C or G, and R is A or G); and
TTN (N is A, T, C or G).

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one exemplary embodiment, when the PAM sequence recognized by the editor protein is 5'-NGG-3', 5'-NAG-3' and/or 5'-NGA-3' (N=A, T, G or C; or A, U, G or C), the target sequence may be a 10 to 25-nt contiguous sequence located adjacent to the 5' end and/or 3' end of the 5'-NGG-3', 5'-NAG-3' and/or 5'-NGA-3' (N=A, T, G or C; or A, U, G or C) sequence(s) in the transcriptional regulatory region of a duplicate gene, or upstream or downstream of the transcriptional regulatory region of a duplicate gene. For example, when the duplicate gene is PMP22, the transcriptional regulatory region may be a promoter, and the promoter may be a P1 promoter, a P2 promoter or both of the promoters. Here, when the PAM sequence recognized by the editor protein is 5'-NGG-3', 5'-NAG-3' and/or 5'-NGA-3' (N=A, T, G or C; or A, U, G or C), the target sequence may be a 10 to 25-nt contiguous sequence located adjacent to the 5' end and/or 3' end of the 5'-NGG-3', 5'-NAG-3' and/or 5'-NGA-3' (N=A, T, G or C; or A, U, G or C) sequence in the promoter (a P1 promoter, a P2 promoter or both of the promoters) of a PMP22 gene, or upstream or downstream of the promoter (a P1 promoter, a P2 promoter or both of the promoters) of a PMP22 gene.

In another exemplary embodiment, when the PAM sequence recognized by the editor protein is 5'-NGGNG-3' and/or 5'-NNAGAAW-3' (W=A or T, N=A, T, G or C; or A, U, G or C), the target sequence may be a 10 to 25-nt contiguous sequence located adjacent to the 5' end and/or 3' end of the 5'-NGGNG-3' and/or 5'-NNAGAAW-3' (W=A or T, N=A, T, G or C; or A, U, G or C) sequence in the transcriptional regulatory region of a duplicate gene, or upstream or downstream of the transcriptional regulatory region of a duplicate gene.

In still another exemplary embodiment, when the PAM sequence recognized by the editor protein is 5'-NNNN-GATT-3' and/or 5'-NNNGCTT-3' (N=A, T, G or C; or A, U, G or C), the target sequence may be a 10 to 25-nt contiguous sequence located adjacent to the 5' end and/or 3' end of the 5'-NNNNGATT-3' and/or 5'-NNNGCTT-3' (N=A, T, G or C; or A, U, G or C) sequence in the transcriptional regulatory region of a duplicate gene, upstream or downstream of the transcriptional regulatory region of a duplicate gene.

In one exemplary embodiment, when the PAM sequence recognized by the editor protein is 5'-NNNVRYAC-3' (V=G, C or A; R=A or G, Y=C or T, N=A, T, G or C; or A, U, G or C), the target sequence may be a 10 to 25-nt contiguous sequence located adjacent to the 5' end and/or 3' end of the 5'-NNNVRYAC-3' (V=G, C or A; R=A or G, Y=C or T, N=A, T, G or C; or A, U, G or C) sequence in the transcriptional regulatory region of a duplicate gene, or upstream or downstream of the transcriptional regulatory region of a duplicate gene.

In another exemplary embodiment, when the PAM sequence recognized by the editor protein is 5'-NAAR-3' (R=A or G, N=A, T, G or C; or A, U, G or C), the target sequence may be a 10 to 25-nt contiguous sequence located adjacent to the 5' end and/or 3' end of the 5'-NAAR-3'(R=A or G, N=A, T, G or C; or A, U, G or C) sequence in the transcriptional regulatory region of a duplicate gene, or upstream or downstream of the transcriptional regulatory region of a duplicate gene.

In still another exemplary embodiment, when the PAM sequence recognized by the editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence located adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the transcriptional regulatory region of a duplicate gene, or upstream or downstream of the transcriptional regulatory region of a duplicate gene.

In one exemplary embodiment, when the PAM sequence recognized by the editor protein is 5'-TTN-3' (N=A, T, G or C; or A, U, G or C), the target sequence may be a 10 to 25-nt contiguous sequence located adjacent to the 5' end and/or 3' end of the 5'-TTN-3' (N=A, T, G or C; or A, U, G or C) sequence in the transcriptional regulatory region of a duplicate gene, or upstream or downstream of the transcriptional regulatory region of a duplicate gene.

Hereinafter, examples of target sequences that can be used in an exemplary embodiment disclosed in the specification are listed in Tables 1, 2, 3, 4, 5, 6, 7, 8 and 9. The target sequences disclosed in Tables 1, 2, 3, 4, 5, 6, 7, 8 and 9 are non-guide nucleic acid-binding sequences, and complementary sequences thereof, which are guide nucleic acid-binding sequences, may be predicted from the sequences listed in the tables. In addition, gRNAs shown in Tables 1, 2, 3, 4, 5 and 6 were named Sp for SpCas9 and Cj for CjCas9 according to an editor protein.

TABLE 1

Target sequences of human PMP22 gene for SpCas9

| gRNA | No. | Target (5' to 3') | SEQ ID NO |
|---|---|---|---|
| hPMP22-TATA-Sp#1 | 1 | GGACCAGCCCCTGAATAAAC | SEQ ID NO: 1 |
| hPMP22-TATA-Sp#2 | 2 | GGCGTCTTTCCAGTTTATTC | SEQ ID NO: 2 |
| hPMP22-TATA-Sp#3 | 3 | GCGTCTTTCCAGTTTATTCA | SEQ ID NO: 3 |
| hPMP22-TATA-Sp#4 | 4 | CGTCTTTCCAGTTTATTCAG | SEQ ID NO: 4 |
| hPMP22-TATA-Sp#5 | 5 | TTCAGGGGCTGGTCCAATGC | SEQ ID NO: 5 |
| hPMP22-TATA-Sp#6 | 6 | TCAGGGGCTGGTCCAATGCT | SEQ ID NO: 6 |
| hPMP22-TATA-Sp#7 | 7 | ACCATGACATATCCCAGCAT | SEQ ID NO: 7 |
| hPMP22-TATA-Sp#8 | 8 | TTTCCAGTTTATTCAGGGGC | SEQ ID NO: 8 |
| hPMP22-TATA-Sp#9 | 9 | CAGTTACAGGGAGCACCACC | SEQ ID NO: 9 |
| hPMP22-TATA-Sp#10 | 10 | CTGGTCTGGCTTCAGTTACA | SEQ ID NO: 10 |
| hPMP22-TATA-Sp#11 | 11 | CCTGGTCTGGCTTCAGTTAC | SEQ ID NO: 11 |

TABLE 1-continued

Target sequences of human PMP22 gene for SpCas9

| gRNA | No. | Target (5' to 3') | SEQ ID NO |
|---|---|---|---|
| hPMP22-TATA-Sp#12 | 12 | AACTGGAAAGACGCCTGGTC | SEQ ID NO: 12 |
| hPMP22-TATA-Sp#13 | 13 | GAATAAACTGGAAAGACGCC | SEQ ID NO: 13 |
| hPMP22-TATA-Sp#14 | 14 | TCCAATGCTGGGATATGTCA | SEQ ID NO: 14 |
| hPMP22-TATA-Sp#15 | 15 | AATGCTGGGATATGTCATGG | SEQ ID NO: 15 |
| hPMP22-TATA-Sp#16 | 16 | ATAGAGGCTGAGAACCTCTC | SEQ ID NO: 16 |
| hPMP22-Enh-Sp#1 | 17 | TTGGGCATGTTTGAGCTGGT | SEQ ID NO: 17 |
| hPMP22-Enh-Sp#2 | 18 | TTTGGGCATGTTTGAGCTGG | SEQ ID NO: 18 |
| hPMP22-Enh-Sp#3 | 19 | GAGCTGGTGGGCGAAGCATA | SEQ ID NO: 19 |
| hPMP22-Enh-Sp#4 | 20 | AGCTGGTGGGCGAAGCATAT | SEQ ID NO: 20 |
| hPMP22-Enh-Sp#5 | 21 | TGGGCGAAGCATATGGGCAA | SEQ ID NO: 21 |
| hPMP22-Enh-Sp#6 | 22 | GGCCTCCATCCTAAACAATG | SEQ ID NO: 22 |
| hPMP22-Enh-Sp#10 | 23 | GGGTTGGGAGGTTTGGGCGT | SEQ ID NO: 23 |
| hPMP22-Enh-Sp#11 | 24 | AGGTTTGGGCGTGGGAGTCC | SEQ ID NO: 24 |
| hPMP22-Enh-Sp#12 | 25 | TTCAGAGACTCAGCTATTT | SEQ ID NO: 25 |
| hPMP22-Enh-Sp#13 | 26 | GGCCACATTGTTTAGGATG | SEQ ID NO: 26 |
| hPMP22-Enh-Sp#14 | 27 | GGCTTTGGGCATGTTTGAG | SEQ ID NO: 27 |
| hPMP22-Enh-Sp#15 | 28 | AACATGCCCAAAGCCCAGC | SEQ ID NO: 28 |
| hPMP22-Enh-Sp#16 | 29 | ACATGCCCAAAGCCCAGCG | SEQ ID NO: 29 |
| hPMP22-CDS-Sp#1 | 30 | CGATGATACTCAGCAACAGG | SEQ ID NO: 30 |
| hPMP22-CDS-Sp#3 | 31 | ATGGACACGCAACTGATCTC | SEQ ID NO: 31 |

TABLE 2

Target sequences of human PMP22 gene for CjCas9

| gRNA | No. | Target (5' to 3') | SEQ ID NO |
|---|---|---|---|
| hPMP22-TATA-Cj#1 | 1 | GCCCTCTGAATCTCCAGTCAAT | SEQ ID NO: 32 |
| hPMP22-TATA-Cj#2 | 2 | AATCTCCAGTCAATTCCAACAC | SEQ ID NO: 33 |
| hPMP22-TATA-Cj#3 | 3 | AATTAGGCAATTCTTGTAAAGC | SEQ ID NO: 34 |
| hPMP22-TATA-Cj#4 | 4 | TTAGGCAATTCTTGTAAAGCAT | SEQ ID NO: 35 |
| hPMP22-TATA-Cj#5 | 5 | AAAGCATAGGCACACATCACCC | SEQ ID NO: 36 |
| hPMP22-TATA-Cj#6 | 6 | GCCTGGTCTGGCTTCAGTTACA | SEQ ID NO: 37 |
| hPMP22-TATA-Cj#7 | 7 | GTGTCCAACTTTGTTTGCTTTC | SEQ ID NO: 38 |
| hPMP22-TATA-Cj#8 | 8 | GTATTCTGGAAAGCAAACAAAG | SEQ ID NO: 39 |
| hPMP22-TATA-Cj#9 | 9 | CAGTCTTGGCATCACAGGCTTC | SEQ ID NO: 40 |
| hPMP22-TATA-Cj#10 | 10 | GGACCTCTTGGCTATTACACAG | SEQ ID NO: 41 |
| hPMP22-TATA-Cj#11 | 11 | GGAGCCAGTGGGACCTCTTGGC | SEQ ID NO: 42 |
| hPMP22-Enh-Cj#1 | 12 | TAAATCACAGAGGCAAAGAGTT | SEQ ID NO: 43 |
| hPMP22-Enh-Cj#2 | 13 | TTGCATAGTGCTAGACTGTTTT | SEQ ID NO: 44 |
| hPMP22-Enh-Cj#3 | 14 | GGGTCATGTGTTTTGAAAACAG | SEQ ID NO: 45 |

TABLE 2-continued

Target sequences of human PMP22 gene for CjCas9

| gRNA | No. | Target (5' to 3') | SEQ ID NO |
|---|---|---|---|
| hPMP22-Enh-Cj#4 | 15 | CCCAAACCTCCCAACCCACAAC | SEQ ID NO: 46 |
| hPMP22-Enh-Cj#5 | 16 | ACTCAGCTATTTCTGGAATGAC | SEQ ID NO: 47 |
| hPMP22-Enh-Cj#6 | 17 | TCATCGCCTTTGTGAGCTCCAT | SEQ ID NO: 48 |
| hPMP22-Enh-Cj#7 | 18 | CAGACACAGGCTTTGCTCTAGC | SEQ ID NO: 49 |
| hPMP22-Enh-Cj#8 | 19 | CAAAGCCTGTGTCTGGCCACTA | SEQ ID NO: 50 |
| hPMP22-Enh-Cj#9 | 20 | AGCAGTTTGTGCCCACTAGTGG | SEQ ID NO: 51 |
| hPMP22-Enh-Cj#10 | 21 | ATGTCAAGGTATTCCAGCTAAC | SEQ ID NO: 52 |
| hPMP22-Enh-Cj#11 | 22 | GAATAACTGTATCAAAGTTAGC | SEQ ID NO: 53 |
| hPMP22-Enh-Cj#12 | 23 | TTCCTAATTAAGAGGCTTTGTG | SEQ ID NO: 54 |
| hPMP22-Enh-Cj#13 | 24 | GAGCTAGTTTGTCAGGGTCTAG | SEQ ID NO: 55 |

TABLE 3

Target sequences of human PLP1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-TATA-Sp-01 | 1 | GACTTTGGGAGCTAATATCTAGG | SEQ ID NO: 56 | + | 1 | 0 | 0 | — |
| hPLP1-wMN1-Sp-01 | 2 | CCCTTTCATCTTCCCATTCGTGG | SEQ ID NO: 57 | + | 1 | 0 | 0 | Up |
| hPLP1-wMN1-Sp-02 | 3 | CCTTTCATCTTCCCATTCGTGGG | SEQ ID NO: 58 | + | 1 | 0 | 0 | Up |
| hPLP1-wMN1-Sp-03 | 4 | CCCACGAATGGGAAGATGAAAGG | SEQ ID NO: 59 | − | 1 | 0 | 0 | Up |
| hPLP1-wMN1-Sp-04 | 5 | CATCTTCCCATTCGTGGGCAAGG | SEQ ID NO: 60 | + | 1 | 0 | 0 | Up |
| hPLP1-wMN1-Sp-05 | 6 | TCTCCACCTTGCCCACGAATGGG | SEQ ID NO: 61 | − | 1 | 0 | 0 | Up |
| hPLP1-wMN1-Sp-06 | 7 | GTCTCCACCTTGCCCACGAATGG | SEQ ID NO: 62 | − | 1 | 0 | 0 | Up |
| hPLP1-wMN1-Sp-07 | 8 | CCCAATGCTTGCACATAAATTGG | SEQ ID NO: 63 | + | 1 | 0 | 0 | Up |
| hPLP1-wMN1-Sp-08 | 9 | CCAATTTATGTGCAAGCATTGGG | SEQ ID NO: 64 | − | 1 | 0 | 0 | Up |
| hPLP1-wMN1-Sp-09 | 10 | TCCAATTTATGTGCAAGCATTGG | SEQ ID NO: 65 | − | 1 | 0 | 0 | Up |
| hPLP1-wMN1-Sp-10 | 11 | TGTGCGCGTCTGAAGAGGAGTGG | SEQ ID NO: 66 | + | 1 | 0 | 0 | Up |

TABLE 3-continued

Target sequences of human PLP1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Sp-11 | 12 | GTGCGCGTCTGAAGAGGAGTGGG | SEQ ID NO: 67 | + | 1 | 0 | 0 | Up |
| hPLP1-wMN1-Sp-12 | 13 | TGCGCGTCTGAAGAGGAGTGGGG | SEQ ID NO: 68 | + | 1 | 0 | 0 | Up |
| hPLP1-wMN1-Sp-13 | 14 | TAGTCCAGATGCTGTTGCCGTGG | SEQ ID NO: 69 | + | 1 | 0 | 0 | Up |
| hPLP1-wMN1-Sp-14 | 15 | ATTACCACGGCAACAGCATCTGG | SEQ ID NO: 70 | - | 1 | 0 | 0 | Up |
| hPLP1-wMN1-Sp-15 | 16 | GACACGATTTAGTATTACCACGG | SEQ ID NO: 71 | - | 1 | 0 | 0 | Up |
| hPLP1-wMN1-Sp-16 | 17 | CTAAATCGTGTCCAAAGAGGAGG | SEQ ID NO: 72 | + | 1 | 0 | 0 | Up |
| hPLP1-wMN1-Sp-17 | 18 | AGGAATCTCAGCCTCCTCTTTGG | SEQ ID NO: 73 | - | 1 | 0 | 0 | Up |
| hPLP1-wMN1-Sp-18 | 19 | GTGGACAAGGTTAACTAAAAAGG | SEQ ID NO: 74 | - | 1 | 0 | 0 | Up |
| hPLP1-wMN1-Sp-19 | 20 | ATAGTCAAATCATGTGGACAAGG | SEQ ID NO: 75 | - | 1 | 0 | 0 | Up |
| hPLP1-wMN1-Sp-20 | 21 | TGCTGGATAGTCAAATCATGTGG | SEQ ID NO: 76 | - | 1 | 0 | 0 | Up |
| hPLP1-wMN1-Sp-21 | 22 | ACATGATTTGACTATCCAGCAGG | SEQ ID NO: 77 | + | 1 | 0 | 0 | Up |
| hPLP1-wMN1-Sp-22 | 23 | ATTTGACTATCCAGCAGGCTTGG | SEQ ID NO: 78 | + | 1 | 0 | 0 | Up |
| hPLP1-wMN1-Sp-23 | 24 | GTCCCGAAGTCTCTGGGGCCTGG | SEQ ID NO: 79 | - | 1 | 0 | 0 | Up |
| hPLP1-wMN1-Sp-24 | 25 | AAAACAGTCCCGAAGTCTCTGGG | SEQ ID NO: 80 | - | 1 | 0 | 0 | Up |
| hPLP1-wMN1-Sp-25 | 26 | GAAAACAGTCCCGAAGTCTCTGG | SEQ ID NO: 81 | - | 1 | 0 | 0 | Up |
| hPLP1-wMN1-Sp-26 | 27 | TATATACCACATTCAAGTGCTGG | SEQ ID NO: 82 | - | 1 | 0 | 0 | Up |
| hPLP1-wMN1-Sp-27 | 28 | TGGATATAACGAAGTTGTGTGGG | SEQ ID NO: 83 | - | 1 | 0 | 0 | Down |
| hPLP1-wMN1-Sp-28 | 29 | ATGGATATAACGAAGTTGTGTGG | SEQ ID NO: 84 | - | 1 | 0 | 0 | Down |

TABLE 3-continued

Target sequences of human PLP1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Sp-29 | 30 | ATATGTTTGTTCACCCCAACAGG | SEQ ID NO: 85 | + | 1 | 0 | 0 | Down |
| hPLP1-wMN1-Sp-30 | 31 | GAAAACTTGAAATCCTGTTGGGG | SEQ ID NO: 86 | − | 1 | 0 | 0 | Down |
| hPLP1-wMN1-Sp-31 | 32 | TAGACATTAGGAGAAACAGAAGG | SEQ ID NO: 87 | − | 1 | 0 | 0 | Down |
| hPLP1-wMN1-Sp-32 | 33 | CTAGCAGTGACATAGACATTAGG | SEQ ID NO: 88 | − | 1 | 0 | 0 | Down |
| hPLP1-wMN1-Sp-33 | 34 | AGCCACCTGACTTTGATGAAAGG | SEQ ID NO: 89 | − | 1 | 0 | 0 | Down |
| hPLP1-wMN1-Sp-34 | 35 | TGAGAAATGTTATTACTATATGG | SEQ ID NO: 90 | + | 1 | 0 | 0 | Down |
| hPLP1-wMN1-Sp-35 | 36 | AGACTGCGAGATGAGAGAGTTGG | SEQ ID NO: 91 | − | 1 | 0 | 0 | Down |
| hPLP1-wMN1-Sp-36 | 37 | CTCGCAGTCTGTACTTAGACTGG | SEQ ID NO: 92 | + | 1 | 0 | 0 | Down |
| hPLP1-wMN1-Sp-37 | 38 | AATGTCTCTTGAGAGAGCCAAGG | SEQ ID NO: 93 | + | 1 | 0 | 0 | Down |

TABLE 4

Target sequences of human PLP1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Cj-01 | 1 | ATGGAAGATGAAAGGGAAGTAACTGGTAC | SEQ ID NO: 94 | − | 1 | 0 | 0 | Up |
| hPLP1-wMN1-Cj-02 | 2 | ACTTTGATTGTTAAAACTTATCCTTGGCAC | SEQ ID NO: 95 | − | 1 | 0 | 0 | Up |
| hPLP1-wMN1-Cj-03 | 3 | AGTCCTACCTCAGCTTCCCAATGCTTGCAC | SEQ ID NO: 96 | + | 1 | 0 | 0 | Up |
| hPLP1-wMN1-Cj-04 | 4 | CAATGCTTGCACATAAATTGGAATGTGTAC | SEQ ID NO: 97 | + | 1 | 0 | 0 | Up |
| hPLP1-wMN1-Cj-05 | 5 | ACACAGAGAGAGACAGAATGAATGATGTAC | SEQ ID NO: 98 | − | 1 | 0 | 0 | Up |
| hPLP1-wMN1-Cj-06 | 6 | TCCTCTTCAGACGCGCACACACACACACAC | SEQ ID NO: 99 | − | 1 | 0 | 0 | Up |
| hPLP1-wMN1-Cj-07 | 7 | ACTCCTCTTCAGACGCGCACACACACACAC | SEQ ID NO: 100 | − | 1 | 0 | 0 | Up |

TABLE 4-continued

Target sequences of human PLP1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Cj-08 | 8 | CCACTCCTCTT CAGACGCGCAC ACACACAC | SEQ ID NO: 101 | − | 1 | 0 | 0 | Up |
| hPLP1-wMN1-Cj-09 | 9 | CCCCACTCCTC TTCAGACGCGC ACACACAC | SEQ ID NO: 102 | − | 1 | 0 | 0 | Up |
| hPLP1-wMN1-Cj-10 | 10 | CTCCCCACTCC TCTTCAGACGC GCACACAC | SEQ ID NO: 103 | − | 1 | 0 | 0 | Up |
| hPLP1-wMN1-Cj-11 | 11 | TACTCCCCACT CCTCTTCAGAC GCGCACAC | SEQ ID NO: 104 | − | 1 | 0 | 0 | Up |
| hPLP1-wMN1-Cj-12 | 12 | TATACTCCCCA CTCCTCTTCAG ACGCGCAC | SEQ ID NO: 105 | − | 1 | 0 | 0 | Up |
| hPLP1-wMN1-Cj-13 | 13 | ACAGCATCTGG ACTATCTTGTTT CCTATAC | SEQ ID NO: 106 | − | 1 | 0 | 0 | Up |
| hPLP1-wMN1-Cj-14 | 14 | ATAGTCCAGAT GCTGTTGCCGT GGTAATAC | SEQ ID NO: 107 | + | 1 | 0 | 0 | Up |
| hPLP1-wMN1-Cj-15 | 15 | AAAAGGAATCT CAGCCTCCTCT TTGGACAC | SEQ ID NO: 108 | − | 1 | 0 | 0 | Up |
| hPLP1-wMN1-Cj-16 | 16 | TGTCACTGCTA GTGTGCTTAAT TCTTGTAC | SEQ ID NO: 109 | + | 1 | 0 | 0 | Down |
| hPLP1-wMN1-Cj-17 | 17 | ATGTGAATTCA GTACAAGAATT AAGCACAC | SEQ ID NO: 110 | − | 1 | 0 | 0 | Down |
| hPLP1-wMN1-Cj-18 | 18 | TTATGTGAATTC AGTACAAGAAT TAAGCAC | SEQ ID NO: 111 | − | 1 | 0 | 0 | Down |
| hPLP1-wMN1-Cj-19 | 19 | CTTTCATTTCTG TTTATGTGAATT CAGTAC | SEQ ID NO: 112 | − | 1 | 0 | 0 | Down |
| hPLP1-wMN1-Cj-20 | 20 | TTCACATAAACA GAAATGAAAGA AAAACAC | SEQ ID NO: 113 | + | 1 | 0 | 0 | Down |
| hPLP1-wMN1-Cj-21 | 21 | ATGCCAACTCT CTCATCTCGCA GTCTGTAC | SEQ ID NO: 114 | + | 1 | 0 | 0 | Down |
| hPLP1-wMN1-Cj-22 | 22 | GAGACATTCTC ACATTTCCAGT CTAAGTAC | SEQ ID NO: 115 | − | 1 | 0 | 0 | Down |

TABLE 5

Target sequences of mouse Plp1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-TATA-Sp-01 | 1 | TGTTTGGTAGTA TAGTAAGTAGG | SEQ ID NO: 116 | + | 1 | 0 | 1 | − |

TABLE 5-continued

Target sequences of mouse Plp1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-wMN1-Sp-01 | 2 | GGTCTAGAAAAGATCAAGCCAGG | SEQ ID NO: 117 | + | 1 | 0 | 0 | Up |
| mPlp1-wMN1-Sp-02 | 3 | GCCAGGACTGTGACCTGATAAGG | SEQ ID NO: 118 | + | 1 | 0 | 0 | Up |
| mPlp1-wMN1-Sp-03 | 4 | TCACCTTCACACTTTAACCAAGG | SEQ ID NO: 119 | + | 1 | 0 | 0 | Up |
| mPlp1-wMN1-Sp-04 | 5 | CAAGGTTGAGACAATGTTCCAGG | SEQ ID NO: 120 | + | 1 | 0 | 0 | Up |
| mPlp1-wMN1-Sp-05 | 6 | CCAATTCATGTGCAAACATTTGG | SEQ ID NO: 121 | - | 1 | 0 | 0 | Up |
| mPlp1-wMN1-Sp-06 | 7 | CATCACAGTTTATACTTAGCTGG | SEQ ID NO: 122 | + | 1 | 0 | 0 | Down |
| mPlp1-wMN1-Sp-07 | 8 | ATCACAGTTTATACTTAGCTGGG | SEQ ID NO: 123 | + | 1 | 0 | 0 | Down |
| mPlp1-wMN1-Sp-08 | 9 | GGAATACCTCAGGCTCAACAGG | SEQ ID NO: 124 | - | 1 | 0 | 0 | Down |
| mPlp1-wMN1-Sp-09 | 10 | TCTCTGTTTCGGAATACCTCAGG | SEQ ID NO: 125 | - | 1 | 0 | 0 | Down |
| mPlp1-wMN1-Sp-10 | 11 | CTGTCGACTACTTTGATGAAAGG | SEQ ID NO: 126 | + | 1 | 0 | 0 | Down |
| mPlp1-wMN1-Sp-11 | 12 | TGAACCAAGATGATTATTTGTGG | SEQ ID NO: 127 | - | 1 | 0 | 1 | Up |
| mPlp1-wMN1-Sp-12 | 13 | ATCTTGGTTCATAGAAATTTGGG | SEQ ID NO: 128 | + | 1 | 0 | 1 | Up |
| mPlp1-wMN1-Sp-13 | 14 | AGCCTTGCATGGCAGAGCTTGG | SEQ ID NO: 129 | - | 1 | 0 | 1 | Up |
| mPlp1-wMN1-Sp-14 | 15 | ACACTTTAACCAAGGAAAGAGGG | SEQ ID NO: 130 | + | 1 | 0 | 1 | Up |
| mPlp1-wMN1-Sp-15 | 16 | TACCAGATCCCCTCTTTCCTTGG | SEQ ID NO: 131 | - | 1 | 0 | 1 | Up |
| mPlp1-wMN1-Sp-16 | 17 | CATTTGGAGGCCAAAATACAAGG | SEQ ID NO: 132 | - | 1 | 0 | 1 | Up |
| mPlp1-wMN1-Sp-17 | 18 | CCAAATGTTTGCACATGAATTGG | SEQ ID NO: 133 | + | 1 | 0 | 1 | Up |
| mPlp1-wMN1-Sp-18 | 19 | AGTCCAGATGCTGTCCCTGAAGG | SEQ ID NO: 134 | + | 1 | 0 | 1 | Up |

TABLE 5-continued

Target sequences of mouse Plp1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-wMN1-Sp-19 | 20 | CGCAAGCCATTCAAACACAAAGG | SEQ ID NO: 135 | + | 1 | 0 | 1 | Down |
| mPlp1-wMN1-Sp-20 | 21 | TCAAACCCTGTTGAGCCTGAGG | SEQ ID NO: 136 | + | 1 | 0 | 1 | Down |
| mPlp1-wMN1-Sp-21 | 22 | CGGAATACCTCAGGCTCAACAG | SEQ ID NO: 137 | − | 1 | 0 | 1 | Down |
| mPlp1-wMN1-Sp-22 | 23 | GTCAAAATGTGAATTCTAACAGG | SEQ ID NO: 138 | − | 1 | 0 | 1 | Down |
| mPlp1-wMN1-Sp-23 | 24 | TTATCTATTCTATTAGAGCTCGG | SEQ ID NO: 139 | − | 1 | 0 | 0 | Down |
| mPlp1-wMN1-Sp-24 | 25 | ATCAAGTAATGAAATGGACAAGG | SEQ ID NO: 140 | − | 1 | 0 | 1 | Down |
| mPlp1-wMN1-Sp-25 | 26 | CTCCCACTGCCTTATTAGGCAGG | SEQ ID NO: 141 | − | 1 | 0 | 0 | Up |
| mPlp1-wMN1-Sp-26 | 27 | AGAGCTCAAATGGGTTCTAAAGG | SEQ ID NO: 142 | − | 1 | 0 | 0 | Up |
| mPlp1-wMN1-Sp-27 | 28 | ACCACATTCAAGAGCTCAAATGG | SEQ ID NO: 143 | − | 1 | 0 | 0 | Up |
| mPlp1-wMN1-Sp-28 | 29 | TTACAGATTGGTTACACTTGGGG | SEQ ID NO: 144 | + | 1 | 0 | 0 | Down |
| mPlp1-wMN1-Sp-29 | 30 | ATCACTGCTGCTACTACTTATGG | SEQ ID NO: 145 | − | 1 | 0 | 0 | Up |
| mPlp1-wMN1-Sp-30 | 31 | ATACCTGCCTAATAAGGCAGTGG | SEQ ID NO: 146 | + | 1 | 0 | 0 | Up |
| mPlp1-wMN1-Sp-31 | 32 | GATCAGGAGAGTCAGTGGGATGG | SEQ ID NO: 147 | + | 1 | 0 | 1 | Down |
| mPlp1-wMN1-Sp-32 | 33 | CTATTGTGAGTCTCAGATTAAGG | SEQ ID NO: 148 | − | 1 | 0 | 1 | Down |
| mPlp1-wMN1-Sp-33 | 34 | TATTACAGATTGGTTACACTTGG | SEQ ID NO: 149 | + | 1 | 0 | 1 | Down |
| mPlp1-wMN1-Sp-34 | 35 | ATTACAGATTGGTTACACTTGGG | SEQ ID NO: 150 | + | 1 | 0 | 1 | Down |
| mPlp1-wMN1-Sp-35 | 36 | TACAGATTGGTTACACTTGGGGG | SEQ ID NO: 151 | + | 1 | 0 | 1 | Down |
| mPlp1-wMN1-Sp-36 | 37 | ACAGATTGGTTACACTTGGGGGG | SEQ ID NO: 152 | + | 1 | 0 | 1 | Down |

TABLE 6

Target sequences of mouse Plp1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-TATA-Cj-01 | 1 | CTACTTACTATACTACCAAACACACCGCAC | SEQ ID NO: 153 | − | 1 | 0 | 0 | − |
| mPlp1-TATA-Cj-02 | 2 | AAAGCCTACTTACTATACTACCAAACACAC | SEQ ID NO: 154 | − | 1 | 0 | 0 | − |
| mPlp1-TATA-Cj-03 | 3 | CAAAAGCCTACTTACTATACTACCAAACAC | SEQ ID NO: 155 | − | 1 | 0 | 0 | − |
| mPlp1-TATA-Cj-04 | 4 | GGGTCTGAATCAAAAGCCTACTTACTATAC | SEQ ID NO: 156 | − | 1 | 0 | 0 | − |
| mPlp1-wMN1-Cj-01 | 5 | AGAGTGGGATTCTACAAGTCACCTTCACAC | SEQ ID NO: 157 | + | 1 | 0 | 0 | Up |
| mPlp1-wMN1-Cj-02 | 6 | GGAAAGAGGGGATCTGGTAGCATAAAGTAC | SEQ ID NO: 158 | + | 1 | 0 | 0 | Up |
| mPlp1-wMN1-Cj-03 | 7 | GGGATCTGGTAGCATAAAGTACAGCTACAC | SEQ ID NO: 159 | + | 1 | 0 | 0 | Up |
| mPlp1-wMN1-Cj-04 | 8 | ATCTGTCACTAGCGACAAGTGTAGCTGTAC | SEQ ID NO: 160 | − | 1 | 0 | 0 | Up |
| mPlp1-wMN1-Cj-05 | 9 | TCATGTGCAAACATTTGGAGGCCAAAATAC | SEQ ID NO: 161 | − | 1 | 0 | 0 | Up |
| mPlp1-wMN1-Cj-06 | 10 | GACATACAGAGAGGGGGCGGAGAGAAATAC | SEQ ID NO: 162 | − | 1 | 0 | 0 | Up |
| mPlp1-wMN1-Cj-07 | 11 | ATACTGACGCCATCACATCACAGTTTATAC | SEQ ID NO: 163 | + | 1 | 0 | 0 | Down |
| mPlp1-wMN1-Cj-08 | 12 | TAAAACTATAAGCTCTCTGTTTCGGAATAC | SEQ ID NO: 164 | − | 1 | 0 | 0 | Down |
| mPlp1-wMN1-Cj-09 | 13 | TCATCAAAGTAGTCGACAGTCAAAGCATAC | SEQ ID NO: 165 | − | 1 | 0 | 0 | Down |
| mPlp1-wMN1-Cj-10 | 14 | TGAATTCTAACAGGAAAACTCAGAACATAC | SEQ ID NO: 166 | − | 1 | 0 | 0 | Down |
| mPlp1-wMN1-Cj-11 | 15 | ACTGCTGCTACTACTTATGGTGACTAGTAC | SEQ ID NO: 167 | − | 1 | 0 | 0 | Up |
| mPlp1-wMN1-Cj-12 | 16 | AGTCACCATAAGTAGTAGCAGCAGTGATAC | SEQ ID NO: 168 | + | 1 | 0 | 0 | Up |
| mPlp1-wMN1-Cj-13 | 17 | CATAAGTAGTAGCAGCAGTGATACTAATAC | SEQ ID NO: 169 | + | 1 | 0 | 0 | Up |
| mPlp1-wMN1-Cj-14 | 18 | TTGAATGGCTTGCGAACAAAGATTAAACAC | SEQ ID NO: 170 | − | 1 | 0 | 0 | Down |
| mPlp1-wMN1-Cj-15 | 19 | TTAATCTTTGTTCGCAAGCCATTCAAACAC | SEQ ID NO: 171 | + | 1 | 0 | 0 | Down |

TABLE 6-continued

Target sequences of mouse Plp1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-wMN1-Cj-16 | 20 | TTGCTGCATCTCTAACGTGAACTCTAACAC | SEQ ID NO: 172 | - | 1 | 0 | 0 | Down |
| mPlp1-wMN1-Cj-17 | 21 | TTCACGTTAGAGATGCAGCAAAGTCTATAC | SEQ ID NO: 173 | + | 1 | 0 | 0 | Down |
| mPlp1-wMN1-Cj-18 | 22 | TGGAAGCAACTCTAAATCACCACCCGATAC | SEQ ID NO: 174 | - | 1 | 0 | 0 | Down |
| mPlp1-wMN1-Cj-19 | 23 | TTCCAAAGTTCTGTCACCCAGTAAAAACAC | SEQ ID NO: 175 | + | 1 | 0 | 0 | Down |
| mPlp1-wMN1-Cj-20 | 24 | TTCAAGAGCTCAAATGGGTTCTAAAGGCAC | SEQ ID NO: 176 | - | 1 | 0 | 0 | Up |
| mPlp1-wMN1-Cj-21 | 25 | TTGAATGTGGTATAAGTGCTAATATCATAC | SEQ ID NO: 177 | + | 1 | 0 | 0 | Up |
| mPlp1-wMN1-Cj-22 | 26 | GTATAAGTGCTAATATCATACAGGAAACAC | SEQ ID NO: 178 | + | 1 | 0 | 0 | Up |
| mPlp1-wMN1-Cj-23 | 27 | GTGTTTCCTGTATGATATTAGCACTTATAC | SEQ ID NO: 179 | - | 1 | 0 | 0 | Up |
| mPlp1-wMN1-Cj-24 | 28 | GACTTTGTGTTTCCTGTATGATATTAGCAC | SEQ ID NO: 180 | - | 1 | 0 | 0 | Up |
| mPlp1-wMN1-Cj-25 | 29 | AAAACAATTATCAGGCAGTGACAGAGACAC | SEQ ID NO: 181 | - | 1 | 0 | 0 | Down |
| mPlp1-wMN1-Cj-26 | 30 | CCAAGATACTAGAGTAGCTGTGACTGGCAC | SEQ ID NO: 182 | - | 1 | 0 | 0 | Down |
| mPlp1-wMN1-Cj-27 | 31 | GGCCTATAGCCATTCAAATGGCCAAGATAC | SEQ ID NO: 183 | - | 1 | 0 | 0 | Down |
| mPlp1-wMN1-Cj-28 | 32 | GTCCCATCTCCCTAAGTCTGAATCTGCAC | SEQ ID NO: 184 | - | 1 | 0 | 0 | Down |

TABLE 7

Target sequences of human P1 promoter for SpCas9

| No. | Target with PAM (5' to 3') | SEQ ID NO | Mismatch 0 | Mismatch 1 | Mismatch 2 |
|---|---|---|---|---|---|
| 1 | AGTTACAGGGAGCACCACCAGGG | SEQ ID NO: 330 | 1 | 0 | 0 |
| 2 | CAGTTACAGGGAGCACCACCAGG | SEQ ID NO: 331 | 1 | 0 | 0 |
| 3 | CTGGTCTGGCTTCAGTTACAGGG | SEQ ID NO: 332 | 1 | 0 | 0 |
| 4 | CCTGGTCTGGCTTCAGTTACAGG | SEQ ID NO: 333 | 1 | 0 | 0 |

TABLE 7-continued

Target sequences of human P1 promoter for SpCas9

| No. | Target with PAM (5' to 3') | SEQ ID NO | Mismatch 0 | Mismatch 1 | Mismatch 2 |
|---|---|---|---|---|---|
| 5 | CCTGGTCTGGCTTCAGTTACAGG | SEQ ID NO: 334 | 1 | 0 | 0 |
| 6 | TCTGCAGAATTCACTGGGAGGGG | SEQ ID NO: 335 | 1 | 0 | 0 |
| 7 | CTCTGCAGAATTCACTGGGAGGG | SEQ ID NO: 336 | 1 | 0 | 0 |
| 8 | TCTCTGCAGAATTCACTGGGAGG | SEQ ID NO: 337 | 1 | 0 | 0 |
| 9 | TAATCTCTGCAGAATTCACTGGG | SEQ ID NO: 338 | 1 | 0 | 0 |
| 10 | TTAATCTCTGCAGAATTCACTGG | SEQ ID NO: 339 | 1 | 0 | 0 |

TABLE 8

Target sequences of human P1 promoter for CjCas9

| No. | Target with PAM (5' to 3') | SEQ ID NO | Mismatch 0 | Mismatch 1 | Mismatch 2 |
|---|---|---|---|---|---|
| 1 | GCCTGGTCTGGCTTCAGTTACAGGGAGCAC | SEQ ID NO: 340 | 1 | 0 | 0 |
| 2 | GTGTCCAACTTTGTTTGCTTTCCAGAATAC | SEQ ID NO: 341 | 1 | 0 | 0 |
| 3 | GTATTCTGGAAAGCAAACAAAGTTGGACAC | SEQ ID NO: 342 | 1 | 0 | 0 |
| 4 | CAGTCTTGGCATCACAGGCTTCAGGCATAC | SEQ ID NO: 343 | 1 | 0 | 0 |
| 5 | GGACCTCTTGGCTATTACACAGGTTGGCAC | SEQ ID NO: 344 | 1 | 0 | 0 |
| 6 | GGAGCCAGTGGGACCTCTTGGCTATTACAC | SEQ ID NO: 345 | 1 | 0 | 0 |
| 7 | CCCAGTGAATTCTGCAGAGATTAAATATAC | SEQ ID NO: 346 | 1 | 0 | 0 |
| 8 | GGAAGGATCTGTGTCTACAGTGTTACATAC | SEQ ID NO: 347 | 1 | 0 | 0 |
| 9 | TTACCTGCACGTATGTAACACTGTAGACAC | SEQ ID NO: 348 | 1 | 0 | 0 |
| 10 | AAATAAAACTTACCTGCACGTATGTAACAC | SEQ ID NO: 349 | 1 | 0 | 0 |
| 11 | AAGTTTATTTAAAATAAAACTTACCTGCAC | SEQ ID NO: 350 | 1 | 0 | 0 |
| 12 | AAAGCATAGGCACACATCACCCAGAGGCAC | SEQ ID NO: 351 | 1 | 0 | 0 |
| 13 | TTAGGCAATTCTTGTAAAGCATAGGCACAC | SEQ ID NO: 352 | 1 | 0 | 0 |
| 14 | AATTAGGCAATTCTTGTAAAGCATAGGCAC | SEQ ID NO: 353 | 1 | 0 | 0 |
| 15 | AATCTCCAGTCAATTCCAACACAAATGCAC | SEQ ID NO: 354 | 1 | 0 | 0 |
| 16 | GCCCTCTGAATCTCCAGTCAATTCCAACAC | SEQ ID NO: 355 | 1 | 0 | 0 |

TABLE 8-continued

Target sequences of human P1 promoter for CjCas9

| No. | Target with PAM (5' to 3') | SEQ ID NO | Mismatch 0 | Mismatch 1 | Mismatch 2 |
|---|---|---|---|---|---|
| 17 | TATATCCTTGGTTAAAAGGTGGATATATAC | SEQ ID NO: 356 | 1 | 0 | 0 |

TABLE 9

Target sequences of mouse P1 promoter for CjCas9

| No. | Target with PAM (5' to 3') | SEQ ID NO | Mismatch 0 | Mismatch 1 | Mismatch 2 |
|---|---|---|---|---|---|
| 1 | CTCTTGGGATCACTCTATCCTGGAAGATAC | SEQ ID NO: 357 | 1 | 0 | 0 |
| 2 | CTTGGGATCACTCTATCCTGGAAGATACAC | SEQ ID NO: 358 | 1 | 0 | 0 |
| 3 | TCTATCCTGGAAGATACACAAGCTGGACAC | SEQ ID NO: 359 | 1 | 0 | 0 |
| 4 | GAGACATCCAAGTGGAGGAAGGGGTTACAC | SEQ ID NO: 360 | 1 | 0 | 0 |
| 5 | CTCTATAAAGCACACCCTACCCAGAGATAC | SEQ ID NO: 361 | 1 | 0 | 0 |
| 6 | ACAAAAACTGAGCCACTCTATAAAGCACAC | SEQ ID NO: 362 | 1 | 0 | 0 |
| 7 | GGACAAAAACTGAGCCACTCTATAAAGCAC | SEQ ID NO: 363 | 1 | 0 | 0 |

Hereinafter, examples of guide sequences that can be used in an exemplary embodiment disclosed in the specification are listed in Tables 10, 11, 12, 13, 14 and 15. In addition, gRNAs shown in Tables 10, 11, 12, 13, 14 and 15 were named Sp for SpCas9 and Cj for CjCas9 according to an editor protein.

TABLE 10

Guide sequences of gRNA for targeting human PMP22 gene

| gRNA | Guide Sequence (5' to 3') | SEQ ID NO |
|---|---|---|
| hPMP22-TATA-Sp#1 | GGACCAGCCCCUGAAUAAAC | SEQ ID NO: 440 |
| hPMP22-TATA-Sp#2 | GGCGUCUUUCCAGUUUAUUC | SEQ ID NO: 441 |
| hPMP22-TATA-Sp#3 | GCGUCUUUCCAGUUUAUUCA | SEQ ID NO: 442 |
| hPMP22-TATA-Sp#4 | CGUCUUUCCAGUUUAUUCAG | SEQ ID NO: 443 |
| hPMP22-TATA-Sp#5 | UUCAGGGGCUGGUCCAAUGC | SEQ ID NO: 444 |
| hPMP22-TATA-Sp#6 | UCAGGGGCUGGUCCAAUGCU | SEQ ID NO: 445 |
| hPMP22-TATA-Sp#7 | ACCAUGACAUAUCCCAGCAU | SEQ ID NO: 446 |
| hPMP22-TATA-Sp#8 | UUUCCAGUUUAUUCAGGGGC | SEQ ID NO: 447 |
| hPMP22-TATA-Sp#9 | CAGUUACAGGGAGCACCACC | SEQ ID NO: 448 |
| hPMP22-TATA-Sp#10 | CUGGUCUGGCUUCAGUUACA | SEQ ID NO: 449 |
| hPMP22-TATA-Sp#11 | CCUGGUCUGGCUUCAGUUAC | SEQ ID NO: 450 |
| hPMP22-TATA-Sp#12 | AACUGGAAAGACGCCUGGUC | SEQ ID NO: 451 |
| hPMP22-TATA-Sp#13 | GAAUAAACUGGAAAGACGCC | SEQ ID NO: 452 |
| hPMP22-TATA-Sp#14 | UCCAAUGCUGGGAUAUGUCA | SEQ ID NO: 453 |
| hPMP22-TATA-Sp#15 | AAUGCUGGGAUAUGUCAUGG | SEQ ID NO: 454 |
| hPMP22-TATA-Sp#16 | AUAGAGGCUGAGAACCUCUC | SEQ ID NO: 455 |

TABLE 10-continued

Guide sequences of gRNA for targeting human PMP22 gene

| gRNA | Guide Sequence (5' to 3') | SEQ ID NO |
|---|---|---|
| hPMP22-Enh-Sp#1 | UUGGGCAUGUUUGAGCUGGU | SEQ ID NO: 456 |
| hPMP22-Enh-Sp#2 | UUUGGGCAUGUUUGAGCUGG | SEQ ID NO: 457 |
| hPMP22-Enh-Sp#3 | GAGCUGGUGGGCGAAGCAUA | SEQ ID NO: 458 |
| hPMP22-Enh-Sp#4 | AGCUGGUGGGCGAAGCAUAU | SEQ ID NO: 459 |
| hPMP22-Enh-Sp#5 | UGGGCGAAGCAUAUGGGCAA | SEQ ID NO: 460 |
| hPMP22-Enh-Sp#6 | GGCCUCCAUCCUAAACAAUG | SEQ ID NO: 461 |
| hPMP22-Enh-Sp#10 | GGGUUGGGAGGUUUGGGCGU | SEQ ID NO: 462 |
| hPMP22-Enh-Sp#11 | AGGUUUGGGCGUGGGAGUCC | SEQ ID NO: 463 |
| hPMP22-Enh-Sp#12 | UUCAGAGACUCAGCUAUUU | SEQ ID NO: 464 |
| hPMP22-Enh-Sp#13 | GGCCACAUUGUUUAGGAUG | SEQ ID NO: 465 |
| hPMP22-Enh-Sp#14 | GGCUUUGGGCAUGUUUGAG | SEQ ID NO: 466 |
| hPMP22-Enh-Sp#15 | AACAUGCCCAAAGCCCAGC | SEQ ID NO: 467 |
| hPMP22-Enh-Sp#16 | ACAUGCCCAAAGCCCAGCG | SEQ ID NO: 468 |
| hPMP22-CDS-Sp#1 | CGAUGAUACUCAGCAACAGG | SEQ ID NO: 469 |
| hPMP22-CDS-Sp#3 | AUGGACACGCAACUGAUCUC | SEQ ID NO: 470 |

TABLE 11

Guide sequences of gRNA for targeting human PMP22 gene

| gRNA | Guide Sequence (5' to 3') | SEQ ID NO |
|---|---|---|
| hPMP22-TATA-Cj#1 | GCCCUCUGAAUCUCCAGUCAAU | SEQ ID NO: 471 |
| hPMP22-TATA-Cj#2 | AAUCUCCAGUCAAUUCCAACAC | SEQ ID NO: 472 |
| hPMP22-TATA-Cj#3 | AAUUAGGCAAUUCUUGUAAAGC | SEQ ID NO: 473 |
| hPMP22-TATA-Cj#4 | UUAGGCAAUUCUUGUAAAGCAU | SEQ ID NO: 474 |
| hPMP22-TATA-Cj#5 | AAAGCAUAGGCACACAUCACCC | SEQ ID NO: 475 |
| hPMP22-TATA-Cj#6 | GCCUGGUCUGGCUUCAGUUACA | SEQ ID NO: 476 |
| hPMP22-TATA-Cj#7 | GUGUCCAACUUUGUUUGCUUUC | SEQ ID NO: 477 |
| hPMP22-TATA-Cj#8 | GUAUUCUGGAAAGCAAACAAAG | SEQ ID NO: 478 |
| hPMP22-TATA-Cj#9 | CAGUCUUGGCAUCACAGGCUUC | SEQ ID NO: 479 |
| hPMP22-TATA-Cj#10 | GGACCUCUUGGCUAUUACACAG | SEQ ID NO: 480 |
| hPMP22-TATA-Cj#11 | GGAGCCAGUGGGACCUCUUGGC | SEQ ID NO: 481 |
| hPMP22-Enh-Cj#1 | UAAAUCACAGAGGCAAAGAGUU | SEQ ID NO: 482 |
| hPMP22-Enh-Cj#2 | UUGCAUAGUGCUAGACUGUUUU | SEQ ID NO: 483 |
| hPMP22-Enh-Cj#3 | GGGUCAUGUGUUUUGAAAACAG | SEQ ID NO: 484 |
| hPMP22-Enh-Cj#4 | CCCAAACCUCCCAACCCACAAC | SEQ ID NO: 485 |
| hPMP22-Enh-Cj#5 | ACUCAGCUAUUUCUGGAAUGAC | SEQ ID NO: 486 |
| hPMP22-Enh-Cj#6 | UCAUCGCCUUUGUGAGCUCCAU | SEQ ID NO: 487 |
| hPMP22-Enh-Cj#7 | CAGACACAGGCUUUGCUCUAGC | SEQ ID NO: 488 |

TABLE 11-continued

Guide sequences of gRNA for targeting human PMP22 gene

| gRNA | Guide Sequence (5' to 3') | SEQ ID NO |
|---|---|---|
| hPMP22-Enh-Cj#8 | CAAAGCCUGUGUCUGGCCACUA | SEQ ID NO: 489 |
| hPMP22-Enh-Cj#9 | AGCAGUUUGUGCCCACUAGUGG | SEQ ID NO: 490 |
| hPMP22-Enh-Cj#10 | AUGUCAAGGUAUUCCAGCUAAC | SEQ ID NO: 491 |
| hPMP22-Enh-Cj#11 | GAAUAACUGUAUCAAAGUUAGC | SEQ ID NO: 492 |
| hPMP22-Enh-Cj#12 | UUCCUAAUUAAGAGGCUUUGUG | SEQ ID NO: 493 |
| hPMP22-Enh-Cj#13 | GAGCUAGUUUGUCAGGGUCUAG | SEQ ID NO: 494 |

TABLE 12

Guide sequences of gRNA for targeting human PLP1 gene

| gRNA | Guide Sequence (5' to 3') | SEQ ID NO |
|---|---|---|
| hPLP1-TATA-Sp-01 | GACUUUGGGAGCUAAUAUCU | SEQ ID NO: 495 |
| hPLP1-wMN1-Sp-01 | CCCUUUCAUCUUCCCAUUCG | SEQ ID NO: 496 |
| hPLP1-wMN1-Sp-02 | CCUUUCAUCUUCCCAUUCGU | SEQ ID NO: 497 |
| hPLP1-wMN1-Sp-03 | CCCACGAAUGGGAAGAUGAA | SEQ ID NO: 498 |
| hPLP1-wMN1-Sp-04 | CAUCUUCCCAUUCGUGGGCA | SEQ ID NO: 499 |
| hPLP1-wMN1-Sp-05 | UCUCCACCUUGCCCACGAAU | SEQ ID NO: 500 |
| hPLP1-wMN1-Sp-06 | GUCUCCACCUUGCCCACGAA | SEQ ID NO: 501 |
| hPLP1-wMN1-Sp-07 | CCCAAUGCUUGCACAUAAAU | SEQ ID NO: 502 |
| hPLP1-wMN1-Sp-08 | CCAAUUUAUGUGCAAGCAUU | SEQ ID NO: 503 |
| hPLP1-wMN1-Sp-09 | UCCAAUUUAUGUGCAAGCAU | SEQ ID NO: 504 |
| hPLP1-wMN1-Sp-10 | UGUGCGCGUCUGAAGAGGAG | SEQ ID NO: 505 |
| hPLP1-wMN1-Sp-11 | GUGCGCGUCUGAAGAGGAGU | SEQ ID NO: 506 |
| hPLP1-wMN1-Sp-12 | UGCGCGUCUGAAGAGGAGUG | SEQ ID NO: 507 |
| hPLP1-wMN1-Sp-13 | UAGUCCAGAUGCUGUUGCCG | SEQ ID NO: 508 |
| hPLP1-wMN1-Sp-14 | AUUACCACGGCAACAGCAUC | SEQ ID NO: 509 |
| hPLP1-wMN1-Sp-15 | GACACGAUUUAGUAUUACCA | SEQ ID NO: 510 |
| hPLP1-wMN1-Sp-16 | CUAAAUCGUGUCCAAAGAGG | SEQ ID NO: 511 |
| hPLP1-wMN1-Sp-17 | AGGAAUCUCAGCCUCCUCUU | SEQ ID NO: 512 |
| hPLP1-wMN1-Sp-18 | GUGGACAAGGUUAACUAAAA | SEQ ID NO: 513 |
| hPLP1-wMN1-Sp-19 | AUAGUCAAAUCAUGUGGACA | SEQ ID NO: 514 |
| hPLP1-wMN1-Sp-20 | UGCUGGAUAGUCAAAUCAUG | SEQ ID NO: 515 |
| hPLP1-wMN1-Sp-21 | ACAUGAUUUGACUAUCCAGC | SEQ ID NO: 516 |
| hPLP1-wMN1-Sp-22 | AUUUGACUAUCCAGCAGGCU | SEQ ID NO: 517 |
| hPLP1-wMN1-Sp-23 | GUCCCGAAGUCUCUGGGGCC | SEQ ID NO: 518 |
| hPLP1-wMN1-Sp-24 | AAAACAGUCCCGAAGUCUCU | SEQ ID NO: 519 |
| hPLP1-wMN1-Sp-25 | GAAAACAGUCCCGAAGUCUC | SEQ ID NO: 520 |
| hPLP1-wMN1-Sp-26 | UAUAUACCACAUUCAAGUGC | SEQ ID NO: 521 |
| hPLP1-wMN1-Sp-27 | UGGAUAUAACGAAGUUGUGU | SEQ ID NO: 522 |

TABLE 12-continued

Guide sequences of gRNA for targeting human PLP1 gene

| gRNA | Guide Sequence (5' to 3') | SEQ ID NO |
|---|---|---|
| hPLP1-wMN1-Sp-28 | AUGGAUAUAACGAAGUUGUG | SEQ ID NO: 523 |
| hPLP1-wMN1-Sp-29 | AUAUGUUUGUUCACCCCAAC | SEQ ID NO: 524 |
| hPLP1-wMN1-Sp-30 | GAAAACUUGAAAUCCUGUUG | SEQ ID NO: 525 |
| hPLP1-wMN1-Sp-31 | UAGACAUUAGGAGAAACAGA | SEQ ID NO: 526 |
| hPLP1-wMN1-Sp-32 | CUAGCAGUGACAUAGACAUU | SEQ ID NO: 527 |
| hPLP1-wMN1-Sp-33 | AGCCACCUGACUUUGAUGAA | SEQ ID NO: 528 |
| hPLP1-wMN1-Sp-34 | UGAGAAAUGUUAUUACUAUA | SEQ ID NO: 529 |
| hPLP1-wMN1-Sp-35 | AGACUGCGAGAUGAGAGAGU | SEQ ID NO: 530 |
| hPLP1-wMN1-Sp-36 | CUCGCAGUCUGUACUUAGAC | SEQ ID NO: 531 |
| hPLP1-wMN1-Sp-37 | AAUGUCUCUUGAGAGAGCCA | SEQ ID NO: 532 |

TABLE 13

Guide sequences of gRNA for targeting human PLP1 gene

| gRNA | Guide Sequence (5' to 3') | SEQ ID NO |
|---|---|---|
| hPLP1-wMN1-Cj-01 | AUGGGAAGAUGAAAGGGAAGUA | SEQ ID NO: 533 |
| hPLP1-wMN1-Cj-02 | ACUUUGAUUGUUAAAACUUAUC | SEQ ID NO: 534 |
| hPLP1-wMN1-Cj-03 | AGUCCUACCUCAGCUUCCCAAU | SEQ ID NO: 535 |
| hPLP1-wMN1-Cj-04 | CAAUGCUUGCACAUAAAUUGGA | SEQ ID NO: 536 |
| hPLP1-wMN1-Cj-05 | ACACAGAGAGACAGAAUGAA | SEQ ID NO: 537 |
| hPLP1-wMN1-Cj-06 | UCCUCUUCAGACGCGCACAC | SEQ ID NO: 538 |
| hPLP1-wMN1-Cj-07 | ACUCCUCUUCAGACGCGCAC | SEQ ID NO: 539 |
| hPLP1-wMN1-Cj-08 | CCACUCCUCUUCAGACGCGCAC | SEQ ID NO: 540 |
| hPLP1-wMN1-Cj-09 | CCCCACUCCUCUUCAGACGCGC | SEQ ID NO: 541 |
| hPLP1-wMN1-Cj-10 | CUCCCCACUCCUCUUCAGACGC | SEQ ID NO: 542 |
| hPLP1-wMN1-Cj-11 | UACUCCCCACUCCUCUUCAGAC | SEQ ID NO: 543 |
| hPLP1-wMN1-Cj-12 | UAUACUCCCCACUCCUCUUCAG | SEQ ID NO: 544 |
| hPLP1-wMN1-Cj-13 | ACAGCAUCUGGACUAUCUUGUU | SEQ ID NO: 545 |
| hPLP1-wMN1-Cj-14 | AUAGUCCAGAUGCUGUUGCCGU | SEQ ID NO: 546 |
| hPLP1-wMN1-Cj-15 | AAAAGGAAUCUCAGCCUCCUCU | SEQ ID NO: 547 |
| hPLP1-wMN1-Cj-16 | UGUCACUGCUAGUGUGCUUAAU | SEQ ID NO: 548 |
| hPLP1-wMN1-Cj-17 | AUGUGAAUUCAGUACAAGAAUU | SEQ ID NO: 549 |
| hPLP1-wMN1-Cj-18 | UUAUGUGAAUUCAGUACAAGAA | SEQ ID NO: 550 |
| hPLP1-wMN1-Cj-19 | CUUUCAUUUCUGUUUAUGUGAA | SEQ ID NO: 551 |
| hPLP1-wMN1-Cj-20 | UUCACAUAAACAGAAAUGAAAG | SEQ ID NO: 552 |
| hPLP1-wMN1-Cj-21 | AUGCCAACUCUCUCAUCUCGCA | SEQ ID NO: 553 |
| hPLP1-wMN1-Cj-22 | GAGACAUUCUCACAUUUCCAGU | SEQ ID NO: 554 |

TABLE 14

Guide sequences of gRNA for targeting human P1 promoter

| gRNA | Guide Sequence (5' to 3') | SEQ ID NO |
|---|---|---|
| hPMP22-P1-Sp-01 | AGUUACAGGGAGCACCACCA | SEQ ID NO: 555 |
| hPMP22-P1-Sp-02 | CAGUUACAGGGAGCACCACC | SEQ ID NO: 556 |
| hPMP22-P1-Sp-03 | CUGGUCUGGCUUCAGUUACA | SEQ ID NO: 557 |
| hPMP22-P1-Sp-04 | CCUGGUCUGGCUUCAGUUAC | SEQ ID NO: 558 |
| hPMP22-P1-Sp-05 | CCUGGUCUGGCUUCAGUUAC | SEQ ID NO: 559 |
| hPMP22-P1-Sp-06 | UCUGCAGAAUUCACUGGGAG | SEQ ID NO: 560 |
| hPMP22-P1-Sp-07 | CUCUGCAGAAUUCACUGGGA | SEQ ID NO: 561 |
| hPMP22-P1-Sp-08 | UCUCUGCAGAAUUCACUGGG | SEQ ID NO: 562 |
| hPMP22-P1-Sp-09 | UAAUCUCUGCAGAAUUCACU | SEQ ID NO: 563 |
| hPMP22-P1-Sp-10 | UUAAUCUCUGCAGAAUUCAC | SEQ ID NO: 564 |

TABLE 15

Guide sequences of gRNA for targeting human P1 promoter

| gRNA | Guide Sequence (5' to 3') | SEQ ID NO |
|---|---|---|
| hPMP22-P1-Cj-01 | GCCUGGUCUGGCUUCAGUUACA | SEQ ID NO: 565 |
| hPMP22-P1-Cj-02 | GUGUCCAACUUUGUUUGCUUUC | SEQ ID NO: 566 |
| hPMP22-P1-Cj-03 | GUAUUCUGGAAAGCAAACAAAG | SEQ ID NO: 567 |
| hPMP22-P1-Cj-04 | CAGUCUUGGCAUCACAGGCUUC | SEQ ID NO: 568 |
| hPMP22-P1-Cj-05 | GGACCUCUUGGCUAUUACACAG | SEQ ID NO: 569 |
| hPMP22-P1-Cj-06 | GGAGCCAGUGGGACCUCUUGGC | SEQ ID NO: 570 |
| hPMP22-P1-Cj-07 | CCCAGUGAAUUCUGCAGAGAUU | SEQ ID NO: 571 |
| hPMP22-P1-Cj-08 | GGAAGGAUCUGUGUCUACAGUG | SEQ ID NO: 572 |
| hPMP22-P1-Cj-09 | UUACCUGCACGUAUGUAACACU | SEQ ID NO: 573 |
| hPMP22-P1-Cj-10 | AAAUAAAACUUACCUGCACGUA | SEQ ID NO: 574 |
| hPMP22-P1-Cj-11 | AAGUUUAUUUAAAAUAAAACUU | SEQ ID NO: 575 |
| hPMP22-P1-Cj-12 | AAAGCAUAGGCACACAUCACCC | SEQ ID NO: 576 |
| hPMP22-P1-Cj-13 | UUAGGCAAUUCUUGUAAAGCAU | SEQ ID NO: 577 |
| hPMP22-P1-Cj-14 | AAUUAGGCAAUUCUUGUAAAGC | SEQ ID NO: 578 |
| hPMP22-P1-Cj-15 | AAUCUCCAGUCAAUUCCAACAC | SEQ ID NO: 579 |
| hPMP22-P1-Cj-16 | GCCCUCUGAAUCUCCAGUCAAU | SEQ ID NO: 580 |
| hPMP22-P1-Cj-17 | UAUAUCCUUGGUUAAAAGGUGG | SEQ ID NO: 581 |

As one aspect disclosed in the specification, the expression control composition may include a guide nucleic acid and an editor protein.

In one exemplary embodiment, the expression control composition may include the following:
(a) a guide nucleic acid capable of targeting a target sequence located in the transcriptional regulatory region of a duplicate gene or a nucleic acid sequence encoding the same; and
(b) one or more editor proteins or a nucleic acid sequence(s) encoding the same.

A description related to the duplicate gene is as described above.

A description related to the transcriptional regulatory region is as described above.

A description related to the target sequence is as described above.

In another exemplary embodiment, the expression control composition may include the following:
i) a first guide nucleic acid capable of targeting a target sequence located upstream of the transcriptional regulatory region of a duplicate gene or a nucleic acid sequence encoding the same;

ii) a second guide nucleic acid capable of targeting a target sequence located downstream of the transcriptional regulatory region of a duplicate gene or a nucleic acid sequence encoding the same; and iii) one or more editor proteins or nucleic acid sequence(s) encoding the same.

A description of the duplicate gene is as described above.

A description of the transcriptional regulatory region is as described above.

A description of the target sequence is as described above.

The expression control composition may include a guide nucleic acid-editor protein complex.

The term "guide nucleic acid-editor protein complex" refers to a complex formed through the interaction between a guide nucleic acid and an editor protein.

A description related to the guide nucleic acid is as described above.

The term "editor protein" refers to a peptide, polypeptide or protein which is able to directly bind to or interact with, without direct binding to, a nucleic acid.

Here, the nucleic acid may be a nucleic acid included in a target nucleic acid, gene or chromosome.

Here, the nucleic acid may be a guide nucleic acid.

The editor protein may be an enzyme.

Here, the term "enzyme" refers to a polypeptide or protein that contains a domain capable of cleaving a nucleic acid, gene or chromosome.

The enzyme may be a nuclease or restriction enzyme.

The editor protein may include a complete active enzyme.

Here, the "complete active enzyme" refers to an enzyme having the same function as the nucleic acid, gene or chromosome cleavage function of a wild-type enzyme. For example, the wild-type enzyme that cleaves double-stranded DNA may be a complete active enzyme that entirely cleaves double-stranded DNA. As another example, when the wild-type enzyme cleaving double-stranded DNA undergoes a deletion or substitution of a partial sequence of an amino acids sequence due to artificial engineering, the artificially engineered enzyme variant cleaves double-stranded DNA like the wild-type enzyme, the artificially engineered enzyme variant may be a complete active enzyme.

In addition, the complete active enzyme may include an enzyme having an improved function, compared to the wild-type enzyme. For example, a specific modified or manipulated form of the wild-type enzyme cleaving double-stranded DNA may have a complete enzyme activity, which is greater than the wild-type enzyme, that is, an increased activity of cleaving double-stranded DNA.

The editor protein may include an incomplete or partially active enzyme.

Here, the "incomplete or partially active enzyme" refers to an enzyme having some of the nucleic acid, gene or chromosome cleavage function of the wild-type enzyme. For example, a specific modified or manipulated form of the wild-type enzyme that cleaves double-stranded DNA may be a form having a first function or a form having a second function. Here, the first function is a function of cleaving the first strand of double-stranded DNA, and the second function may be a function of cleaving the second strand of double-stranded DNA. Here, the enzyme with the first function or the enzyme with the second function may be an incomplete or partially active enzyme.

The editor protein may include an inactive enzyme.

Here, the "inactive enzyme" refers to an enzyme in which the nucleic acid, gene or chromosome cleavage function of the wild-type enzyme is entirely inactivated. For example, a specific modified or manipulated form of the wild-type enzyme may be a form in which both of the first and second functions are lost, that is, both of the first function of cleaving the first strand of double-stranded DNA and the second function of cleaving the second strand thereof are lost. Here, the enzyme in which all of the first and second functions are lost may be inactive enzyme.

The editor protein may be a fusion protein.

Here, the term "fusion protein" refers to a protein produced by fusing an enzyme with an additional domain, peptide, polypeptide or protein.

The additional domain, peptide, polypeptide or protein may be a functional domain, peptide, polypeptide or protein, which has a function the same as or different from the enzyme.

The fusion protein may be a form in which the functional domain, peptide, polypeptide or protein is added to one or more of the amino end of an enzyme or the proximity thereof; the carboxyl end of the enzyme or the proximity thereof; the middle part of the enzyme; or a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase. The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV (SEQ ID NO: 312); NLS derived from nucleoplasmin (e.g., nucleoplasmin bipartite NLS with a sequence KRPAATKKAGQAKKKK (SEQ ID NO: 313)); c-myc NLS with an amino acid sequence PAAKRVKLD (SEQ ID NO: 314) or RQRRNELKRSP (SEQ ID NO: 315); hRNPA1 M9 NLS with a sequence NQSSNFGPMKGGNFG-GRSSGPYGGGGQYFAKPRNQGGY (SEQ ID NO: 316); an importin-α-derived IBB domain sequence RMRIZFKNKGKDTAELRRRRVEVSVELRKAKKD-EQILKRRNV (SEQ ID NO: 317); myoma T protein sequences VSRKRPRP (SEQ ID NO: 318) and PPKKARED (SEQ ID NO: 319); human p53 sequence PQPKKKPL (SEQ ID NO: 320); a mouse c-abl IV sequence SALIKKKKKMAP (SEQ ID NO: 321); influenza virus NS1 sequences DRLRR (SEQ ID NO: 322) and PKQKKRK (SEQ ID NO: 323); a hepatitis virus-δ antigen sequence RKLKKKIKKL (SEQ ID NO: 324); a mouse Mx1 protein sequence REKKKFLKRR (SEQ ID NO: 325); a human poly(ADP-ribose) polymerase sequence KRKGDEVDGVDEVAKKKSKK (SEQ ID NO: 326); or steroid hormone receptor (human) glucocorticoid sequence RKCLQAGMNLEARKTKK (SEQ ID NO: 327), but the present invention is not limited thereto.

The additional domain, peptide, polypeptide or protein may be a non-functional domain, peptide, polypeptide or protein that does not perform a specific function. Here, the non-functional domain, peptide, polypeptide or protein may be a domain, peptide, polypeptide or protein that does not affect the enzyme function.

The fusion protein may be a form in which the non-functional domain, peptide, polypeptide or protein is added to one or more of the amino end of an enzyme or the proximity thereof; the carboxyl end of the enzyme or the proximity thereof; the middle part of the enzyme; or a combination thereof.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

Alternatively, the modification may be substitution, removal, addition of some nucleotides in the nucleotide sequence encoding the editor protein, or a combination thereof.

In addition, optionally, the expression control composition may further include a donor having a desired specific nucleotide sequence, which is to be inserted, or a nucleic acid sequence encoding the same.

Here, the nucleic acid sequence to be inserted may be a partial nucleotide sequence in the transcriptional regulatory region of the duplicate gene.

Here, the nucleic acid sequence to be inserted may be a nucleic acid sequence used to introduce a mutation into the transcriptional regulatory region of the duplication gene. Here, the mutation may be a mutation that interferes with the transcription of a duplicate gene.

The term "donor" refers to a nucleotide sequence that helps homologous recombination (HR)-based repair of a damaged gene or nucleic acid.

The donor may be a double- or single-stranded nucleic acid.

The donor may be present in a linear or circular shape.

The donor may include a nucleotide sequence having homology with a nucleic acid in the transcriptional regulatory region of a target gene.

For example, the donor may include a nucleotide sequence having homology with each of nucleotide sequences at a location into which a specific nucleotide sequence is to be inserted, for example, upstream (left) and downstream (right) of a damaged nucleic acid. Here, the specific nucleotide sequence to be inserted may be located between a nucleotide sequence having homology with a nucleotide sequence downstream of the damaged nucleic acid and a nucleotide sequence having homology with a nucleotide sequence upstream of the damaged nucleic acid. Here, the nucleotide sequence having homology may have at least 50%, 55%, 60%, 65%, 70%, 75%, 80%, 85%, 90% or 95% or more homology or complete homology.

The donor may include a specific nucleic acid sequence.

Here, the specific nucleic acid sequence may be a partial nucleotide sequence of a target gene or a similar nucleotide sequence thereto. The partial nucleotide sequence of the target gene may include, for example, a normal nucleic acid sequence in which a mutation for editing a target gene having a mutation is edited. Alternatively, the partial similar nucleotide sequence of a target gene may include a mutation-induced nucleic acid sequence in which a part of the partial normal nucleic acid sequence of a target gene for mutating the normal target gene is modified.

Here, the specific nucleic acid sequence may be an exogenous nucleic acid sequence. For example, the exogenous nucleic acid sequence may be an exogenous gene desired to be expressed in cells having a target gene.

Here, the specific nucleic acid sequence may be a nucleic acid sequence desired to be expressed in cells having a target gene. For example, the specific nucleic acid sequence may be a specific gene expressed in cells having a target gene, and in this case, the specific gene may be increased in copy number in cells due to an expression control composition having the donor, and thus highly expressed.

Optionally, the donor may include an additional nucleotide sequence. Here, the additional nucleotide sequence may serve to increase the stability of the donor, the efficiency of insertion into a target, or homologous recombination efficiency.

For example, the additional nucleotide sequence may be an A and T nucleotide-rich nucleic acid sequence, that is, an A-T rich domain. For example, the additional nucleotide sequence may be a scaffold/matrix attachment region (SMAR).

The guide nucleic acid, editor protein or guide nucleic acid-editor protein complex disclosed in the specification may be delivered or introduced into a subject in various ways.

Here, the term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including a target gene or chromosome of a guide nucleic acid-editor protein complex.

The organism may be an animal, animal tissue or an animal cell.

The organism may be a human, human tissue or a human cell.

The tissue may be eyeball, skin, liver, kidney, heart, lung, brain, muscle tissue, or blood.

The cell may be a fibroblast, a Schwann cell, a nerve cell, an oligodendrocyte, a myoblast, a glial cell, a macrophage, an immune cell, a hepatocyte, a retinal pigment epithelial cell, a cancer cell or a stem cell.

The specimen or sample may be acquired from an organism including a target gene or chromosome and may be saliva, blood, retinal tissue, brain tissue, a Schwann cell, an oligodendrocyte, a myoblast, a fibroblast, a neuron, a glial cell, a macrophage, a hepatocyte, an immune cell, a cancer cell, or a stem cell.

Preferably, the subject may be an organism including a duplicate gene. Here, the subject may be an organism in which a duplicate gene is in a gene duplication state.

The guide nucleic acid, editor protein or guide nucleic acid-editor protein complex may be delivered or introduced into a subject in the form of DNA, RNA or a mixed form.

Here, the guide nucleic acid and/or editor protein may be delivered or introduced into a subject in the form of DNA, RNA or a mixed form by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

In one exemplary embodiment, the nucleic acid sequence encoding the guide nucleic acid and/or editor protein may be delivered or introduced into a subject by a vector.

The vector may include a nucleic acid sequence encoding a guide nucleic acid and/or editor protein.

In one example, the vector may simultaneously include nucleic acid sequences, which encode the guide nucleic acid and the editor protein, respectively.

In another example, the vector may include the nucleic acid sequence encoding the guide nucleic acid.

As an example, domains included in the guide nucleic acid may be contained all in one vector, or may be divided and then contained in different vectors.

In another example, the vector may include the nucleic acid sequence encoding the editor protein.

As an example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase Ill.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant lentivirus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

In another exemplary embodiment, the nucleic acid sequence encoding the guide nucleic acid and/or editor protein may be delivered or introduced into a subject by a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, gene gun, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

In one example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

In a certain embodiment, the non-vector may be delivered using a lipid shell.

In a certain embodiment, the non-vector may be delivered using an exosome. The exosome is an endogenous nano-vesicle for transferring a protein and RNA, which can deliver RNA to the brain and another target organ.

In a certain embodiment, the non-vector may be delivered using a liposome. The liposome is a spherical vesicle structure which is composed of single or multiple lamellar lipid bilayers surrounding internal aqueous compartments and an external, lipophilic phospholipid bilayer which is relatively non-transparent. While the liposome may be made from several different types of lipids; phospholipids are most generally used to produce the liposome as a drug carrier.

In addition, the composition for delivery of the non-vector may be include other additives.

The editor protein may be delivered or introduced into a subject in the form of a peptide, polypeptide or protein.

The editor protein may be delivered or introduced into a subject in the form of a peptide, polypeptide or protein by a method known in the art.

The peptide, polypeptide or protein form may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

The guide nucleic acid and the editor protein may be delivered or introduced into a subject in the form of mixing a nucleic acid and a protein.

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

The guide nucleic acid-editor protein complex disclosed in the specification may modify a target nucleic acid, gene or chromosome.

For example, the guide nucleic acid-editor protein complex induces a modification in the sequence of a target nucleic acid, gene or chromosome. As a result, a protein expressed by the target nucleic acid, gene or chromosome may be modified in structure and/or function, or the expression of the protein may be controlled or inhibited.

The guide nucleic acid-editor protein complex may act at the DNA, RNA, gene or chromosome level.

In one example, the guide nucleic acid-editor protein complex may manipulate or modify the transcriptional regulatory region of a target gene to control (e.g., suppress, inhibit, reduce, increase or promote) the expression of a protein encoded by a target gene, or express a protein whose activity is controlled (e.g., suppressed, inhibited, reduced, increased or promoted) or modified.

The guide nucleic acid-editor protein complex may act at the transcription and translation stage of a gene.

In one example, the guide nucleic acid-editor protein complex may promote or inhibit the transcription of a target gene, thereby controlling (e.g., suppressing, inhibiting, reducing, increasing or promoting) the expression of a protein encoded by the target gene.

In another example, the guide nucleic acid-editor protein complex may promote or inhibit the translation of a target gene, thereby controlling (e.g., suppressing, inhibiting, reducing, increasing or promoting) the expression of a protein encoded by the target gene.

In one exemplary embodiment disclosed in the specification, the expression control composition may include gRNA and a CRISPR enzyme.

In one example, the expression control composition may include the following:
  (a) a gRNA that can target a target sequence located in the transcriptional regulatory region of a duplicate gene or a nucleic acid sequence encoding the same; and
  (b) one or more CRISPR enzymes or a nucleic acid sequence(s) encoding the same.

A description related to the duplicate gene is as described above.

A description related to the transcriptional regulatory region is as described above.

A description related to the target sequence is as described above.

In another example, the expression control composition may include:
  i) a first guide nucleic acid capable of targeting a target sequence located upstream of the transcriptional regulatory region of a duplicate gene or a nucleic acid sequence encoding the same;
  ii) a second guide nucleic acid capable of targeting a target sequence located downstream of the transcriptional regulatory region of a duplicate gene or a nucleic acid sequence encoding the same; and
  iii) one or more editor proteins or nucleic acid sequence(s) encoding the same.

A description of the duplicate gene is as described above.

A description of the transcriptional regulatory region is as described above.

A description of the target sequence is as described above.

The expression control composition may include a gRNA-CRISPR enzyme complex.

The term "gRNA-CRISPR enzyme complex" refers to a complex formed by the interaction between gRNA and a CRISPR enzyme.

A description related to the gRNA is as described above.

The term "CRISPR enzyme" is a main protein component of a CRISPR-Cas system, and forms a complex with gRNA, resulting in the CRISPR-Cas system.

The CRISPR enzyme may be a nucleic acid having a sequence encoding the CRISPR enzyme or a polypeptide (or a protein).

The CRISPR enzyme may be a Type II CRISPR enzyme.

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes a RuvC domain, an HNH domain and a PAM-interaction (PI) domain. Here, the RuvC domain encompasses RuvC-like domains, and the HNH domain encompasses HNH-like domains.

Here, the RuvC domain shares structural similarity with members of the microorganism family existing in nature having the type II CRISPR enzyme, and cleaves a single strand, for example, a non-complementary strand of a nucleic acid in the transcriptional regulatory region of a target gene, that is, a strand not forming a complementary bond with gRNA. The RuvC domain is sometimes referred to as a RuvCI domain, RuvCII domain or RuvCIII domain in the art, and generally called an RuvC I, RuvCII or RuvCIII.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs.

The PI domain recognizes a specific nucleotide sequence in the transcriptional regulatory region of a target gene, that is, a protospacer adjacent motif (PAM), or interacts with PAM. Here, the PAM may vary according to the origin of a Type II CRISPR enzyme. For example, when the CRISPR enzyme is SpCas9, the PAM may be 5'-NGG-3', and when the CRISPR enzyme is *Streptococcus thermophilus* Cas9 (StCas9), the PAM may be 5'-NNAGAAW-3' (W=A or T), when the CRISPR enzyme is *Neisseria meningiditis* Cas9 (NmCas9), the PAM may be 5'-NNNNGATT-3', and when the CRISPR enzyme is *Campylobacter jejuni* Cas9 (CjCas9), the PAM may be 5'-NNNVRYAC-3' (V=G or C or A, R=A or G, Y=C or T), herein, N is A, T, G or C; or A, U, G or C). However, while it is generally understood that PAM is determined according to the origin of the above-described enzyme, as the study of a mutant of an enzyme derived from the corresponding origin progresses, the PAM may be changed.

The Type II CRISPR enzyme may be Cas9.

The Cas9 may be derived from various microorganisms such as *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus* and *Acaryochloris marina*.

The Cas9 is an enzyme which binds to gRNA so as to cleave or modify a target sequence or position on the transcriptional regulatory region of a target gene, and may consist of an HNH domain capable of cleaving a nucleic acid strand forming a complementary bond with gRNA, an RuvC domain capable of cleaving a nucleic acid strand forming a non-complementary bond with gRNA, an REC domain interacting the target and a PI domain recognizing a PAM. Hiroshi Nishimasu et al. (2014) Cell 156:935-949 may be referenced for specific structural characteristics of Cas9.

The Cas9 may be isolated from a microorganism existing in nature or non-naturally produced by a recombinant or synthetic method.

In addition, the CRISPR enzyme may be a Type V CRISPR enzyme.

The type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a nucleic acid in the transcriptional regulatory region of a target gene is dependent on the PAM sequence.

The PAM sequence may be a sequence present in the transcriptional regulatory region of a target gene, and recognized by the PI domain of a Type V CRISPR enzyme. The PAM sequence may have different sequences according to the origin of the Type V CRISPR enzyme. That is, each species has a specifically recognizable PAM sequence. For example, the PAM sequence recognized by Cpf1 may be 5'-TTN-3' (N is A, T, C or G). While it has been generally understood that PAM is determined according to the origin of the above-described enzyme, as the study of mutants of the enzyme derived from the corresponding origin progresses, the PAM may be changed.

The Type V CRISPR enzyme may be Cpf1.

The Cpf1 may be derived from *Streptococcus, Campylobacter, Nitratifractor, Staphylococcus, Parvibaculum, Roseburia, Neisseria, Gluconacetobacter,* Azospirillum, *Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacillus, Methylobacterium* or *Acidaminococcus*.

The Cpf1 may consist of a RuvC-like domain corresponding to the RuvC domain of Cas9, a Nuc domain instead of the HNH domain of Cas9, an REC and WED domains recognizing a target, and a PI domain recognizing PAM. For specific structural characteristics of Cpf1, Takashi Yamano et al. (2016) Cell 165:949-962 may be referenced.

The Cpf1 may be isolated from a microorganism existing in nature or non-naturally produced by a recombinant or synthetic method.

The CRISPR enzyme may be a nuclease or restriction enzyme having a function of cleaving a double-stranded nucleic acid in the transcriptional regulatory region of a target gene.

The CRISPR enzyme may be a complete active CRISPR enzyme.

The term "complete active" refers to a state in which an enzyme has the same function as that of a wild-type CRISPR enzyme, and the CRISPR enzyme in such a state is named a complete active CRISPR enzyme. Here, the "function of the wild-type CRISPR enzyme" refers to a state in which an enzyme has functions of cleaving double-stranded DNA, that is, the first function of cleaving the first strand of double-stranded DNA and a second function of cleaving the second strand of double-stranded DNA.

The complete active CRISPR enzyme may be a wild-type CRISPR enzyme that cleaves double-stranded DNA.

The complete active CRISPR enzyme may be a CRISPR enzyme variant formed by modifying or manipulating the wild-type CRISPR enzyme that cleaves double-stranded DNA.

The CRISPR enzyme variant may be an enzyme in which one or more amino acids of the amino acid sequence of the wild-type CRISPR enzyme are substituted with other amino acids, or one or more amino acids are removed.

The CRISPR enzyme variant may be an enzyme in which one or more amino acids are added to the amino acid sequence of the wild-type CRISPR enzyme. Here, the location of the added amino acids may be the N-end, the C-end or the amino acid sequence of the wild-type enzyme.

The CRISPR enzyme variant may be a complete active enzyme with an improved function compared to the wild-type CRISPR enzyme.

For example, a specifically modified or manipulated form of the wild-type CRISPR enzyme, that is, the CRISPR enzyme variant may cleave double-stranded DNA while not binding to the double-stranded DNA to be cleaved or maintaining a certain distance therefrom. In this case, the modified or manipulated form may be a complete active CRISPR enzyme with an improved functional activity, compared to the wild-type CRISPR enzyme.

The CRISPR enzyme variant may be a complete active CRISPR enzyme with a reduced function, compared to the wild-type CRISPR enzyme.

For example, the specific modified or manipulated form of the wild-type CRISPR enzyme, that is, the CRISPR enzyme variant may cleave double-stranded DNA while very close to the double-stranded DNA to be cleaved or forming a specific bond therewith. Here, the specific bond may be, for example, a bond between an amino acid at a specific region of the CRISPR enzyme and a DNA sequence at the cleavage location. In this case, the modified or manipulated form may be a complete active CRISPR enzyme with a reduced functional activity, compared to the wild-type CRISPR enzyme.

The CRISPR enzyme may be an incomplete or partially active CRISPR enzyme.

The term "incomplete or partially active" refers to a state in which an enzyme has one selected from the functions of the wild-type CRISPR enzyme, that is, a first function of cleaving the first strand of double-stranded DNA and a second function of cleaving the second strand of double-stranded DNA. The CRISPR enzyme in this state is named an incomplete or partially active CRISPR enzyme. In addition, the incomplete or partially active CRISPR enzyme may be referred to as a nickase.

The term "nickase" refers to a CRISPR enzyme manipulated or modified to cleave only one strand of the double strand of a nucleic acid in the transcriptional regulatory region of a target gene, and the nickase has nuclease activity of cleaving a single strand, for example, a strand that is complementary or non-complementary to gRNA of a nucleic acid in the transcriptional regulatory region of a target gene. Therefore, to cleave the double strand, nuclease activity of the two nickases is needed.

The nickase may have nuclease activity by the RuvC domain. That is, the nickase may not include nuclease activity of the HNH domain, and to this end, the HNH domain may be manipulated or modified.

In one example, when the CRISPR enzyme is a Type II CRISPR enzyme, the nickase may be a Type II CRISPR enzyme including a modified HNH domain.

For example, provided that the Type II CRISPR enzyme is a wild-type SpCas9, the nickase may be a SpCas9 variant in which nuclease activity of the HNH domain is inactivated by mutation that the $840^{th}$ amino acid in the amino acid sequence of the wild-type SpCas9 is mutated from histidine to alanine. Since the nickase produced thereby, that is, the SpCas9 variant has nuclease activity of the RuvC domain, it is able to cleave a strand which is a non-complementary strand of a nucleic acid in the transcriptional regulatory region of a target gene, that is, a strand not forming a complementary bond with gRNA.

For another example, provided that the Type II CRISPR enzyme is a wild-type CjCas9, the nickase may be a CjCas9 variant in which nuclease activity of the HNH domain is inactivated by mutation that the $559^{th}$ amino acid in the amino acid sequence of the wild-type CjCas9 is mutated from histidine to alanine. Since the nickase produced thereby, that is, the CjCas9 variant has nuclease activity of the RuvC domain, it is able to cleave a strand which is a non-complementary strand of a nucleic acid in the transcriptional regulatory region of a target gene, that is, a strand not forming a complementary bond with gRNA.

In addition, the nickase may have nuclease activity by the HNH domain of a CRISPR enzyme. That is, the nickase may not include the nuclease activity of the RuvC domain, and to this end, the RuvC domain may be manipulated or modified.

In one example, when the CRISPR enzyme is a Type II CRISPR enzyme, the nickase may be a Type II CRISPR enzyme including a modified RuvC domain.

For example, provided that the Type II CRISPR enzyme is a wild-type SpCas9, the nickase may be a SpCas9 variant in which nuclease activity of the RuvC domain is inactivated by mutation that the $10^{th}$ amino acid in the amino acid sequence of the wild-type SpCas9 is mutated from aspartic acid to alanine. Since the nickase produced thereby, that is the SpCas9 variant has nuclease activity of the HNH domain, it is able to cleave a strand which is a complementary strand of a nucleic acid in the transcriptional regulatory region of a target gene, that is, a strand forming a complementary bond with gRNA.

For another example, provided that the Type II CRISPR enzyme is a wild-type CjCas9, the nickase may be a CjCas9 variant in which nuclease activity of the RuvC domain is inactivated by mutation that the $8^{th}$ amino acid in the amino acid sequence of the wild-type CjCas9 is mutated from aspartic acid to alanine. Since the nickase produced thereby, that is, the CjCas9 variant has nuclease activity of the HNH domain, it is able to cleave a strand which is a complementary strand of a nucleic acid in the transcriptional regulatory region of a target gene, that is, a strand forming a complementary bond with gRNA.

The CRISPR enzyme may be an inactive CRISPR enzyme.

The term "inactive" refers to a state in which both of the functions of the wild-type CRISPR enzyme, that is, the first function of cleaving the first strand of double-stranded DNA and the second function of cleaving the second strand of double-stranded DNA are lost. The CRISPR enzyme in such a state is named an inactive CRISPR enzyme.

The inactive CRISPR enzyme may have nuclease inactivity due to variations in the domain having nuclease activity of a wild-type CRISPR enzyme.

The inactive CRISPR enzyme may have nuclease inactivity due to variations in a RuvC domain and an HNH domain. That is, the inactive CRISPR enzyme may not have nuclease activity generated by the RuvC domain and HNH domain of the CRISPR enzyme, and to this end, the RuvC domain and the HNH domain may be manipulated or modified.

In one example, when the CRISPR enzyme is a Type II CRISPR enzyme, the inactive CRISPR enzyme may be a Type II CRISPR enzyme having a modified RuvC domain and HNH domain.

For example, when the Type II CRISPR enzyme is a wild-type SpCas9, the inactive CRISPR enzyme may be a SpCas9 variant in which the nuclease activities of the RuvC domain and the HNH domain are inactivated by mutations of both aspartic acid 10 and histidine 840 in the amino acid sequence of the wild-type SpCas9 to alanine. Here, since, in the produced inactive CRISPR enzyme, that is, the SpCas9 variant, the nuclease activities of the RuvC domain and the HNH domain are inactivated, a double-stranded nucleic acid in the transcriptional regulatory region of a target gene may be entirely cleaved.

In another example, when the Type II CRISPR enzyme is a wild-type CjCas9, the inactive CRISPR enzyme may be a CjCas9 variant in which the nuclease activities of the RuvC domain and the HNH domain are inactivated by mutations of both aspartic acid 8 and histidine 559 in the amino acid sequence of the wild-type CjCas9 to alanine. Here, since, in the produced inactive CRISPR enzyme, that is, the CjCas9 variant, the nuclease activities of the RuvC domain and HNH domain are inactivated, a double-stranded nucleic acid in the transcriptional regulatory region of a target gene may not be entirely cleaved.

The CRISPR enzyme may have helicase activity, that is, an ability to anneal the helix structure of the double-stranded nucleic acid, in addition to the above-described nuclease activity.

In addition, the CRISPR enzyme may be modified to complete activate, incomplete or partially activate, or inactivate the helicase activity.

The CRISPR enzyme may be a CRISPR enzyme variant produced by artificially manipulating or modifying the wild-type CRISPR enzyme.

The CRISPR enzyme variant may be an artificially manipulated or modified CRISPR enzyme variant for modifying the functions of the wild-type CRISPR enzyme, that is, the first function of cleaving the first strand of double-stranded DNA and/or the second function of cleaving the second strand of double-stranded DNA.

For example, the CRISPR enzyme variant may be a form in which the first function of the functions of the wild-type CRISPR enzyme is lost.

Alternatively, the CRISPR enzyme variant may be a form in which the second function of the functions of the wild-type CRISPR enzyme is lost.

For example, the CRISPR enzyme variant may be a form in which both of the functions of the wild-type CRISPR enzyme, that is, the first function and the second function, are lost.

The CRISPR enzyme variant may form a gRNA-CRISPR enzyme complex by interactions with gRNA.

The CRISPR enzyme variant may be an artificially manipulated or modified CRISPR enzyme variant for modifying a function of interacting with gRNA of the wild-type CRISPR enzyme.

For example, the CRISPR enzyme variant may be a form having reduced interactions with gRNA, compared to the wild-type CRISPR enzyme.

Alternatively, the CRISPR enzyme variant may be a form having increased interactions with gRNA, compared to the wild-type CRISPR enzyme.

For example, the CRISPR enzyme variant may be a form having the first function of the wild-type CRISPR enzyme and reduced interactions with gRNA.

Alternatively, the CRISPR enzyme variant may be a form having the first function of the wild-type CRISPR enzyme and increased interactions with gRNA.

For example, the CRISPR enzyme variant may be a form having the second function of the wild-type CRISPR enzyme and reduced interactions with gRNA.

Alternatively, the CRISPR enzyme variant may be a form having the second function of the wild-type CRISPR enzyme and increased interactions with gRNA.

For example, the CRISPR enzyme variant may be a form not having the first and second functions of the wild-type CRISPR enzyme, and having reduced interactions with gRNA.

Alternatively, the CRISPR enzyme variant may be a form not having the first and second functions of the wild-type CRISPR enzyme and having increased interactions with gRNA.

Here, according to the interaction strength between gRNA and the CRISPR enzyme variant, various gRNA-CRISPR enzyme complexes may be formed, and according to the CRISPR enzyme variant, there may be a difference in function of approaching or cleaving the target sequence.

For example, the gRNA-CRISPR enzyme complex formed by a CRISPR enzyme variant having reduced interactions with gRNA may cleave a double or single strand of a target sequence only when very close to or localized to the target sequence completely complementarily bind to gRNA.

The CRISPR enzyme variant may be in a form in which at least one amino acid of the amino acid sequence of the wild-type CRISPR enzyme is modified.

As an example, the CRISPR enzyme variant may be in a form in which at least one amino acid of the amino acid sequence of the wild-type CRISPR enzyme is substituted.

As another example, the CRISPR enzyme variant may be in a form in which at least one amino acid of the amino acid sequence of the wild-type CRISPR enzyme is deleted.

As still another example, the CRISPR enzyme variant may be in a form in which at least one amino acid of the amino acid sequence of the wild-type CRISPR enzyme is added.

In one example, the CRISPR enzyme variant may be in a form in which at least one amino acid of the amino acid sequence of the wild-type CRISPR enzyme is substituted, deleted and/or added.

In addition, optionally, the CRISPR enzyme variant may further include a functional domain, in addition to the original functions of the wild-type CRISPR enzyme, that is, the first function of cleaving the first strand of double-stranded DNA and the second function of cleaving the second strand thereof. Here, the CRISPR enzyme variant may have an additional function, in addition to the original functions of the wild-type CRISPR enzyme.

The functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

The functional domain may be a deaminase.

For example, cytidine deaminase may be further included as a functional domain to an incomplete or partially-active CRISPR enzyme. In one exemplary embodiment, a fusion protein may be produced by adding a cytidine deaminase, for example, apolipoprotein B editing complex 1 (APOBEC1) to a SpCas9 nickase. The [SpCas9 nickase]-[APOBEC1] formed as described above may be used in nucleotide editing of C to T or U, or nucleotide editing of G to A.

In another example, adenine deaminase may be further included as a functional domain to the incomplete or partially-active CRISPR enzyme. In one exemplary embodiment, a fusion protein may be produced by adding adenine deaminases, for example, TadA variants, ADAR2 variants or ADAT2 variants to a SpCas9 nickase. The [SpCas9 nickase]-[TadA variant], [SpCas9 nickase]-[ADAR2 variant] or [SpCas9 nickase]-[ADAT2 variant] formed as described above may be used in nucleotide editing of A to G, or nucleotide editing of T to C, because the fusion protein modifies nucleotide A to inosine, the modified inosine is recognized as nucleotide G by a polymerase, thereby substantially exhibiting nucleotide editing of A to G.

The functional domain may be a nuclear localization sequence or signal (NLS) or a nuclear export sequence or signal (NES).

In one example, the CRISPR enzyme may include one or more NLSs. Here, one or more NLSs may be included at an N-terminus of a CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 312); NLS from nucleoplasmin (e.g., nucleoplasmin bipartite NLS having the sequence KRPAATKKAGQAKKKK (SEQ ID NO: 313)); c-myc NLS having the amino acid sequence PAAKRVKLD (SEQ ID NO: 314) or RQRRNELKRSP (SEQ ID NO: 315); hRNPA1 M9 NLS having the sequence NQSSNFGPMKGGNFGGRSSGPYGGGGQYFAKPRNQGGY (SEQ ID NO: 316); the sequence RMRIZFKNKGKDTAELRRRRVEVSVELRKAKKDEQILKRRNV (SEQ ID NO: 317) of the IBB domain from importin-α; the sequences VSRKRPRP (SEQ ID NO: 318) and PPKKARED (SEQ ID NO: 319) of a myoma T protein; the sequence PQPKKKPL (SEQ ID NO: 320) of human p53; the sequence SALIKKKKKMAP (SEQ ID NO: 321) of mouse c-abl IV; the sequences DRLRR (SEQ ID NO: 322) and PKQKKRK (SEQ ID NO: 323) of influenza virus NS1; the sequence RKLKKKIKKL (SEQ ID NO: 324) of a hepatitis delta virus antigen; the sequence REKKKFLKRR (SEQ ID NO: 325) of a mouse Mx1 protein; the sequence KRKGDEVDGVDEVAKKKSKK (SEQ ID NO: 326) of a human poly (ADP-ribose) polymerase; or the NLS sequence RKCLQAGMNLEARKTKK (SEQ ID NO: 327), derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

The split-type CRISPR enzyme may be a complete, incomplete or partially active enzyme or inactive enzyme.

For example, when the CRISPR enzyme is a SpCas9, the SpCas9 may be divided into two parts between the residue 656, tyrosine, and the residue 657, threonine, thereby generating split SpCas9.

The split-type CRISPR enzyme may selectively include an additional domain, peptide, polypeptide or protein for reconstitution.

The additional domain, peptide, polypeptide or protein for reconstitution may be assembled for formation of the split-type CRISPR enzyme to be structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, when the CRISPR enzyme is a SpCas9, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycine is present, thereby producing a reconstituted CRISPR enzyme.

The CRISPR enzyme or CRISPR enzyme variant disclosed in the specification may be a polypeptide, protein or nucleic acid having a sequence encoding the same, and may be codon-optimized for a subject to introduce the CRISPR enzyme or CRISPR enzyme variant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized for optimal gene expression in a given organism based on codon optimization.

The gRNA, CRISPR enzyme or gRNA-CRISPR enzyme complex disclosed in the specification may be delivered or introduced into a subject by various delivering methods and various forms.

The subject related description is as described above.

In one exemplary embodiment, a nucleic acid sequence encoding the gRNA and/or CRISPR enzyme may be delivered or introduced into a subject by a vector.

The vector may include the nucleic acid sequence encoding the gRNA and/or CRISPR enzyme.

In one example, the vector may simultaneously include the nucleic acid sequences encoding the gRNA and the CRISPR enzyme.

In another example, the vector may include the nucleic acid sequence encoding the gRNA.

For example, domains contained in the gRNA may be contained in one vector, or may be divided and then contained in different vectors.

In another example, the vector may include the nucleic acid sequence encoding the CRISPR enzyme.

For example, in the case of the CRISPR enzyme, the nucleic acid sequence encoding the CRISPR enzyme may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase Ill.

The promoter may be an inducible promoter.

The promoter may be a subject-specific promoter.

The promoter may be a viral or non-viral promoter.

The promoter may use a suitable promoter according to a control region (that is, a nucleic acid sequence encoding the gRNA and/or CRISPR enzyme).

For example, a promoter useful for the gRNA may be a H1, EF-1a, tRNA or U6 promoter. For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus. The virus may be a retrovirus, a lentivirus, an adenovirus, adeno-associated virus (AAV), vaccinia virus, a poxvirus or a herpes simplex virus, but the present invention is not limited thereto.

In one example, a nucleic acid sequence encoding gRNA and/or a CRISPR enzyme may be delivered or introduced by a recombinant lentivirus.

In another example, a nucleic acid sequence encoding gRNA and/or a CRISPR enzyme may be delivered or introduced by a recombinant adenovirus. In still another example, a nucleic acid sequence encoding gRNA and/or a CRISPR enzyme may be delivered or introduced by recombinant AAV. In yet another example, a nucleic acid sequence encoding gRNA and/or a CRISPR enzyme may be delivered or introduced by one or more hybrids of hybrid viruses, for example, the viruses described herein.

In one exemplary embodiment, the gRNA-CRISPR enzyme complex may be delivered or introduced into a subject.

For example, the gRNA may be present in the form of DNA, RNA or a mixture thereof. The CRISPR enzyme may be present in the form of a peptide, polypeptide or protein.

In one example, the gRNA and CRISPR enzyme may be delivered or introduced into a subject in the form of a gRNA-CRISPR enzyme complex including RNA-type gRNA and a protein-type CRISPR, that is, a ribonucleoprotein (RNP).

The gRNA-CRISPR enzyme complex may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The gRNA-CRISPR enzyme complex disclosed in the specification may be used for artificial manipulation or modification, or deletion of the transcriptional regulatory region of a target gene, that is, a duplicate gene.

The transcriptional regulatory region of a target gene may be manipulated or modified using the above-described gRNA-CRISPR enzyme complex, that is, the CRISPR complex. Here, the manipulation or modification of the transcriptional regulatory region of a target gene may include both of i) cleaving or damaging of the transcriptional regulatory region of a target gene and ii) repairing of the damaged transcriptional regulatory region.

The i) cleaving or damaging of the transcriptional regulatory region of the target gene may be cleavage or damage of the transcriptional regulatory region of the target gene using the CRISPR complex, and particularly, cleavage or damage of a target sequence of the transcriptional regulatory region The target sequence nay become a target of the gRNA-CRISPR enzyme complex, and the target sequence may or may not include a PAM sequence recognized by the CRISPR enzyme. Such a target sequence may provide a critical standard to one who is involved in the designing of gRNA.

The target sequence may be specifically recognized by gRNA of the gRNA-CRISPR enzyme complex, and therefore, the gRNA-CRISPR enzyme complex may be located near the recognized target sequence.

The "cleavage" at a target site refers to the breakage of a covalent backbone of a polynucleotide. The cleavage includes enzymatic or chemical hydrolysis of a phosphodiester bond, but the present invention is not limited thereto. Other than this, the cleavage may be performed by various methods. Both of single strand cleavage and double strand cleavage are possible, wherein the double strand cleavage may result from two distinct single strand cleavages. The double strand cleavage may produce a blunt end or a staggered end (or a sticky end).

In one example, the cleavage or damage of the transcriptional regulatory region of a target gene using the CRISPR complex may be the entire cleavage or damage of the double strand of a target sequence.

In one exemplary embodiment, when the CRISPR enzyme is a wild-type SpCas9, the double strand of a target sequence forming a complementary bond with gRNA may be completely cleaved by the CRISPR complex.

In another exemplary embodiment, when the CRISPR enzymes are SpCas9 nickase (D10A) and SpCas9 nickase (H840A), the two single strands of a target sequence forming a complementary bond with gRNA may be respectively cleaved by the each CRISPR complex. That is, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In another example, the cleavage or damage of the transcriptional regulatory region of a target gene using the CRISPR complex may be the cleavage or damage of only a single strand of the double strand of a target sequence. Here, the single strand may be a guide nucleic acid-binding sequence of the target sequence complementarily binding to gRNA, that is, a complementary single strand, or a non-guide nucleic acid-binding sequence not complementarily binding to gRNA, that is, a non-complementary single strand with gRNA.

In one exemplary embodiment, when the CRISPR enzyme is a SpCas9 nickase (D10A), the CRISPR complex may cleave the guide nucleic acid-binding sequence of a target sequence complementarily binding to gRNA, that is, a complementary single strand, by a SpCas9 nickase (D10A), and may not cleave a non-guide nucleic acid-binding sequence not complementarily binding to gRNA, that is, a non-complementary single strand with gRNA.

In another exemplary embodiment, when the CRISPR enzyme is a SpCas9 nickase (H840A), the CRISPR complex may cleave the non-guide nucleic acid-binding sequence of a target sequence not complementarily binding to gRNA, that is, a non-complementary single strand with gRNA by a SpCas9 nickase (H840A), and may not cleave the guide nucleic acid-binding sequence of a target sequence complementarily binding to gRNA, that is, a complementary single strand.

In still another example, the cleavage or damage of the transcriptional regulatory region of a target gene using the CRISPR complex may be partial removal of a nucleic acid fragment.

In one exemplary embodiment, when the CRISPR complexes consist of wild-type SpCas9 and two gRNAs having different target sequences, a double strand of a target sequence forming a complementary bond with the first gRNA may be cleaved, and a double strand of a target sequence forming a complementary bond with the second gRNA may be cleaved, resulting in the removal of nucleic acid fragments by the first and second gRNAs and SpCas9.

For example, when two CRISPR complexes consist of two gRNAs complementarily binding to different target sequences, such as one gRNA complementarily binding to a target sequence present upstream of an enhancer and the other gRNA complementarily binding to a target sequence present downstream of the enhancer, and wild-type SpCas9, the double strand of the target sequence present upstream of the enhancer complementarily binding to the first gRNA may be cleaved, and the double strand of the target sequence present downstream of the enhancer complementarily binding to the second gRNA may be cleaved, thereby removing a nucleic acid fragment, that is, an enhancer region by the first gRNA, the second gRNA and SpCas9.

In still another example, the transcriptional regulatory region of a target gene may be removed using the CRISPR complex.

In one exemplary embodiment, when the CRISPR complex consists of two gRNAs complementarily binding to different target sequences and wild-type SpCas9, a double strand of the target sequence capable of complementarily binding to first gRNA (e.g., the target sequence located upstream of the promoter of a target gene) may be cleaved, and a double strand of the target sequence capable of complementarily binding to second gRNA (e.g., the target sequence located downstream of the promoter of a target gene) may be cleaved, thereby a nucleic acid fragment or a specific region (e.g., the promoter of a target sequence) may be removed using the first gRNA, the second gRNA and SpCas9.

For example, when each of two CRISPR complexes consist of two gRNAs complementarily binding to different target sequences, for example, first gRNA complementarily binding to a target sequence present upstream of a promoter controlling the transcription of a duplicate gene (e.g., PMP22 gene) and second gRNA complementarily binding to a target sequence present downstream of the promoter, and wild-type SpCas9, a double strand of the target sequence present upstream of the promoter complementarily binding to the first gRNA may be cleaved, and a double strand of the target sequence present downstream of the promoter complementarily binding to the second gRNA may be cleaved, thereby removing a nucleic acid fragment, that is, a promoter region, using the first gRNA, the second gRNA and SpCas9.

For example, when each of two CRISPR complexes consist of two gRNAs complementarily binding to different target sequences, for example, first gRNA complementarily binding to a target sequence present upstream of an enhancer controlling the transcription of a duplicate gene (e.g., PMP22 gene) and second gRNA complementarily binding to a target sequence present downstream of the enhancer, and wild-type SpCas9, the double strand of the target sequence present upstream of the enhancer complementarily binding to the first gRNA may be cleaved, and the double strand of the target sequence present downstream of the enhancer complementarily binding to the second gRNA may be cleaved, thereby removing a nucleic acid fragment, that is, an enhancer region, using the first gRNA, the second gRNA and SpCas9.

The ii) repairing of the damaged transcriptional regulatory region may be repairing or restoring performed through non-homologous end joining (NHEJ) and homology-directed repair (HDR).

The non-homologous end joining (NHEJ) is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because mutation in a significant functional domain is probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a target gene in which the expression is controlled by the transcriptional regulatory region targeted by the CRISPR complex may be performed using such NHEJ. A double strand or two single strands of the transcriptional regulatory region of a target gene may be cleaved using the CRISPR enzyme such as Cas9 or Cpf1, and the broken double strand or two single strands may have indels through the NHEJ, thereby inducing specific knockout of the target gene in which the expression is controlled by the transcriptional regulatory region.

In one example, the double strand of the transcriptional regulatory region of a target gene may be cleaved using the CRISPR complex, and various indels (insertions and deletions) may be generated at a repaired region by repairing through NHEJ.

The term "indel" refers to a variation formed by inserting or deleting a partial nucleotide into/from the nucleotide sequence of DNA. Indels may be introduced into the target sequence during repair by HDR or NHEJ, when the gRNA-CRISPR enzyme complex, as described above, cleaves a target sequence in the transcriptional regulatory region of a target gene.

The homology directed repairing (HDR) is a correction method without an error, which uses a homologous sequence as a template to repair or restore the damaged transcriptional regulatory region, and generally, to repair or restoration broken DNA, that is, to restore innate information of cells, the broken DNA is repaired using information of a complementary nucleotide sequence which is not modified or information of a sister chromatid. The most common type of HDR is homologous recombination (HR). HDR is a repair or restore method usually occurring in the S or G2/M phase of actively dividing cells.

To repair or restore damaged DNA using HDR, rather than using a complementary nucleotide sequence or sister chromatin of the cells, a DNA template artificially synthesized using information of a complementary nucleotide sequence or homologous nucleotide sequence, that is, a nucleic acid template including a complementary nucleotide sequence or homologous nucleotide sequence may be provided to the cells, thereby repairing the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be a nucleic acid sequence or nucleic acid fragment for correcting the transcriptional regulatory region of the target gene modified by a mutation to a normal gene, or a gene or nucleic acid to be expressed in cells, but the present invention is not limited thereto.

In one example, a double or single strand of the transcriptional regulatory region of a target gene acid may be cleaved using the CRISPR complex, a nucleic acid template including a nucleotide sequence complementary to a nucleotide sequence adjacent to the cleavage site may be provided to cells, and the cleaved nucleotide sequence of the transcriptional regulatory region of the target gene may be repaired or restored through HDR.

Here, the nucleic acid template including the complementary nucleotide sequence may have a complementary nucleotide sequence of the broken DNA, that is, a cleaved double or single strand, and further include a nucleic acid sequence or nucleic acid fragment to be inserted into the broken DNA. An additional nucleic acid sequence or nucleic acid fragment may be inserted into the broken DNA, that is, a cleaved site of the transcriptional regulatory region of the target gene using the nucleic acid template including the complementary nucleotide sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting the transcriptional regulatory region of a target gene modified by a mutation to a normal gene or a gene or nucleic acid to be expressed in cells. The complementary nucleotide sequence may be a nucleotide sequence having complementary bonds with broken DNA, that is, right and left nucleotide sequences of the cleaved double or single strand of the transcriptional regulatory region of the target gene. Alternatively, the complementary nucleotide sequence may be a nucleotide sequence having complementary bonds with broken DNA, that is, 3' and 5' ends of the cleaved double or single strand of the transcriptional regulatory region of the target gene. The complementary nucleotide sequence may be a 15 to 3000-nt sequence, a length or size of the complementary nucleotide sequence may be suitably designed according to a size of the nucleic acid template or the transcriptional regulatory region of the target gene. Here, the nucleic acid template may be a double- or single-stranded nucleic acid, and may be linear or circular, but the present invention is not limited thereto.

In another example, a double- or single-strand of the transcriptional regulatory region of a target gene is cleaved using the CRISPR complex, a nucleic acid template including a homologous nucleotide sequence with a nucleotide sequence adjacent to a cleavage site is provided to cells, and the cleaved nucleotide sequence of the transcriptional regulatory region of the target gene may be repaired or restored by HDR.

Here, the nucleic acid template including the homologous nucleotide sequence may have a homologous nucleotide sequence of the broken DNA, that is, a cleaved double- or single-strand, and further include a nucleic acid sequence or nucleic acid fragment to be inserted into the broken DNA. An additional nucleic acid sequence or nucleic acid fragment may be inserted into broken DNA, that is, a cleaved site of the transcriptional regulatory region of a target gene using the nucleic acid template including a homologous nucleotide sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting the transcriptional regulatory region of a target gene or nucleic acid modified by a mutation to a normal gene, or a gene or nucleic acid to be expressed in cells. The homologous nucleotide sequence may be a nucleotide sequence having homology with the broken DNA, that is, the right and left nucleotide sequence of the cleaved double-strand of the transcriptional regulatory region. Alternatively, the complementary nucleotide sequence may be a nucleotide sequence having homology with broken DNA, that is, the 3' and 5' ends of a cleaved double or single strand of the transcriptional regulatory region. The homologous nucleotide sequence may be a 15 to 3000-nt sequence, and a length or size of the homologous nucleotide sequence may be suitably designed according to a size of the nucleic acid template or the transcriptional regulatory region of a target gene. Here, the nucleic acid template may be a double- or single-stranded nucleic acid, and may be linear or circular, but the present invention is not limited thereto.

Other than the NHEJ and HDR, there are various methods for repairing or restoring a damaged transcriptional regulatory region. For example, the method of repairing or restoring a damaged transcriptional regulatory region may be single-strand annealing, single-strand break repair, mismatch repair, nucleotide cleavage repair or a method using the nucleotide cleavage repair.

The single-strand annealing (SSA) is a method of repairing double strand breaks between two repeat sequences present in a target nucleic acid, and generally uses a repeat sequence of more than 30 nucleotides. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

The SSA, similar to HDR, utilizes a complementary sequence, that is, a complementary repeat sequence, and in contrast, does not requires a nucleic acid template for modifying or correcting a target nucleic acid sequence.

Single strand breaks in a genome are repaired through a separate mechanism, single-strand break repair (SSBR), from the above-described repair mechanisms. In the case of single-strand DNA breaks, PARP1 and/or PARP2 recognizes the breaks and recruits a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing is generally involved in repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a single nucleotide. After DNA gap filling, a DNA ligase promotes end joining.

The mismatch repair (MMR) works on mismatched DNA nucleotides. Each of an MSH2/6 or MSH2/3 complex has ATPase activity and thus plays an important role in recognizing a mismatch and initiating a repair, and the MSH2/6 primarily recognizes nucleotide-nucleotide mismatches and identifies one or two nucleotide mismatches, but the MSH2/3 primarily recognizes a larger mismatch.

The base excision repair (BER) is a repair method which is active throughout the entire cell cycle, and used to remove a small non-helix-distorting base damaged region from the genome. In the damaged DNA, damaged nulceotides are removed by cleaving an N-glycoside bond joining a nucleotide to the phosphate-deoxyribose backbone, and then the phosphodiester backbone is cleaved, thereby generating breaks in single-strand DNA. The broken single strand ends formed thereby were removed, a gap generated due to the removed single strand is filled with a new complementary nucleotide, and then an end of the newly-filled complementary nucleotide is ligated with the backbone by a DNA ligase, resulting in repair of the damaged DNA.

The nucleotide excision repair (NER) is an excision mechanism important for removing large helix-distorting damage from DNA, and when the damage is recognized, a short single-strand DNA segment containing the damaged region is removed, resulting in a single strand gap of 22 to 30 nucleotides. The generated gap is filled with a new complementary nucleotide, and an end of the newly filled complementary nucleotide is ligated with the backbone by a DNA ligase, resulting in the repair of the damaged DNA.

Effects of artificially manipulating the transcriptional regulatory region of a target gene by the gRNA-CRISPR enzyme complex may be largely knockout (knock-out), knockdown, knockin (knock-in) and increased expression.

The term "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when the transcriptional regulatory region of a target gene is edited using the gRNA-CRISPR enzyme complex, that is, the CRISPR complex, the transcriptional regulatory region of the target gene may be cleaved using the CRISPR complex. The transcriptional regulatory region damaged using the CRISPR complex may be repaired by NHEJ. In the damaged transcriptional regulatory region, an indel is generated by NHEJ and thus the damaged transcriptional regulatory region is inactivated, thereby inducing target gene or chromosome-specific knockout.

In another example, when the transcriptional regulatory region of a target gene is edited using the gRNA-CRISPR enzyme complex, that is, the CRISPR complex and a donor, the transcriptional regulatory region of the target gene may be cleaved using the CRISPR complex. The transcriptional regulatory region damaged using the CRISPR complex may be repaired by HDR using a donor. Here, the donor includes a homologous nucleotide sequence and a nucleotide sequence desired to be inserted. Here, the number of nucleotide sequences to be inserted may vary according to an insertion location or purpose. When the damaged transcriptional regulatory region is repaired using a donor, a nucleotide sequence to be inserted is inserted into the damaged nucleotide sequence region, and therefore, the transcriptional regulatory region may be inactivated, thereby inducing target gene or chromosome-specific knockout.

The term "knockdown" refers to a decrease in transcription and/or translation of a target gene or nucleic acid or the expression of a target protein. The onset of a disease may be prevented or a disease may be treated by regulating the overexpression of a gene or protein through the knockdown.

For example, when the transcriptional regulatory region of a target gene edited using the gRNA-CRISPR enzyme complex, that is, the CRISPR complex, the transcriptional regulatory region of the target gene may be cleaved using the CRISPR complex. The transcriptional regulatory region damaged using the CRISPR complex may be repaired by NHEJ. In the damaged transcriptional regulatory region, an indel is generated by NHEJ and thus the damaged transcriptional regulatory region is inactivated, thereby inducing target gene or chromosome-specific knockdown.

In another example, when the transcriptional regulatory region, for example, a promoter, of a target gene is deleted using two gRNA-CRISPR enzyme complexes, that is, two CRISPR complexes, a target sequence present upstream of the promoter and a target sequence present downstream of the promoter may be cleaved using the two CRISPR complexes. The promoter region cleaved by the two CRISPR complexes may be deleted, a cleaved end upstream of the cleaved promoter and a cleaved end downstream of the cleaved promoter may be repaired, and through this, the promoter is lost, resulting in inhibition of the transcription of a target gene or chromosome and induction of specific knockdown.

In another example, when the transcriptional regulatory region of a target gene is edited using the gRNA-CRISPR enzyme complex, that is, the CRISPR complex and a donor, the transcriptional regulatory region of the target gene may be cleaved using the CRISPR complex. The transcriptional regulatory region damaged using the CRISPR complex may be repaired by HDR using a donor. Here, the donor includes a homologous nucleotide sequence and a nucleotide sequence desired to be inserted. Here, the number of the nucleotide sequences to be inserted may vary according to an insertion location or purpose. When the damaged transcriptional regulatory region is repaired using a donor, a nucleotide sequence to be inserted is inserted into the damaged nucleotide sequence region, and therefore, the transcriptional regulatory region may be inactivated, thereby inducing target gene or chromosome-specific knockdown.

For example, when the transcriptional regulatory region of a target gene is edited using a gRNA-CRISPR inactive enzyme-transcription inhibitory activity domain complex, that is, a CRISPR-inactive complex including a transcription inhibitory activity domain, the CRISPR-inactive complex may specifically bind to the transcriptional regulatory region of the target gene, and the activity of the transcriptional regulatory region is inhibited by the transcription inhibitory activity domain included in the CRISPR-inactive complex, thereby inducing knockdown in which the expression of a target gene or chromosome is inhibited.

The term "knockin" refers to insertion of a specific nucleic acid or gene into a target gene or nucleic acid, and here, the "specific nucleic acid or gene" refers to a gene or nucleic acid of interest to be inserted or expressed. A mutant gene triggering a disease may be utilized in disease treatment by correction to normal or insertion of a normal gene to induce expression of the normal gene through the knockin.

In addition, the knockin may further need a donor.

For example, when a target gene or nucleic acid is edited using the gRNA-CRISPR enzyme complex, that is, the CRISPR complex and a donor, the target gene or nucleic acid may be cleaved using the CRISPR complex. The target gene or nucleic acid damaged using the CRISPR complex may be repaired by HDR using a donor. Here, the donor may include a specific nucleic acid or gene, and may be used to insert a specific nucleic acid or gene into the damaged gene or chromosome. Here, the inserted specific nucleic acid or gene may induce the expression of a protein.

The "increased expression" refers to an increase in the transcription and/or translation of a target gene or nucleic acid or the expression of a target protein, compared to before artificially manipulation. A disease may be prevented or treated by controlling the expression of an underexpressed or non-expressed gene or protein.

For example, when the transcriptional regulatory region of a target gene is edited using the gRNA-CRISPR enzyme complex, that is, the CRISPR complex, the transcriptional regulatory region of the target gene may be cleaved using the CRISPR complex. The transcriptional regulatory region damaged using the CRISPR complex may be repaired by NHEJ. In the damaged transcriptional regulatory region, an indel is generated by NHEJ, thereby increasing the activity of the transcriptional regulatory region and inducing the expression of a normal target gene or chromosome.

In one exemplary embodiment disclosed in the specification, the gRNA-CRISPR enzyme complex may add an artificial manipulation or modification to the transcriptional regulatory region of a duplicate gene and/or a region adjacent to the transcriptional regulatory region.

The gRNA-CRISPR enzyme complex may specifically recognize a target sequence in the transcriptional regulatory region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The target sequence may be specifically recognized by gRNA of the gRNA-CRISPR enzyme complex, and therefore, the gRNA-CRISPR enzyme complex may be located near the recognized target sequence.

The target sequence may be a site or region in which an artificial modification occurs in the transcriptional regulatory region of a duplicate gene.

The target sequence may be a site or region in which an artificial modification occurs in the transcriptional regulatory region of a duplicate gene, or upstream and/or downstream of the transcriptional regulatory region.

A description of the target sequence is as described above.

In one exemplary embodiment, the target sequence may be one or more nucleotide sequences selected from the nucleotide sequences shown in Tables 1 to 9.

The gRNA-CRISPR enzyme complex may consist of a gRNA and a CRISPR enzyme.

The gRNA may include a guide domain capable of partially or completely complementarily binding to the guide nucleic acid-binding sequence of the target sequence in the transcriptional regulatory region of a duplicate gene.

The gRNA may include a guide domain capable of partially or completely complementarily binding with the guide nucleic acid-binding sequence of a target sequence located in the transcriptional regulatory region of a duplicate gene or in the region adjacent to the transcriptional regulatory region thereof.

The guide domain may be at least 70%, 75%, 80%, 85%, 90%, 95% or more complementary, or completely complementary to the guide nucleic acid-binding sequence.

The guide domain may include a nucleotide sequence complementary to the guide nucleic acid-binding sequence of the target sequence located in the transcriptional regulatory region of a duplicate gene or a region adjacent to the transcriptional regulatory region. Here, the complementary nucleotide sequence may include 0 to 5, 0 to 4, 0 to 3, or 0 to 2 mismatches.

The guide domain may include a guide sequence complementary to the guide nucleic acid-binding sequence of the target sequence located in the transcriptional regulatory region of a duplicate gene or a region adjacent to the transcriptional regulatory region.

In one exemplary embodiment, the guide sequence may be one or more nucleotide sequences selected from the nucleotide sequences shown in Tables 10 to 15.

The gRNA may include one or more domains selected from the group consisting of a first complementary domain, a linker domain, a second complementary domain, a proximal domain and a tail domain.

The CRISPR enzyme may be one or more selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein. In one example, the editor protein may be a *Campylobacter jejuni*-derived Cas9 protein or a *Staphylococcus aureus*-derived Cas9 protein.

The gRNA-CRISPR enzyme complex may add various artificial manipulations or modifications to the transcriptional regulatory region of a duplicate gene and/or a region adjacent to the transcriptional regulatory region.

The artificially manipulated or modified transcriptional regulatory region of a duplicate gene and/or region adjacent to the transcriptional regulatory region may have one or more of the following modifications to a 1 to 50-bp contiguous nucleotide sequence located in a target sequence or adjacent to the 5' end and/or 3' end of the target sequence:
 i) deletion of one or more nucleotides,
 ii) substitution of one or more nucleotides to nucleotides different from a wild-type gene,
 iii) insertion of one or more nucleotides, or
 iv) a combination of two or more selected from i) to iii).

For example, the artificially manipulated or modified transcriptional regulatory region of a duplicate gene may include deletion of one or more nucleotides in the 1b to 50-bp contiguous nucleotide sequence region located in a target sequence or adjacent to the 5' end and/or 3' end of the target sequence. In one example, the deleted nucleotides may be 1, 2, 3, 4 or 5 consecutive or non-consecutive base pairs. In another example, the deleted nucleotides may be a nucleotide fragment consisting of 2-bp or more consecutive nucleotides. Here, the nucleotide fragment may be 2 to 5, 6 to 10, 11 to 15, 16 to 20, 21 to 25, 26 to 30, 31 to 35, 36 to 40, 41 to 45, or 46 to 50 base pairs. In still another example, the deleted nucleotide may be two or more nucleotide fragments. Here, the two or more nucleotide fragments may be nucleotide fragments each having a non-consecutive nucleotide sequence, that is, one or more nucleotide sequence gaps, and may have two or more deletion sites due to the two or more deleted nucleotide fragments.

Alternatively, for example, the artificially manipulated or modified transcriptional regulatory region of a duplicate gene may include insertion of one or more nucleotides in the 1b to 50-bp contiguous nucleotide sequence region located in a target sequence or adjacent to the 5' end and/or 3' end of the target sequence. In one example, the inserted nucleotide may be 1, 2, 3, 4, or 5 consecutive base pairs. In another example, the inserted nucleotide may be a nucleotide fragment consisting of 5 or more consecutive base pairs. Here, the nucleotide fragment may be 5 to 10, 11 to 50, 50 to 100, 100 to 200, 200 to 300, 300 to 400, 400 to 500, 500 to 750, or 750 to 1000 base pairs. In still another example, the inserted nucleotides may be a partial or entire nucleotide sequence of a specific gene. Here, the specific gene may be a gene input from the outside, which is not included in a subject, such as human cells, with a duplication gene. Alternatively, the specific gene may be a gene included in a subject, such as human cells, with a duplication gene, for example, a gene present in the genome of a human cell.

Alternatively, for example, the artificially manipulated or modified transcriptional regulatory region of a duplicate gene may include the deletion and insertion of one or more nucleotides from/in a 1 to 50-bp contiguous nucleotide sequence region located in a target sequence or adjacent to the 5' end and/or 3' end of the target sequence. In one example, the deleted nucleotides may be 1, 2, 3, 4 or 5 consecutive or non-consecutive base pairs. Here, the inserted nucleotides may be 1, 2, 3, 4 or 5 base pairs; a nucleotide fragment; or a partial or entire nucleotide sequence of a specific gene, and the deletion and insertion may sequentially or simultaneously occur. Here, the inserted nucleotide fragment may be 5 to 10, 11 to 50, 50 to 100, 100 to 200, 200 to 300, 300 to 400, 400 to 500, 500 to 750, or 750 to 1000 base pairs. Here, the specific gene may be a gene input from the outside of a subject, such as human cells, with a duplication gene. Alternatively, the specific gene may be a gene included in a subject, such as human cells, with a duplication gene, for example, a gene present in the genome of a human cell. In another example, the deleted nucleotide may be a nucleotide fragment consisting of 2 base pairs or more. Here, the deleted nucleotide fragment may be 2 to 5, 6 to 10, 11 to 15, 16 to 20, 21 to 25, 26 to 30, 31 to 35, 36 to 40, 41 to 45, or 46 to 50 base pairs. Here, the inserted nucleotide may be 1, 2, 3, 4 or 5 base pairs; a nucleotide fragment; or a partial or entire nucleotide sequence of a specific gene, and the deletion and insertion may sequentially or simultaneously occur. In still another example, the deleted nucleotides may be two or more nucleotide fragments. Here, the inserted nucleotides may be 1, 2, 3, 4 or 5 base pairs; a nucleotide fragment; or a partial or entire nucleotide sequence of a specific gene, and the deletion and insertion may sequentially or simultaneously occur. In addition, the insertion may occur in a part or all of the deleted two or more sites.

The gRNA-CRISPR enzyme complex may add a variety of artificial manipulations or modifications to the transcriptional regulatory region of a duplicate gene according to the types of gRNA and a CRISPR enzyme.

In one example, when the CRISPR enzyme is a SpCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NGG-3' (N is A, T, G or C) PAM sequence present in a target region:
 i) deletion of one or more nucleotides,
 ii) substitution of one or more nucleotides to nucleotides different from the wild-type gene,
 iii) insertion of one or more nucleotides, or
 iv) a combination of two or more selected from i) to iii).

In another example, when the CRISPR enzyme is a CjCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNNNRYAC-3' (N is each independently A, T, C or G, R is A or G, and Y is C or T) PAM sequence present in a target sequence:
 i) deletion of one or more nucleotides,
 ii) substitution of one or more nucleotides to nucleotides different from the wild-type gene,
 iii) insertion of one or more nucleotides, or
 iv) a combination of two or more selected from i) to iii).

In still another example, when the CRISPR enzyme is a StCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNAGAAW-3' (N is each independently A, T, C or G, and W is A or T) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In one example, when the CRISPR enzyme is a NmCas9 protein, the artificially manipulated or modified transcriptional regulatory region of a duplicate gene may one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNNNGATT-3' (N is each independently A, T, C or G) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In another example, when the CRISPR enzyme is a SaCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNGRR(T)-3' (refers to a sequence in which N is each independently A, T, C or G, R is A or G, and (T) is arbitrarily included) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In still another example, when the CRISPR enzyme is a Cpf1 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-TTN-3' (N is A, T, C or G) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

The effect of artificially manipulating the transcriptional regulatory region of a duplicate gene by the gRNA-CRISPR enzyme complex may be knockout.

The expression of a protein encoded by a duplicate gene by the gRNA-CRISPR enzyme complex may be inhibited.

The effect of artificially manipulating the transcriptional regulatory region of a duplicate gene by the gRNA-CRISPR enzyme complex may be knockdown.

The expression of a protein encoded by a duplicate gene by the gRNA-CRISPR enzyme complex may be reduced.

The effect of artificially manipulating the transcriptional regulatory region of a duplicate gene by the gRNA-CRISPR enzyme complex may be knockin.

Here, the knockin effect may be induced by the gRNA-CRISPR enzyme complex and a donor additionally including an exogenous nucleotide sequence or gene.

The effect of artificially manipulating the transcriptional regulatory region of a duplicate gene by the gRNA-CRISPR enzyme complex and the donor may be induced by expressing a peptide or protein encoded by the exogenous nucleotide sequence or gene.

Here, the knockin effect may be induced by the gRNA-CRISPR enzyme complex and the donor including a nucleotide sequence desired to be inserted.

In one exemplary embodiment disclosed in the specification, the gRNA-CRISPR enzyme complex may add an artificial manipulation or modification to delete the transcriptional regulatory region of a duplicate gene.

The gRNA-CRISPR enzyme complex may specifically recognize a target sequence located upstream and/or downstream of the transcriptional regulatory region of a duplicate gene.

Here, the gRNA-CRISPR enzyme complex may include two types of gRNA-CRISPR enzyme complexes.

One of the two types of gRNA-CRISPR enzyme complexes may be a first gRNA-CRISPR enzyme complex specifically recognizing a target sequence located upstream of the transcriptional regulatory region of a duplicate gene.

The other one of the two types of gRNA-CRISPR enzyme complexes may be a second gRNA-CRISPR enzyme complex specifically recognizing a target sequence located downstream of the transcriptional regulatory region of the duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The target sequence may be specifically recognized by gRNA of the gRNA-CRISPR enzyme complex, and therefore, the gRNA-CRISPR enzyme complex may be located near the recognized target sequence.

The target sequence may be a site or region in which artificial cleavage occurs by the gRNA-CRISPR enzyme complex(es) located upstream and/or downstream of the transcriptional regulatory region of the duplicate gene.

A description of the target sequence is as described above.

In one exemplary embodiment, the target sequence may be one or more nucleotide sequences selected from the nucleotide sequences shown in Tables 7, 8 and 9.

The gRNA-CRISPR enzyme complex may consist of a gRNA and a CRISPR enzyme.

The gRNA may include a guide domain capable of partially or completely complementarily binding to the guide nucleic acid-binding sequence of the target sequence located upstream and/or downstream of the transcriptional regulatory region of the duplicate gene.

The guide domain may be at least 70%, 75%, 80%, 85%, 90%, 95% or more complementary, or completely complementary to the guide nucleic acid-binding sequence.

The guide domain may include a nucleotide sequence complementary to the guide nucleic acid-binding sequence of the target sequence located upstream and/or downstream of the transcriptional regulatory region of the duplicate gene. Here, the complementary nucleotide sequence may include 0 to 5, 0 to 4, 0 to 3, or 0 to 2 mismatches.

The gRNA may include one or more domains selected from the group consisting of a first complementary domain, a linker domain, a second complementary domain, a proximal domain and a tail domain.

The CRISPR enzyme may be one or more selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein. In one example, the editor protein may be a *Campylobacter jejuni*-derived Cas9 protein or a *Staphylococcus aureus*-derived Cas9 protein.

The gRNA-CRISPR enzyme complex may add an artificial manipulation or modification to delete the transcriptional regulatory region of a duplicate gene.

The artificial manipulation or modification may include the cleavage of a 1 to 50-bp contiguous nucleotide sequence, which is located in each of the target sequences located upstream and downstream of the artificially manipulated or modified transcriptional regulatory region of the duplicate gene or adjacent to the 5' end and/or 3' end of each target sequence.

Here, the cleavage may be double strand or single strand cleavage, which is generated by the gRNA-CRISPR enzyme complex.

The cleavage may occur upstream and downstream of the transcriptional regulatory region of a duplicate gene by the two types of gRNA-CRISPR enzyme complexes.

Here, one of the two types of gRNA-CRISPR enzyme complexes may be a first gRNA-CRISPR enzyme complex specifically recognizing the target sequence located upstream of the transcriptional regulatory region of the duplicate gene.

The other one of gRNA-CRISPR enzyme complexes may be a second gRNA-CRISPR enzyme complex specifically recognizing the target sequence located downstream of the transcriptional regulatory region of the duplicate gene.

Here, the first cleavage may take place upstream of the transcriptional regulatory region of the duplicate gene by the first gRNA-CRISPR enzyme complex.

The second cleavage may take place downstream of the transcriptional regulatory region of the duplicate gene by the second gRNA-CRISPR enzyme complex.

Here, the first cleavage and the second cleavage may take place simultaneously.

Here, the first cleavage and the second cleavage may take place sequentially.

Here, the first cleavage and the second cleavage may take place in reverse order.

The first cleavage and the second cleavage may take place upstream and downstream of the transcriptional regulatory region of the duplicate gene, and due to these cleavages, a fragment of the transcriptional regulatory region may be generated.

The fragment of the transcriptional regulatory region, which is generated by the first and second cleavages may be deleted or lost in DNA repairing.

Cleavage positions made by the two types of gRNA-CRISPR enzyme complexes, that is, a first cleavage part (a cleavage position upstream of the transcriptional regulatory region) and a second cleavage part (a cleavage position downstream of the transcriptional regulatory region), may be repaired through DNA repairing.

Here, the repairing may be repairing for linking the first cleavage part (3' end) and the second cleavage part (5' end).

For example, a promoter of a duplicate gene may be deleted using a first gRNA-CRISPR enzyme complex targeting upstream of the promoter (e.g., P1 promoter, P2 promoter or both thereof) of the duplicate gene (e.g., PMP22) and a second gRNA-CRISPR enzyme complex targeting downstream of the promoter. Here, a part upstream of the promoter of the duplicate gene may be cleaved by the first gRNA-CRISPR enzyme complex, and a part downstream of the promoter of the duplicate gene may be cleaved by the second gRNA-CRISPR enzyme complex. Here, the first cleavage part (3' end) and the second cleavage part (5' end) are generated by the cleavages, and a nucleic acid fragment, that is, a promoter fragment (5'-promoter-3'), between the first cleavage part and the second cleavage part may be generated. The cleavage by the gRNA-CRISPR enzyme complex may be repaired through DNA repairing. Here, the repairing may be repairing for linking the first cleavage part (3' end) and the second cleavage part (5' end). A nucleic acid fragment, that is, the promoter fragment (5'-promoter-3') between the first cleavage part and the second cleavage part may be deleted through the repairing (FIG. 39). The deletion of the nucleic acid fragment, that is, the promoter fragment (5'-promoter-3'), may induce a knockdown effect of reducing the expression of the duplicate gene or a knockout effect of inhibiting or suppressing the expression.

One aspect disclosed in the specification relates to a method of controlling expression.

One exemplary embodiment disclosed in the specification relates to a method of controlling the expression of a duplicate gene, which may be performed in vivo, ex vivo or in vitro.

In some embodiments, the method may include sampling a cell or a colony of cells from a human or non-human animal, and modifying the cell or cells. Culturing may occur in any step ex vivo. The cell or cells may be even reintroduced into a non-human animal or plant.

The method may be a method of artificially engineering eukaryotic cells, which includes introducing an expression control composition into a eukaryotic cell having a duplicate gene.

A description of the expression control composition is as described above.

In one embodiment, the expression control composition may include the following:
 (a) a guide nucleic acid capable of targeting a target sequence located in the transcriptional regulatory region of a duplicate gene or a nucleic acid sequence encoding the same; and
 (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The guide nucleic acid and the editor protein may be present in one or more vectors in the form of individual nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

The guide nucleic acid, the editor protein and/or a donor may be present in one or more vectors in the form of individual nucleic acid sequence.

The introduction step may be performed in vivo or ex vivo.

For example, the introduction step may be performed by one or more methods selected from electroporation, liposomes, plasmids, viral vectors, nanoparticles and a protein translocation domain (PTD) fusion protein method.

For example, the viral vector may be one or more selected from the group consisting of a retrovirus, a lentivirus, an adenovirus, an adeno-associated virus (AAV), a vaccinia virus, a poxvirus and a herpes virus.

In another exemplary embodiment, the expression control composition may include:
  i) a first guide nucleic acid capable of targeting a target sequence located upstream of the transcriptional regulatory region of a duplicate gene or a nucleic acid sequence encoding the same;
  ii) a second guide nucleic acid capable of targeting a target sequence located downstream of the transcriptional regulatory region of a duplicate gene or a nucleic acid sequence encoding the same; and
  iii) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The first guide nucleic acid, the second guide nucleic acid and the editor protein may be present in one or more vectors in the form of a nucleic acid sequence, or present by forming a complex by coupling of the guide nucleic acid and the editor protein.

Optionally, the expression control composition may further include a donor including a nucleic acid sequence desired to be inserted or a nucleic acid sequence encoding the same.

The first guide nucleic acid, the second guide nucleic acid and the editor protein, and/or a donor may be present in one or more vectors in the form of a nucleic acid sequence.

The introduction step may be performed in vivo or ex vivo.

For example, the introduction step may be performed by one or more methods selected from electroporation, liposomes, plasmids, viral vectors, nanoparticles and a protein translocation domain (PTD) fusion protein method.

For example, the viral vector may be one or more selected from the group consisting of a retrovirus, a lentivirus, an adenovirus, an adeno-associated virus (AAV), a vaccinia virus, a poxvirus and a herpes virus.

One aspect disclosed in the specification relates to a method of treating a gene duplication disease using a composition for controlling expression to treat a gene duplication disease.

One exemplary embodiment disclosed in the specification relates to a use for treating a gene duplication disease using a method including administration of an expression control composition for artificially manipulating the transcriptional regulatory region of a duplicate gene into a subject to be treated.

Here, the subject to be treated may include mammals including a human, a primate such as monkey, and a rodent such as a mouse and a rat.

A description of the gene duplication disease is as described above.

In one exemplary embodiment, a gene duplication disease may be a disease generated by the duplication of a PMP22 gene.

In one example, a disease generated by the duplication of the PMP22 gene may be Charcot-Marie-Tooth Type 1A (CMT1A), Dejerine-Sottas disease (Dejerine-Sottas syndrome, DSS), congenital hypomyelination neuropathy (CHN), or Roussy-Levy syndrome (RLS).

Charcot-Marie-Tooth Disease (CMT)

CMT disease is a hereditary disease caused by gene duplication that occurs in human chromosomes, and genes involved in the development of peripheral nerves in the hands and feet are duplicated by mutations, thereby causing a deformation such as a shape like an inverted champagne bottle. The CMT disease is a relatively common neurological genetic disease that occurs in 36 out of 100,000 people in the United States, and the number of patients is 2.8 million worldwide and estimated to be around 17,000 even in Korea. The CMT disease is largely classified into a total of 5 types of CMT1, CMT2, CMT3, CMT4, and CMTX according to the inherited aspect, CMT1, CMT2 and CMT3 are dominant and inherited with a 50% probability in children, and CMT4 is recessive and inherited with a probability of 25%. CMT1 and CMT2 are dominantly inherited in most domestic patients (80% and 20 to 40%, respectively), and CMT3 and CMT4 are extremely rare. CMTX is inherited through the maternal line along X chromosomes, but the frequency thereof is 10 to 20%. CMT1 is a disease caused by the inability to perform the normal process of gene expression due to gene duplication involved in the formation of proteins of the myelin sheath surrounding the neuronal axon. CMT1 is classified into 3 types. CMT1A is an autosomal dominant genetic disease, caused by duplication of the PMP22 gene located on chromosome No. 17 17p11.2-p12, resulting in the structural and functional abnormalities of the myelin sheath caused by the overexpression of the PMP22, which is an important component of the myelin sheath.

CMT2 is associated with axonal abnormalities, and is a neuropathy with a considerably reduced action potential of motor sensory nerves while the nerve conduction velocity is close to the normal state, and CMT3 occurs in early childhood as an extremely rare autosomal recessive genetic disease and is a type in which clinical symptoms and a decrease in nerve conduction velocity are very severe. CMT4 is also a type in which the onset age is early and clinical symptoms are severe, is autosomal recessive inherited, and CMTX occurs while being associated with X chromosomes and the symptoms thereof in men are more severe than those in women.

Dejerine-Sottas Disease (Dejerine-Sottas Syndrome, DSS)

DSS is a demyelinating motor sensory neuropathy occurring at an early age and is a disease which is usually autosomal dominantly inherited but is also autosomal recessively inherited, exhibits a severe demyelinating neuropathy, exhibits abnormalities of motor nerves from infancy, and is characterized by exhibiting very slow nerve conduction and an increase in specific proteins in cerebrospinal fluid. Dejerine-Sottas disease has a very rapid rate of progression, and is characterized in that gait disturbance starts from an early age and is also inherited, but also occurs sporadically. Similarly to CMT1A, PMP22 duplication is found among some patients with DSS, and in addition, it was confirmed that a missense mutation of the corresponding gene was present.

Congenital Hypomyelination Neuropathy (CHN)

CHN is a nervous system disease whose symptoms appear immediately after birth, and as the main symptoms thereof, respiratory failure, muscle weakness, muscle movement dissonance, a decrease in muscle tonicity, areflexia, motor incoordination (kinesioneurosis; ataxia), paralysis or dysesthesia appear, and affect men and women at the same rate. CHN is a genetic disease, in which a disorder occurs in motor and sensory nerves, and is characterized by a reduction in myelin sheath formation while demyelination and remyelination of the myelin sheath are repeated.

Roussy-Levy Syndrome (RLS)

RLS is a rare type of hereditary motor sensory neuropathy and was first described by Roussy and Levy, et al., in 1926, and is a case where tremors of limbs, gait loss, and the like are more severe than other hereditary motor sensory neuropathies, but the same symptoms were later found in various hereditary motor sensory neuropathy subtypes, so that RLS is currently regarded as one symptom that appears in the hereditary motor sensory neuropathy. For RLS, a mutation of an MPZ gene as a myelin protein zero gene was found in a genetic test of patients who were first reported to have RLS, and in other patients, a case where there is a duplication of the PMP22 gene as a gene of myelin protein 22 of the peripheral nerves has been reported.

In one exemplary embodiment, the gene duplication disease may be a disease generated by the duplication of a PLP1 gene.

In one example, the disease generated by the duplication of the PLP1 gene may be Pelizaeus-Merzbacher disease (PMD).

Pelizaeus-Merzbacher Disease (PMD)

Pelizaeus-Merzbacher disease (PMD) is a very rare sudanophilic leukodystrophy exhibiting various neurological symptoms due to dysmyelination of the white matter of the central nervous system. The prevalence thereof is estimated to be approximately 1/400,000. In 1885, Pelizaeus first reported one family having developmental cerebral diplegia, which is inherited chromosome X-dependently, and characterized by nystagmus, ataxia, stiffness, and acquired microcephaly, shown at the beginning of the disease. The clinical signs of PMD appear early in infancy and childhood, and the characteristic clinical symptoms of PMD are pendular nystagmus, wheezing, psychomotor development disorder or degeneration, ataxia, irregular movement, involuntary movement, oral dysfunction, and mental retardation.

PMD is a neurodegenerative disease or leukodystrophy caused by the dysmyelination of the white matter of the central nervous system due to the decrease in oligodendrocytes and the synthetic disorder of proteolipid protein (PLP). Proteolipid protein (PLP) is a protein most abundantly present in the myelin sheath of the central nervous system, and is abnormally expressed or produced due to the mutation of the PLP1 gene (Xq22) located on the long arm of chromosome X, causing dysmyelination in the central nervous system. PMD has affinity to Sudan Red in brain tissue pathology, which is caused by some azo compounds reacting with lipids, refers to the breakdown of the myelin sheath, and is observed in the centrum semiovale, the cerebellum, and the brain stem. However, since breakdown products are not found, the cause of PMD is considered to be dysmyelination or hypomyelination, rather than demyelination. Generally, the connate form of PMD is characterized by total dysmyelination, and the classic form of PMD is characterized by partial dysmyelination. When partial dysmyelination occurs, the normal medullated white matter shows a tigroid appearance. Axons and neurons of lesions with dysmyelination are generally well preserved, the number of rare oligodendrocytes is reduced, increases in astrocytes and fibrous gliosis are found in the white matter, and atrophy is found in the micropolygyria and the granular layer of the cerebellum. In 80% or more of male patients, the mutation of the PLP1 gene (Xq22) located on the long arm of chromosome X is found. Among these patients, 10 to 30% have a point mutation in the gene, and in this case, are known to exhibit more severe clinical symptoms. A phenomenon of duplicating an entire PLP1 gene is more frequently found in 60 to 70% or more of PMD patients. Recently, since PLP1 gene is located on chromosome X, generally, PMD is chromosome X-dependently inherited, has a family history, and mostly occurs in males. However, the pathogenesis of PMD may not be explained only with the PLP1 gene, and sometimes, the connate form of PMD is autosomal recessive, the adult form of PMD is autosomal dominant, or PMD sporadically occurs without a family history. Rarely, it has been reported that the symptoms of PMD are rarely expressed even in females.

In one exemplary embodiment, a gene duplication disease may be a disease that occurs due to the duplication of an MECP2 gene.

In one example, the disease caused by the duplication of the MECP2 gene may be an MECP2 duplication syndrome.

MECP2 Duplication Syndrome

A brain disease, called MECP2 duplication syndrome, is caused by the duplication of genetic material, which occurs in a specific region of chromosome X having the MECP2 gene. This disease is accompanied by a variety of symptoms, and includes symptoms such as low muscle tone, developmental delays, respiratory infection, speech abnormalities, seizures, autistic behaviors and serious intellectual disability.

This disease is a genetic disorder, but even occurs without a family history. MECP2 duplication syndrome mainly occurs in males, and Rett Syndrome occurring due to the MECP2 gene deficiency mainly occurs in females.

In one exemplary embodiment, the gene duplication disease may be a disease caused by the duplication of an RAI1 gene.

In one example, a disease caused by the RAI1 gene duplication may be Potocki-Lupski syndrome (PTLS).

Potocki-Lupski Syndrome (PTLS)

PTLS is a contiguous gene syndrome having microduplication of 11.2 region (17p11.2) on the short arm of chromosome 17, and the first study case for PTLS was reported in 1996. PTLS is known to occur due to 1.3-3.7 Mb duplication at 17p11.2 having a retinoic acid induced-1 (RAI1) gene. PTLS is considered a rare disease, and its incidence is expected to be one in 20,000 newborn babies. PTLS is characterized by various connate abnormalities and mental retardation, and 80% of the cases of PTLS have autism spectrum disorder. In addition, other unique characteristics of PTLS include sleep apnea, structural cardiovascular abnormalities, abnormal social behavior, learning disability, attention deficit disorder, obsessive behavior, and a small height.

In one exemplary embodiment, the gene duplication disease may be a disease caused by the duplication of an ELN gene.

In one example, a disease caused by the ELN gene duplication may be Williams Beuren syndrome (WBS).

Williams Beuren Syndrome (WBS)

WBS is a proximal gene syndrome associated with the abnormality of chromosome 7 having characteristic clinical findings, and the incidence of WBS is one out of 20,000 newborn babies. As the cause of microdeletion of the proximal part of the long arm of chromosome 7 (7q11.23), in this region, various genes including an elastin gene associated with the production of an elastin protein forming elastic tissue such as blood vessel walls and an LIMK1 gene associated with cognitive ability are located. Due to the deletion of such genes, various and characteristic appearances and clinical symptoms are shown. The microdeletion of 7q11.23 naturally occurs in most cases, and a family history of the microdeletion is rarely shown. Children with WBS have characteristic appearances such as a slightly raised, small nose tip, a long philtrum, a wide mouth, full lips, small cheeks (Malar hypoplasia), puffy eyes, failure of nail formation, and hallux valgus.

In one exemplary embodiment, the gene duplication disease may be a disease caused by the duplication of a JAGGED1 gene.

In one example, the disease caused by the JAGGED1 gene duplication may be Alagille syndrome (AS).

Alagille Syndrome (AS)

AS is a syndrome in which the number of bile ducts in the liver is considerably reduced, induces cholestasis, and is accompanied with abnormalities in the cardiovascular system, skeletal system, eye balls, face, pancreas, and nerve development. According to foreign reports, the incidence of AS is 1/100,000, and due to the characteristic of the disease, if including patients with minor symptoms, the incidence thereof is expected to be higher. AS occurs due to the abnormality of the JAGGED1 gene located on the short arm of chromosome 20. It is currently known that causative mutation or duplication can be found in 50 to 70% of cases through genetic testing.

The clinical symptoms of AS are generally expressed within three months after birth. AS is commonly found in the neonatal period because of contiguous jaundice and cholestasis, and found in the childhood because of chronic liver disease, and even found in the late adulthood. Since AS has various clinical symptoms and can be inherited incompletely, it may be difficult to be diagnosed. Most patients have symptoms of jaundice and cholestasis, itching resulting therefrom and progressive liver failure in infancy. Jaundice is observed in most patients, and lasts until late childhood in more than half of the patients. Itching resulting from cholestasis occurs, and some children have xanthoma in subcutaneous tissue. While the synthesis function in the liver is relatively well preserved, approximately 20% of the patients develop cirrhosis and liver failure.

In one exemplary embodiment, the gene duplication disease may be a disease caused by the duplication of a SNCA gene.

In one example, the disease caused by the SNCA gene duplication may be Parkinson's disease.

Parkinson's Disease

Parkinson's disease is a disease commonly exhibiting tremors, muscle stiffness, and movement disorders such as slowness of movement. If Parkinson's disease is not properly treated, movement disorders gradually progress, resulting in difficulty in walking and daily activity. Parkinson's disease is a disease that occurs mainly in the elderly, and with age, the risk of the onset of the disease may increase gradually. Although there is no accurate statistical data in Korea, it is estimated that Parkinson's disease occurs at a rate of 1 to 2 out of 1,000 people. Most cases of Parkinson's disease, which occur in the elderly, have been known to be less influenced by genetic factors through various studies. However, some cases of Parkinson's disease, which occur at younger ages under 40, have been known to be associated with genetic factors.

Parkinson's disease is a disease caused by a lowered dopamine concentration as dopamine neurons present in the substantia nigra gradually die. Another pathological characteristic of Parkinson's disease is the formation of a protein aggregate, which is called a Lewy body, observed in brain autopsies. The Lewy body has a protein called α-synuclein, which is the major component, and the Lewy body and α-synuclein are also associated with other diseases such as Lewy body dementia and synucleinopathy. The α-synuclein aggregation begins in the vagus nerve and anterior olfactory nucleus, rather than the midbrain, and then spreads to the cerebral cortex at the last stage via the midbrain. The hypothesis in which α-synuclein widely spreads to various regions of the brain according to the progression of Parkinson's disease is supported by recent reports in which α-synuclein is released from one cell and then transmitted to another cell.

The heritability of Parkinson's disease was first suggested by the report in which mutants (A53T and A30P) of α-synuclein, which is the major component of the Lewy body, induce Parkinson's disease. Afterward, duplication and triplication of an α-synuclein gene (SNCA) had been reported to be other causes of Parkinson's disease. This means that overexpression of a normal protein, in addition to the mutation of an α-synuclein protein, leads to accumulation of α-synuclein in cells and formation of an aggregate, resulting in the onset of Parkinson's disease.

In one exemplary embodiment, the gene duplication disease may be a disease caused by the duplication of an APP gene.

In one example, the disease caused by the APP gene duplication may be Alzheimer's disease.

Alzheimer's Disease

Alzheimer's disease is a disease caused by a brain abnormality leading to progressive degeneration of memory. In addition, Alzheimer's disease leads to dementia, which brings serious loss of intellectual functions (thinking, memory and reasoning) which is enough to interfere with daily life. In most cases, Alzheimer's disease occurs at ages beyond 65, but may rarely occur before 65. In the United States, approximately 3% of people at the age of 65 to 74, approximately 19% of people at the age of 75 to 84, and approximately 50% of people at the age of 85 or more suffer from Alzheimer's disease. In Korea, according to a recent study based on rural areas, it has been reported that approximately 21% of people at the age of 60 or more have dementia, and approximately 63% of the affected people have Alzheimer's dementia. In 2006, 266,000 people suffered from Alzheimer's disease in the world. It is anticipated that Alzheimer's disease will affect one out of 85 people by 2050.

The characteristics of the disease vary from person to person, but some of them are common in all affected people. Early symptoms tend to be mistaken for simple symptoms caused by aging or symptoms caused by stress. In the early stages of the illness, the affected people undergo common short-term memory loss, in which names, dates and places disappear from memory. If the disease becomes worse, symptoms of confusion, intensive behavior, a bipolar disorder, a speech disorder, and long-term memory loss are shown. Consequently, physical functions are lost, leading to death. Because of different symptoms per individual, it is difficult to predict how the disease will affect a person. When Alzheimer's disease is suspected, diagnosis in which thinking or acting ability is tested is usually performed, and if necessary, a brain test is performed. However, for accurate diagnosis, it is necessary to investigate cranial nerves. Although Alzheimer's disease occurs, it generally takes much time until the disease is completely diagnosed, and therefore the disease may progress for several years without diagnosis. When the disease occurs, average life expectancy is 7 years, and less than 3% of the affected people live 14 years after diagnosis.

Alzheimer's disease is classified as a neurodegenerative disease. The cause of the disease has not been fully understood, but is estimated that amyloid plaques modify a normal Alzheimer's disease protein to form a plaque mass, resulting in the loss of an intrinsic function. Alzheimer's disease has histopathological features including overall brain atrophy, ventricular enlargement, neurofibrillary tangle and neuritic plaques.

In one exemplary embodiment, the gene duplication disease may be a disease caused by the duplication of a SOX3 gene, TBX1 gene, NSD1 gene, MMP23 gene or LMB1 gene.

In one example, the gene duplication disease may be X-linked hypopituitarism (XLHP), velocardiofacial syndrome (VCFS), growth retardation syndrome, premature closure cranial sutures or autosomal dominant leukodystrophy (ADLD).

In one exemplary embodiment, the gene duplication disease may be a cancer generated by the duplication of an oncogene.

Here, the cancer gene may be an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene or an AKT2 gene.

In one example, the cancer may be breast cancer, cervical cancer, colorectal cancer, esophageal cancer, gastric cancer, glioblastoma, head and neck cancer, hepatocellular cancer, neuroblastoma, ovarian cancer, sarcoma or small cell lung cancer.

One exemplary embodiment disclosed in the specification provides a pharmaceutical composition including an expression control composition that may artificially manipulate or delete the transcriptional regulatory region of a duplicate gene.

A description of the expression control composition is as described above.

In one exemplary embodiment, the expression control composition may include the following:
 (a) a guide nucleic acid capable of targeting a target sequence located in the transcriptional regulatory region of a duplicate gene or a nucleic acid sequence encoding the same; and
 (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

Each of the guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the guide nucleic acid, the editor protein and/or a donor may be present in one or more vectors in the form of a nucleic acid sequence.

The pharmaceutical composition may further include an additional element.

The additional element may include a suitable carrier for the delivery into the body of a subject.

In one exemplary embodiment, the expression control composition may include the following:
 i) a first guide nucleic acid capable of targeting a target sequence located upstream of the transcriptional regulatory region of a duplicate gene or a nucleic acid sequence encoding the same;
ii) a second guide nucleic acid capable of targeting a target sequence located downstream of the transcriptional regulatory region of a duplicate gene or a nucleic acid sequence encoding the same; and
iii) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

Each of the first guide nucleic acid, the second guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the first guide nucleic acid, the second guide nucleic acid and the editor protein, and/or a donor may be present in one or more vectors in the form of a nucleic acid sequence.

The pharmaceutical composition may further include an additional element.

The additional element may include a suitable carrier for the delivery into the body of a subject.

One exemplary embodiment disclosed in the specification provides a method of treating a gene duplication disease, which includes administering a composition for gene engineering to an organism having a gene duplication disease to treat the gene duplication disease.

The treatment method may be a treatment method for controlling the expression of a duplicate gene by manipulating or deleting the transcriptional regulatory region of a duplicate gene present in the living body. Such a treatment method may be performed by directly injecting the expression control composition for manipulating or deleting the transcriptional regulatory region of a duplication gene present in the living body.

A description of the expression control composition is as described above.

In one exemplary embodiment, the expression control composition may include the following:
(a) a guide nucleic acid capable of targeting a target sequence located in the transcriptional regulatory region of a duplicate gene or a nucleic acid sequence encoding the same; and
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

Each of the guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the guide nucleic acid, the editor protein and/or a donor may be present in one or more vectors in the form of a nucleic acid sequence.

Here, the vector may be a plasmid or viral vector.

Here, the viral vector may be one or more selected from the group consisting of a retrovirus, a lentivirus, an adenovirus, an adeno-associated virus (AAV), a vaccinia virus, a poxvirus and a herpes virus.

In another exemplary embodiment, the expression control composition may include the following:
i) a first guide nucleic acid capable of targeting a target sequence located upstream of the transcriptional regulatory region of a duplicate gene or a nucleic acid sequence encoding the same;
ii) a second guide nucleic acid capable of targeting a target sequence located downstream of the transcriptional regulatory region of a duplicate gene or a nucleic acid sequence encoding the same; and
iii) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

Each of the first guide nucleic acid, the second guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the first guide nucleic acid, the second guide nucleic acid and the editor protein, and/or a donor may be present in one or more vectors in the form of a nucleic acid sequence.

Here, the vector may be a plasmid or viral vector.

Here, the viral vector may be one or more selected from the group consisting of a retrovirus, a lentivirus, an adenovirus, an adeno-associated virus (AAV), a vaccinia virus, a poxvirus and a herpes virus.

A description of the gene duplication disease is as described above.

The gene duplication disease may be Charcot-Marie-Tooth Type 1A (CMT1A), Dejerine-Sottas disease (DSD), congenital hypomyelination neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), velocardiofacial syndrome (VCFS), Williams Beuren syndrome (WBS), Alagille syndrome (AS), growth retardation syndrome, premature closure cranial sutures, autosomal dominant leukodystrophy (ADLD), Parkinson's disease or Alzheimer's disease.

In addition, the gene duplication disease may be breast cancer, cervical cancer, colorectal cancer, esophageal cancer, gastric cancer, glioblastoma, head and neck cancer, hepatocellular cancer, neuroblastoma, ovarian cancer, a sarcoma or small cell lung cancer.

The expression control composition may be administered to a treatment subject with a gene duplication disease.

The treatment subject may include mammals including a human, a primate such as monkey, and a rodent such as a mouse and a rat.

The expression control composition may be administered to the treatment subject.

The administration may be performed by injection, transfusion, implantation or transplantation.

The administration may be performed via an administration route selected from intraneural, subretinal, subcutaneously, intradermal, intraocular, intravitreal, intratumoral, intranodal, intramedullary, intramuscular, intravenous, intralymphatic, and intraperitoneal routes.

A dose of the expression control composition (a pharmaceutically effective amount to obtain a predetermined, desired effect) is approximately $10^4$ to $10^9$ cells/kg (body weight of an administration subject), for example, approximately $10^5$ to $10^6$ cells/kg (body weight), and may be selected from all integers in the numerical range, but the present invention is not limited thereto. The composition may be suitably prescribed in consideration of an age, health condition and body weight of an administration subject, the type of concurrent treatment, and if possible, the frequency of treatment and a desired effect.

When the transcriptional regulatory region of a duplicate gene is artificially manipulated or deleted by the method and composition according to some exemplary embodiments disclosed in the specification, the expression of mRNA and/or a protein of the duplicate gene may be controlled, thereby achieving an effect of normally controlling the expression of a duplicate gene abnormally expressed.

EXAMPLES

Hereinafter, the present invention will be described in further detail with reference to examples.

These examples are merely provided to describe the present invention in further detail, and it might be obvious to those of ordinary skill in the art that the scope of the present invention is not limited to the following examples.

Experimental Method 1. gRNA Design

CRISPR/Cas9 target regions of a human PMP22 gene, human PLP1 gene and mouse PLP1 gene were screened using CRISPR RGEN Tools (www.rgenome.net). The target regions of the PMP22 gene and the PLP1 gene may vary according to the type of CRISPR enzyme. Target sequences of a promoter region (TATA-box) and an enhancer region (for example, EGR2-, SOX10- or TEAD1-binding region); or a distal enhancer region B or C of the human PMP22 gene for SpCas9 are summarized in Table 1 above, and target sequences of a promoter region (TATA-box) and an enhancer region (for example, EGR2- or SOX10-binding region) of the human PMP22 gene for CjCas9 are summarized in Table 2. In addition, target sequences of a promoter region (TATA-box region) and an enhancer region (for example, wmN1 enhancer) of the human PLP1 gene for SpCas9 are summarized in Table 3 above, and target sequences of a promoter region (TATA-box region) and an enhancer region (For example, wmN1 enhancer) of the human PLP1 gene for CjCas9 are summarized in Table 4 above. Target sequences of a promoter region (TATA-box region) and an enhancer region (for example, wmN1 enhancer) of the mouse PLP1 gene for SpCas9 are summarized in Table 5 above, and target sequences of a promoter region (TATA-box region) and an enhancer region (for example, wmN1 enhancer) of the mouse PLP1 gene for CjCas9 are summarized in Table 6 above.

Moreover, target sequences located upstream and downstream of the promoter 1 (P1) of the human PMP22 gene and the mouse PMP22 gene are summarized in Tables 7, 8 and 9 above.

All gRNAs was generated in the form of chimeric single stranded RNA (sgRNA). The backbone sequences of Cj- and Sp-specific sgRNAs, excluding the target sequences, are 5'-GUUUUAGUCCCUGAAAAGGGAC-UAAAAUAAAGAGUUUGCGGGACUCUGCGGGG UUACAAUCCCCUAAAACCGCUUUU-3' (SEQ ID NO: 328) and 5'-GUUUUAGAGCUA-GAAAUAGCAAGUUAAAAUAAGGCUAGU-CCGUUAUCAACUUGA AAAAGUGGCACCGAGUCG-GUGC-3' (SEQ ID NO: 329).

2. Construction and Synthesis of gRNA sgRNA was packed into an AAV vector or synthesized with RNA. In order to insert the sgRNA into a viral vector, a DNA oligonucleotide corresponding to 20 to 22 base sequences of the sgRNA was designed and annealed, and ligated into a pRGEN-CAS9 (developed in-house) vector using a BsmBI site. Cas9 and the sgRNA including a variable target sequence at the 5' end were expressed through the CMV and U6 promoters, respectively.

Furthermore, for a delivery system by RNP, the sgRNA was transcribed by T7 RNA polymerase after a template was produced by annealing two partially complementary oligonucleotides produced by Phusion Taq-mediated polymerization. The transcribed sgRNA was purified and quantified using spectrometry.

3. Purification of Cas9 Protein

Codon-optimized Cas9 DNA sequences including NLS and HA epitopes were subcloned into a pET28 vector and expressed in BL21 (DE3) using IPTG under optimal culture conditions. The expressed Cas9 protein was purified using Ni-NTA agarose beads and dialyzed with an appropriate buffer. The activity of Cas9 was confirmed through an in vitro cleavage test using a well-known effective sgRNA.

4. Cell Culture

A human Schwann-like cell line (ATCC) and human primary Schwann cells (ScienCell) were cultured according to the manufacturer's manual. The human Schwann-like cells were cultured in Dulbecco's modified Eagle's medium (DMEM) (WelGene) containing a high concentration of glucose supplemented with 1×penicillin/streptomycin (WelGene) and 10% fetal calf serum (WelGene).

The human primary Schwann cells were maintained in a Schwann cell culture solution (ScienCell) provided by a vendor. For differentiation, the cells were cultured in DMEM (WelGene) containing a low concentration of glucose supplemented with a 1% fetal calf serum (WelGene), 100 ng/mL Nrg1 (Peprotech) for myelin sheath formation (myelination) signals, and 100 μM dbcAMP (Sigma-Aldrich) for 7 days.

5. Transduction (Transfection)

For transduction (transfection), an RNP complex containing 4 μg of the Cas9 protein (ToolGen) and 1 μg of sgRNA was incubated at room temperature for 15 minutes. Thereafter, the RNP complex was electroporated by using a 10 μl electroporation tip and a Neon electroporator (ThermoFisher) and delivered to 2×10⁵ cells. For targeted deep sequencing, genomic DNA (gDNA) was collected from transduced cells 72 hours after transduction.

6. In Vitro Real Time PCR (qRT-PCR)

mRNA was extracted from human primary Schwann cells according to the manufacturer's protocol using an RNeasy minikit (Qiagen). Thereafter, 100 ng mRNA was reverse transcribed using a high-capacity cDNA reverse transcription kit (ThermoFisher). qRT-PCR was performed with 100 ng of Taqman Gene expression master mix according to the manufacturer's protocol using QuantStudio 3 (ThermoFisher). PMP22 expression levels were calculated using Ct values, and GAPDH was used as an endogenous control. The Taqman probes (ThermoFisher) used in the present study are summarized in Table 16 below.

TABLE 16

| Target Gene | Taqman Gene Experssion Assay | Accession number |
|---|---|---|
| PMP22 | Hs00165556_m1 | NM_000304.3 |
| GAPDH | HS02786624_g1 | NM_001256799.2 |

7. Targeted Deep Sequencing

An on-target site was amplified by PCR from gDNA extracted from transduced cells using Phusion polymerase taq (New England BioLabs). Thereafter, paired-end deep sequencing was performed using Mi-Seq (Illumina) as the PCR amplification product. The deep sequencing results were analyzed using an online Cas-Analyzer tool (www.rgenome.net). It was confirmed whether a mutation occurred at 3 bp upstream from a PAM sequence as a result of indels by Cas9. The primers used in the present study are summarized in Table 17 below.

TABLE 17

| | Target site | Primer-F (5' to 3') | | Primer-R (5' to 3') | |
|---|---|---|---|---|---|
| On-Target | hPMP22-TATA | CACAGGGCAGTCAGAGACCC | SEQ ID NO: 185 | GCAAACAAAGTTGGACACTG | SEQ ID NO: 186 |
| | mRosa26 | AGACTCCCGCCCATCTTCTAGAAA | SEQ ID NO: 187 | AAGTCGCTCTGAGTTGTTATCAGT | SEQ ID NO: 188 |
| | AAVS1 | CAGTGAAACGCACCAGACG | SEQ ID NO: 189 | AATCTGCCTAACAGGAGGTG | SEQ ID NO: 190 |
| Off-target (In silico, in vitro) | hPMP22-TATA Off1 | GAGGGAATGGGGACCAAAGGCATT | SEQ ID NO: 191 | TCATGTGGGGTGATGTTCAGGAAG | SEQ ID NO: 192 |
| | hPMP22-TATA Off2 | AGAGCAGCTGACCTGAGGTCCAA | SEQ ID NO: 193 | CCCAAGGGTAGAGTGCAAGTAAAC | SEQ ID NO: 194 |
| | hPMP22-TATA Off3 | GCATCCTAGCTCATTTGGTCTGCT | SEQ ID NO: 195 | GAGAGGATTCCTCATGAATGGGAT | SEQ ID NO: 196 |
| | hPMP22-TATA Off4 | ACCAAACACTACACTTGGTTACTG | SEQ ID NO: 197 | CTCCCACTAGCAATTTTAAAGTCT | SEQ ID NO: 198 |
| | hPMP22-TATA Off5 | GAATGTTCAGCACAGGTTTCCTTG | SEQ ID NO: 199 | GGTCAAAAGGAGCTCCATATTTGA | SEQ ID NO: 200 |
| | hPMP22-TATA Off6 | CAGGACACCCATGGCCAAATCCAG | SEQ ID NO: 201 | CAGAGCCTCCTGCAGGGATGTCAA | SEQ ID NO: 202 |
| | hPMP22-TATA Off7 | GCCTGCCAAGGTGACTCTCATCTA | SEQ ID NO: 203 | TGCCCAGGCTGATCTTGAACTCCT | SEQ ID NO: 204 |
| | hPMP22-TATA Off8 | CCCAGAGTTAAGAGGTTCTTTCCT | SEQ ID NO: 205 | GAAGCTACTCCAGTGCAACTAGCT | SEQ ID NO: 206 |
| | hPMP22-TATA Off9 | ACGCAGTCTGTTCTGTGCAGTGT | SEQ ID NO: 207 | AGGCCTTCCCAAGGAAGACCCTGA | SEQ ID NO: 208 |
| | hPMP22-TATA Off10 | GCTGATCACTGGCCAAATCCAGCT | SEQ ID NO: 209 | GGGAAACAATGGGATCAGCTGCA | SEQ ID NO: 210 |
| | hPMP22-TATA Off11 | GCCCCTTTGTAAGTTGAGGAGCAT | SEQ ID NO: 211 | CCCTCTACCTCTCTCAATGGGCTT | SEQ ID NO: 212 |
| | hPMP22-TATA Off12 | CAGACAAGCAAATGCTGAGAGATT | SEQ ID NO: 213 | CCTGTCATTATGATGTTCGCTAGT | SEQ ID NO: 214 |

TABLE 17-continued

| Target site | | Primer-F (5' to 3') | | Primer-R (5' to 3') | |
|---|---|---|---|---|---|
| | hPMP22-TATA Off13 | CCAGAGTTGGCCTCCT ACAGAGAT | SEQ ID NO: 215 | GTGGATGCCCCACTACT GTTCATT | SEQ ID NO: 216 |
| | hPMP22-TATA Off14 | TACCCAATTTGCCAGT CTGTGTCT | SEQ ID NO: 217 | ACCACCAGGCCTGCCC TACAAGA | SEQ ID NO: 218 |
| | hPMP22-TATA Off15 | TGTGAATTTGATCCTG GCATTATG | SEQ ID NO: 219 | TACAGACAAGCAGATGC TGAGAGA | SEQ ID NO: 220 |
| | hPMP22-TATA Off16 | CAGTCAACAGAGCTCT AACCTCCT | SEQ ID NO: 221 | AGCACCTGGTTGCACAT CAACTT | SEQ ID NO: 222 |
| | hPMP22-TATA Off17 | CATGTGGTCCCTGAAC GTGAATGA | SEQ ID NO: 223 | GTCTGTCGCTTGCCCTC TTCTCT | SEQ ID NO: 224 |
| | hPMP22-TATA Off18 | ATGCAGGGCCTCTAGA CCATTTCA | SEQ ID NO: 225 | CTCAGCCCTTTGTGCAC TCACCT | SEQ ID NO: 226 |
| Off-target (Digenome-seq, in vitro) | hPMP22-TATA Off1 | TGCACATCGCAAACAT TTCG | SEQ ID NO: 227 | TGGGTATCGCACTGTGT CAG | SEQ ID NO: 228 |
| | hPMP22-TATA Off2 | AGGTTCACATGGCTTG TGGT | SEQ ID NO: 229 | ATATCTGAAATGCCCGC AGG | SEQ ID NO: 230 |
| | hPMP22-TATA Off3 | TGCACATCGCAAACAT TTCG | SEQ ID NO: 231 | TGGGTATCGCACTGTGT CAG | SEQ ID NO: 232 |
| | hPMP22-TATA Off4 | TCTTTAAAGGCCTTAT CTCC | SEQ ID NO: 233 | TTCTGCTTGAGAATTCA TCC | SEQ ID NO: 234 |
| | hPMP22-TATA Off5 | CTCCTAATCTTTCACTT AGG | SEQ ID NO: 235 | CAAAGCCTGGTATAACA TAG | SEQ ID NO: 236 |
| | hPMP22-TATA Off6 | TCACTTCGAGCATCTG TGG | SEQ ID NO: 237 | CCAAATGACAGGCTGAG CT | SEQ ID NO: 238 |
| | hPMP22-TATA Off7 | AGCAGGAAGTGAAGG CTAAG | SEQ ID NO: 239 | ATGTAACGTGGCAACTC TGG | SEQ ID NO: 240 |
| | hPMP22-TATA Off8 | GTGTTGCTCTCGTCAA TTAG | SEQ ID NO: 241 | AGGTGTTGTACATGGAG AAG | SEQ ID NO: 242 |
| | hPMP22-TATA Off9 | TGTGAGCCACCATACC CAGC | SEQ ID NO: 243 | CCTGCAGTCCTTTGCGG ATC | SEQ ID NO: 244 |
| Off-target (In silico, In vivo) | hPMP22-TATA Off1 | TCGCTGCCAGTATAAC ATGC | SEQ ID NO: 245 | AACTCCAGTCTCTAGAC TCG | SEQ ID NO: 246 |
| | hPMP22-TATA Off2 | AATAGTTTGACGTTGG AGCC | SEQ ID NO: 247 | ACTCCCAACATGTTCTC CTG | SEQ ID NO: 248 |
| | hPMP22-TATA Off3 | ATCATCGCTCACAGAG TCC | SEQ ID NO: 249 | ACGACTGCAGGATCTTA ATG | SEQ ID NO: 250 |
| | hPMP22-TATA Off4 | TGGATGGAGGTTGGG AATCC | SEQ ID NO: 251 | TTGAGGCAGCAGCACTC TCC | SEQ ID NO: 252 |
| | hPMP22-TATA Off5 | AGTCTATCCTAGCAGC TCC | SEQ ID NO: 253 | ACTGAGACCAGATAATG CAG | SEQ ID NO: 254 |
| | hPMP22-TATA Off6 | AAGAGATGCGAGTTGT TCC | SEQ ID NO: 255 | CCTCTTCTACTCTGAGT GG | SEQ ID NO: 256 |
| | hPMP22-TATA Off7 | ACCTGGTTTATCACAA GCTA | SEQ ID NO: 257 | AACGTGAACAGAAGGAT TTC | SEQ ID NO: 258 |
| | hPMP22-TATA Off8 | ATCACTCCATCAGAGT CAGG | SEQ ID NO: 259 | TGGCTCCTTCTATTCTC TCC | SEQ ID NO: 260 |

8. Design of in Silica Off-Target Site

An off-target potential site was designed in silico using an online tool (www.rgenome.net). A maximum of a 3 bp mismatch was considered as an off-target site.

9. Digenome-Seq

Genomic DNA of HeLa cells was purified according to the vendor's protocol using a DNeasy Blood & Tissue Kit (Qiagen). The Cas9 protein (100 nM) and the sgRNA (300 nM) incubated in advance were mixed with genomic DNA (10 µg) in 1 mL of a reaction solution (100 mM NaCl, 50 mM Tris-HCl, 10 mM MgCl2, 100 µg/ml BSA, pH 7.9) at 37° C. for 8 hours. Cleaved genomic DNA was treated with RNase A (50 µg/mL), and purified again using a DNeasy Tissue Kit (Qiagen). 1 µg of the cleasved genomic DNA was split into fragments using a Covaris system, and an adaptor for producing a library was connected to the DNA fragments. Thereafter, the library was subjected to whole genome sequencing (WGS) using a HiSeqxTen Sequencer (Illumina) at a sequencing depth of 30 to 40×(Macrogen). In vitro cleavage scores were calculated by a DNA cleavage scoring system at the positions of each base sequence cleaved in the genome.

10. Mice and Intraneural Injection

C22 mouse lines (B6; CBACa-Tg(PMP22)C22Clh/H) used in the present study were purchased from MRC Harwell (Oxfordshire, UK). C22 mice (4 males and 7 females) were treated with PMP22-TATA RNP. Intraneural injection was performed in the same manner as a previous study (Daisuke Ino., J Vis Exp., (2016) 115). 6-day old mice were anesthetized, and the mouse sciatic nerves were exposed by surgery. In order to minimize nerve damage, intraneural injection was immediately performed at the end of the sciatic notch was immediately using a pulled glass micropipettes attached to a microinjector. An RNP complex of 11 µg of the Cas9 protein and 2.75 µg of sgRNA per mouse was injected into the mice along with Lipofectamine 3000 (Invitrogen, Carlsbad, CA, USA). The management, use, and treatment of all animals used in the present study were performed under the guidelines prepared by the Samsung Animal Management and Use Committee (SMC-20170206001) in accordance with the Association for Assessment and Accreditation of Laboratory Animal Care International.

11. Rotarod Experiment (Rotarod Test)

Motor coordination was evaluated using a rotarod device (B.S. Technolab INC., Korea). This experiment was performed to evaluate the balance and motor coordination of the mice. Prior to the experiment, mice went through a 3-day training period. In the experiment, a horizontal rotating rod (21 rpm) was used for the rotarod experiment. The retention time on the rotating rod of the mouse was measured, and the mouse was allowed to stay on the rod for up to 300 seconds.

12. Electrophysiological Test

In order to evaluate the electrophysiological state, a nerve conduction test (NCS) was performed in the same manner as in a previous study (Jinho Lee., J Biomed Sci., (2015) 22, 43). In summary, mice were anesthetized with carbon dioxide gas, and the anesthesia was maintained using a nose cone to supply 1.5% isoflurane during the experiment. Hair was completely removed from the end to the hind paw. The NCS was performed using a Nicolet VikingQuest device (Natus Medical). For a motor nerve conduction test of the sciatic nerve, responses from a distal part and a proximal part were each determined by placing an activity recording needle electrode on the gastrocnemius muscle with a reference electrode attached to the tendon, and disposing a stimulating negative electrode at a position close to a recording electrode at a distance of 6 mm toward the body center inside the hip and the center line of the post-orbital portion thigh. The distal latency (DL), the motor nerve conduction velocity (MNCV), and the amplitude of the compound muscle action potential (CMAP) were measured. The CMAP was measured at the maximal overstimulation.

13. Nerve Histology and Images

The sciatic nerves of the mice were biopsied and a pathological examination of the affected sample was performed by analysis with a microscope. The samples were respectively fixed using a 25 mM cacodylate buffer containing 2% glutaraldehyde. Semi-thin sections were stained with toluidine blue. After incubation in 1% OsO4 for 1 hour, the samples were dehydrated in an ethanol series, and then allowed to pass through propylene oxide and embedded in an epoxy resin (Epon 812, Oken, Nagano, Japan). The cells were sliced to a certain thickness (1 μm) using Leica ultra-microtome (Leica Microsystems), and stained with toluidine blue for 30 to 45 seconds. The g-ratio (axon diameter/fiber diameter) was calculated by measuring the inner diameter and the outer diameter of myelin using the Zeiss Zen 2 program (Carl Zeiss, Oberkochen, Germany).

14. Statistical Analysis

The statistical significance of data associated with mRNA expression levels was evaluated by a one-way ANOVA using multiple comparisons of post-hoc Tukey's. Other types of presented data were calculated using a Mann-Whitney U test (http://www.socscistatistics.com/tests/mann-whitney/Default2.aspx). Data and graphs produced from the present study were analyzed using GraphPad Prism. The significance level was set at 0.05.

15. sgRNA Screening for Plp1 Gene Targeting

Mouse fibroblast cells, NIH-3T3 (ATCC, CRL-1658), myoblast cells, that is, a C2C12 line, (ATCC, CRL-1772) and oligodendrocyte cells, N20.1 (Cedarlane Laboratories, CLU108-P) were cultured according to the manuals of the manufacturers. The cells were cultured in a high-concentration glucose-containing Dulbecco's modified Eagle's medium (DMEM) supplemented with 1×penicillin/streptomycin (WelGene) and 10% fetus bovine serum (WelGene) at 37° C. and 5% $CO_2$. For transfection of a CRISPR/Cas9 composition, an RNP complex (SpCas9) consisting of 4 μg of a Cas9 protein and 1 μg of sgRNA or a CjCas9 plasmid (FIG. 30) was prepared. Afterward, the RNP complex or CjCas9 plasmid was delivered to 2×10⁵ cells by electroporation using a 10 μl electroporation tip and a Neon electroporator (ThermoFisher). For targeted deep sequencing, 72 hours after transfection, genomic DNA (gDNA) was collected from the transfected cells.

16. Downregulation Assay for Plp1 Gene mRNAs were extracted from the N20.1 cell line using a RNeasy mini kit (Qiagen) according to the protocol of the manufacturer. Afterward, 1 μg of mRNA was reverse-transcribed using a high-capacity cDNA reverse transcription kit (ThermoFisher). Real-time quantitative reverse transcription polymerase chain reaction (qRT-PCR) was performed with 100 ng of a Taqman Gene expression master mix using QuantStudio 3 (ThermoFisher) according to the protocol of the manufacturer. A Plp1 expression level was calculated using a $C_T$ value, and Gapdh was used as an endogenous control. Taqman probes (ThermoFisher) used in this study are summarized in Table 18 below.

TABLE 18

| Target Gene | Taqman Gene Experssion Assay | Accession number |
| --- | --- | --- |
| Plp1 | Mm01297210_m1 | NM_001290561.1 |
| Gapdh | Mm99999915_g1 | NM_001289726.1 |

17. sgRNA Screening for PLP1 Gene Targeting

A human lymphoblast Jurkat cell line (ATCC, TIB-152) and a human epithelial 293T cell line (ATCC, CRL-3216) were cultured according to the manual of the manufacturer. The cells were cultured in a high-concentration glucose-containing Dulbecco's modified Eagle's medium (DMEM) supplemented with 1×penicillin/streptomycin (WelGene) and 10% fetus bovine serum (WelGene) at 37° C. and 5% $CO_2$. For transfection of a CRISPR/Cas9 composition, an RNP complex (SpCas9) consisting of 4 μg of a Cas9 protein and 1 μg of sgRNA or a CjCas9 plasmid (FIG. 30) was prepared. Afterward, the RNP complex or CjCas9 plasmid was delivered to 2×10⁵ cells by electroporation using a 10 μl electroporation tip and a Neon electroporator (ThermoFisher). For targeted deep sequencing, 72 hours after transfection, genomic DNA (gDNA) was collected from the transfected cells.

18. In Vitro Primary Schwann Cell Culture, CRISPR/Cas9 Transfection and DNA/RNA Analysis 18-1. Preparation of sgRNA sgRNAs were generated by in vitro transcription using T7 polymerase (New England BioLabs) according to the manufacturer's protocol.

18-2. In Vitro Primary Schwann Cell Culture and CRISPR/Cas9 Transfection

About 3-4 weeks old C22 mice (6-10 mice/preparation) were sacrificed by a CO2 gas chamber. The accompanying procedure requires a sterile environment, equipment and cell culture tools. Both sciatic nerves were exposed, dissected out. Then, the surrounding membranes and muscular tissue of isolated nerves were carefully removed under a stereomicroscope. The epineurium was stripped off with fine forceps. The remaining nerves were then transferred to tube containing ice-cold phosphate-buffered saline (PBS) and centrifuged at 1500 rpm for 10 min. For single cell dissociation, enzymatic digestion was performed with 0.05% collagenase-A solution (Sigma) for 30 min at 37° C. Enzymatic activity was stopped by fetal bovine serum (Welgene) and centrifuged for 5 min at 1500 rpm. Dissociated cells were then seeded onto poly-L-ornithine- (Sigma) and laminin (ThermoFisher) coated dishes and allowed to adhere overnight. To eliminate contaminating fibroblasts, 10 µM AraC (Sigma) was added to the medium. After 48 h, the medium was replaced by DMEM (Welgene) containing 3% FBS with 3 µM forskolin (Sigma) and 20 ng/ml neuregulin (R&D systems) to expand the cells. For transfection of CRISPR/Cas9 components, 2×105 cells were electroporated with the RNP complexes using a Neon electroporator (ThermoFisher).

18-3. Real Time PCR (qRT-PCR)

For gene expression analysis, total RNA of the primary Schwann cells were extracted using RNeasy Mini Kit (QIAGEN) according to manufacturer's protocol, 5 days post transfection. cDNA was obtained using SuperScript II according to the manufacturer's protocol (Thermo Fisher) as total mRNA extracted. qRT-PCR was performed using Power SYBR® Green Master Mix (Thermo Fisher) protocol with the following primers: Human P1-PMP22-F, 5'-CTTAGTCTGTCGGCTGCGGG-3' (SEQ ID NO: 364); Human P1-PMP22-R: 5'-GGCCAAACAGCGTAACCCCT-3' (SEQ ID NO: 365); Human P2-PMP22-F: 5'-CGTTAAAGGGGAACGCCAGGA-3' (SEQ ID NO: 366); Human P2-PMP22-R: 5'-CAGGGTGGCCTCAAACACAA-3' (SEQ ID NO: 367); Mouse Mpz-F: 5'-CGGACAGGGAAATCTATGGTGC-3' (SEQ ID NO: 368); Mouse Mpz-R: 5'-GCGCCAGGTAAAAGAGATGTCA-3' (SEQ ID NO: 369); Mouse P1-Pmp22-F: 5'-AGCTCCACCAGAGAACCTCTCA-3' (SEQ ID NO: 370); Mouse P1-Pmp22-R: 5'-TGAGGAGTAGCAGTGTTGGACGG-3' (SEQ ID NO: 371); Mouse P2-Pmp22-F: 5'-TGACCCGCAGCACAGCTGTCTTTG-3' (SEQ ID NO: 372); Mouse P2-Pmp22-R: 5'-TGAGGAGTAGCAGTGTTGGACGG-3' (SEQ ID NO: 373).

18-4. Targeted Deep Sequencing

The on-target region was PCR amplified from gDNA extracted from transfected cells using Phusion polymerase (New England BioLabs). The resulting PCR amplicons were then subjected to paired-end deep sequencing using Mi-Seq (Illumina). Data from deep sequencing were analysed using the online Cas-Analyzer tool (www.rgenome.net). Indels in the region 3 bp upstream of the protospacer-adjacent motif (PAM) sequence were considered to be mutations resulting from Cas9.

Example 1. sgRNA Screening for PMP22 Gene

In order to screen for therapeutically effective sgRNA sequences which may reduce the expression of human PMP22 to a normal range, human cell lines were transduced with various sgRNAs and Cas9s designed to target the promoter (TATA-box) and intronic enhancer binding site of a PMP gene. In brief, Jurkat human T cells were used for SpCas9 screening, and HEK293T cells were used for CjCas9. gDNA was collected from the cells and subjected to targeted deep sequencing. Various patterns of mutations induced by the sgRNA sequences were identified by an NHEJ-mediated indel. Several SpCas9-sgRNAs strongly induced indels in two regulatory sites (FIGS. 1 and 2). It was confirmed that 30 to 40% of indels were induced in a specific CjCas9-sgRNA (FIGS. 3 and 4).

Example 2. Gene Manipulation of Schwann-Like Cells

Figure 7:
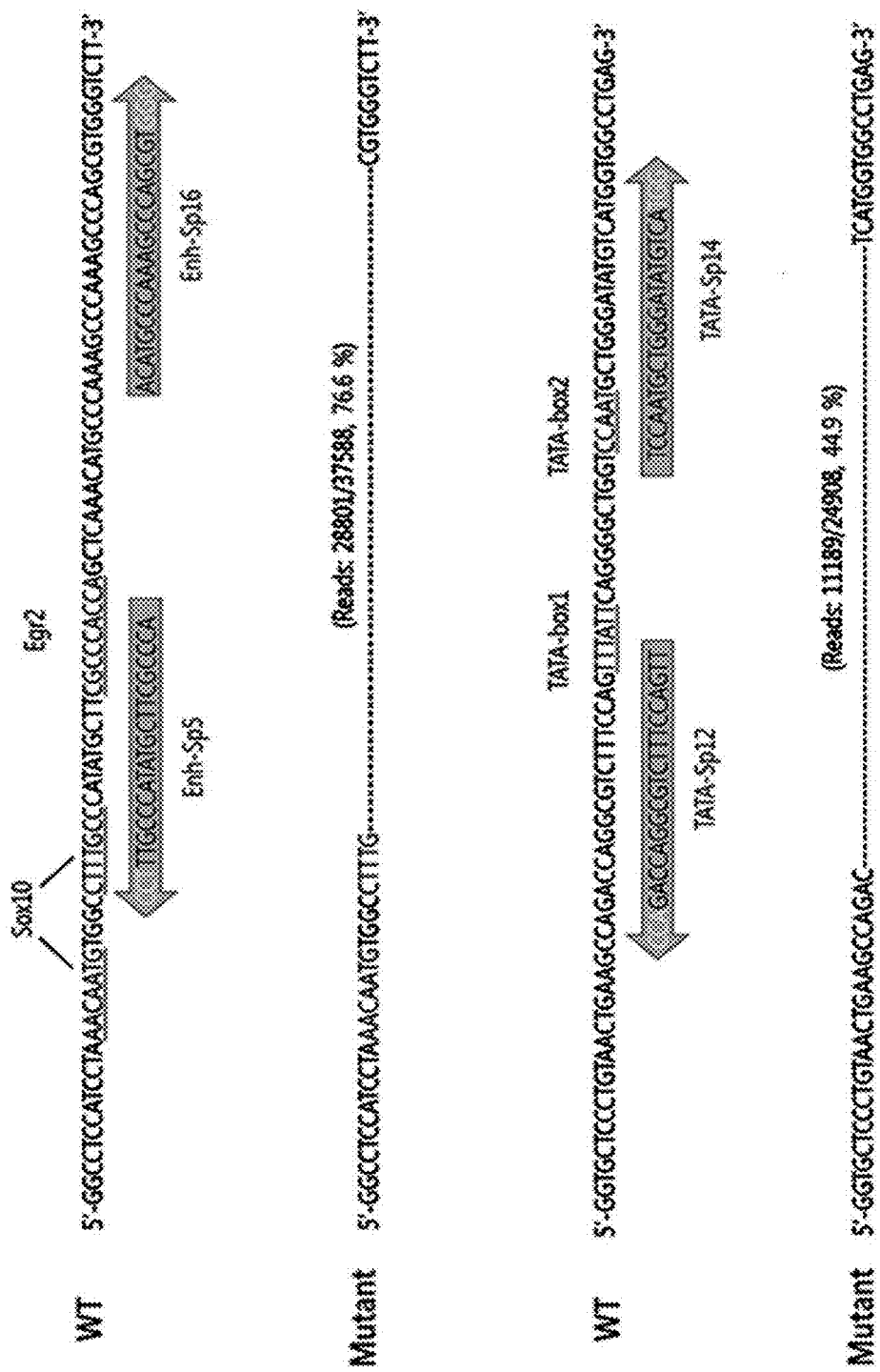
FIG. 7 illustrates Deletions of a small part of human PMP22 by the treatments of the dual sgRNAs. The WT sequence including sequences for Sox10 and Egr2 is a SEQ ID NO: 582, and the mutant sequence deleted a part thereof is a SEQ ID NO: 583. The target sequences for the Enh-Sp5 and the Enh-Sp16 are SEQ ID NOs: 584 and 585. In addition, the WT sequence including TATA-boxes is a SEQ ID NO: 586, and the mutant sequence deleted a part thereof is a SEQ ID NO: 587. The target sequences for the TATA-Sp12 and the TATA-Sp14 are SEQ ID NOs: 588 and 589.

Although effective indel mutations caused by sgRNA were identified in human cells, it is uncertain whether the effect would also be possible in Schwann cells. Thus, in order to investigate the effects of PMP22 expression inhibition and gene manipulation in Schwann cells, the SpCas9-sgRNA effect was confirmed using sNF2.0 cells, which are Schwann-like cells. The effective SpCas9-sgRNA identified in Jurkat cells was repeatedly tested in sNF02.0 cells. After transduction, it was confirmed through deep sequencing analysis that the same high indel frequency was obtained by the same sgRNA. Transduction of a single sgRNA targeting the promoter (TATA-box) site and enhancer-binding site induced indels of 31% and 59%, respectively (FIG. 7). Interestingly, a 40 to 50 bp small deletion containing a main controlling factor (for example, EGR or SOX10-binding site) of a myelin gene, or an important TATA-box was found in a very large number of cells of cells treated with dual sgRNA (FIG. 7).

Example 3. Expression Control of PMP22 by Gene Manipulation

Figure 8:
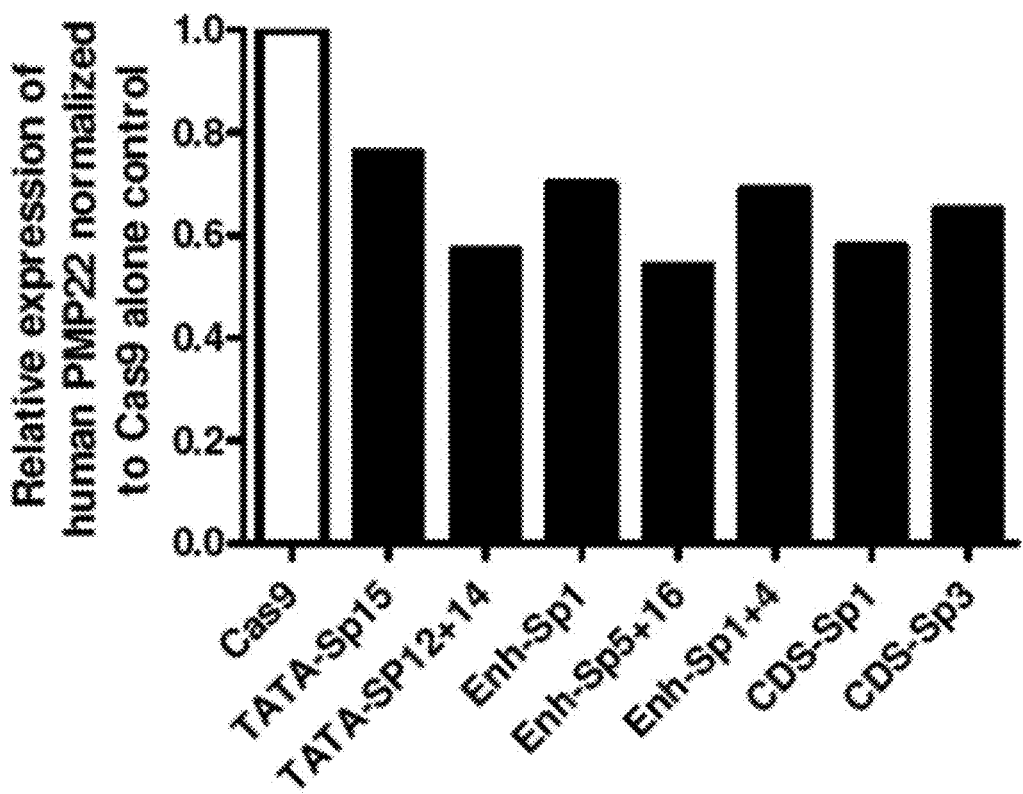
FIG. 8 is a graph illustrating a decrease in mRNA expression of human PMP22 by SpCas9-sgRNA in human Schwann-like cells.

In order to evaluate the change in expression of PMP22 by an effective sgRNA, Schwann-like cells were differentiated, and qRT-PCR was performed. As a result, most of the sgRNAs targeting PMP22 effectively inhibited the expression of PMP22 (FIG. 8). When single sgRNA was used, the expression of PMP22 was decreased by about 30% as compared to a control treated with only Cas9, and when dual sgRNA was used, the expression of PMP22 was decreased by about 50% as compared to the control treated with only Cas9.

Example 4. Gene Manipulation of Schwann Cells

Figure 9:
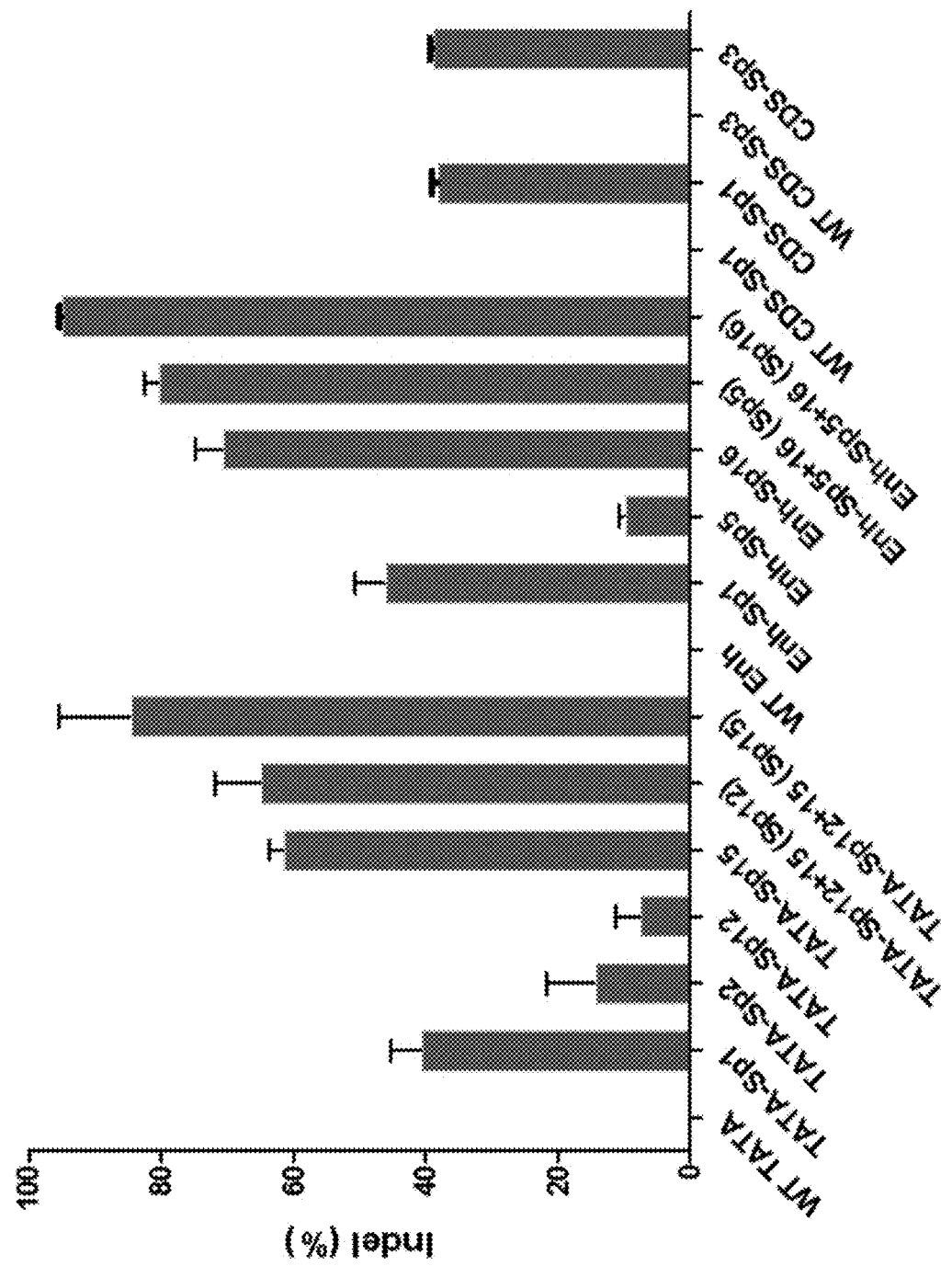
FIG. 9 illustrates indel frequency measurement results by SpCas9-sgRNA at each target site of a human PMP22 gene in human primary Schwann cells.
Figure 11:
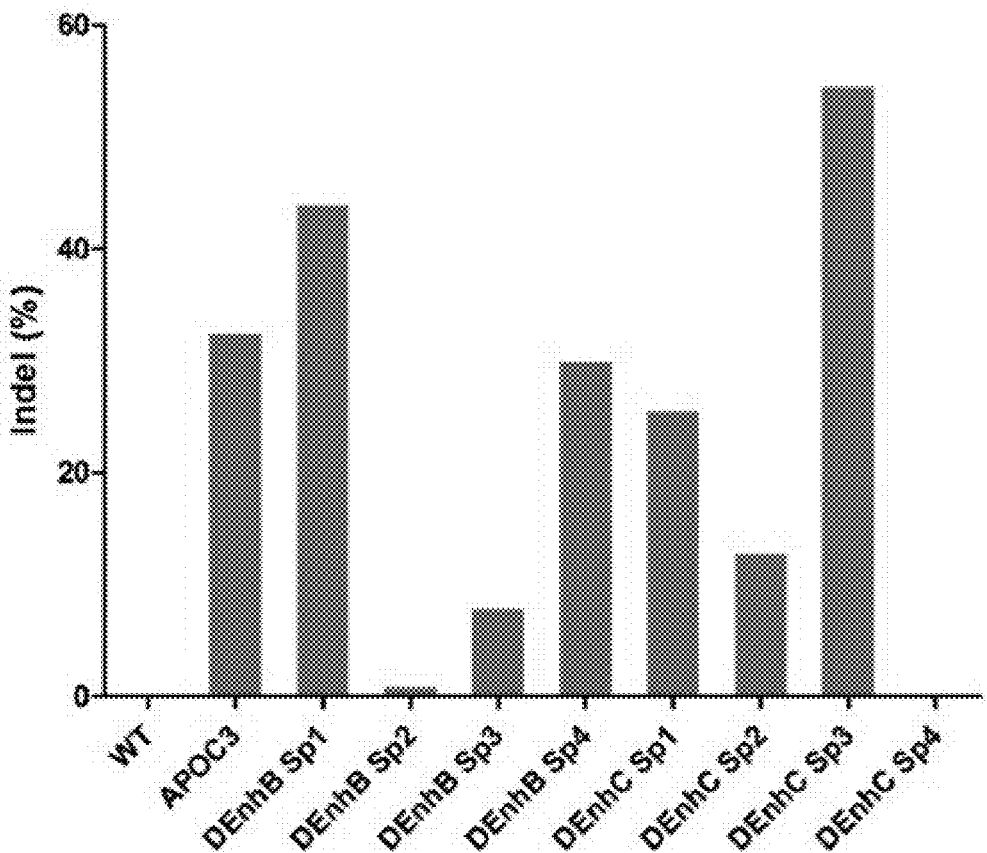
FIG. 11 illustrates indel frequency measurement results by SpCas9-sgRNA targeting distal enhancer sites (distal enhancer regions) B and C of a human PMP22 gene in human primary Schwann cells.
Figure 12:
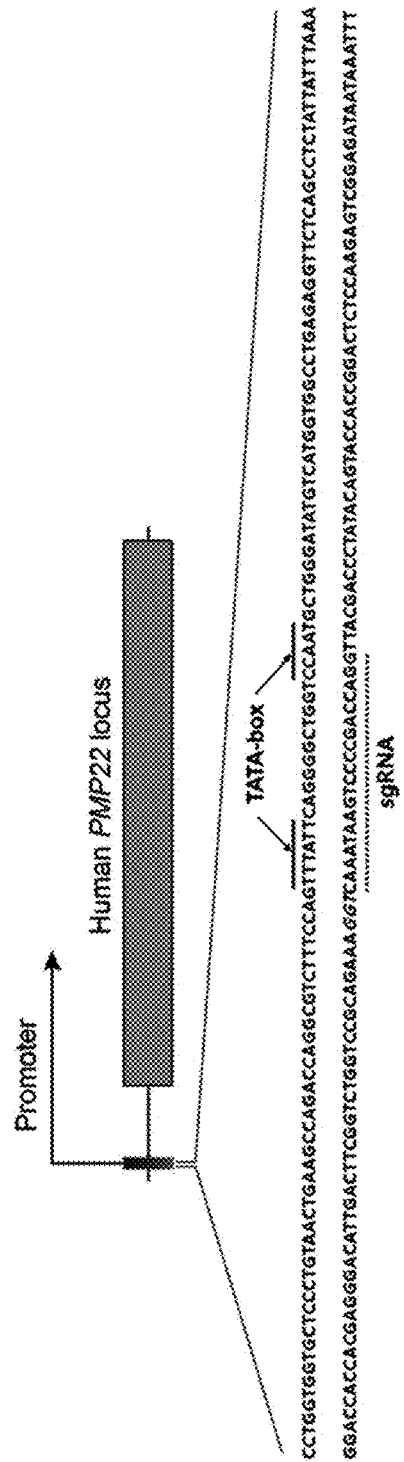
FIG. 12 illustrates a target sequence targeting a promoter region including a TATA-box site of a human PMP22 position. The sequences of a part of the promoter region are SEQ ID NOs: 590 (top strand) and 591 (bottom strand).

After expression inhibition and gene manipulation effects of PMP22 were previously confirmed in Schwann-like cells, it was confirmed whether the previous result exhibited a similar effect in human primary Schwann cells. The indel frequency according to the target site was observed using the SpCas9-sgRNA at each target site of the human PMP22 gene in human primary Schwann cells. As a result, it was confirmed that the indel frequency was high at the target site in most of the sgRNAs targeting TATA-box, enhancer, and coding sequences of the PMP22 gene (FIG. 9). Further, even when dual sgRNAs each targeting TATA-box and an enhancer was used, a high indel frequency was exhibited. It was confirmed that an indel occurred at the target site additionally using an sgRNA targeting sequences encoding distal enhancer sites B and C (FIG. 11), and in this case, an sgRNA targeting APOC3 was used as a control.

Figure 10:
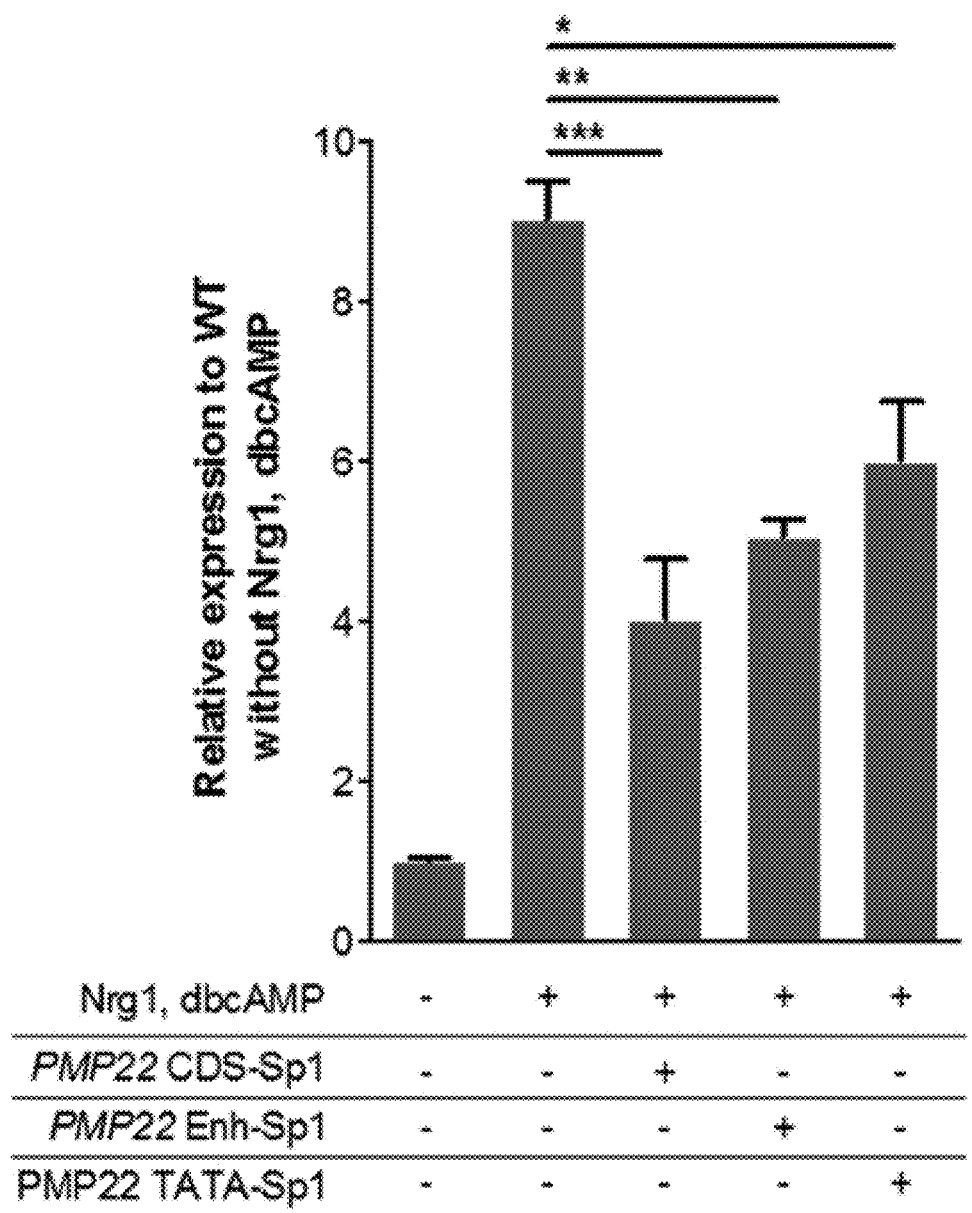
FIG. 10 is a graph illustrating effective and specific expression decreases of PMP22 by SpCas9-sgRNA at each target site of a human PMP22 gene in human primary Schwann cells, and illustrates relative mRNA expression comparison results of PMP22, which are measured by qRT-PCR with or without a treatment of a myelination signal factor and an RNP complex for each target site (n=3, One-way ANOVA and Tukey post-hoc tests: *p<0.05).

In addition, in order to confirm whether the SpCas9-sgRNA at each target site causes a decrease in expression of the PMP22 gene, a qRT-PCR analysis was performed. Since PMP22 is transcribed at the final stage of differentiation of Schwann cells, human primary Schwann cells were treated with a well-known differentiation signal factor including Neuregulin-1 (Nrg1) and dibutryral cyclic AMP (dbcAMP) for 7 days. As a result, it was confirmed that the expression of PMP22 was increased by 9 times in cells treated with Nrg1 and dbcAMP as compared to cells which were not treated with Nrg1 nor dbcAMP. In contrast, when cells were treated with SpCas9-sgRNA at each target site, it was confirmed that the expression of PMP22 was induced 4 to 6-fold. This is determined to be due to the expression inhibition of PMP22 due to each target site modification of PMP22 by SpCas9-sgRNA at each target site (FIG. 10).

Example 5. Effects of Decrease in Effective and Specific Expression of PMP22 Using CRISPR/Cas9 Targeting TATA-Box Site of Human PMP22 Gene An experiment was performed in human primary Schwann cells by selecting sgRNA_TATA_Sp #1 (hereinafter, described as PMP22-TATA sgRNA) which exhibits a high indel efficiency among sgRNAs targeting a TATA-box site previously screened and may target the TATA-box. An indel was induced by transducing human primary Schwann cells with an RNP complex including an sgRNA and Cas9 protein (FIG. 13), and it was confirmed through a targeted deep sequencing analysis that 89.54±1.39% of the total indels were generated at the TATA-box site of human PMP22 (FIG. 13).

In addition, to confirm whether a mutation formed at the TATA-box of PMP22 caused a decrease in expression of the PMP22 gene, a qRT-PCR analysis was performed. Since PMP22 is transcribed at the final stage of differentiation of Schwann cells, human primary Schwann cells were treated with a well-known differentiation signal factor including Neuregulin-1 (Nrg1) and dibutryral cyclic AMP (dbcAMP) for 7 days. As a result, it was confirmed that the expression of PMP22 was increased by 9 times in cells treated with Nrg1 and dbcAMP as compared to cells which were not treated with Nrg1 nor dbcAMP. In contrast, it was confirmed that when cells were treated together with PMP22-TATA RNP, the expression of PMP22 was induced 6-fold. This is determined to be due to expression inhibition of PMP22 by TATA modification of PMP22 by CRISPR/Cas9 (FIG. 13). In a control treated with both the differentiation signal factor and the AAVS1 target RNP, no difference in expression of the PMP22 gene could be confirmed.

In order to confirm the specificity of PMP22-TATA RNP, an in silico-based off-target analysis was performed. Through the targeted deep sequencing, no indel mutation exceeding a sequencing error ratio (0.1% on average) was confirmed at the off-target site confirmed by an in silico analysis (FIG. 14). Since the in silico-based off-target analysis may be a biased approach, Digenome-seq (a whole sequencing-based off-target analysis which is not biased) was also performed. As a result, it was possible to confirm nine off-target sites cleaved by PMP22-TATA RNP in vitro (FIG. 17, FIG. 18). However, as a result of a re-analysis through the targeted deep sequencing, an abnormal indel mutation was not found at the off-target sites (FIG. 19).

These results show that the effective and specific modification of the TATA-box of PMP22 by PMP22-TATA RNP may control the transcription level of PMP22 in human primary Schwann cells.

Example 6. Alleviation Effects of Disease Phenotype by Expression Inhibition of CRISPR/Cas9-Mediated PMP22 in CMT1A Mice In order to test the PMP22 transcription control by PMP22-TATA RNP in vivo, PMP22-TATA RNP enclosed by liposomes was directly injected into the sciatic nerve of the C22 mouse (FIG. 20). In this case, an RNP complex targeting Rosa26 (mRosa26) was used as a control. mRosa26 RNP or PMP22-TATA RNP was injected intraneurally into and delivered to the left sciatic nerve (ipsilateral) of a 6-day old (p6) mouse, and the right sciatic nerve was used as an internal control (contralateral). Four weeks after injection, the intraneural delivery efficiency of the RNP complex was confirmed through targeted deep sequencing by collecting genomic DNA from the sciatic nerve. As a result, all the sciatic nerves respectively treated with mRosa26 RNP and PMP22-TATA RNP showed indel efficiencies of about 11% (FIG. 21). Further, a TATA-box mutation of 98.48±0.15% was confirmed in the overall indel sequencing read consistent with the in vitro results (FIG. 21).

In addition, in order to confirm the expression inhibition of PMP22 by the TATA-box mutation in vivo, a qRT-PCR analysis of mRNA extracted from the whole sciatic nerve was performed on the RNP-treated sciatic nerve. Similar to the in vitro results, it was confirmed that the expression of the PMP22 gene was reduced by 38% as compared to the control (FIG. 21).

In order to confirm whether the off-target mutation occurred in the sciatic nerve by PMP22-TATA RNP, an in silico-based off-target analysis was performed. As a result, eight off-targets including 3 bp or more mismatches were confirmed from the mouse genome (FIG. 22), and as a result of performing targeted deep sequencing, no indel mutation exceeding the sequencing error ratio was confirmed from the nerve (ipsilateral) treated with PMP22-TATA RNP (FIG. 23).

In order to test whether a decrease in transcription of PMP22 caused by PMP22-TATA RNA could prevent demyelination, the sciatic nerve of the C22 mouse treated with PMP22-TATA RNP or mRosa26 RNP was obtained, and the semi-thin cross sections thereof were stained with toluidine-blue (myelin staining). Furthermore, in order to measure the g-ratio, the axon diameter and the fiber (axon including myelin) diameter were measured. As a result, it could be confirmed that a thicker myelin sheet was formed in an experimental group treated with PMP22-TATA RNP (FIG. 24, FIG. 25). In addition, when the experimental group was treated with PMP22-TATA RNP, as compared to a control treated with mRosa26 RNP, it was found that the number of axons having a large diameter was increased (FIG. 24, FIG. 25). A result of measuring the number of large myelinated fibers having a diameter of 6 μm or more in an experimental group (16.5%) treated with PMP22-TATA RNP exhibits a clearer therapeutic effect than that in the control (2.6%, $p<0.01$).

In consideration of a considerable improvement in myelination histological analysis, electrophysiological profiles of the two groups were investigated. As a result, it was confirmed that the distal latency (DL) was decreased and the motor nerve conduction velocity (NCV) was increased in the sciatic nerve of the experimental group treated with PMP22-TATA RNP as compared to a control treated with mRosa26 RNP (FIG. 26), and the results correspond to the increases in myelin thickness and axon diameter in the nerve treated with PMP22-TATA RNP. Further, it was confirmed that the amplitude of the compound muscle action potential (CMAP) was considerably increased in the nerve treated with PMP22-TATA RNP (FIG. 26), which corresponds to the previous result.

In consideration of the histologically and electrophysiologically improved effects by PMP22-TATA RNP, the locomotor behavior of mice was analyzed by a rotarod experiment. As a result, it was confirmed that mice (11 to 16 week old) treated with PMP22-TATA RNP remained longer on the rod than mice (11 to 16 week old) treated with mRosa26 RNP (FIG. 27). Further, it was confirmed that mice treated with MP22-TATA RNP were increased in muscle as compared to mice treated with mRosa26 RNP (FIG. 28).

These results show a therapeutic effect of PMP22-TATA RNP for alleviating or treating demyelination by overexpression of PMP22, such as CMT1A.

Accordingly, the aforementioned results show the expression inhibition effect of PMP22 using CRISPR/Cas9 targeting the promoter site of PMP22. Furthermore, the results show that a direct non-viral delivery of PMP22-TATA RNP to the sciatic nerve of the C22 mouse may improve the clinical and neuropathological phenotypes associated with the demyelination caused by the overexpression of PMP22. Therefore, it is believed that the CRISPR/Cas9-mediated modification of the transcriptional regulatory region of PMP22 may be a good strategy for the treatment of CMT1A and other diseases that exhibit demyelinating neuropathies.

Example 7. PLP Gene Expression Regulatory Effect

When a PLP1 gene is duplicated, the PLP1 gene is overexpressed, which becomes the major cause of a PMD disease. Therefore, to control PLP1 transcription for the treatment of the PMD disease, the transcriptional regulatory region of the PLP gene was artificially modified using CRISPR/Cas9 to confirm its effect.

To this end, SpCas9 and CjCas9 screening was performed for a TATA-box of the promoter sequence and the enhancer (wMN1) of mouse Plp1, sgRNA with the highest activity was selected, and then Plp1 downregulation was confirmed by qRT-PCR (FIG. 29). Here, the enhancer of Plp1 may be an ASE (Hamdan et al., 2015; Meng et al., 2005; Wight, 2017) or wMN1 (Hamdan et al., 2018; Tuason et al., 2008) region.

Based on the sgRNA screening result, each of sgRNAs for SpCas9 and CjCas9 with high indel ratios was selected (FIGS. 31 to 34 and Table 19), when the TATA-box and wMN1 enhancer regions of Plp1 were targeted using oligodendrocytes, that is, an N20.1 cell line expressing a Plp1 gene, a study on what could lead to the downregulation of the Plp1 gene was performed by qRT-PCR.

TABLE 19

Screened sgRNA list (mPlp1-TATA, mPlp1-wmN1 SpCas9 and CjCas9 lead sgRNA list)

| | mPlp1-TATA-SpCas9 | |
|---|---|---|
| No. #RGEN Target (5' to 3') | | Indel ratio (%) |
| 1 TGTTTGGTAGTATAGTAAGTAGG (SEQ ID NO: 116) | | 74.6 |

| | mPlp1-WmN1-SpCas9 | | |
|---|---|---|---|
| No. #RGEN Target (5' to 3') | | Indel ratio (%) | location |
| 26 CTCCCACTGCCTTATTAGGCAGG (SEQ ID NO: 141) | | 98.9 | Up |
| 27 AGAGCTCAAATGGGTTCTAAAGG (SEQ ID NO: 142) | | 99.1 | Up |
| 28 ACCACATTCAAGAGCTCAAATGG (SEQ ID NO: 143) | | 98.6 | Up |
| 8 ATCACAGTTTATACTTAGCTGGG (SEQ ID NO: 123) | | 48.4 | Down |
| 9 GGAATACCTCAGGCTCAACAGGG (SEQ ID NO: 124) | | 66.6 | Down |

| | mPlp1-TATA-CjCas9 | |
|---|---|---|
| No. #RGEN Target (5' to 3') | | Indel ratio (%) |
| 2 AAAGCCTACTTACTATACTACCAAACACAC (SEQ ID NO: 154) | | 27.9 |
| 3 CAAAAGCCTACTTACTATACTACCAAACAC (SEQ ID NO: 155) | | 33.6 |

| | mPlp1-wMN1-CjCas9 | | |
|---|---|---|---|
| No. #RGEN Target (5' to 3') | | Indel ratio (%) | location |
| 10 GACATACAGAGAGGGGGGGAGAGAAATAC (SEQ ID NO: 162) | | 28.5 | Up |
| 25 TTGAATGTGGTATAAGTGCTAATATCATAC (SEQ ID NO: 177) | | 33.7 | Up |
| 13 TCATCAAAGTAGTCGACAGTCAAAGCATAC (SEQ ID NO: 165) | | 13.8 | Down |
| 14 TGAATTCTAACAGGAAAACTCAGAACATAC (SEQ ID NO: 166) | | 15.7 | Down |
| 23 TTCCAAAGTTCTGTCACCCAGTAAAAACAC (SEQ ID NO: 175) | | 5.4 | Down |

As a result, it was confirmed that the targeting of the TATA box or wmN1 enhancer region of Plp1 using SpCas9 and CjCas9 leads to the significant downregulation of Plp1 (FIG. 35). In addition, SpCas9 and CjCas9 screening for the wmN1 enhancer region of a human PLP1 gene was performed to confirm an indel ratio (%) (FIGS. 36 and 37).

Therefore, it is considered that CRISPR/Cas9-mediated artificial modification of the transcriptional regulatory region of PLP1 can be a good strategy for PMD treatment.

Example 8. Manipulation of Promoter (P1) of PMP22 Gene Using SpCas9-sgRNAs and Effect of Controlling PMP22 Expression Mouse (C22 mice) primary Schwann cells overexpressing human PMP22 were treated with SpCas9-sgRNA targeting each of a P1 promoter and a P2 promoter of a human PMP22 gene, thereby confirming the expression level of PMP22.

As a result, it was confirmed that, when SpCas9-sgRNA targeting the P1 promoter of the PMP22 is treated, a PMP22 expression level is reduced (FIG. 38). Contrarily, it was confirmed that, when SpCas9-sgRNA targeting the P2 promoter of the human PMP22 gene is treated, there is no significant change in a PMP22 expression level. Therefore, it can be confirmed that, since the P1 promoter plays a pivotal role in the control of the PMP22 expression, it can be an important target for controlling the PMP22 expression.

Example 9. sgRNA Screening for Deleting Promoter 1 (P1) of PMP22 Gene

To screen a therapeutically effective sgRNA sequence for reducing human PMP22 expression to a normal range, a human cell line was transduced with various sgRNAs and Cas9s, which are designed to target upstream and downstream of the promoter 1 (P1) of the PMP22 gene. gDNA was collected from the cells, and then subjected to targeted deep sequencing. Mutations with various patterns induced by the sgRNA sequence were identified by NHEJ-mediated indels. Some SpCas9-sgRNAs and CjCas9-sgRNAs highly induced indels in all regions upstream and downstream of promoter1 (P1) (FIGS. 40 and 41). SpCas9-sgRNAs (hPMP22-P1-Sp1 targeting an upstream region and hPMP22-P1-Sp9 targeting a downstream region) and CjCas9-sgRNAs (hPMP22-P1-Cj12 targeting an upstream region and hPMP22-P1-Cj8 targeting a downstream region), which highly generate indels, were selected, and then a subsequent experiment was conducted.

Example 10. Deletion of Promoter of PMP22 Gene Using SpCas9-sgRNAs and Effect of Controlling PMP22 Expression To confirm whether the promoter of the PMP22 gene in human cells can be deleted using the selected SpCas9-sgRNAs, a promoter deleting effect was confirmed by the selected SpCas9-sgRNAs using Schwann-like cells (sNF02.0 cells). The sizes of products obtained by amplifying target genes using PCR of gDNAs of the cells collected after transduction were compared by electrophoresis. As a result, when the selected SpCas9-sgRNAs were introduced, it can be confirmed that approximately 310 bp was deleted by the selected SpCas9-sgRNAs, compared to the wild-type PMP22 gene (FIG. 42). Therefore, it can be seen that the promoter region of the PMP22 gene was deleted by the selected SpCas9-sgRNAs. In addition, as a result of comparing mRNA expression levels of the PMP22 gene, it can be confirmed that, when the promoter was deleted using the selected SpCas9-sgRNAs, the mRNA expression level of the PMP22 gene was considerably reduced (FIG. 43). Therefore, it was confirmed that the deletion of the promoter using the selected SpCas9-sgRNAs leads to knockdown of the expression of the PMP22 gene.

This result shows that, when an expression level increases due to a duplicate gene, since the expression level of the duplicate gene can be controlled by deleting or losing the transcriptional regulatory region, for example, a promoter, of the corresponding duplicate gene, the deletion of the transcriptional regulatory region may be utilized as one strategy to treat a disease caused by a duplicate gene.

This application contains references to amino acid sequences and/or nucleic acid sequences which have been submitted concurrently herewith as the sequence listing text file entitled "000013uscob SequenceListinq.XML", file size 581 kilobytes (KB), created on 28 Dec. 2022. The aforementioned sequence listing is hereby incorporated by reference in its entirety pursuant to 37 C.F.R. § 1.52(e)(5).

What is claimed is:

1. A method for treating Pelizaeus-Merzbacher disease (PMD) of a subject, the method comprises:
    administering an expression control composition into the subject, wherein the expression control composition comprises:
        a *Campylobacter jejuni*-derived Cas9 protein, or a nucleic acid encoding the Cas9 protein;
        a first guide RNA comprising a first crRNA and a first tracrRNA, or a nucleic acid encoding the first guide RNA,
            wherein the first crRNA comprises a first guide domain, and a first first complementary domain,
            wherein the first guide domain and the first first complementary domain are linked sequentially from 5' to 3' end,
            wherein the first guide domain is capable of targeting a target sequence of an upstream region of an wmN1 enhancer region of the PLP1 gene selected from the group consisting of SEQ ID NOs: 94, 96, 97, 99, and 100-108, and
            wherein the first first complementary domain and the first tracrRNA are capable of interacting with the Cas9 protein; and
        a second guide RNA comprising a second crRNA and a second tracrRNA, or a nucleic acid encoding the second guide RNA,
    wherein the second crRNA comprises a second guide domain, and a second first complementary domain,
        wherein the second guide domain and the second first complementary domain are linked sequentially from 5' to 3 end,
        wherein the second guide domain is capable of targeting a target sequence of downstream region of wmN1 enhancer region of the PLP1 gene, which is selected from the group consisting of SEQ ID NOs: 111 and 113,
        wherein the second first complementary domain and the second tracrRNA are capable of interacting with the Cas9 protein.

2. The method of claim 1, wherein the first guide RNA is a single guide RNA, and the second guide RNA is a single guide RNA.

3. The method of claim 1, wherein the first first complementary domain and the second first complementary domain of the crRNA both have a sequence of SEQ ID NO: 297, and
    wherein the first tracrRNA and the second tracrRNA both have a sequence such that SEQ ID NO: 300, SEQ ID NO: 303, and SEQ ID NO: 305 are linked sequentially from 5' to 3' end.

4. The method of claim 1, wherein the expression control composition includes:
    a ribonucleoprotein comprising the first guide RNA and the Cas9 protein; and
    a ribonucleoprotein comprising the second guide RNA and the Cas9 protein.

5. The method of claim 1, wherein the expression control composition is in a form of a vector comprising:
    the nucleic encoding Cas9 protein;
    the nucleic acid encoding the first guide RNA; and
    the nucleic acid encoding the second guide RNA.

* * * * *